(12) United States Patent
Cheng et al.

(10) Patent No.: US 7,960,547 B2
(45) Date of Patent: Jun. 14, 2011

(54) TRANSITION METAL COMPLEXES WITH CARBENE LIGANDS AND THEIR APPLICATION

(75) Inventors: Chien-Hong Cheng, Hsinchu (TW);
Cheng-Han Hsieh, Hsinchu (TW);
Kun-Yi Lu, Hsinchu (TW)

(73) Assignee: Chien-Hong Cheng, Hsinchu (TW)

( * ) Notice: Subject to any disclaimer, the term of this patent is extended or adjusted under 35 U.S.C. 154(b) by 837 days.

(21) Appl. No.: 11/949,430

(22) Filed: Dec. 3, 2007

(65) Prior Publication Data
US 2009/0149653 A1   Jun. 11, 2009

(51) Int. Cl.
*C07F 15/00* (2006.01)
*H01L 51/50* (2006.01)
(52) U.S. Cl. ............ 546/2; 428/690; 428/917; 313/504
(58) Field of Classification Search ...... 546/2; 428/690, 428/917; 313/504
See application file for complete search history.

(56) References Cited

U.S. PATENT DOCUMENTS
7,193,088 B2 * 3/2007 Cheng et al. ............ 548/103
2006/0258043 A1  11/2006 Bold et al.

FOREIGN PATENT DOCUMENTS
WO     2006056418      6/2006

OTHER PUBLICATIONS
Taiwan Intellectual Property Office "Office Action", Oct. 14, 2010, Taipei, Taiwan.

* cited by examiner

*Primary Examiner* — Charanjit S Aulakh
(74) *Attorney, Agent, or Firm* — WPAT, PC; Justin King

(57) ABSTRACT

The present invention discloses a transition metal complex having carbene ligands. The disclosed transition metal complex has a structure of a center transition metal surrounded by two identical carbene ligands and one double-chilating ligand which is a nitrogen-contain heteroaryl group compound with pyridyl group. The disclosed transition metal complex can be represented by the following formula:

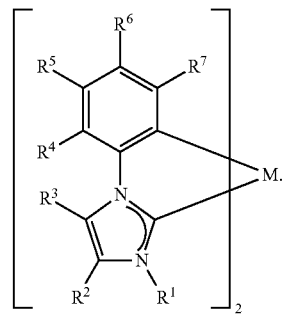

26 Claims, 2 Drawing Sheets

TRANSITION METAL COMPLEXES WITH CARBENE LIGANDS AND THEIR APPLICATION

BACKGROUND OF THE INVENTION

1. Field of the Invention

The present invention is generally related to a transition metal complex, especially to a transition metal complex having carbene ligands, and applications thereof in organic electronic devices.

2. Description of the Prior Art

Organic light-emitting diode (OLED) is an electronic device which emits light through the use of organic semiconductor materials and emitting materials. OLED works on the principal of electroluminescence, where a bias is applied to an electrode pair causing the electrons and holes to diffuse through an electron transport layer (ETL) and hole transport layer (HTL), respectively, to enter an emitting material region. The electrons and holes recombine in the emitting region and form a particle generally referred as exciton. In order for the exciton to come back to the ground state, the energy is given off in the form of photo radiation. The color of the radiation can be tuned by using different emitting materials.

Recently, organic emitting materials with an emissive triplet state, also referred to as organic phosphorescent materials, have drawn much attention as an OLED material. Theoretically, phosphorescent materials are three times in efficiency compared to conventional fluorescent materials which have an emissive singlet state. Common organic compounds have either no phosphorescent properties or can only be observed of this property at a very low temperature, such as 77 K. Investigation has suggested that addition of heavy atoms can overcome this drawback; however, not all heavy atoms are suitable for this purpose. Researchers have reported that transition metals such as rhenium (Re), osmium (Os), iridium (Ir) and platinum (Pt) are the most suitable candidates.

Metal complexes have been used as the phosphorescent dopants of OLEDs. In some metal complexes, the presence of heavy atoms causes strong spin-orbital coupling, leading to the mixing of the singlet and triplet excited states. This greatly reduces the lifetime of the triplet state and thereby the phosphorescence efficiency is promoted. Among these metal complexes used in the light-emitting layer of the organic light emitting diode, iridium complexes have been extensively researched due to the strong spin-orbit coupling resulting from their electron configurations.

Cyclometalated iridium complexes are the one of the most efficient and bright organic phosphorescent materials currently known. Among them, Iridium(III) bis(4,6-difluorophenylpyridinato)picolate (FIrpic) is a common blue phosphorescent material having triplet state. FIrpic renders high device efficiency, but its color saturation is poor. Its CIE coordination locates in the region around (0.16, 0.30). The high Y value leads to a color that lies between blue and green, rather than a deep blue color which is required in a full-color display.

In 2005, professor Thompson announced a novel iridium metal complex which has carbene ligands[1,2]. The disclosed material gave a CIE coordination of (0.17, 0.06), not quite met the required (0.15, 0.15) or (0.15, 0.09); moreover, the external quantum efficiency only reached 5.8%, and its brightness only reached 1.7 μm/W. More similar compounds were disclosed in 2005, 2006 and 2007, with substantially same structure, only differed in the substituents on the carbene ligands.

It has been no longer than 7~8 years since the first phosphorescent material was reported, in which the development of blue phosphorescent material has only been of 3~4 years. Recently, phosphorescent material has been a key to technical breakthrough for OLED devices. Especially, the OLED-based white lighting really depends on availability of more efficient and saturated blue phosphorescent materials.

In summary, blue phosphorescent material plays an important role in whether OLED can applied in the next generation white lighting. Therefore, a blue phosphorescent material having high external quantum efficiency, great hue, brightness and saturation is mostly desired by the industry.

SUMMARY OF THE INVENTION

Therefore, in accordance with the previous summary, objects, features and advantages of the present disclosure will become apparent to one skilled in the art from the subsequent description and the appended claims taken in conjunction with the accompanying drawings.

The present invention discloses a transition metal complex with carbene ligands and application thereof as a host material, electron transport material or hole transport material in organic electroluminescent devices.

One objective of the present invention is to provide a transition meal complex with high thermal stability, thereby extending its lifetime of application organic devices.

Another objective of the present invention is to provide a transition metal complex with carbene ligands which has a high triplet energy level and can be used to compose all blue, red or green emissive metal complex materials based on Ir, Pt or Os. The disclosed transition metal complex makes a blue phosphorescent organic electroluminescent device with high external quantum efficiency, great hue, brightness and saturation.

Accordingly, the present invention discloses transition metal complex with carbene ligands which comprises a moiety represented by the following formula:

Wherein M is a transition metal, $R^1 \sim R^7$ can be identical or different, and at one of the adjacent pair $R^2$ and $R^3$, $R^4$ and $R^5$, $R^5$ and $R^6$, $R^6$ and $R^7$ forms an aromatic ring, heterocyclic aromatic group, cycloalkenyl group, or heterocyclic alkenyl group.

The disclosed transition metal complex has a structure of a center transition metal surrounded by two identical carbene ligands and one double-chilating ligand which is a nitrogen-contain heteroaryl group compound with pyridyl group. The double-chilating ligand introduced into the chemical structure results in red-shift on the spectrum.

The present invention also discloses the potential applications of the disclosed transition metal complex, especially as the host material, electron transport material and hole transport material in an organic electroluminescent and/or phosphorescent device, or other organic electronic devices.

BRIEF DESCRIPTION OF THE DRAWINGS

The accompanying drawings incorporated in and forming a part of the specification illustrate several aspects of the present invention, and together with the description serve to explain the principles of the disclosure. In the drawings.

DETAILED DESCRIPTION OF THE PREFERRED EMBODIMENTS

Figure 1:
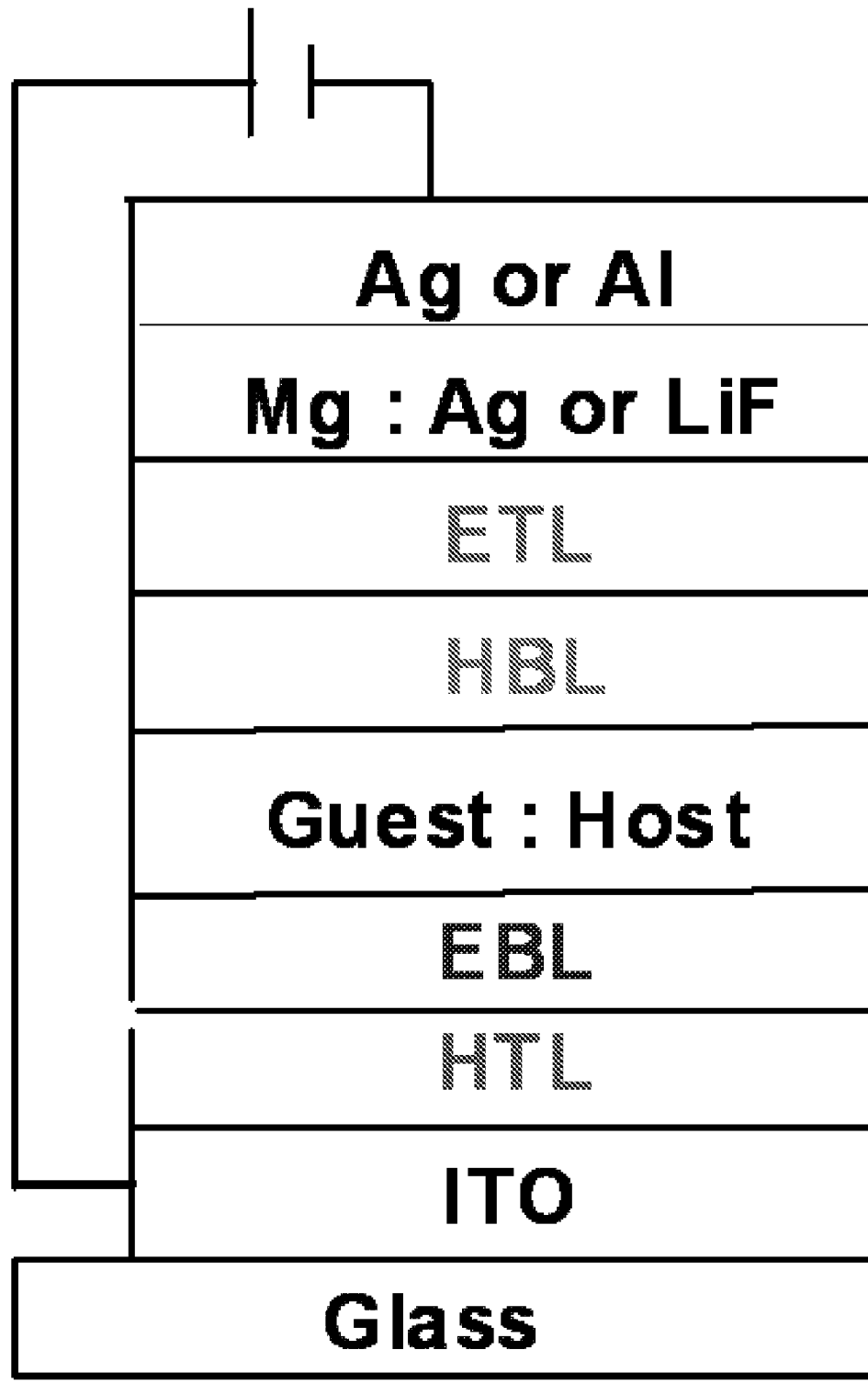
FIG. 1 is a schematic of the structure of an electroluminescent device.

The present disclosure can be described by the embodiments given below. It is understood, however, that the embodiments below are not necessarily limitations to the present disclosure, but are used to a typical implementation of the invention.

Having summarized various aspects of the present invention, reference will now be made in detail to the description of the invention as illustrated in the drawings. While the invention will be described in connection with these drawings, there is no intent to limit it to the embodiment or embodiments disclosed therein. On the contrary the intent is to cover all alternatives, modifications and equivalents included within the spirit and scope of the invention as defined by the appended claims.

It is noted that the drawings presents herein have been provided to illustrate certain features and aspects of embodiments of the invention. It will be appreciated from the description provided herein that a variety of alternative embodiments and implementations may be realized, consistent with the scope and spirit of the present invention.

It is also noted that the drawings presents herein are not consistent with the same scale. Some scales of some components are not proportional to the scales of other components in order to provide comprehensive descriptions and emphasizes to this present invention.

The first embodiment of the present invention discloses a transition metal complex with carbene ligand, the disclosed transition metal complex comprises a moiety represented by the following formula:

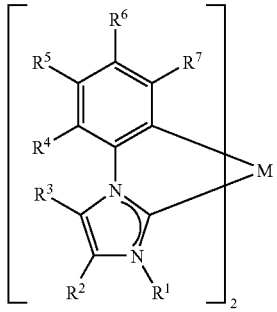

In the above formula, M is a transition metal and is selected from the group consisting of the following: ruthenium, rhodium, tungsten, rhenium, osmium, iridium, platinum; $R^1$ is selected from the group consisting of the following: C1-C20 alkyl group, C1-C20 cycloalkyl group, cycloalkenyl group, conjugated aromatic group, heterocyclic aromatic group; $R^2$~$R^7$ can be identical or different, and are independently selected from the group consisting of the following: H atom, halogen atom, C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group (—CN), nitro group, conjugated aromatic group, heterocyclic aromatic group, and cycloalkenyl group.

In one preferred example of this embodiment, at least one of the pairs of $R^2$-$R^3$, $R^4$-$R^5$, $R^5$-$R^6$, $R^6$-$R^7$ forms an aromatic ring, heterocyclic aromatic group, cycloalkenyl group, or heterocyclic alkenyl group; these aromatic ring, heterocyclic aromatic group, cycloalkenyl group, or heterocyclic alkenyl group can be a five-membered, six-membered or seven-membered ring. Moreover, they optionally comprise one or more substituent, wherein the substituent(s) can be identical or different and is independently selected from the group consisting of the following: H atom, halogen atom such as fluorine (Fl), chlorine (Cl), bromine (Br), iodine (Id), aryl group, halogen substituted aryl group, halogen substituted aralkyl group, haloalkyl substituted aryl group, haloalkyl substituted aralkyl group, aryl substituted C1-C20 alkyl group, electron donating group such as C1-C20 alkyl group and C1-C20 cycloalkyl group (for example methyl, ethyl, butyl, and cyclohexyl group), C1-C20 alkoxy group, C1-C20 substituted amino group, substituted arylamino group (for example aniline), or electron withdrawing group such as halogen atoms, nitrile group, nitro group, carbonyl group, cyano group (—CN), halogen substituted C1-C20 alkyl group (for example trifluoromethyl group, $CF_3$), and heterocyclic ring.

The remaining ones of $R^2$~$R^7$ which do not form a cyclic group can be identical or different, and are independently selected from the group consisting of the following: H atom, halogen atom, C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group (—CN), nitro group, conjugated aromatic group, heterocyclic aromatic group.

The following formula is an example of the disclosed moiety, wherein $R^2$ and $R^3$ forms an aromatic ring. It is noted that this formula is merely an example and is not to limit the scope of the present invention, which should be determined in accordance with the claims.

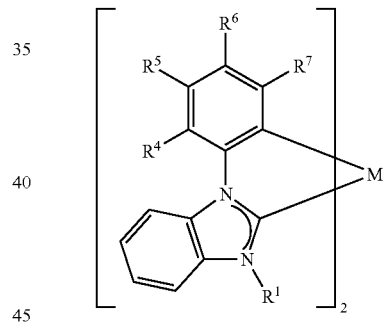

In another preferred example of this embodiment, the transition metal complex is represented by the following formula:

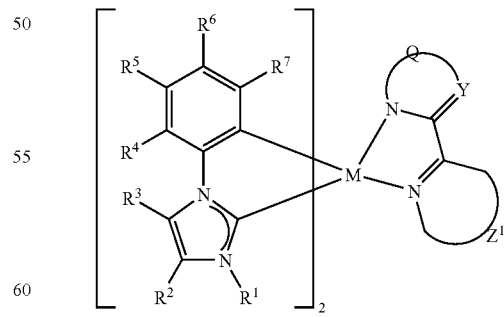

In the above formula, M is a transition metal and is selected from the group consisting of the following: ruthenium, rhodium, tungsten, rhenium, osmium, iridium, platinum; $R^1$ is selected from the group consisting of the following: C1-C20 alkyl group, C1-C20 cycloalkyl group, cycloalkenyl group, conjugated aromatic group, heterocyclic aromatic group; $R^2 \sim R^7$ can be identical or different, and are independently selected from the group consisting of the following: H atom, halogen atom, C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group (—CN), nitro group, conjugated aromatic group, heterocyclic aromatic group, cycloalkenyl group.

Preferably, at least one of the pairs $R^2$-$R^3$, $R^4$-$R^5$, $R^5$-$R^6$, $R^6$-$R^7$ forms an aromatic ring, heterocyclic aromatic group, cycloalkenyl group, or heterocyclic alkenyl group, these aromatic ring, heterocyclic aromatic group, cycloalkenyl group, or heterocyclic alkenyl group can be a five-membered, six-membered or seven-membered ring. Moreover, they optionally comprise one or more substituent.

The remaining ones of $R^2 \sim R^7$ which do not form a cyclic group can be identical or different, and are independently selected from the group consisting of the following: H atom, halogen atom, C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group (—CN), nitro group, conjugated aromatic group, heterocyclic aromatic group.

$Z^1$ can be any moiety which contributes to a nitrogen-containing heterocyclic aromatic ring or nitrogen-containing cycloalkenyl group which can be a five-membered, six-membered, or seven-membered ring. $Z^1$ can optionally comprise one or more substituent which can be identical or different, and is selected from the group consisting of the following: H atom, halogen atom such as fluorine (Fl), chlorine (Cl), bromine (Br), iodine (Id), aryl group, halogen substituted aryl group, halogen substituted aralkyl group, haloalkyl substituted aryl group, haloalkyl substituted aralkyl group, aryl substituted C1-C20 alkyl group, electron donating group such as C1-C20 alkyl group and C1-C20 cycloalkyl group (for example methyl, ethyl, butyl, and cyclohexyl group), C1-C20 alkoxy group, C1-C20 substituted amino group, substituted arylamino group (for example aniline), or electron withdrawing group such as halogen atoms, nitrile group, nitro group, carbonyl group, cyano group (—CN), halogen substituted C1-C20 alkyl group (for example trifluoromethyl group, $CF_3$), and heterocyclic ring.

Y is selected from the group consisting of the following: nitrogen (N), carbon (C), oxygen (O), sulfur (S); and Y optionally comprises a substituent. Q is a moiety comprising at least 2 atoms which contributes to a nitrogen-containing heterocycle, wherein Q comprises atom(s) selected from the group consisting of the following, or any combination thereof: nitrogen, carbon, oxygen, sulfur. The nitrogen-containing heterocycle optionally comprises one or more substituent. The substituent(s) can be identical or different, and are independently selected from the group consisting of the following: H atom, halogen atom such as fluorine (Fl), chlorine (Cl), bromine (Br), iodine (Id), aryl group, halogen substituted aryl group, halogen substituted aralkyl group, haloalkyl substituted aryl group, haloalkyl substituted aralkyl group, aryl substituted C1-C20 alkyl group, electron donating group such as C1-C20 alkyl group and C1-C20 cycloalkyl group (for example methyl, ethyl, butyl, and cyclohexyl group), C1-C20 alkoxy group, C1-C20 substituted amino group, substituted arylamino group (for example aniline), or electron withdrawing group such as halogen atoms, nitrile group, nitro group, carbonyl group, cyano group (—CN), halogen substituted C1-C20 alkyl group (for example trifluoromethyl group, $CF_3$), and heterocyclic ring.

In another preferred example of this embodiment, the transition metal complex is represented by the following formula:

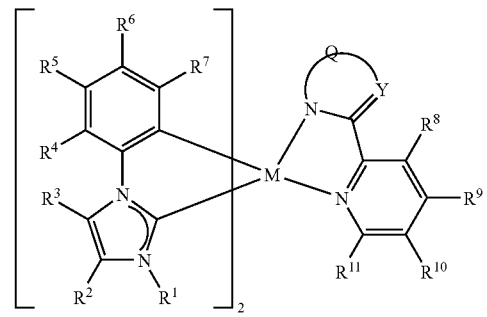

In the above formula, M is a transition metal and is selected from the group consisting of the following: ruthenium, rhodium, tungsten, rhenium, osmium, iridium, platinum; $R^1$ is selected from the group consisting of the following: C1-C20 alkyl group, C1-C20 cycloalkyl group, cycloalkenyl group, conjugated aromatic group, heterocyclic aromatic group; $R^2 \sim R^{11}$ can be identical or different, and are independently selected from the group consisting of the following: H atom, halogen atom, C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group (—CN), nitro group, conjugated aromatic group, heterocyclic aromatic group, cycloalkenyl group.

Preferably, at least one of the pairs $R^2$-$R^3$, $R^4$-$R^5$, $R^5$-$R^6$, $R^6$-$R^7$, $R^8$-$R^9$, $R^9$-$R^{10}$, $R^{10}$-$R^{11}$ forms an aromatic ring, heterocyclic aromatic group, cycloalkenyl group, or heterocyclic alkenyl group, these aromatic ring, heterocyclic aromatic group, cycloalkenyl group, or heterocyclic alkenyl group can be a five-membered, six-membered or seven-membered ring. Moreover, they optionally comprise one or more substituent, wherein the substituent(s) can be identical or different and is independently selected from the group consisting of the following: H atom, halogen atom such as fluorine (Fl), chlorine (Cl), bromine (Br), iodine (Id), C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group (—CN), nitro group, conjugated aromatic group, heterocyclic aromatic group.

The remaining ones of $R^2 \sim R^7$ which do not form a cyclic group can be identical or different, and are independently selected from the group consisting of the following: H atom, halogen atom, C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group (—CN), nitro group, conjugated aromatic group, heterocyclic aromatic group.

Y is selected from the group consisting of the following: nitrogen (N), carbon (C), oxygen (O), sulfur (S), and Y optionally comprises a substituent. Q is a moiety comprising at least 2 atoms which contributes to a nitrogen-containing heterocycle, wherein Q comprises atom(s) selected from the group consisting of the following, or any combination thereof: nitrogen, carbon, oxygen, sulfur. The nitrogen-containing heterocycle optionally comprises one or more substituent. The substituent(s) can be identical or different, and are independently selected from the group consisting of the following: H atom, halogen atom such as fluorine (Fl), chlorine (Cl), bromine (Br), iodine (Id), aryl group, halogen substituted aryl group, halogen substituted aralkyl group, haloalkyl substituted aryl group, haloalkyl substituted aralkyl group, aryl substituted C1-C20 alkyl group, electron donating group such as C1-C20 alkyl group and C1-C20 cycloalkyl group (for example methyl, ethyl, butyl, and cyclohexyl group), C1-C20 alkoxy group, C1-C20 substituted amino group, substituted arylamino group (for example aniline), or electron withdrawing group such as halogen atoms, nitrile group, nitro group, carbonyl group, cyano group (—CN), halogen substituted C1-C20 alkyl group (for example trifluoromethyl group, $CF_3$), and heterocyclic ring.

Another example of this embodiment discloses a forming path of the above transition metal complex from a transition metal dimer; the forming path is as the following:

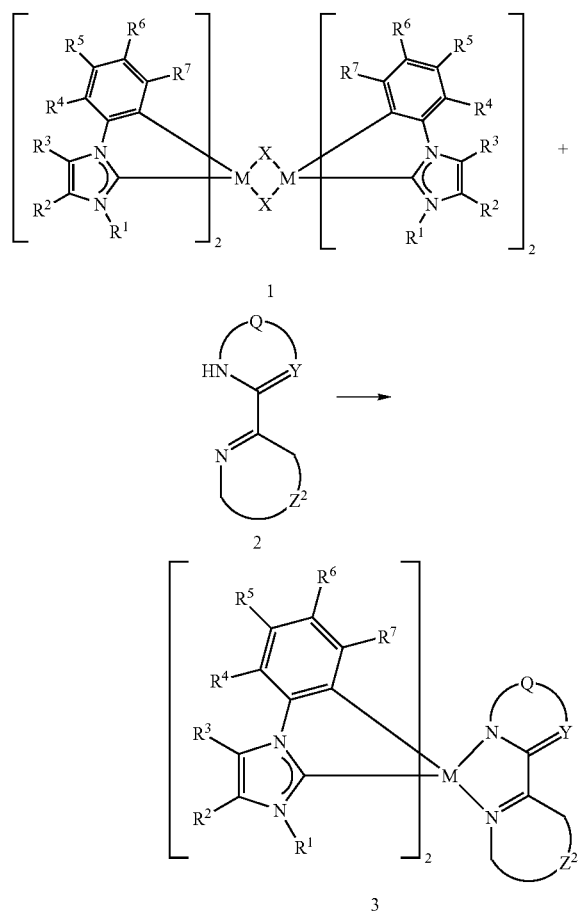

M is a transition metal and is selected from the group consisting of the following: ruthenium, rhodium, tungsten, rhenium, osmium, iridium, platinum; $R^1$ is selected from the group consisting of the following: C1-C20 alkyl group, C1-C20 cycloalkyl group, cycloalkenyl group, conjugated aromatic group, heterocyclic aromatic group; $R^2$~$R^7$ can be identical or different, and are independently selected from the group consisting of the following: H atom, halogen atom, C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group (—CN), nitro group, conjugated aromatic group, heterocyclic aromatic group, cycloalkenyl group.

Preferably, at least one of the pairs $R^2$-$R^3$, $R^4$-$R^5$, $R^5$-$R^6$, $R^6$-$R^7$ forms an aromatic ring, heterocyclic aromatic group, cycloalkenyl group, or heterocyclic alkenyl group, these aromatic ring, heterocyclic aromatic group, cycloalkenyl group, or heterocyclic alkenyl group can be a five-membered, six-membered or seven-membered ring. Moreover, they optionally comprise one or more substituent, wherein the substituent(s) can be identical or different and is independently selected from the group consisting of the following: H atom, halogen atom such as fluorine (Fl), chlorine (Cl), bromine (Br), iodine (Id), aryl group, halogen substituted aryl group, halogen substituted aralkyl group, haloalkyl substituted aryl group, haloalkyl substituted aralkyl group, aryl substituted C1-C20 alkyl group, electron donating group such as C1-C20 alkyl group and C1-C20 cycloalkyl group (for example methyl, ethyl, butyl, and cyclohexyl group), C1-C20 alkoxy group, C1-C20 substituted amino group, substituted arylamino group (for example aniline), or electron withdrawing group such as halogen atoms, nitrile group, nitro group, carbonyl group, cyano group (—CN), halogen substituted C1-C20 alkyl group (for example trifluoromethyl group, $CF_3$), and heterocyclic ring.

The remaining ones of $R^2$~$R^7$ which do not form a cyclic group can be identical or different, and are independently selected from the group consisting of the following: H atom, halogen atom, C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group (—CN), nitro group, conjugated aromatic group, heterocyclic aromatic group.

X is a halogen atom, such as fluorine, bromine, iodine. $Z^2$ is any moiety which contributes to a nitrogen-containing cyclic aromatic group or nitrogen-containing cycloalkenyl group which can be a five-membered, six-membered, or seven-membered ring. Moreover, $Z^2$ optionally comprises one or more substituent. The substituent(s) can be identical or different, and are independently selected from the group consisting of the following: H atom, halogen atom such as fluorine (Fl), chlorine (Cl), bromine (Br), iodine (Id), aryl group, halogen substituted aryl group, halogen substituted aralkyl group, haloalkyl substituted aryl group, haloalkyl substituted aralkyl group, aryl substituted C1-C20 alkyl group, electron donating group such as C1-C20 alkyl group and C1-C20 cycloalkyl group (for example methyl, ethyl, butyl, and cyclohexyl group), C1-C20 alkoxy group, C1-C20 substituted amino group, substituted arylamino group (for example aniline), or electron withdrawing group such as halogen atoms, nitrile group, nitro group, carbonyl group, cyano group (—CN), halogen substituted C1-C20 alkyl group (for example trifluoromethyl group, $CF_3$), and heterocyclic ring.

Y is selected from the group consisting of the following: nitrogen (N), carbon (C), oxygen (O), sulfur (S); and Y optionally comprises a substituent. Q is a moiety comprising at least 2 atoms which contributes to a nitrogen-containing heterocycle, wherein Q comprises atom(s) selected from the group consisting of the following, or any combination thereof: nitrogen, carbon, oxygen, sulfur. The above nitrogen-containing heterocycle optionally comprises one or more substituent. The substitutent(s) can be identical or different, and are independently selected from the group consisting of the following: H atom, halogen atom such as fluorine (Fl), chlorine (Cl), bromine (Br), iodine (Id), aryl group, halogen substituted aryl group, halogen substituted aralkyl group, haloalkyl substituted aryl group, haloalkyl substituted aralkyl group, aryl substituted C1-C20 alkyl group, electron donating group such as C1-C20 alkyl group and C1-C20 cycloalkyl group (for example methyl, ethyl, butyl, and cyclohexyl group), C1-C20 alkoxy group, C1-C20 substituted amino group, substituted arylamino group (for example aniline), or electron withdrawing group such as halogen atoms, nitrile group, nitro group, carbonyl group, cyano group (—CN), halogen substituted C1-C20 alkyl group (for example trifluoromethyl group, $CF_3$), and heterocyclic ring.

The aryl group is one selected from the group consisting of the following: phenyl, naphthyl, diphenyl, anthryl, pyrenyl, phenanthryl, fluorenyl group or other type of multi-phenyl group. The cycloalkenyl group is one selected from the group consisting of the following: cyclohexene, cyclohexadiene, cyclopentene, cyclopentadiene or other type of cycloalkenyl group. The heterocyclic aromatic group is one selected from the group consisting of the following: pyrane, pyrroline, furan, benzofuran, thiophene, benzothiophene, pyridine, quinoline, isoquinoline, pyrazine, pyrimidine, pyrrole, pyrazole, imidazole, indole, thiazole, isothiazole, oxazole, isoxazole, benzothiazole, benzoxazole, phenanthroline or other type of heterocyclic aromatic group. The above nitrogen-containing heterocycle is one selected from the group consisting of the following: pyridine, quinoline, isoquinoline, pyrazine, pyrimidine, pyrrole, pyrazole, imidazole, indole, thiazole, isothiazole, oxazole, isoxazole, benzothiazole, benzoxazole, phenanthroline or other type of heterocyclic group.

Preferably, the above reaction path can be represented as the following:

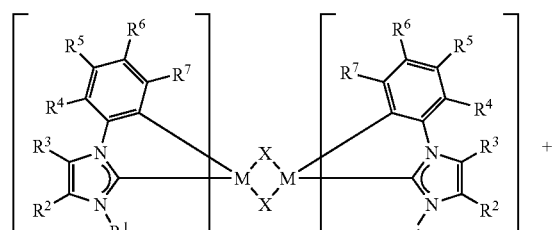

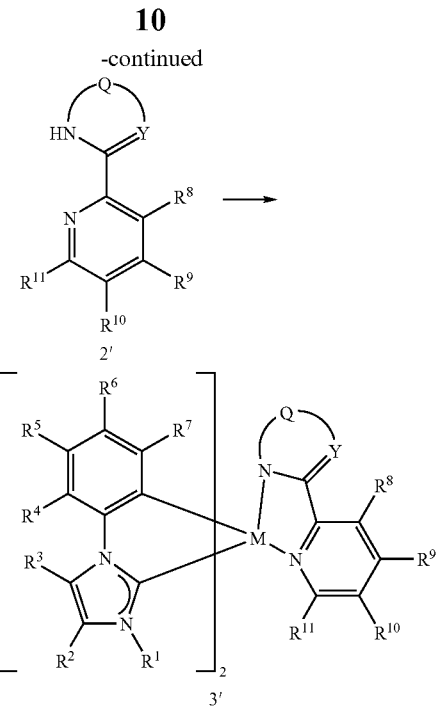

wherein $R^8 \sim R^{11}$ can be identical or different, and are independently selected from the group consisting of the following: H atom, halogen atom, C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group (—CN), nitro group, conjugated aromatic group, heterocyclic aromatic group.

Preferably, at least one of the pairs $R^8$-$R^9$, $R^9$-$R^{10}$, $R^{10}$-$R^{11}$ forms an aromatic ring, heterocyclic aromatic group, cycloalkenyl group, these aromatic ring, heterocyclic aromatic group, cycloalkenyl group, or heterocyclic alkenyl group can be a five-membered, six-membered or seven-membered ring. Moreover, they optionally comprise one or more substituent, wherein the substituent(s) can be identical or different and is independently selected from the group consisting of the following: H atom, halogen atom such as fluorine (Fl), chlorine (Cl), bromine (Br), iodine (Id), C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group (—CN), nitro group, conjugated aromatic group, heterocyclic aromatic group.

The remaining ones of $R^8 \sim R^{11}$ which do not form a cyclic group can be identical or different, and are independently selected from the group consisting of the following: H atom, halogen atom, C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group (—CN), nitro group, conjugated aromatic group, heterocyclic aromatic group.

Several transition metal complexes will be given below as examples constructed according to the presented invention. It is noted that these examples are not to limit the scope of the present invention, which should be determined in accordance with the claims.

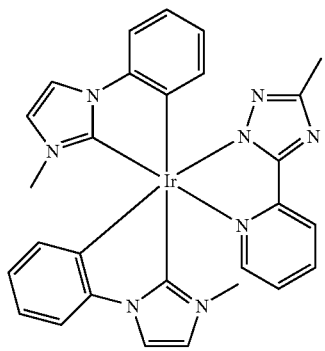

Ir(pmi)₂(mptz)

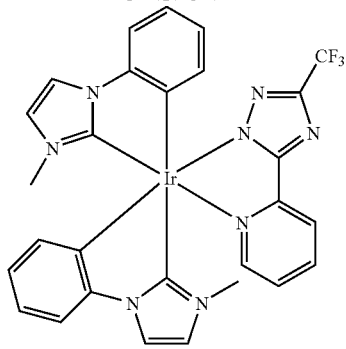

Ir(pmi)₂(tfptz)

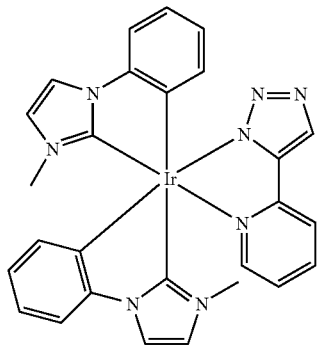

Ir(pmi)₂(pytz)

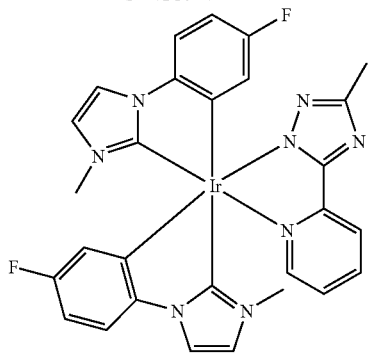

Ir(fpmi)₂(mptz)

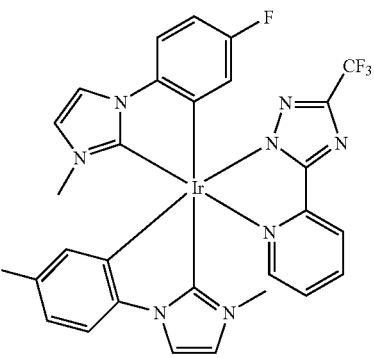

Ir(fpmi)₂(tfptz)

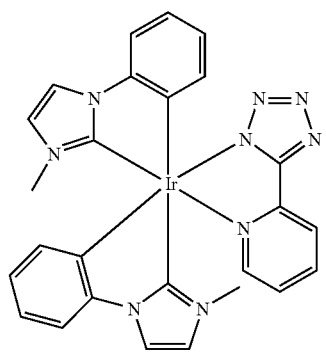

Ir(pmi)₂(pytrz)

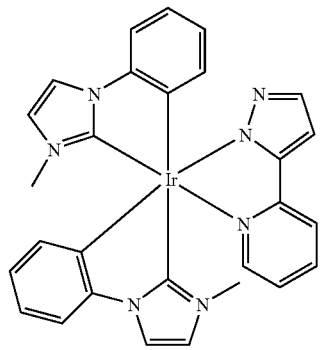

Ir(pmi)₂(pypz)

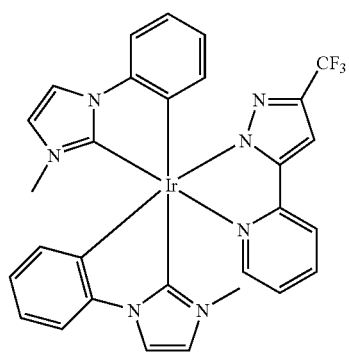

Ir(pmi)₂(tfpypz)

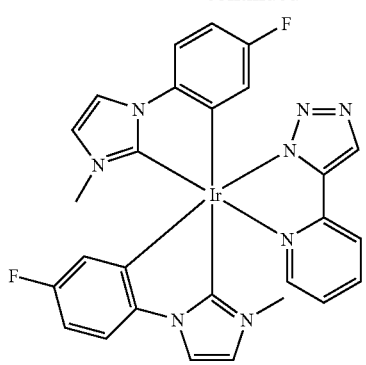
Ir(fpmi)₂(pytz)
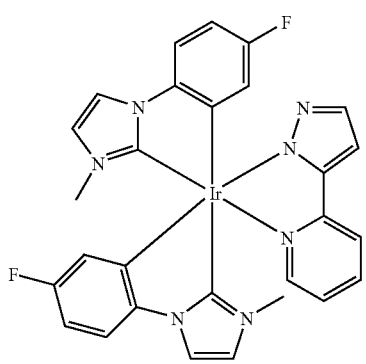
Ir(fpmi)₂(pypz)
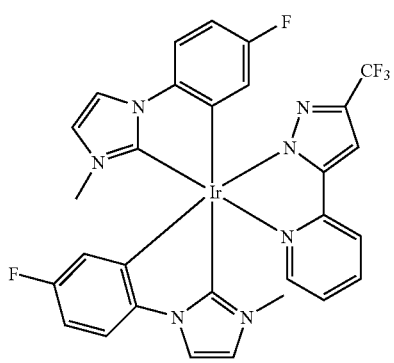
Ir(fpmi)₂(tfpypz)
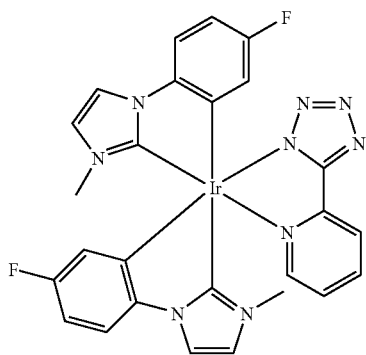
Ir(fpmi)₂(pytrz)
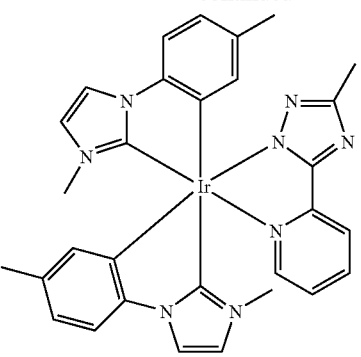
Ir(mpmi)₂(mptz)
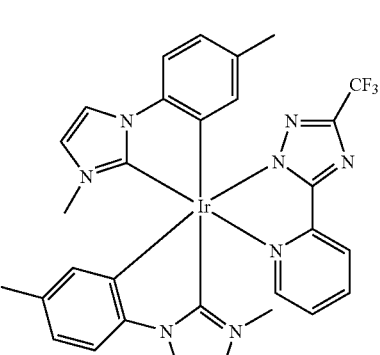
Ir(mpmi)₂(tfptz)
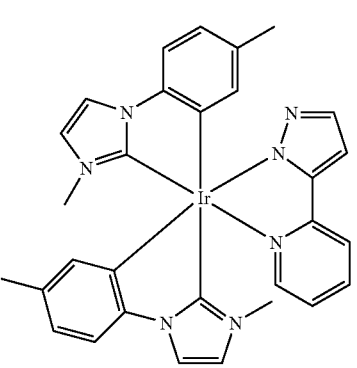
Ir(mpmi)₂(pypz)
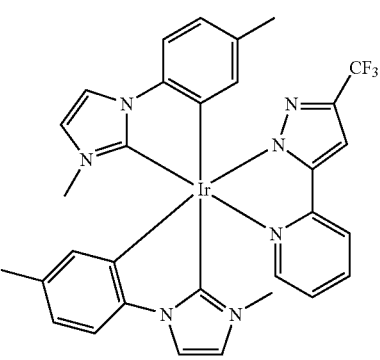
Ir(mpmi)₂(tfpypz)

-continued
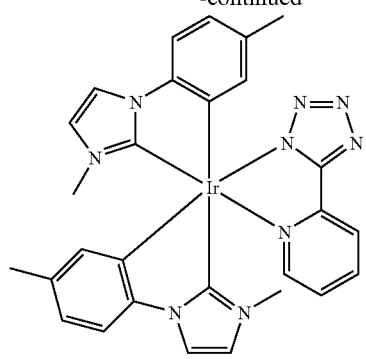
Ir(mpmi)₂(pytrz)
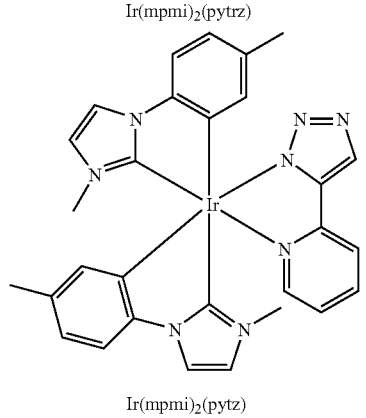
Ir(mpmi)₂(pytz)
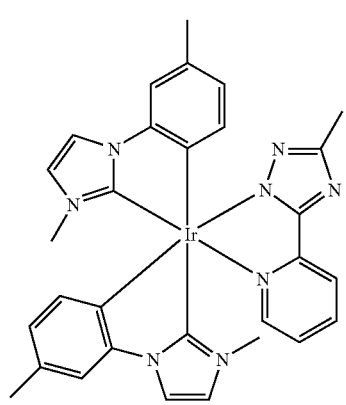
Ir(mmpmi)₂(mptz)
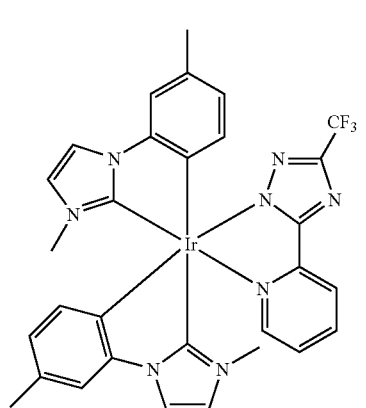
Ir(mmpmi)₂(tfptz)
-continued
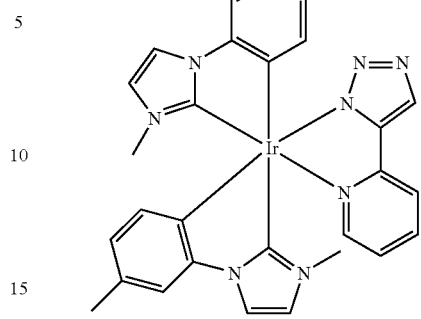
Ir(mmpmi)₂(pytz)
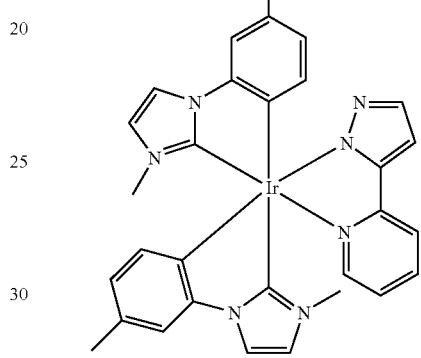
Ir(mmpmi)₂(pypz)
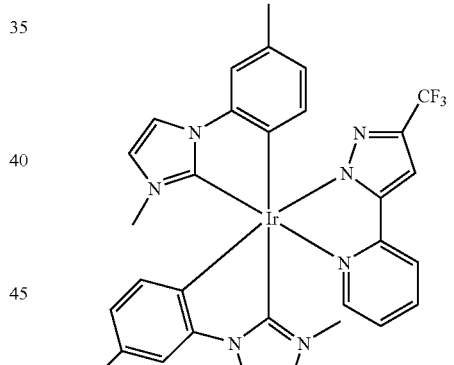
Ir(mmpmi)₂(tfpypz)
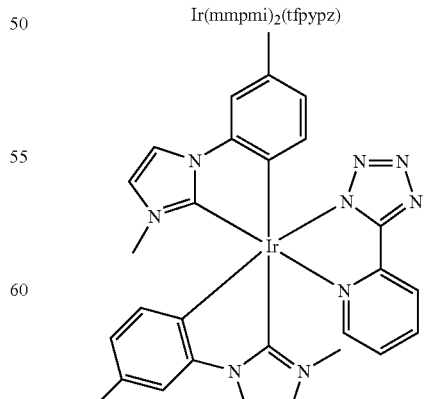
Ir(mmpmi)₂(pytrz)

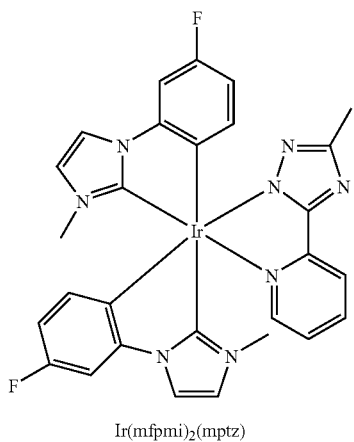
Ir(mfpmi)₂(mptz)
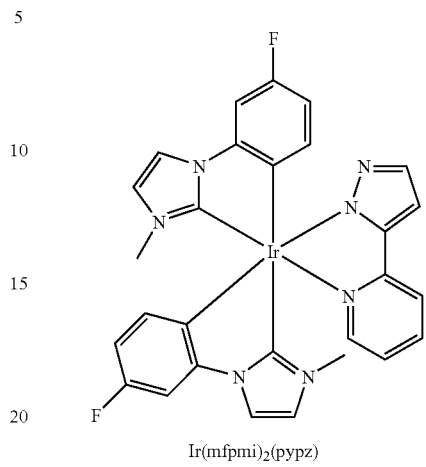
Ir(mfpmi)₂(pypz)
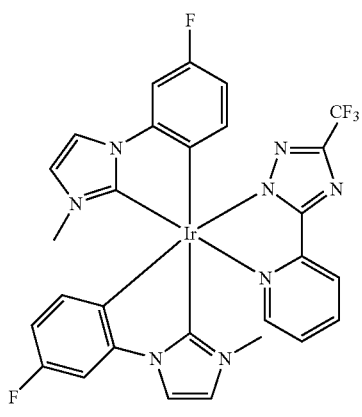
Ir(mfpmi)₂(tfptz)
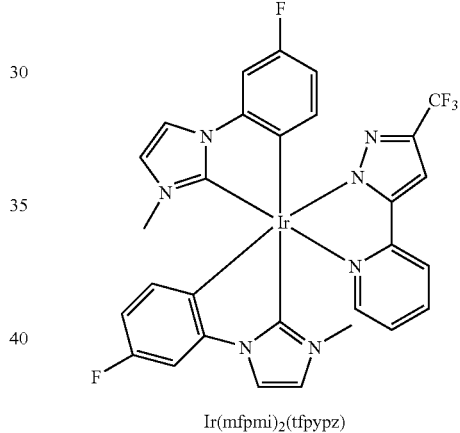
Ir(mfpmi)₂(tfpypz)
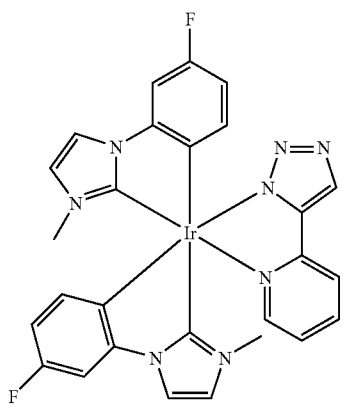
Ir(mfpmi)₂(pytz)
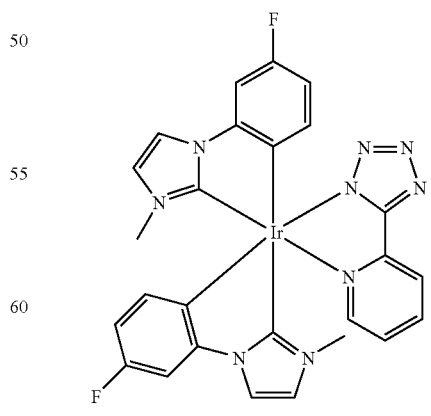
Ir(mfpmi)₂(pytrz)

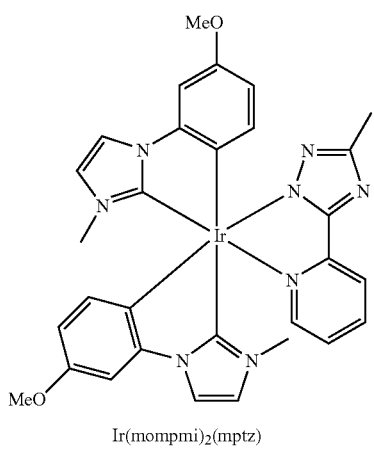
Ir(mompmi)₂(mptz)
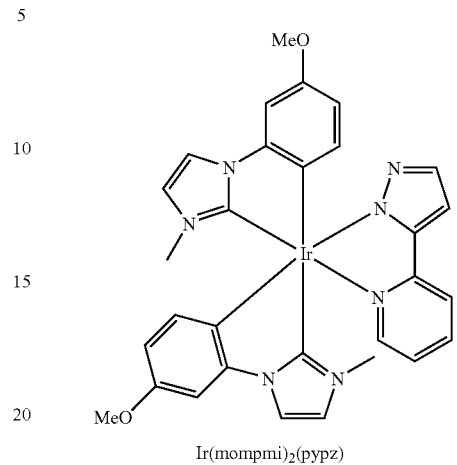
Ir(mompmi)₂(pypz)
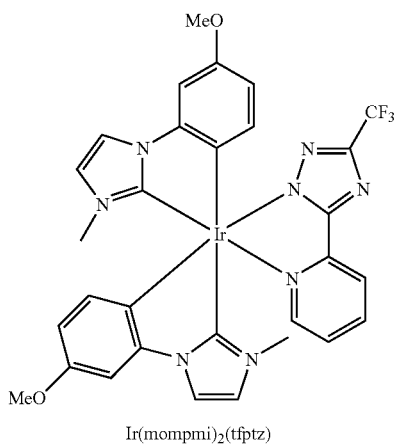
Ir(mompmi)₂(tfptz)
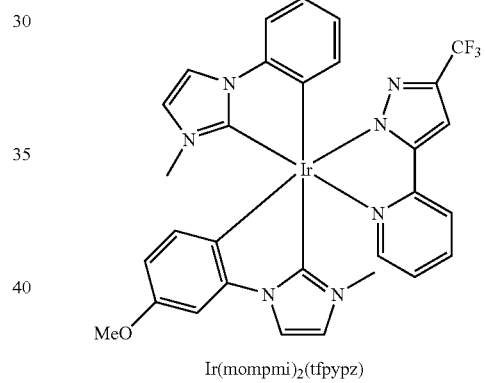
Ir(mompmi)₂(tfpypz)
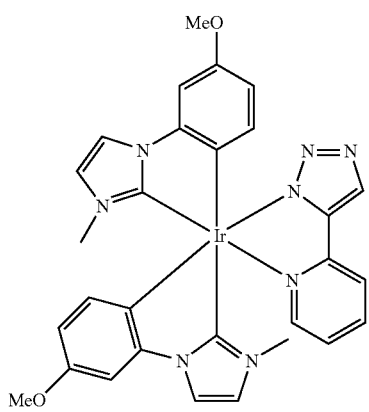
Ir(mompmi)₂(pytz)
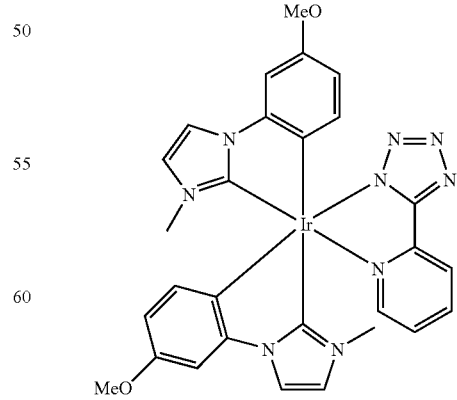
Ir(mompmi)₂(pytrz)

-continued
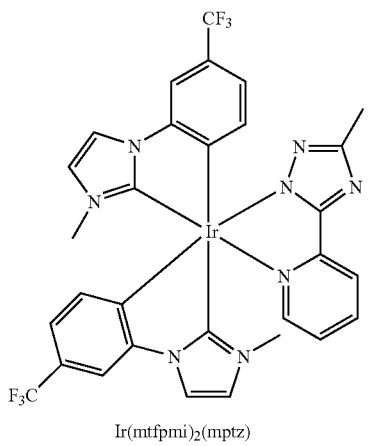
Ir(mtfpmi)₂(mptz)
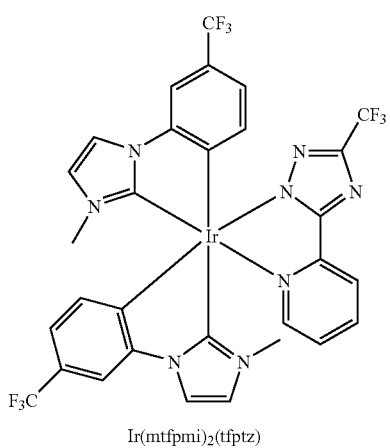
Ir(mtfpmi)₂(tfptz)
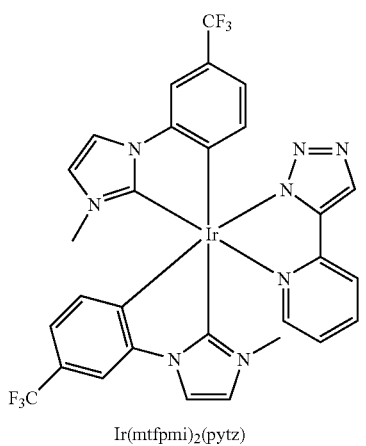
Ir(mtfpmi)₂(pytz)
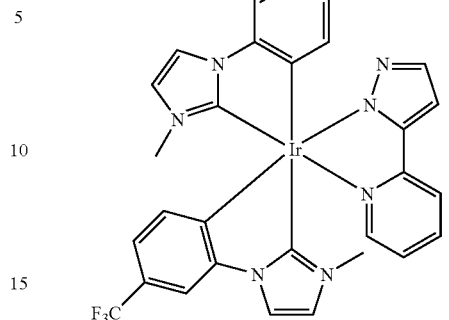
Ir(mfpmi)₂(pypz)
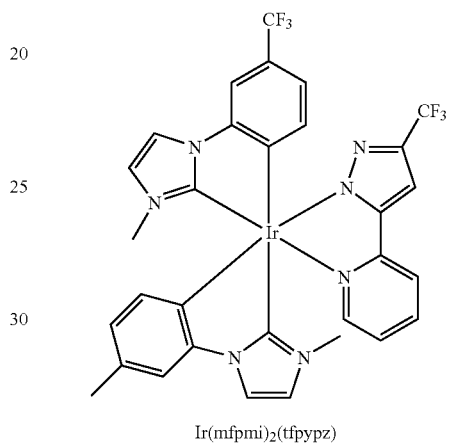
Ir(mfpmi)₂(tfpypz)
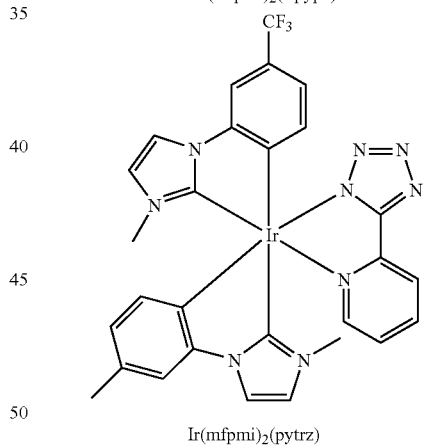
Ir(mfpmi)₂(pytrz)
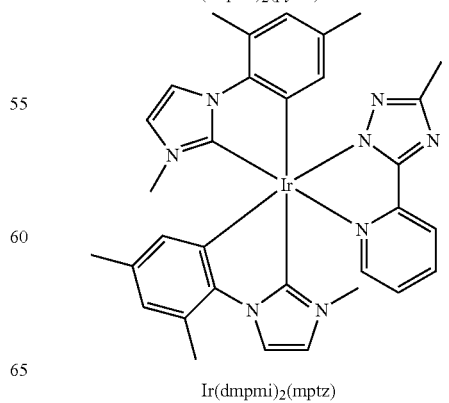
Ir(dmpmi)₂(mptz)

-continued
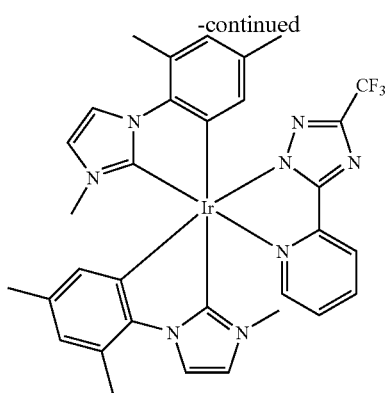
Ir(dmpmi)₂(tfptz)
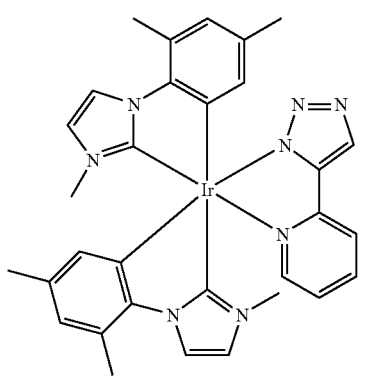
Ir(dmpmi)₂(pytz)
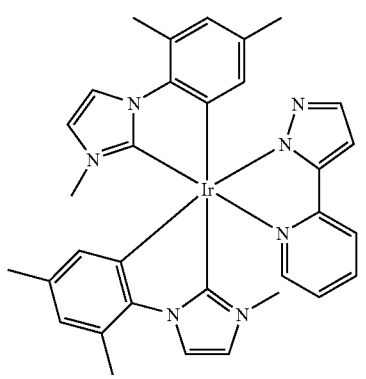
Ir(dmpmi)₂(pypz)
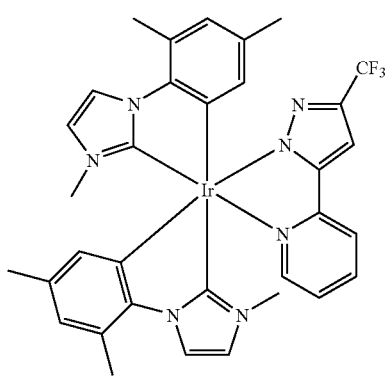
Ir(dmpmi)₂(tfpypz)
-continued
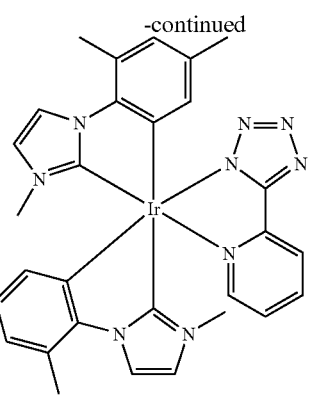
Ir(dmpmi)₂(pytrz)
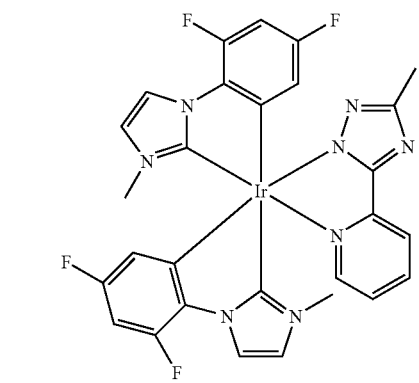
Ir(dfpmi)₂(mptz)
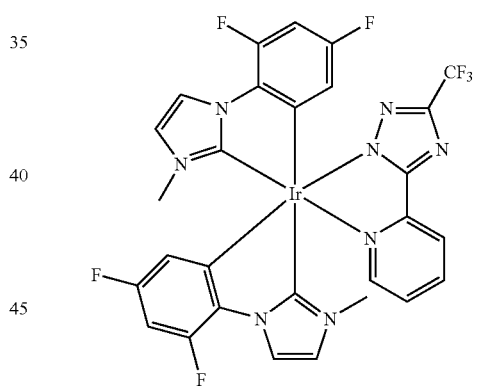
Ir(dfpmi)₂(tfptz)
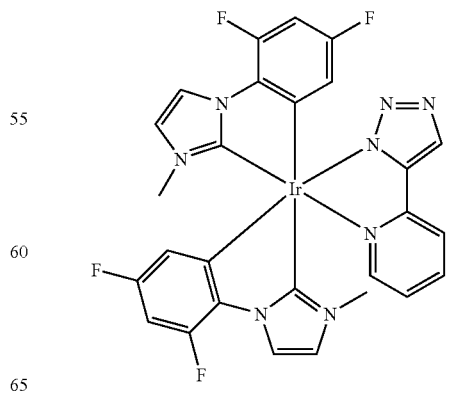
Ir(dfpmi)₂(pytz)

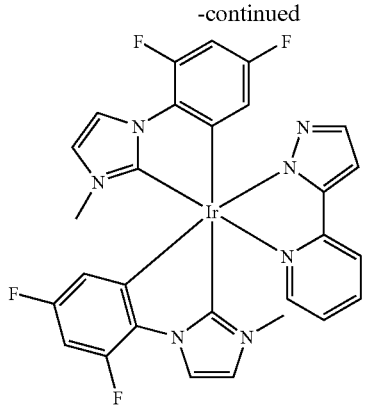
Ir(dfpmi)₂(pypz)
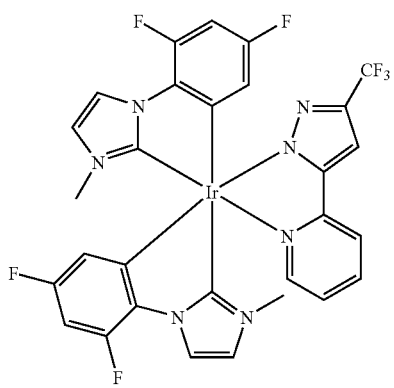
Ir(dfpmi)₂(tfpypz)
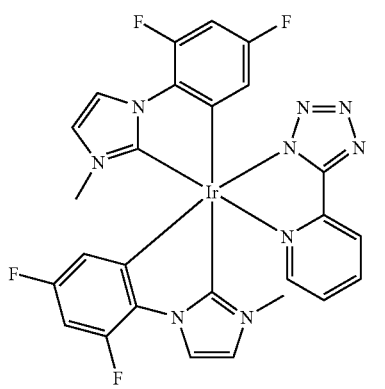
Ir(dfpmi)₂(pytrz)
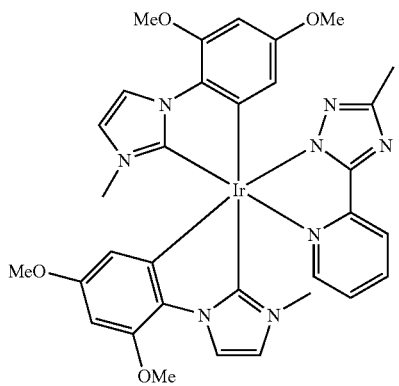
Ir(dmopmi)₂(mptz)
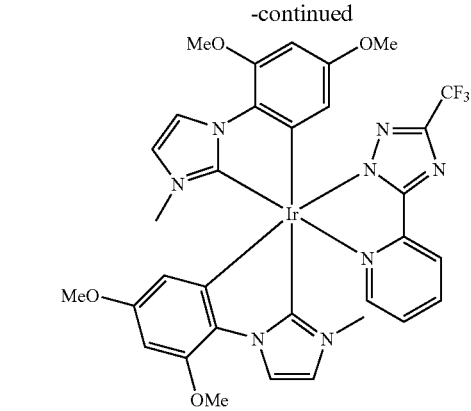
Ir(dmopmi)₂(tfptz)
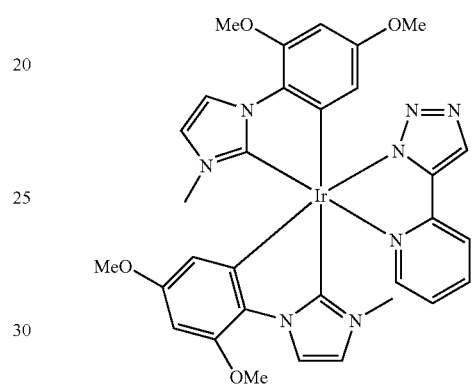
Ir(dmopmi)₂(pytz)
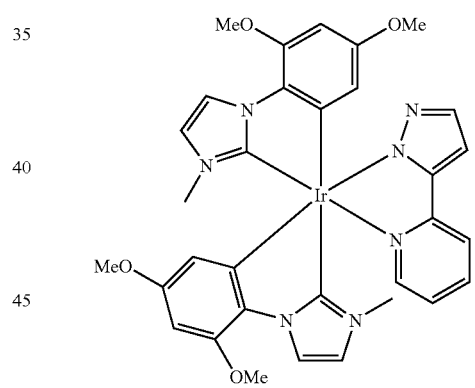
Ir(dmopmi)₂(pypz)
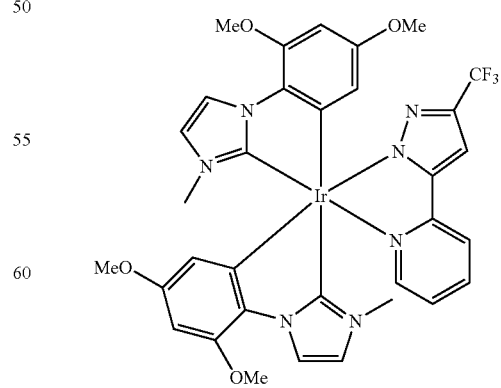
Ir(dmopmi)₂(tfpypz)

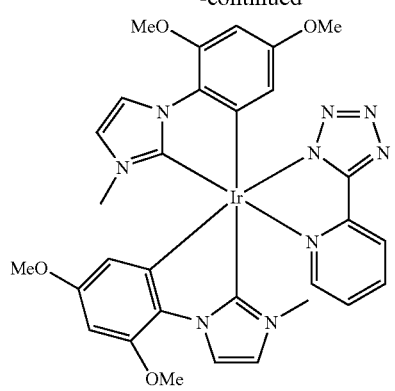
Ir(dmopmi)₂(pytrz)
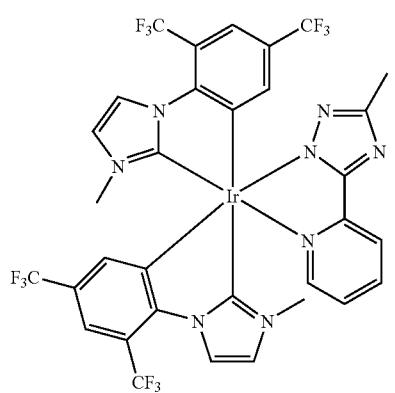
Ir(dfpmi)₂(mptz)
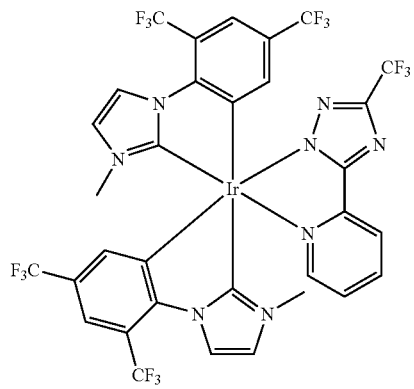
Ir(dfpmi)₂(tfptz)
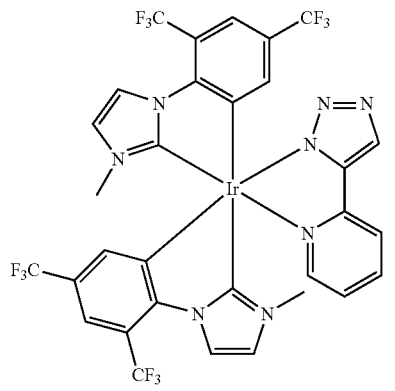
Ir(dfpmi)₂(pytz)
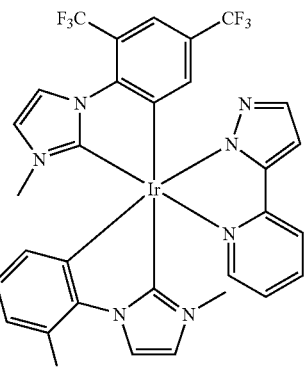
Ir(dfpmi)₂(pypz)
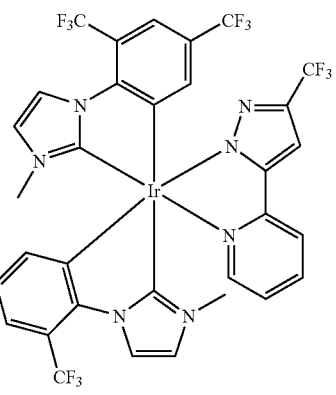
Ir(dfpmi)₂(tfpypz)
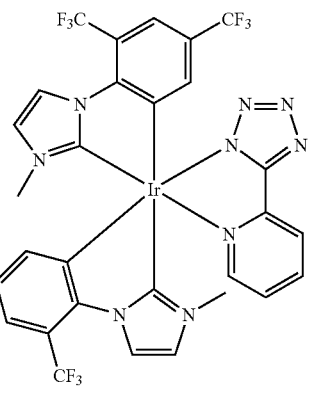
Ir(dfpmi)₂(pytrz)

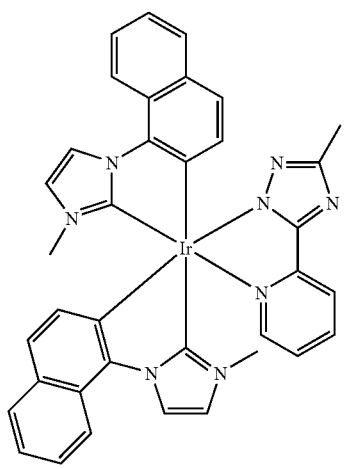
Ir(nmi)₂(mptz)
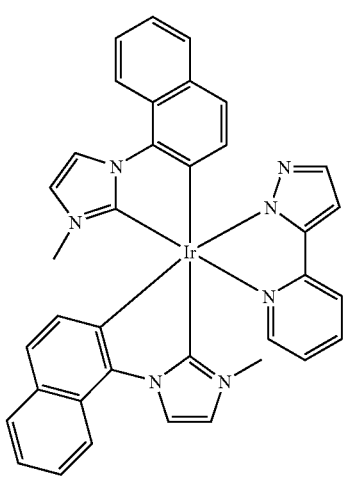
Ir(nmi)₂(pypz)
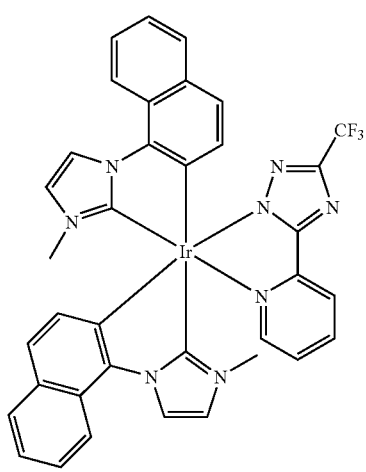
Ir(nmi)₂(tfptz)
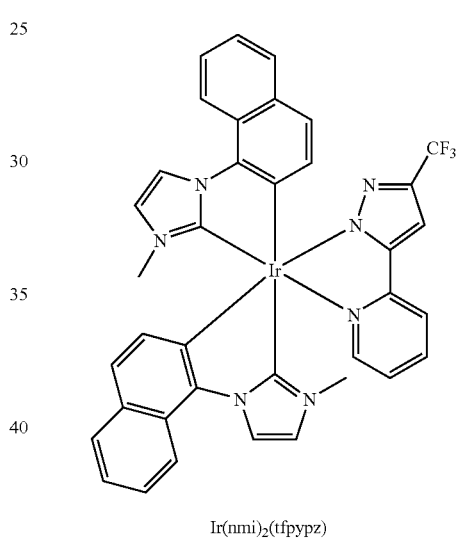
Ir(nmi)₂(tfpypz)
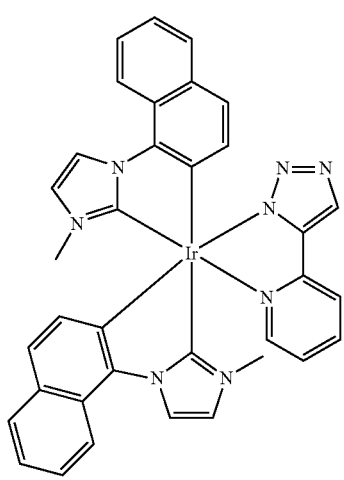
Ir(nmi)₂(pytz)
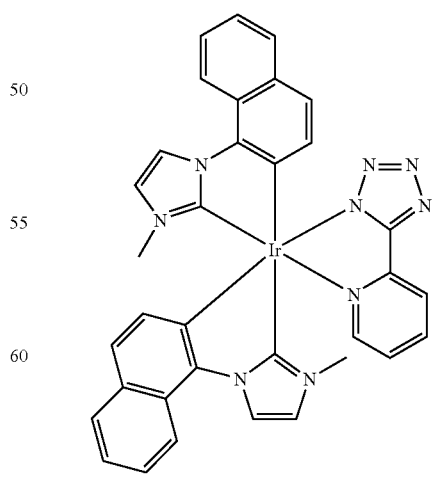
Ir(nmi)₂(pytrz)

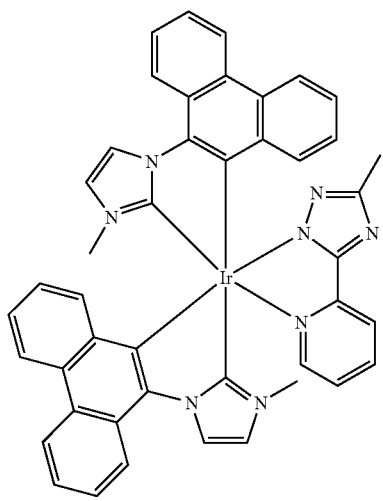
Ir(pnmi)₂(mptz)
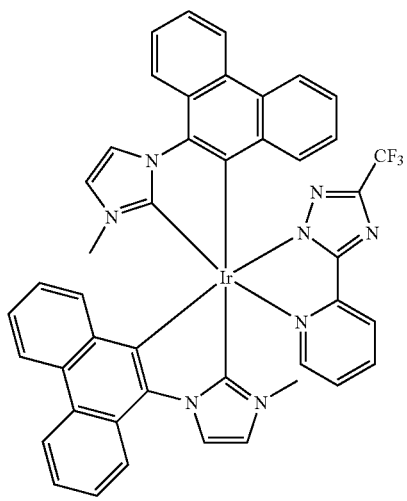
Ir(pnmi)₂(tfptz)
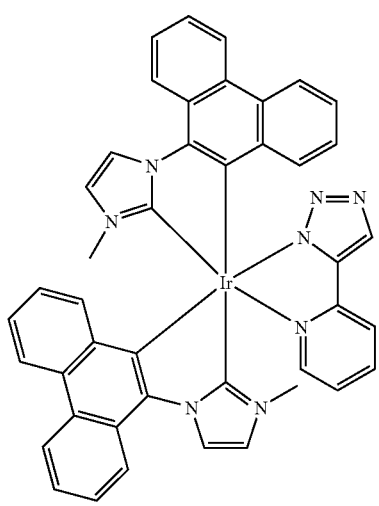
Ir(pnmi)₂(pytz)
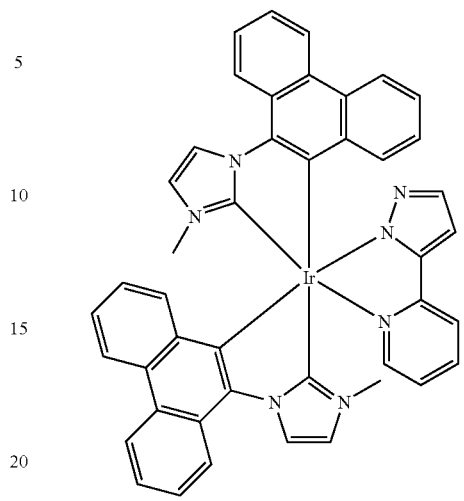
Ir(pnmi)₂(pypz)
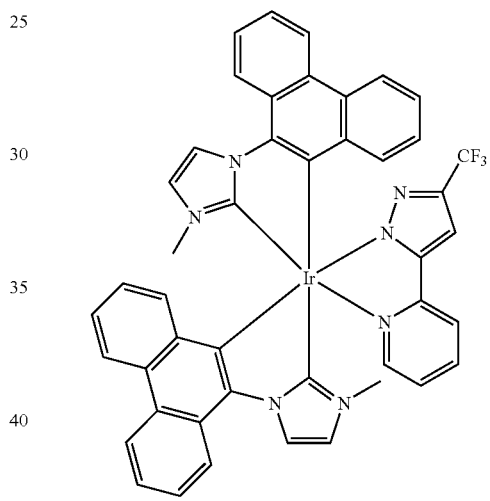
Ir(pnmi)₂(tfpypz)
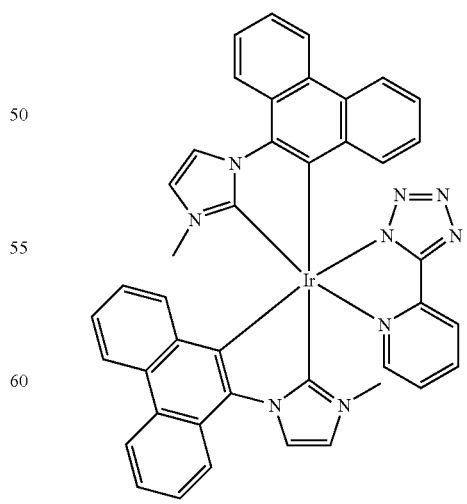
Ir(pnmi)₂(pytrz)

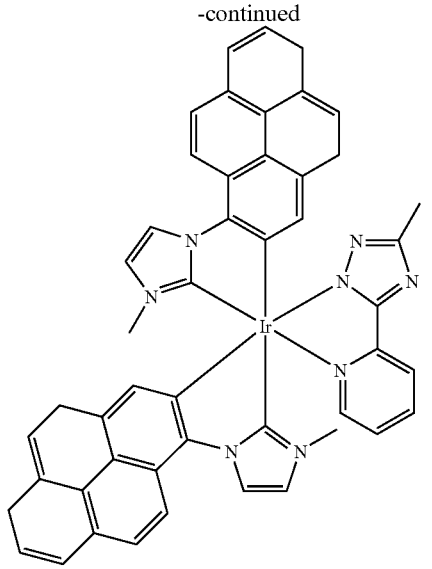
Ir(pymi)₂(mptz)
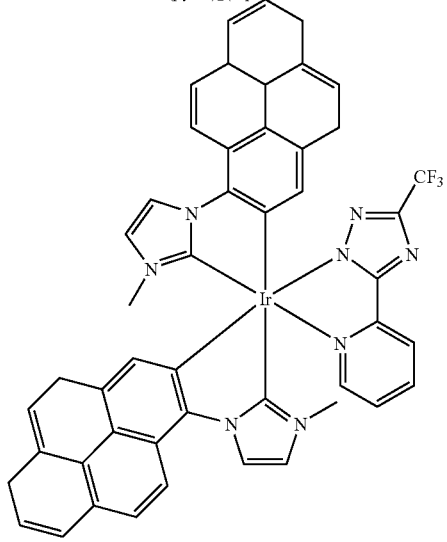
Ir(pymi)₂(tfptz)
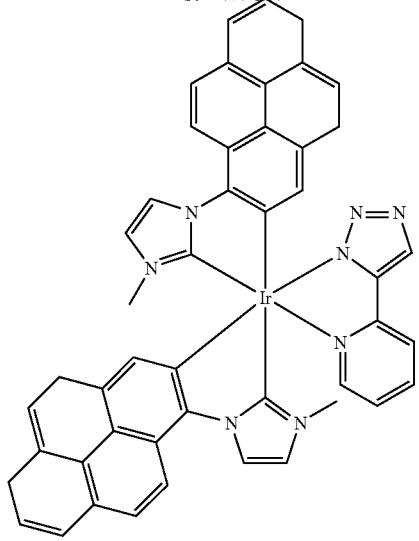
Ir(pymi)₂(pytz)
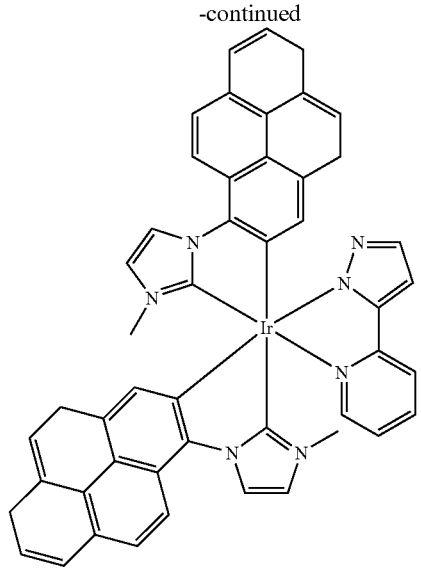
Ir(pymi)₂(pypz)
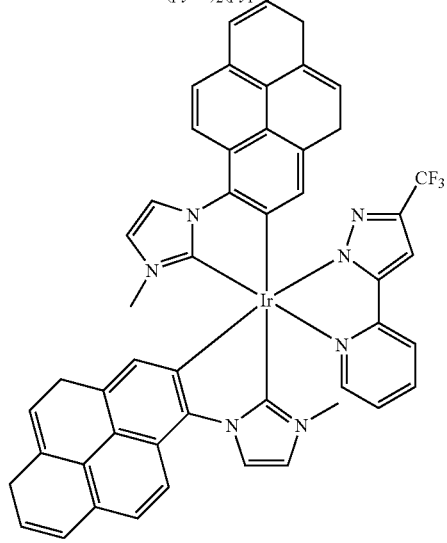
Ir(pymi)₂(tfpypz)
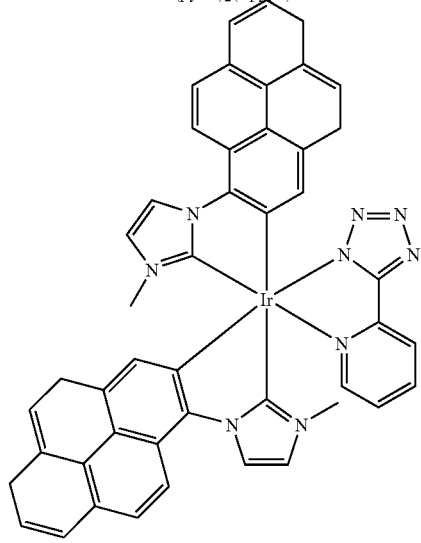
Ir(pymi)₂(pytrz)

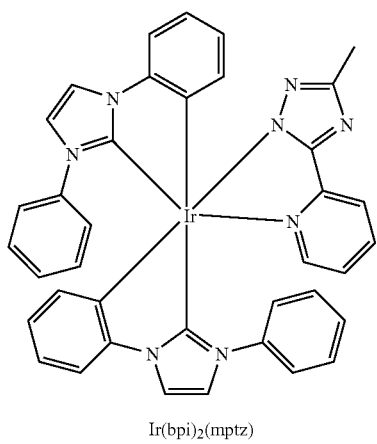
Ir(bpi)₂(mptz)
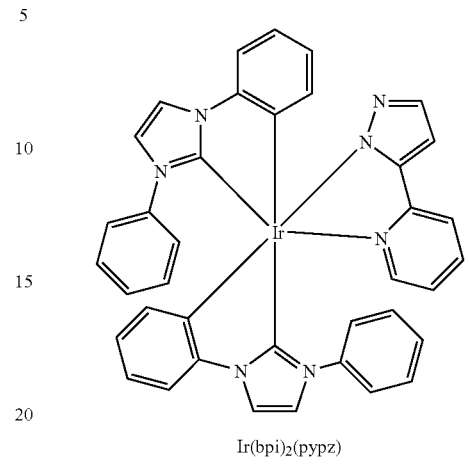
Ir(bpi)₂(pypz)
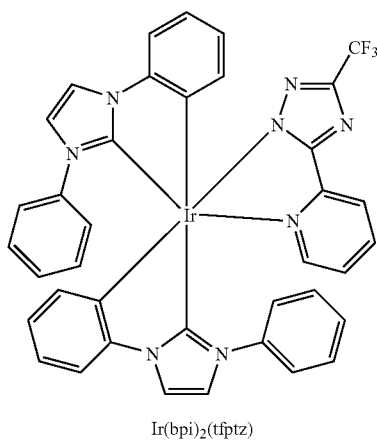
Ir(bpi)₂(tfptz)
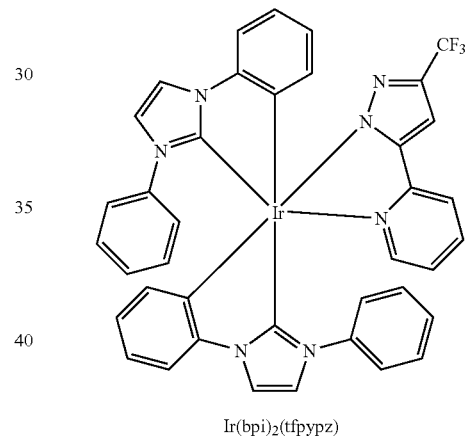
Ir(bpi)₂(tfpypz)
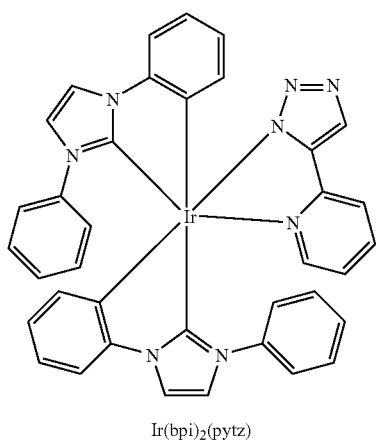
Ir(bpi)₂(pytz)
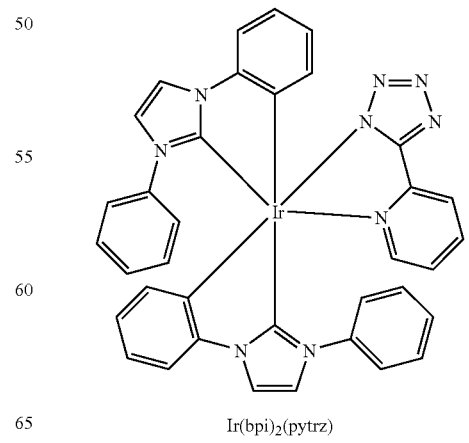
Ir(bpi)₂(pytrz)

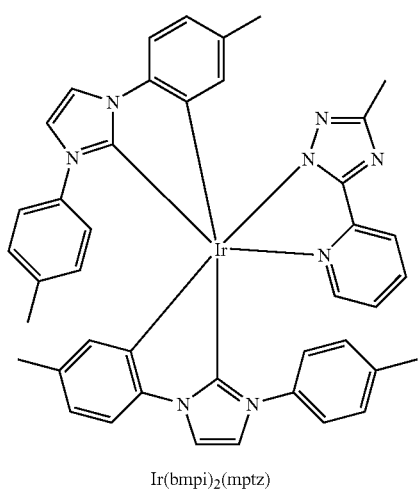
Ir(bmpi)₂(mptz)
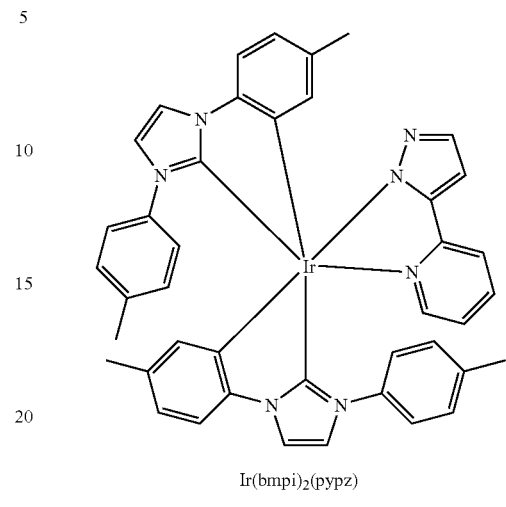
Ir(bmpi)₂(pypz)
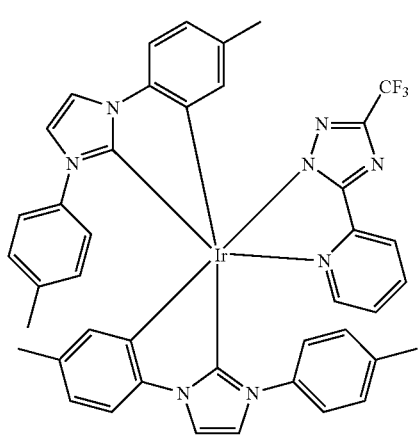
Ir(bmpi)₂(tfptz)
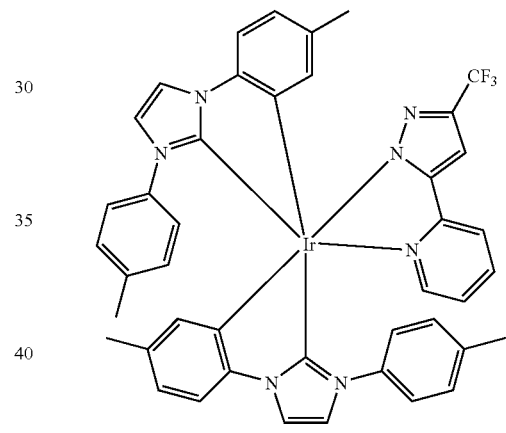
Ir(bmpi)₂(tfpypz)
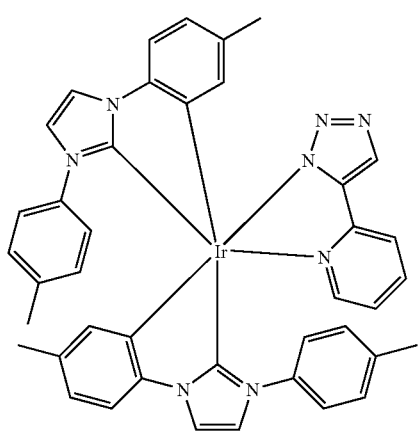
Ir(bmpi)₂(pytz)
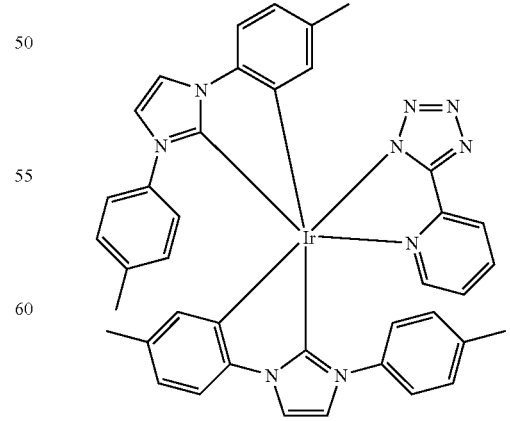
Ir(bmpi)₂(pytrz)

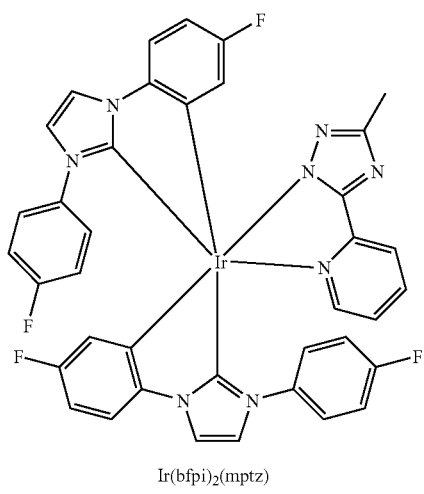
Ir(bfpi)₂(mptz)
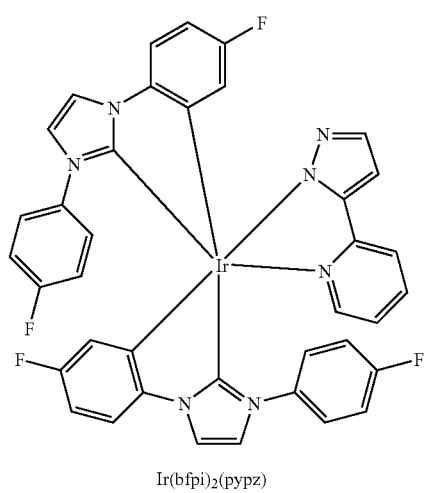
Ir(bfpi)₂(pypz)
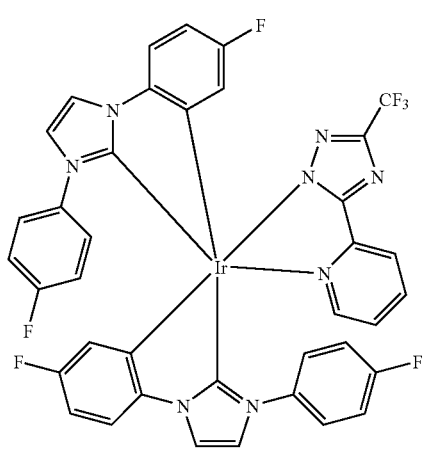
Ir(bfpi)₂(tfptz)
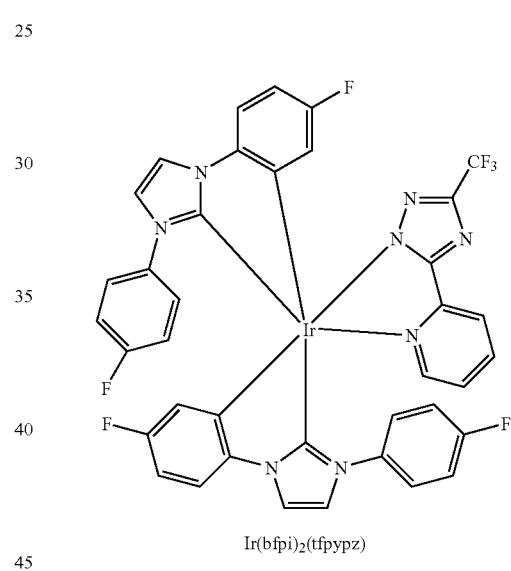
Ir(bfpi)₂(tfpypz)
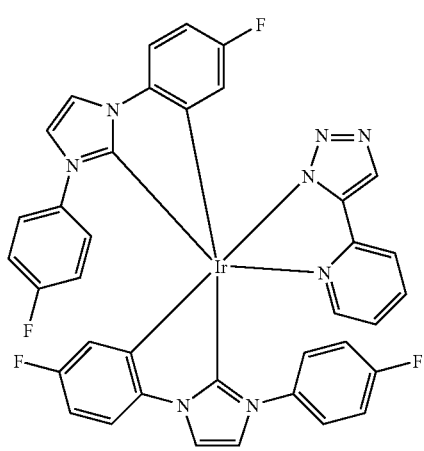
Ir(bfpi)₂(pytz)
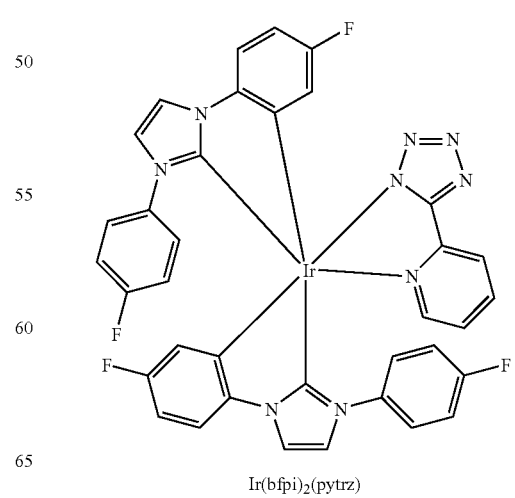
Ir(bfpi)₂(pytrz)

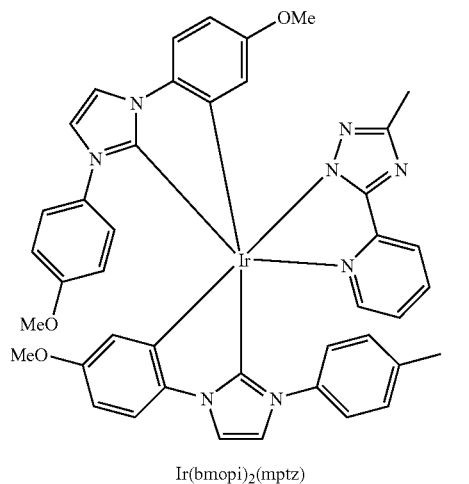
Ir(bmopi)₂(mptz)
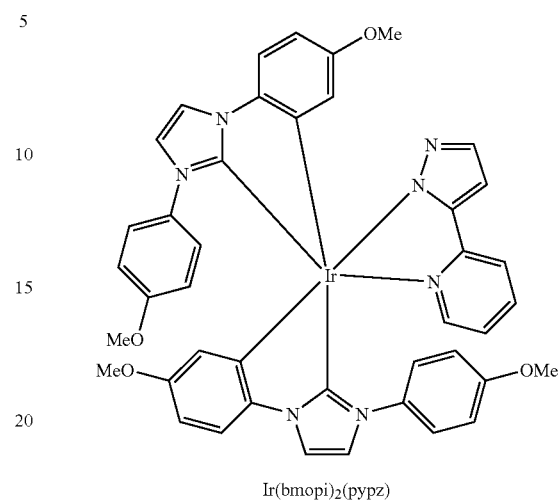
Ir(bmopi)₂(pypz)
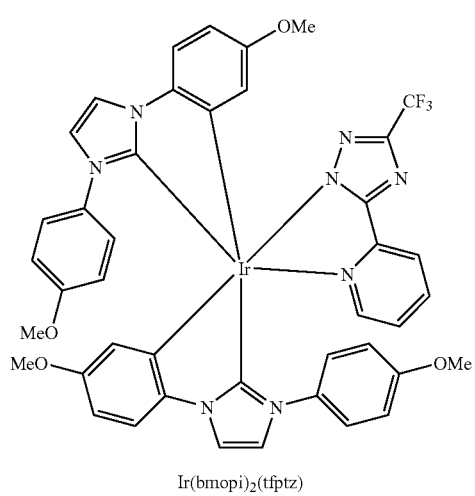
Ir(bmopi)₂(tfptz)
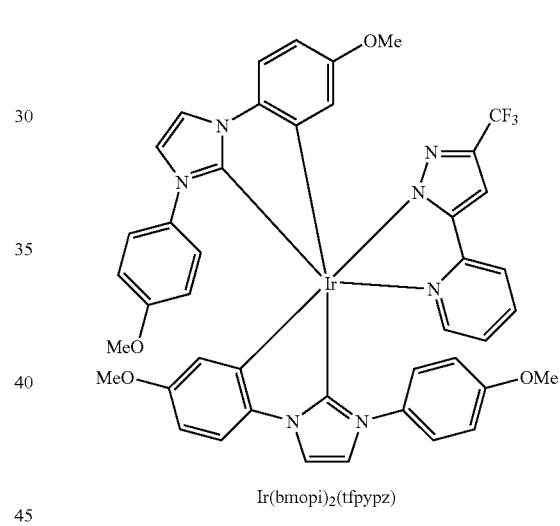
Ir(bmopi)₂(tfpypz)
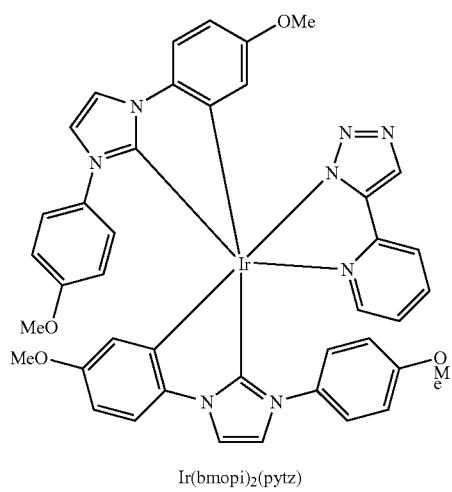
Ir(bmopi)₂(pytz)
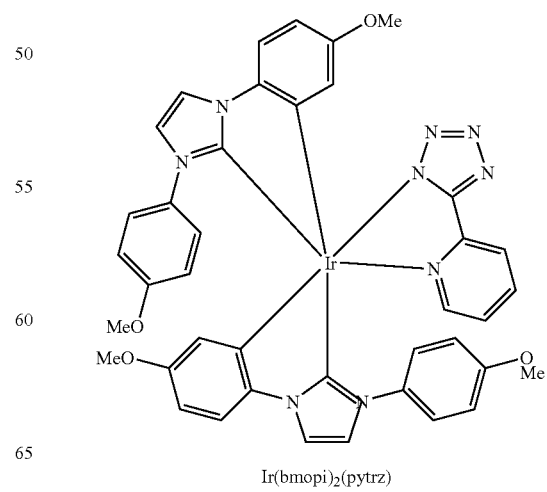
Ir(bmopi)₂(pytrz)

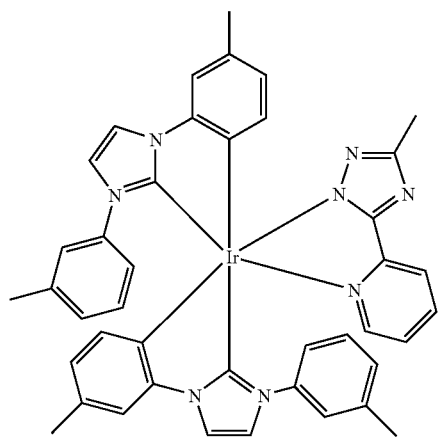
Ir(bmmpi)₂(mptz)
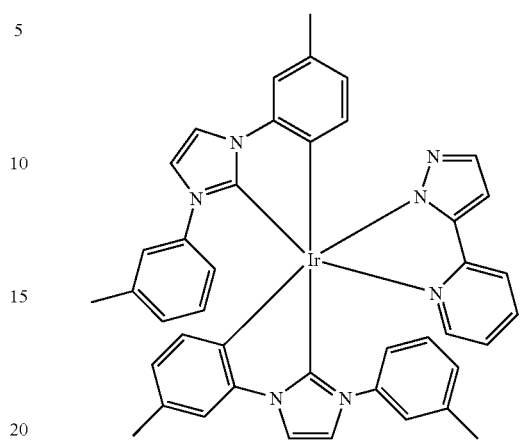
Ir(bmmpi)₂(pypz)
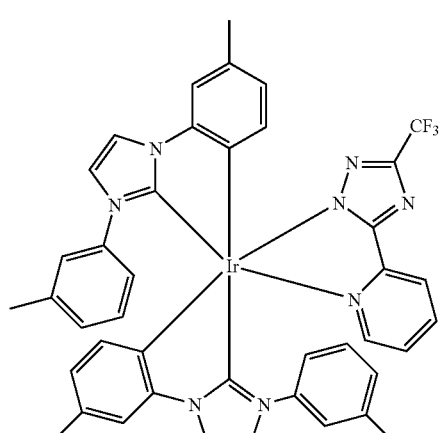
Ir(bmmpi)₂(tfptz)
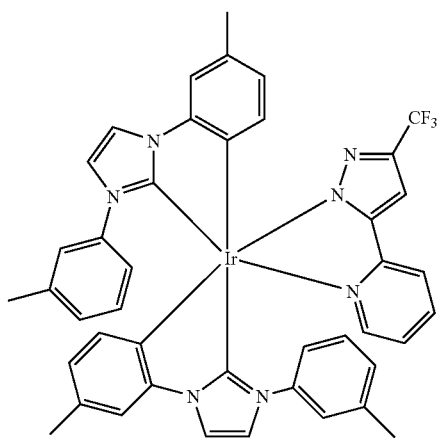
Ir(bmmpi)₂(tfpypz)
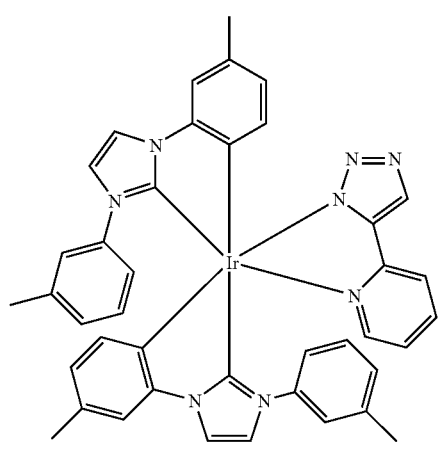
Ir(bmmpi)₂(pytz)
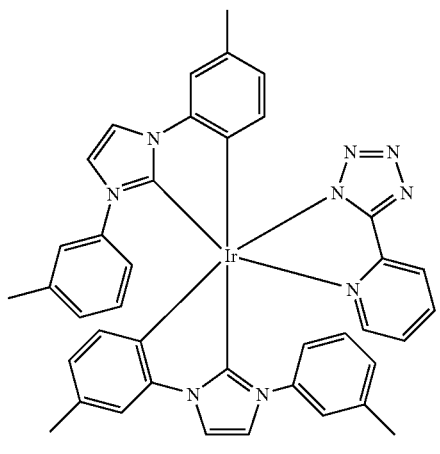
Ir(bmmpi)₂(pytrz)

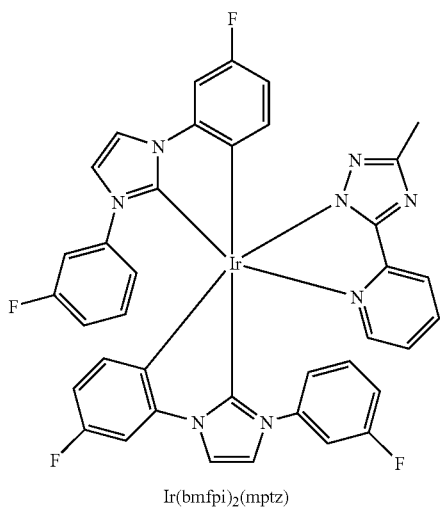
Ir(bmfpi)₂(mptz)
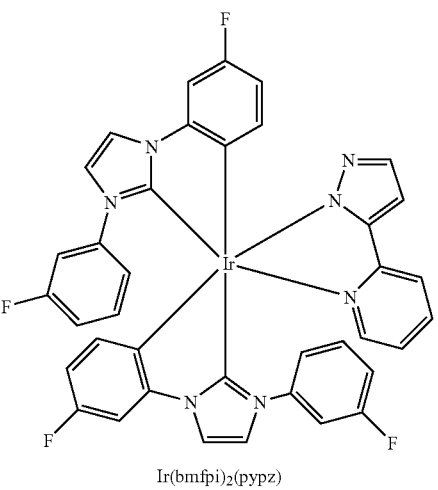
Ir(bmfpi)₂(pypz)
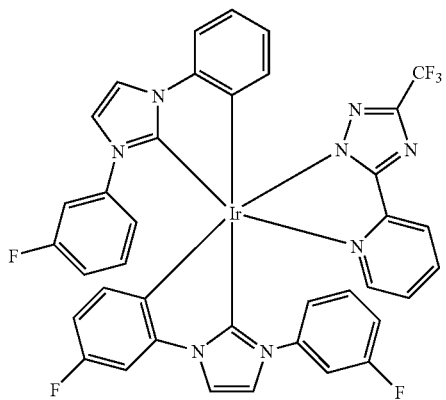
Ir(bmfpi)₂(tfptz)
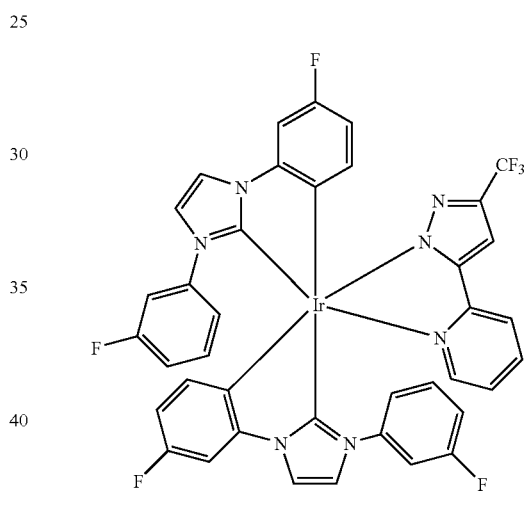
Ir(bmfpi)₂(tfpypz)
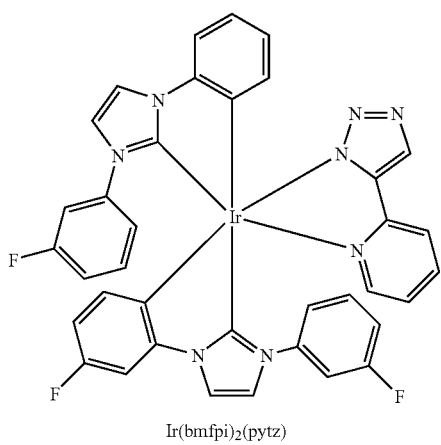
Ir(bmfpi)₂(pytz)
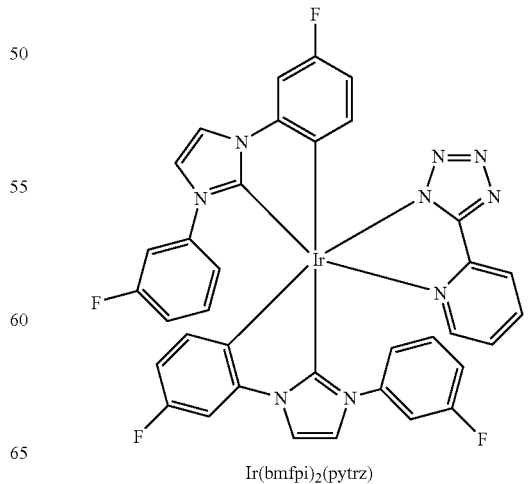
Ir(bmfpi)₂(pytrz)

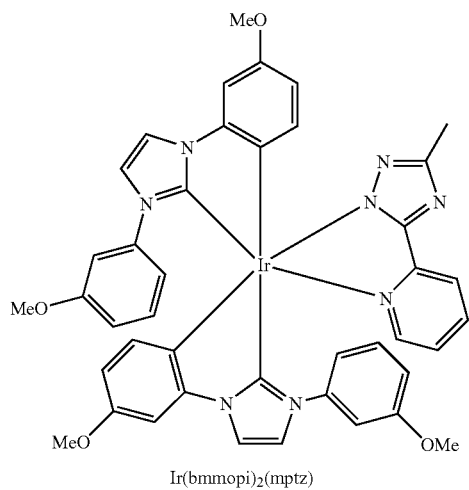
Ir(bmmopi)₂(mptz)
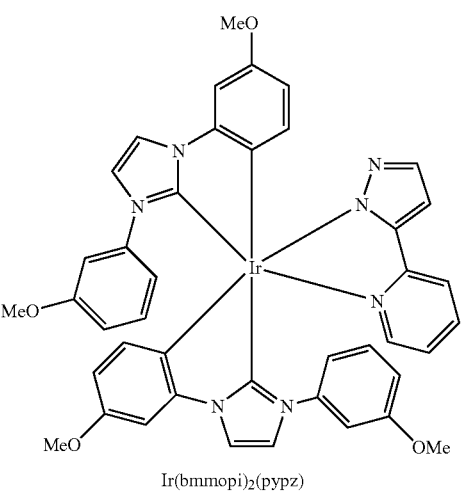
Ir(bmmopi)₂(pypz)
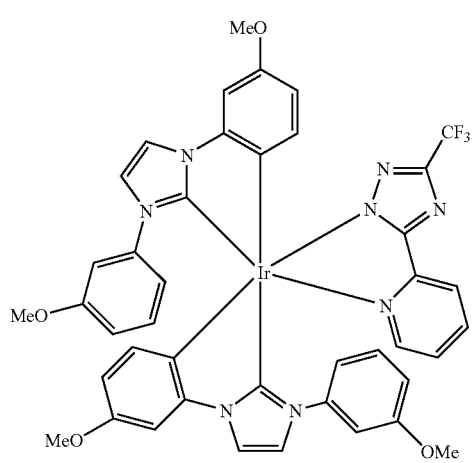
Ir(bmmopi)₂(tfptz)
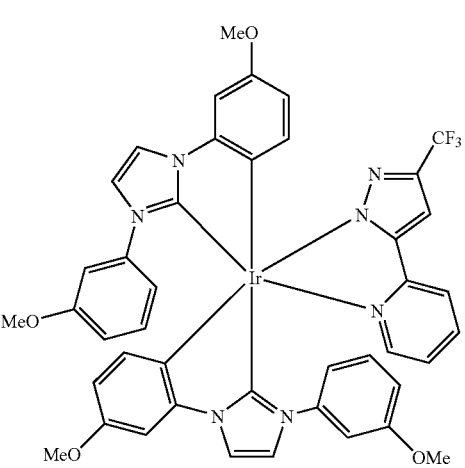
Ir(bmmopi)₂(tfpypz)
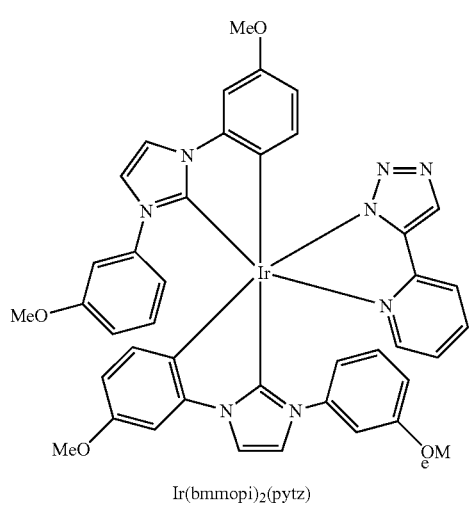
Ir(bmmopi)₂(pytz)
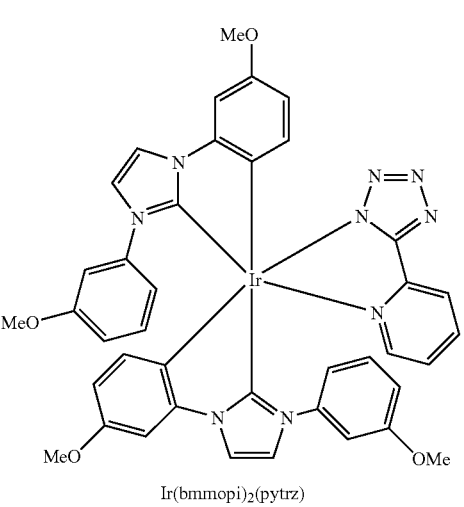
Ir(bmmopi)₂(pytrz)

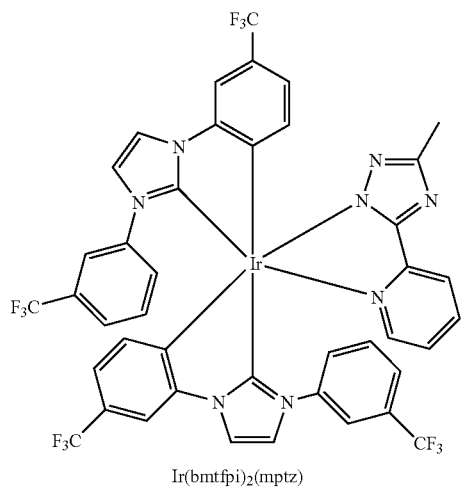
Ir(bmtfpi)₂(mptz)
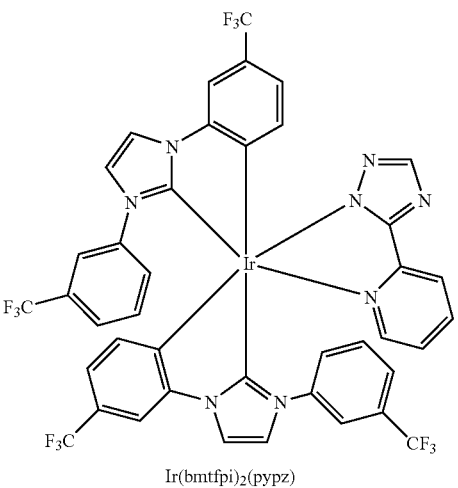
Ir(bmtfpi)₂(pypz)
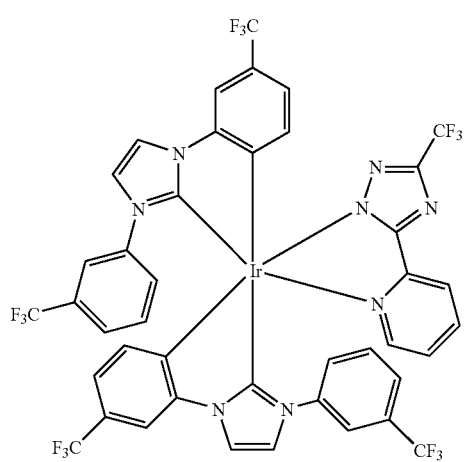
Ir(bmtfpi)₂(tfptz)
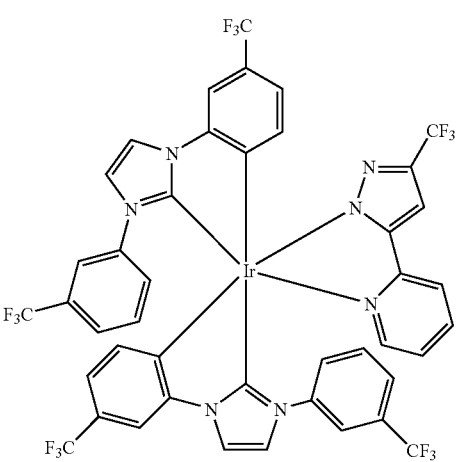
Ir(bmtfpi)₂(tfpypz)
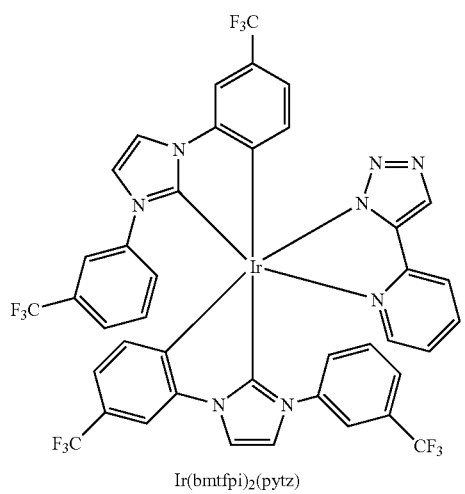
Ir(bmtfpi)₂(pytz)
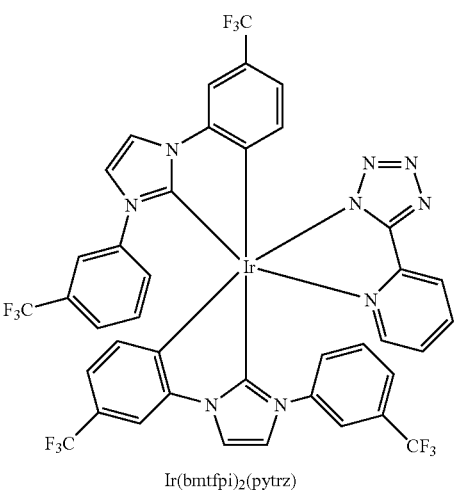
Ir(bmtfpi)₂(pytrz)

-continued
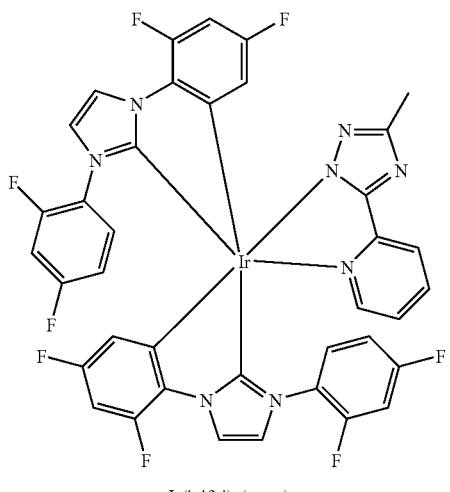
Ir(bdfpi)₂(mptz)
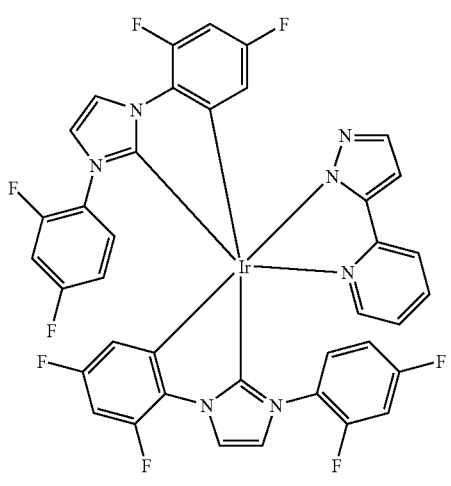
Ir(bdfpi)₂(pypz)
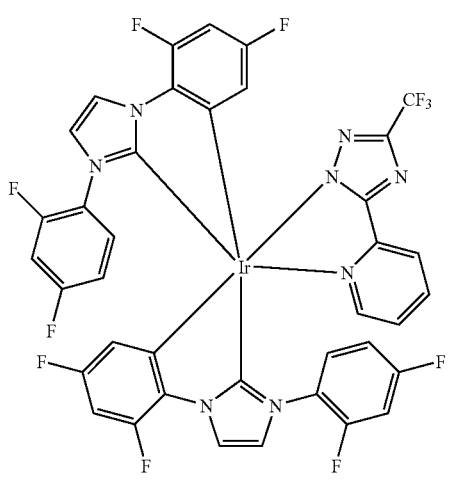
Ir(bdfpi)₂(tfptz)
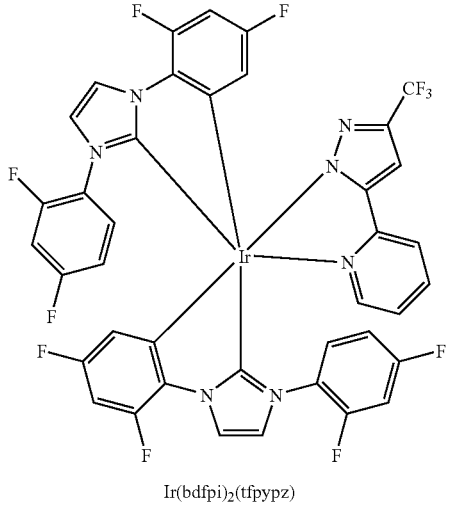
Ir(bdfpi)₂(tfpypz)
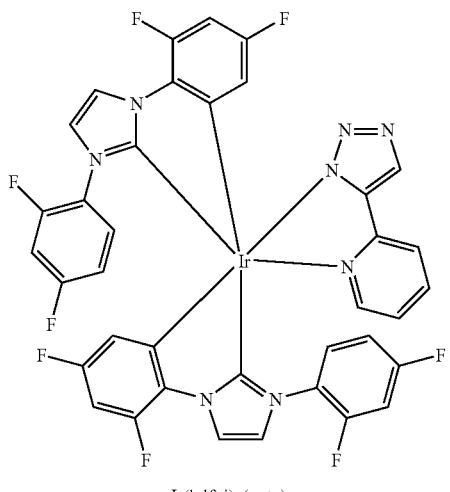
Ir(bdfpi)₂(pytz)
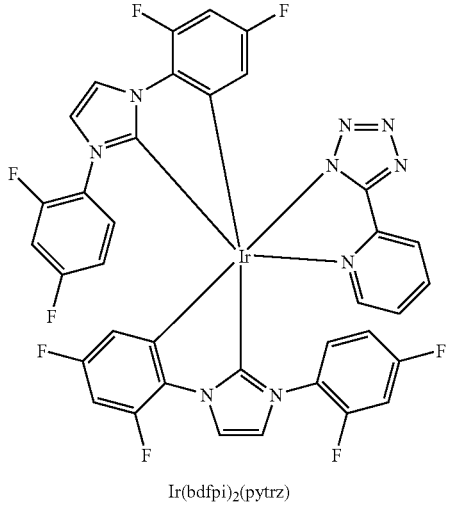
Ir(bdfpi)₂(pytrz)

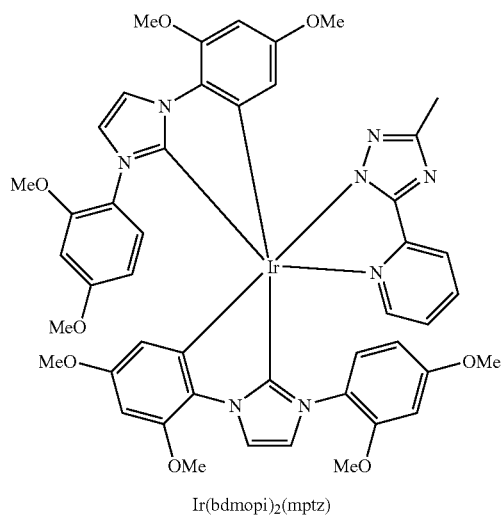
Ir(bdmopi)₂(mptz)
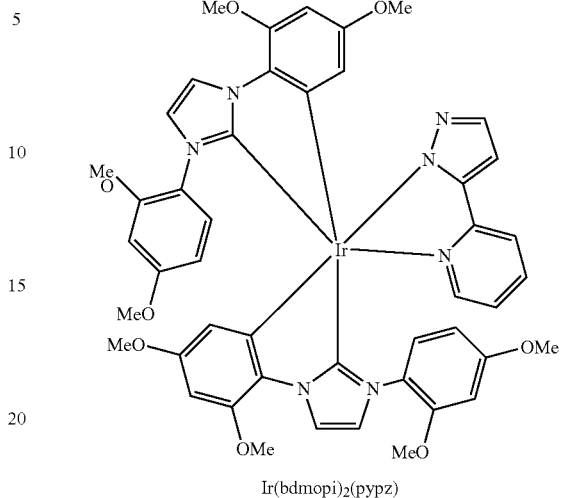
Ir(bdmopi)₂(pypz)
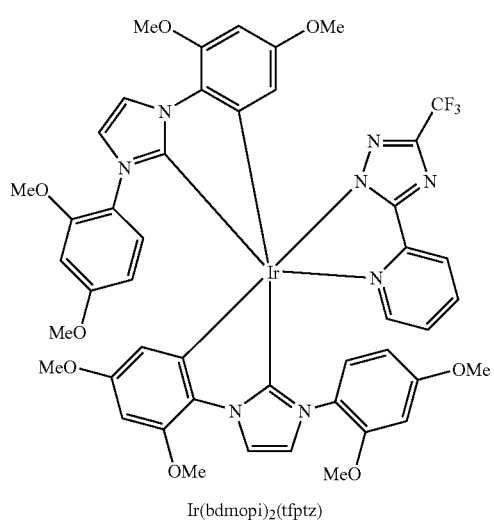
Ir(bdmopi)₂(tfptz)
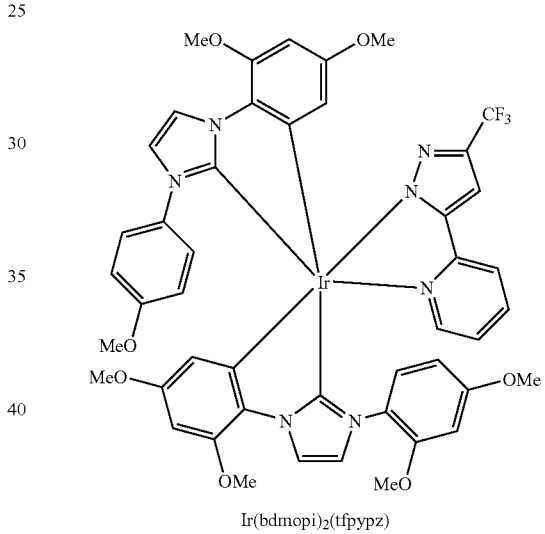
Ir(bdmopi)₂(tfpypz)
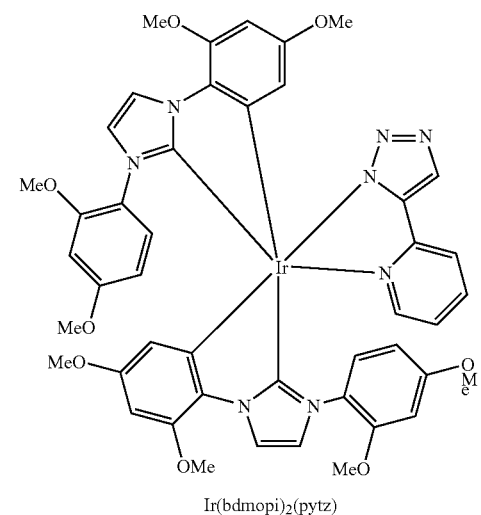
Ir(bdmopi)₂(pytz)
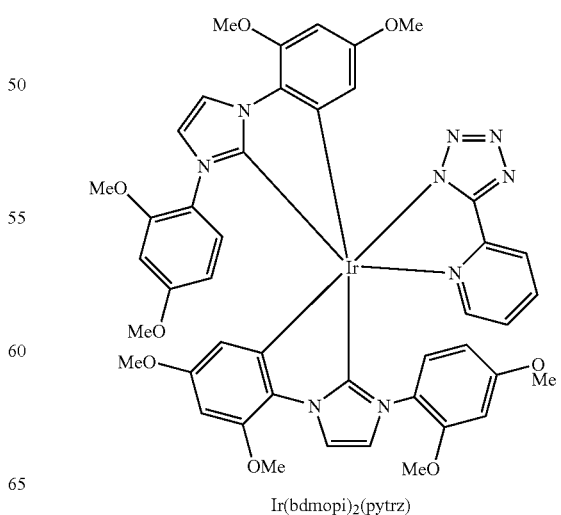
Ir(bdmopi)₂(pytrz)

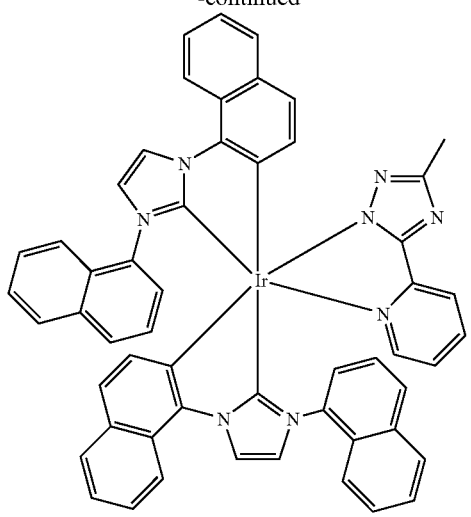
Ir(bni)₂(mptz)
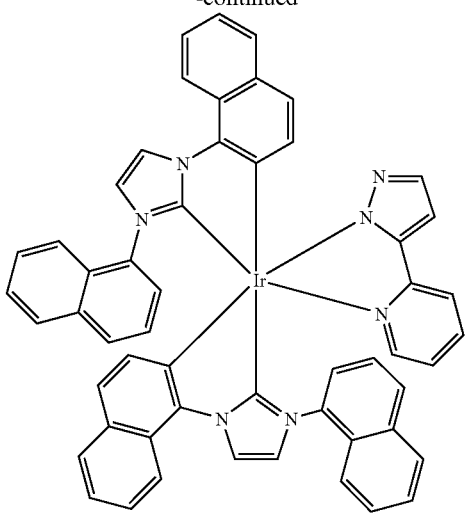
Ir(bni)₂(pypz)
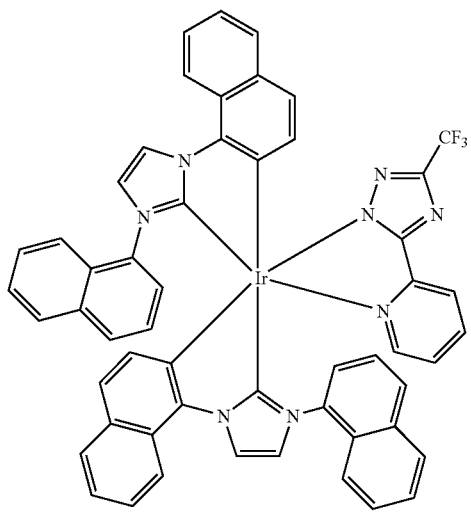
Ir(bni)₂(tfptz)
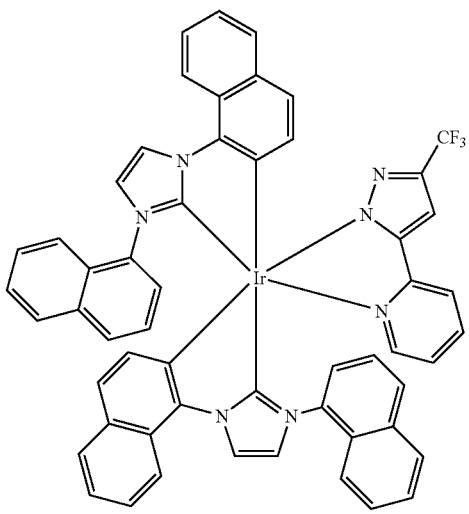
Ir(bni)₂(tfpypz)
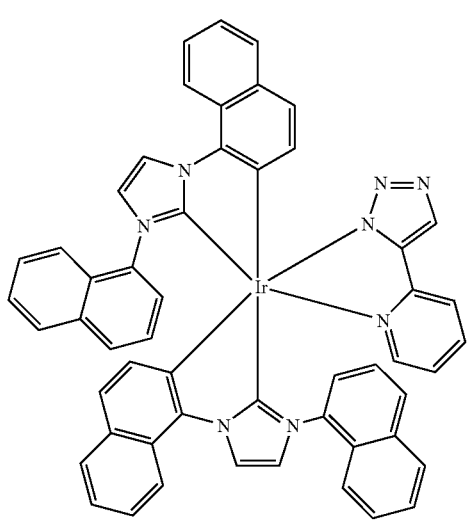
Ir(bni)₂(pytz)
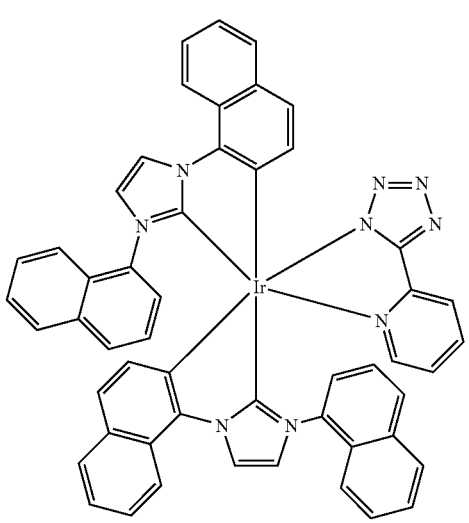
Ir(bni)₂(pytrz)

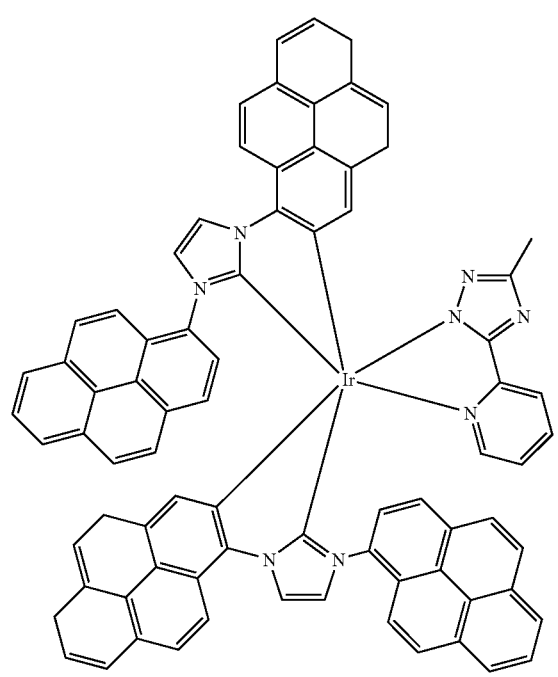
Ir(bpyi)₂(mptz)
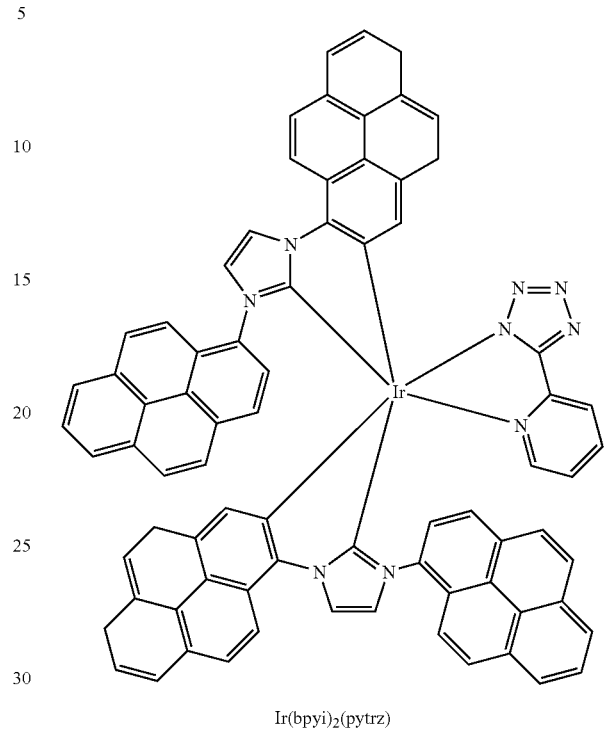
Ir(bpyi)₂(pytrz)
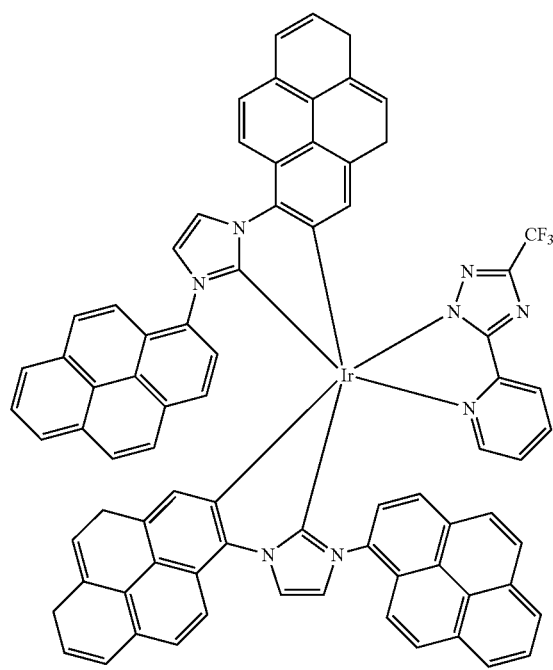
Ir(bpyi)₂(tfptz)
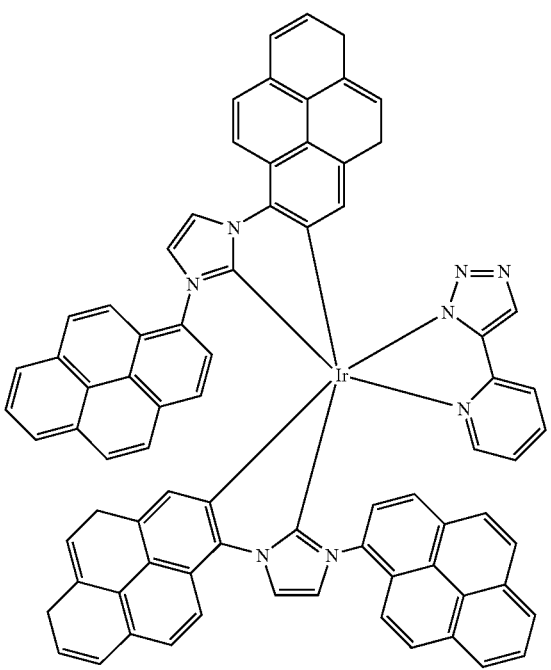
Ir(bpyi)₂(pytz)

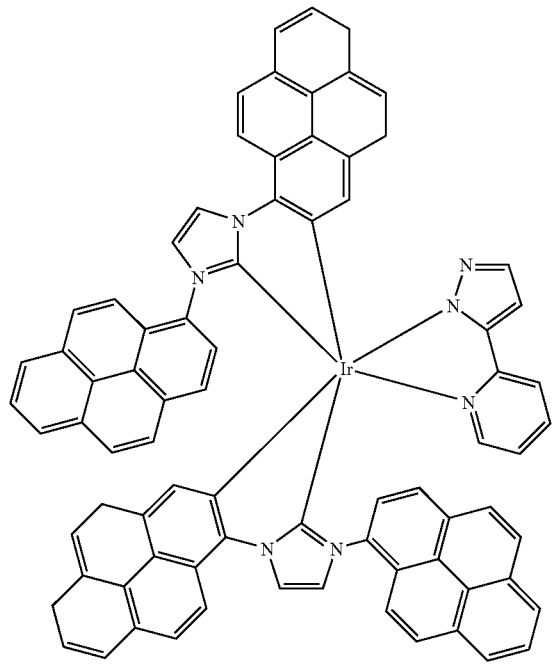
Ir(bpyi)₂(pypz)
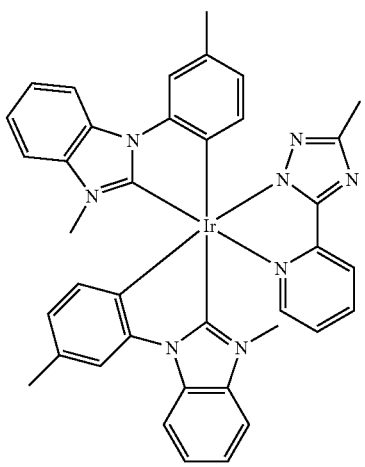
Ir(mmpmi)₂(mptz)
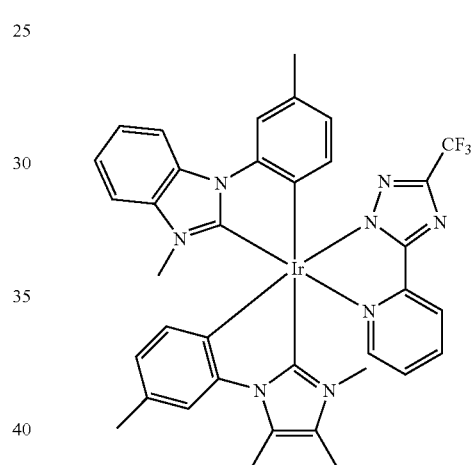
Ir(mmpmi)₂(tfptz)
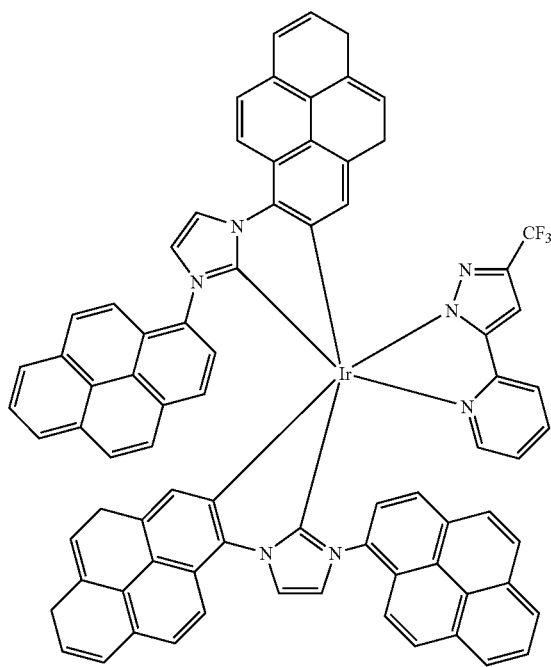
Ir(bpyi)₂(tfpyz)
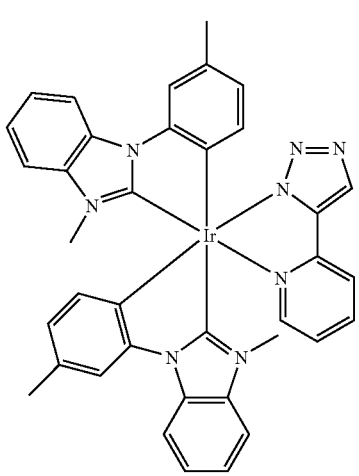
Ir(mmpmi)₂(pytz)

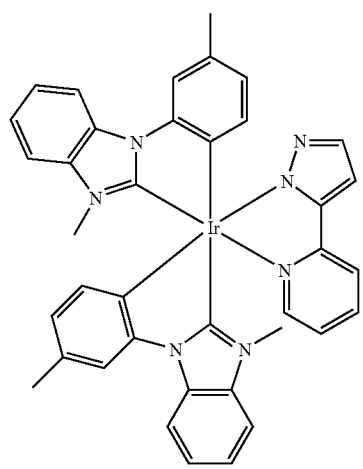
Ir(mmpmbi)₂(pypz)
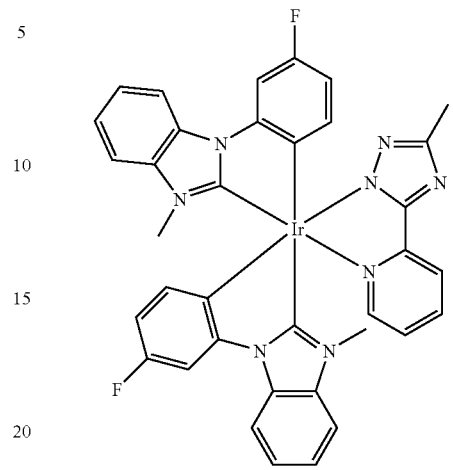
Ir(mfpmbi)₂(mptz)
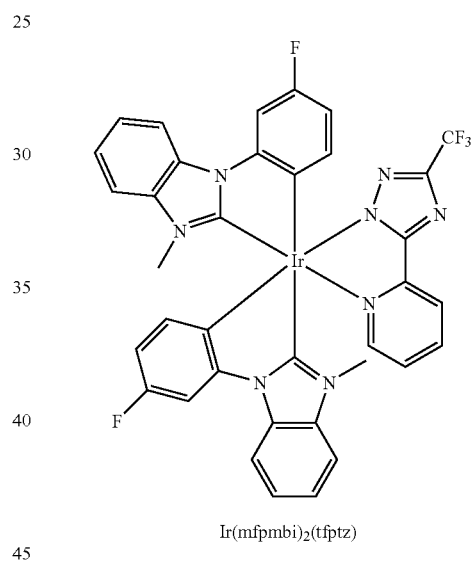
Ir(mmpmbi)₂(tfpypz)
Ir(mfpmbi)₂(tfptz)
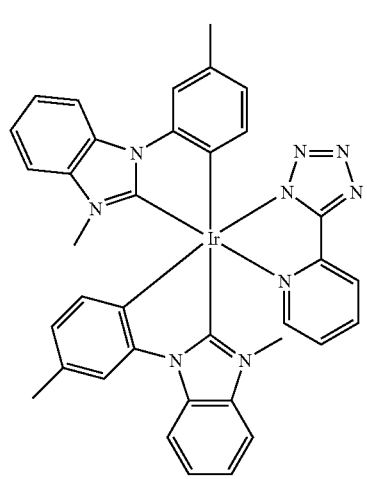
Ir(mmpmbi)₂(pytrz)
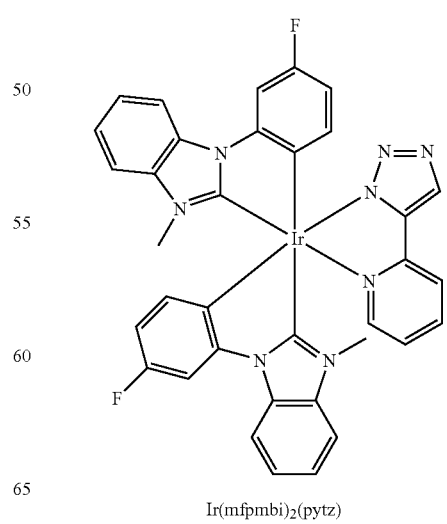
Ir(mfpmbi)₂(pytz)

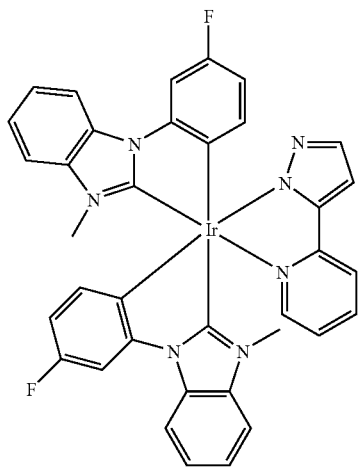
Ir(mfpmbi)₂(pypz)
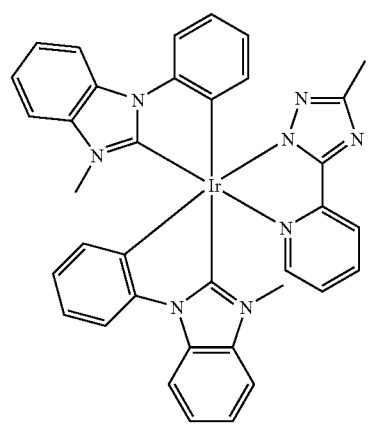
Ir(pmbi)₂(mptz)
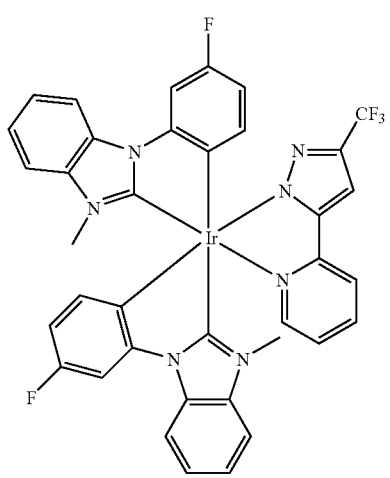
Ir(mfpmbi)₂(tfpypz)
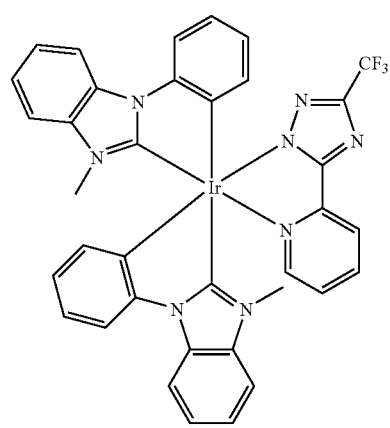
Ir(pmbi)₂(tfptz)
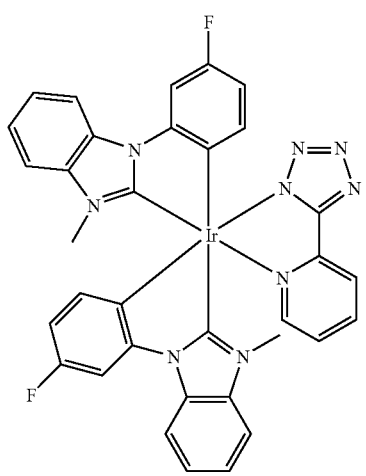
Ir(mfpmbi)₂(pytrz)
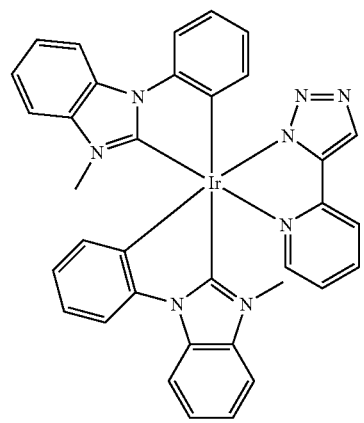
Ir(pmbi)₂(pytz)

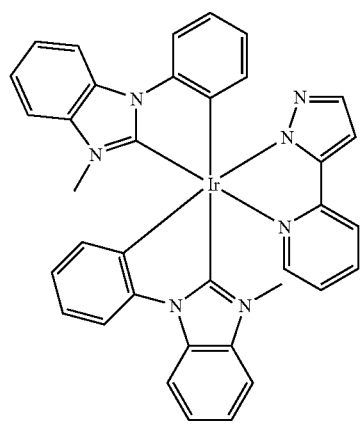
Ir(pmbi)₂(pypz)
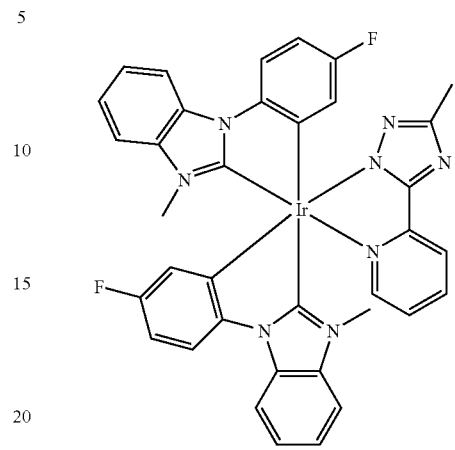
Ir(fpmbi)₂(mptz)
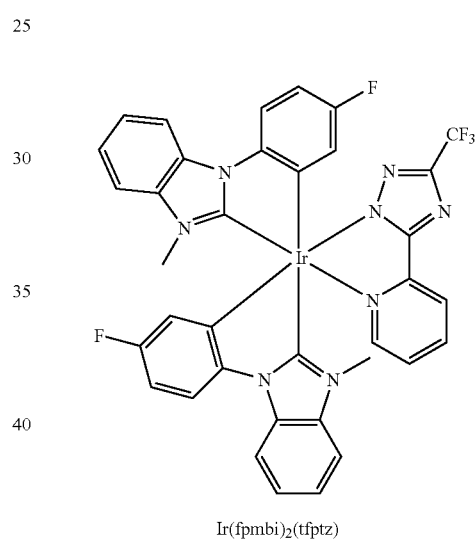
Ir(pmbi)₂(tfpypz)
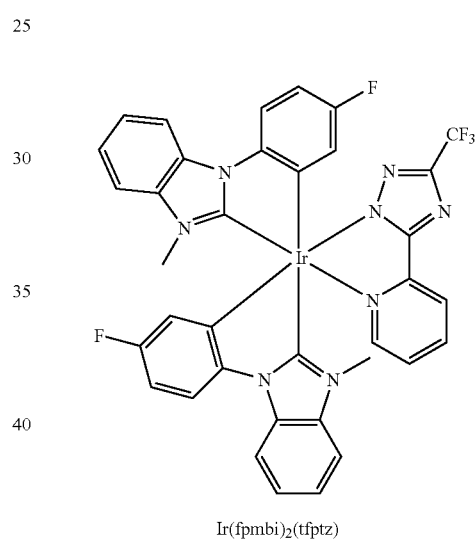
Ir(fpmbi)₂(tfptz)
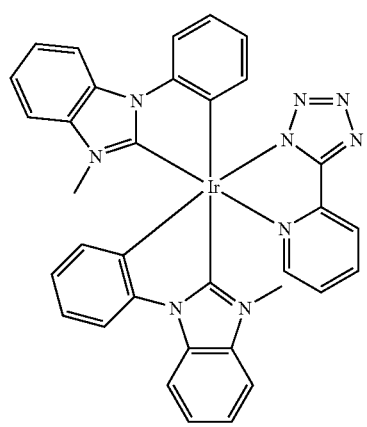
Ir(pmbi)₂(pytrz)
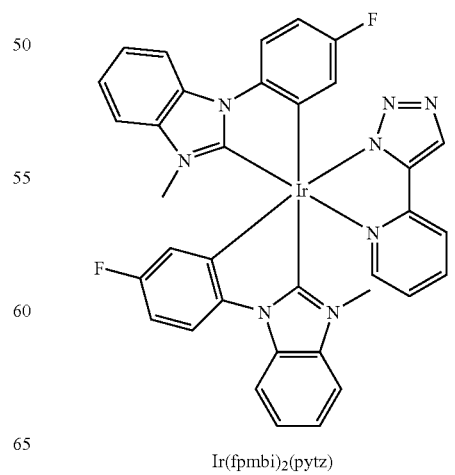
Ir(fpmbi)₂(pytz)

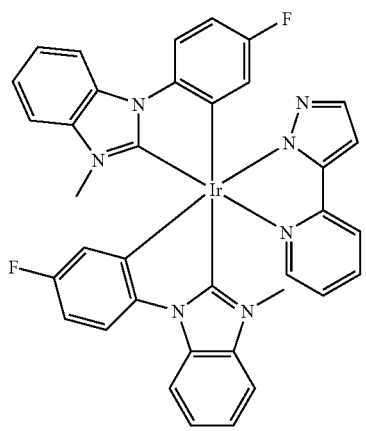
Ir(fpmbi)₂(pypz)
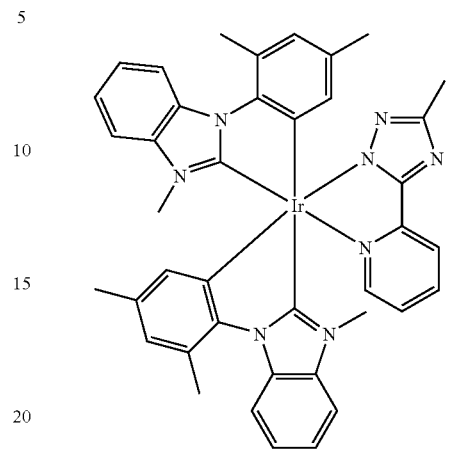
Ir(dmpmbi)₂(mptz)
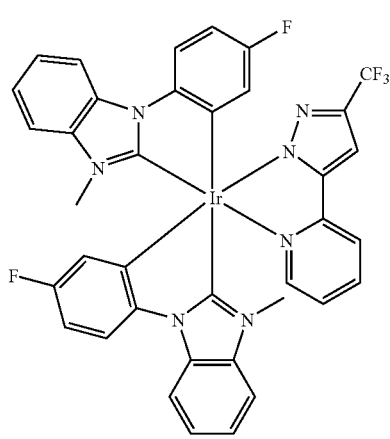
Ir(fpmbi)2(tfpypz)
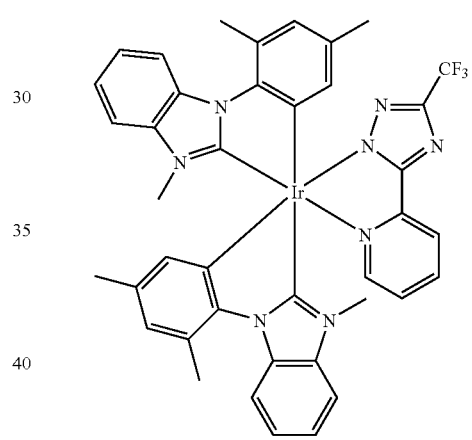
Ir(dmpmbi)₂(tfptz)
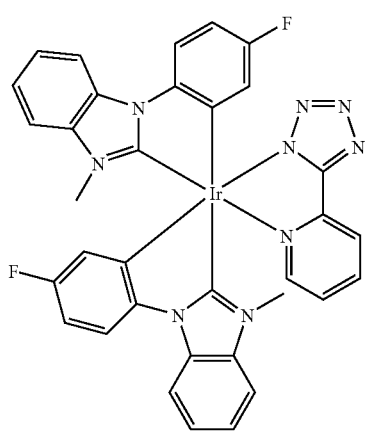
Ir(fpmbi)₂(pytrz)
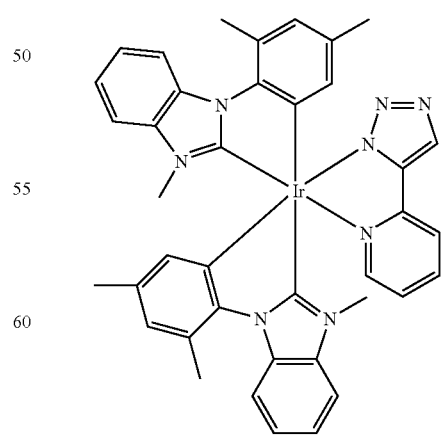
Ir(dmpmbi)2(pytz)

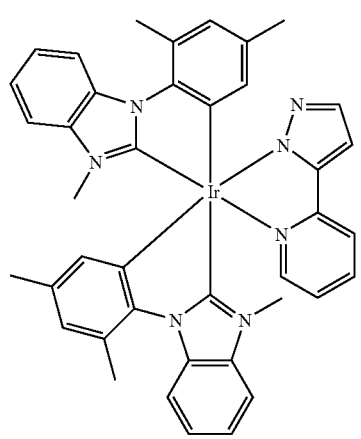
Ir(dmpmbi)₂(pypz)
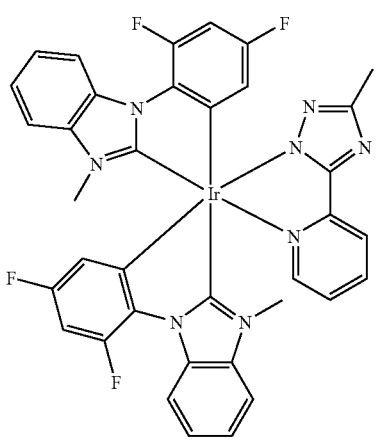
Ir(dfpmbi)₂(mptz)
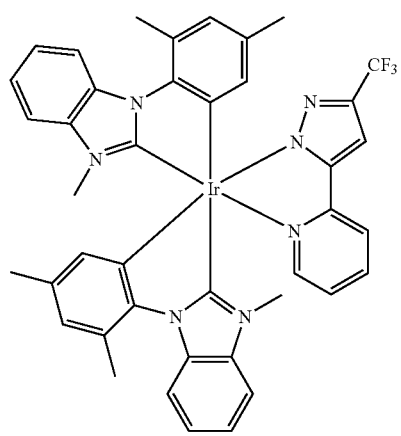
Ir(dmpmbi)₂(tfpypz)
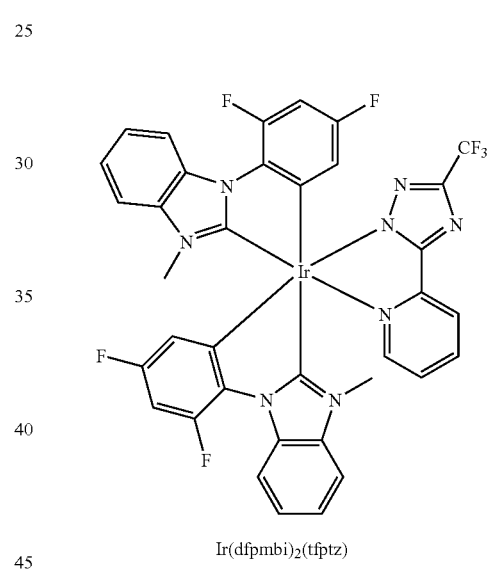
Ir(dfpmbi)₂(tfptz)
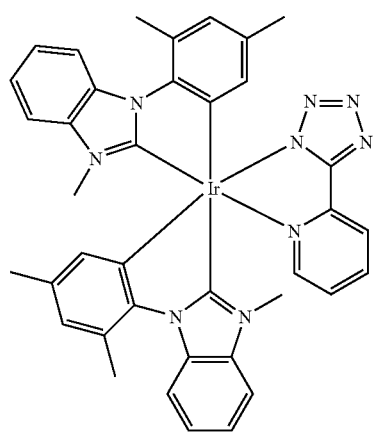
Ir(dmpmbi)₂(pytrz)
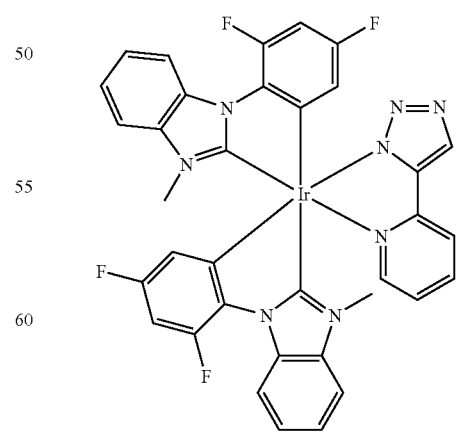
Ir(dfpmbi)₂(pytz)

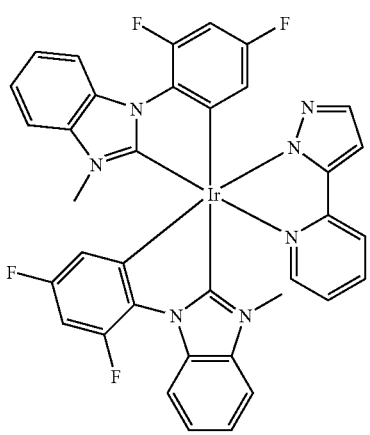
Ir(dfpmbi)₂(pypz)
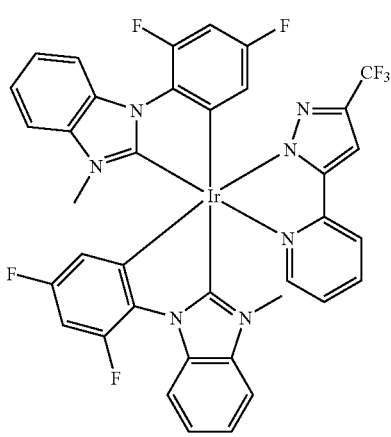
Ir(dfpmbi)₂(tfpypz)
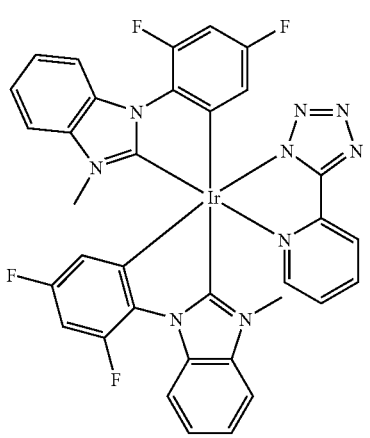
Ir(dfpmbi)₂(pytrz)
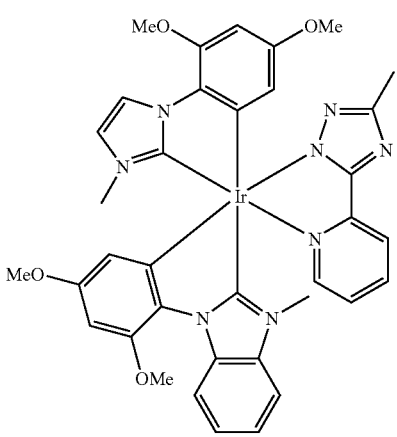
Ir(dmopmbi)₂(mptz)
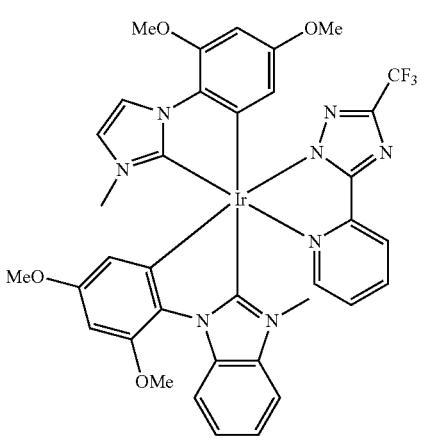
Ir(dmopmbi)₂(tfptz)
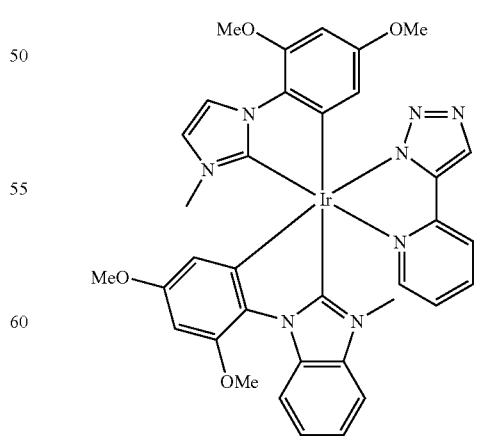
Ir(dmopmbi)₂(pytz)

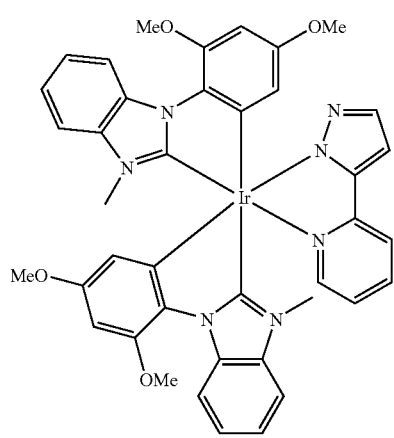
Ir(dmopmbi)₂(pypz)
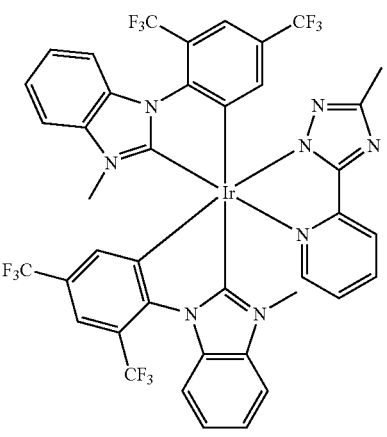
Ir(dfpmbi)₂(mptz)
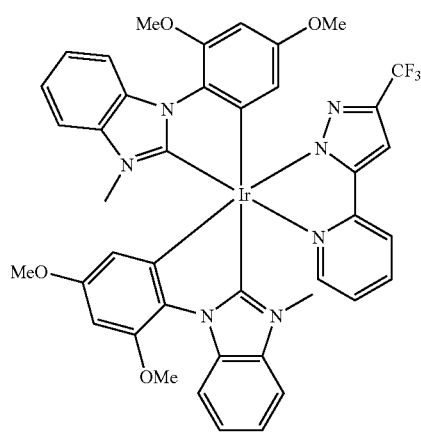
Ir(dmopmbi)₂(tfpypz)
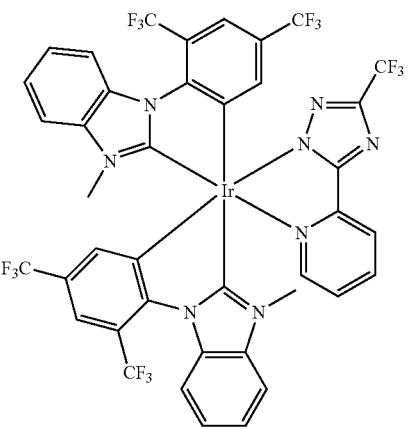
Ir(dfpmbi)₂(tfptz)
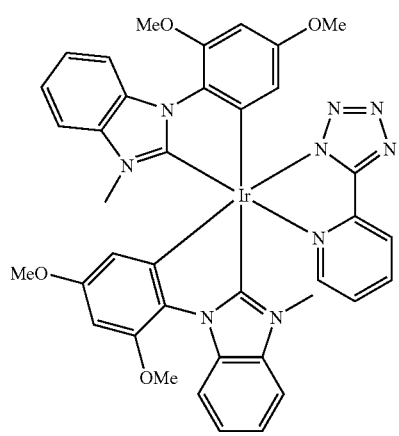
Ir(dmopmbi)₂(pytrz)
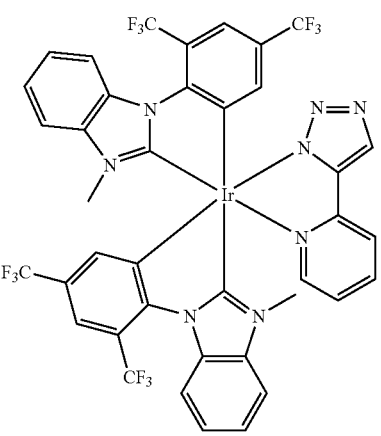
Ir(dfpmbi)₂(pytz)

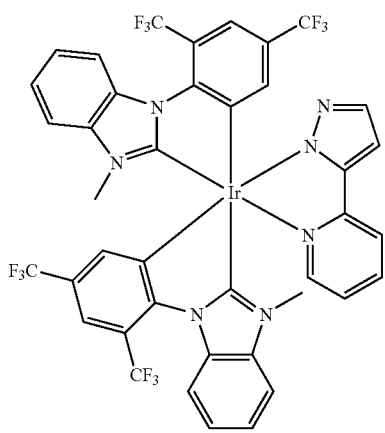
Ir(dfpmbi)₂(pypz)
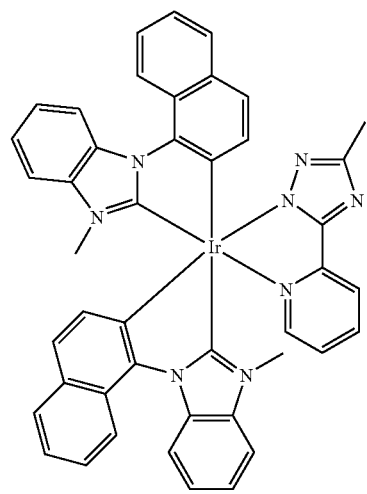
Ir(nmbi)₂(mptz)
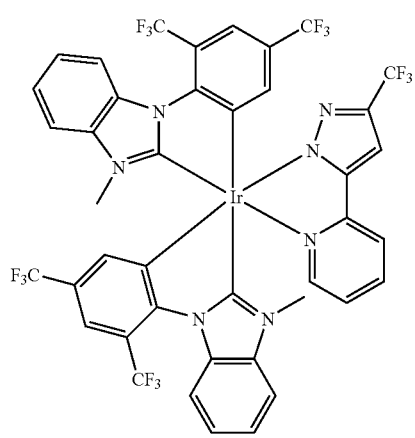
Ir(dfpmbi)₂(tfpypz)
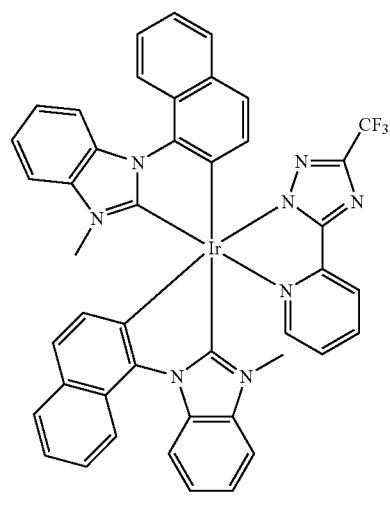
Ir(nmbi)₂(tfptz)
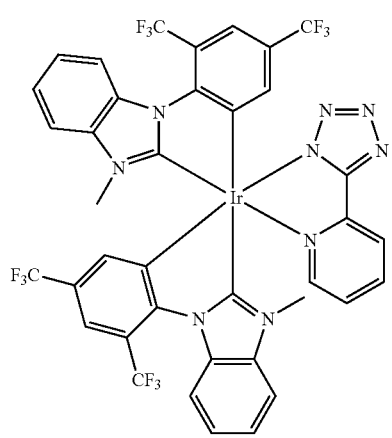
Ir(dfpmbi)₂(pytrz)
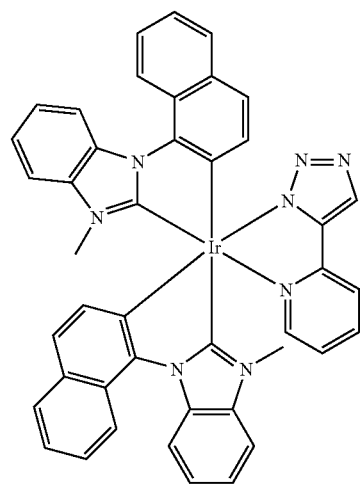
Ir(nmbi)₂(pytz)

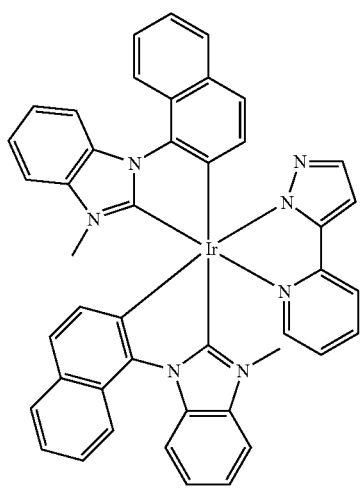
Ir(nmbi)₂(pypz)
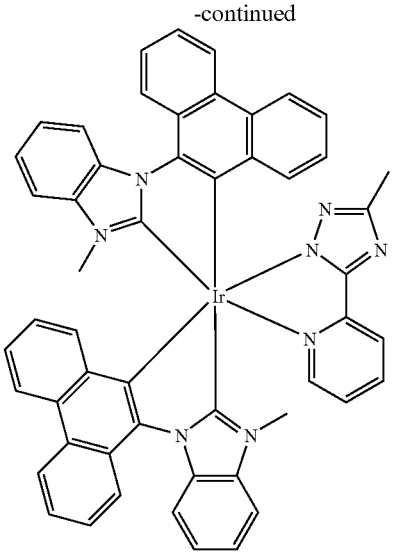
Ir(pnmbi)₂(mptz)
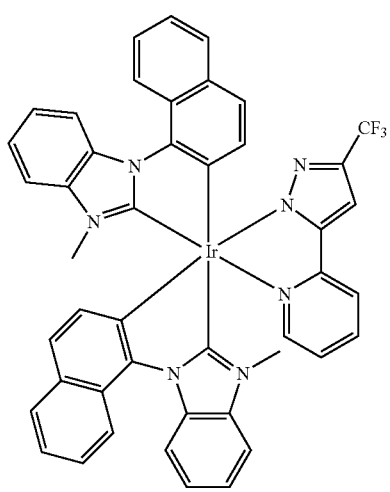
Ir(nmbi)₂(tfpypz)
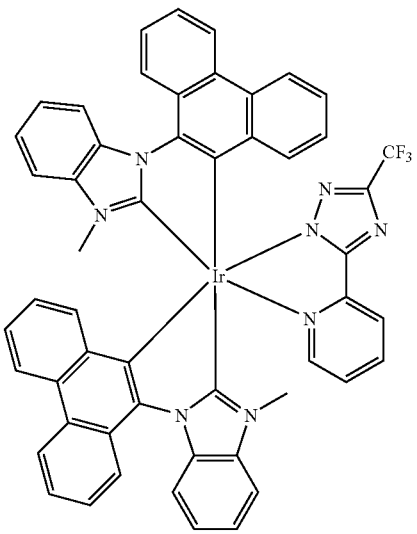
Ir(pnmbi)₂(tfptz)
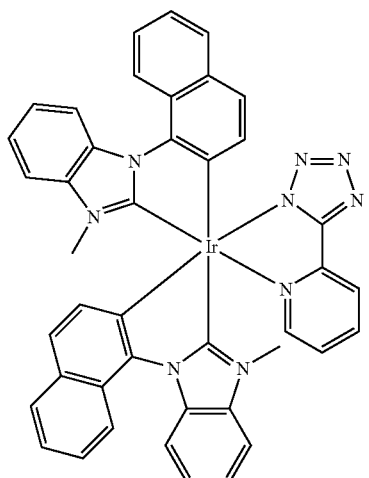
Ir(nmbi)₂(pytrz)
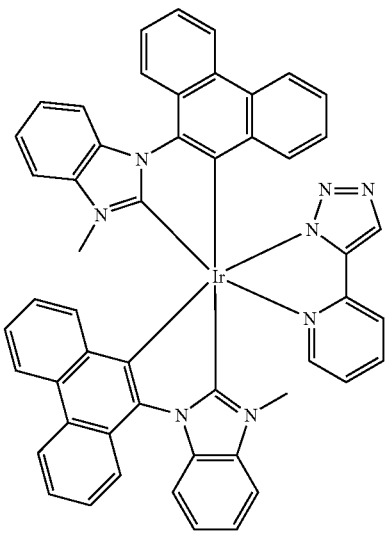
Ir(pnmbi)₂(pytz)

-continued
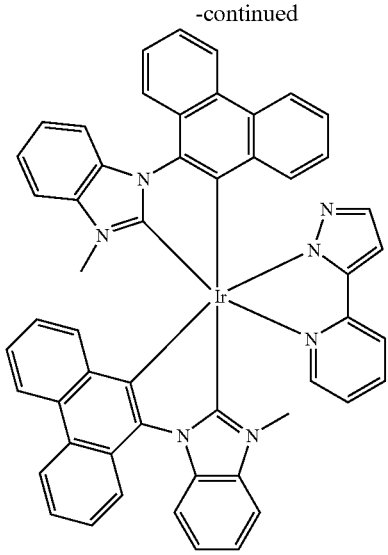
Ir(pnmbi)₂(pypz)
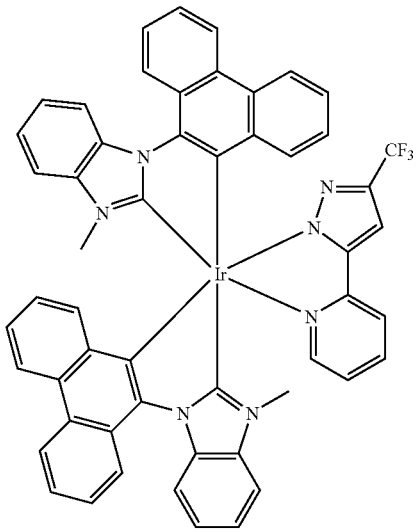
Ir(pnmbi)₂(tfpypz)
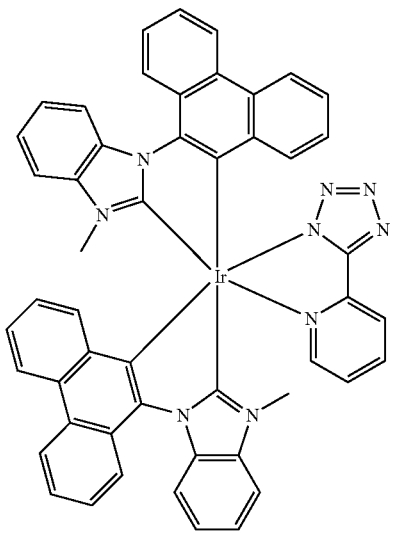
Ir(pnmbi)₂(pytrz)
-continued
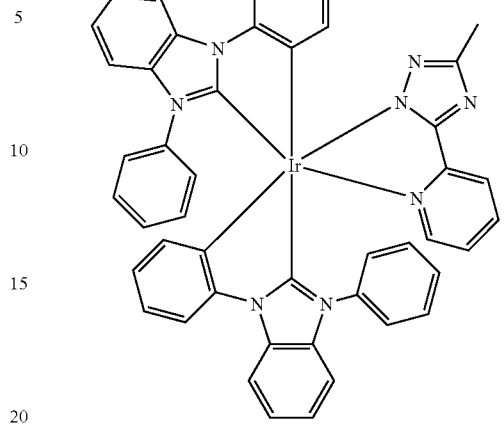
Ir(bpbi)₂(mptz)
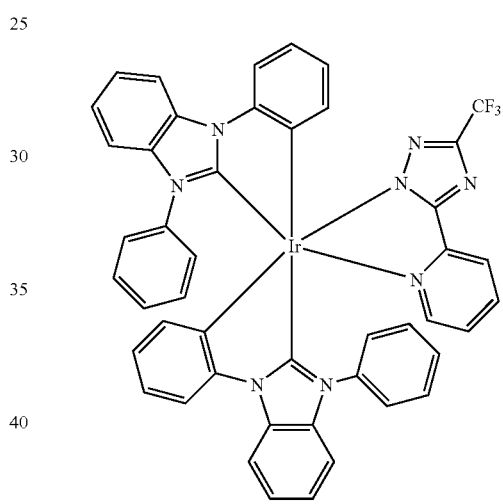
Ir(bpbi)₂(tfptz)
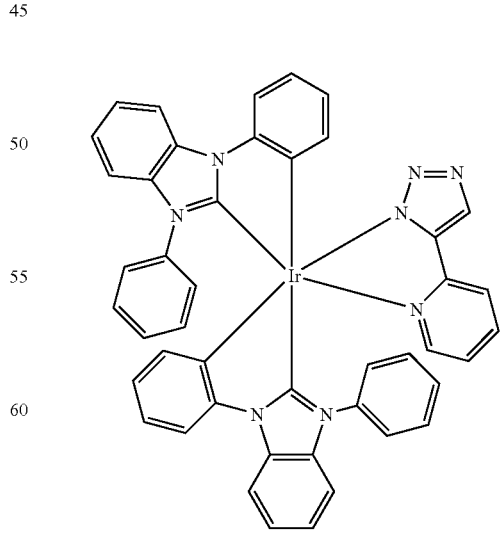
Ir(bpbi)₂(pytz)

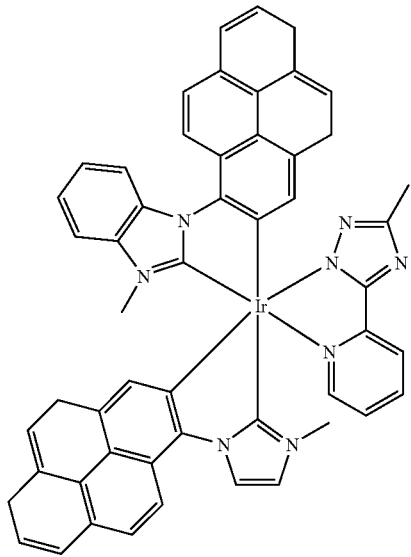
Ir(pymbi)₂(mptz)
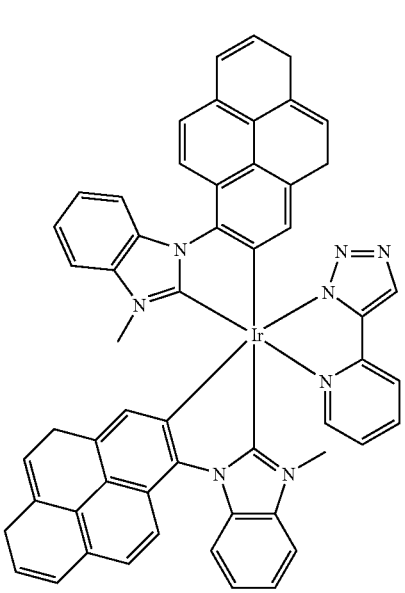
Ir(pymbi)₂(pytz)
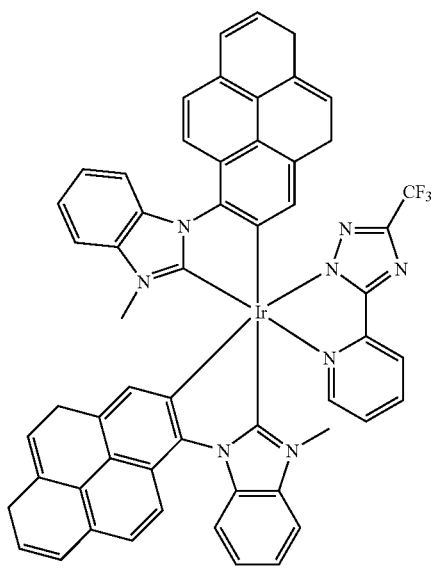
Ir(pymbi)₂(tfptz)
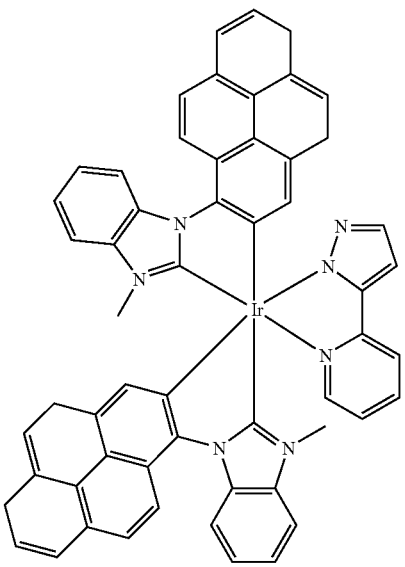
Ir(pymbi)₂(pypz)

-continued
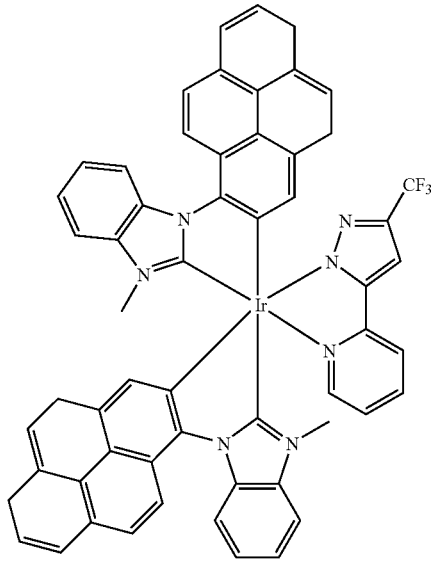
Ir(pymbi)₂(tfpypz)
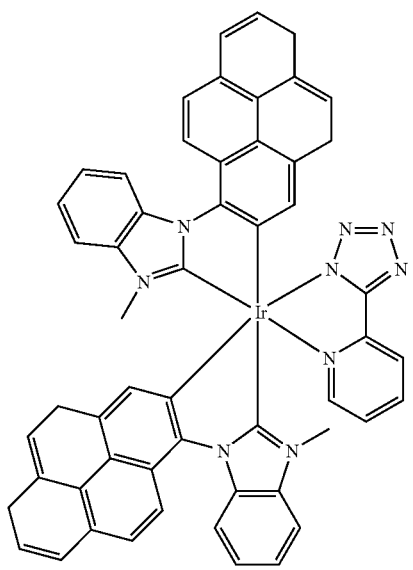
Ir(pymbi)₂(pytrz)
-continued
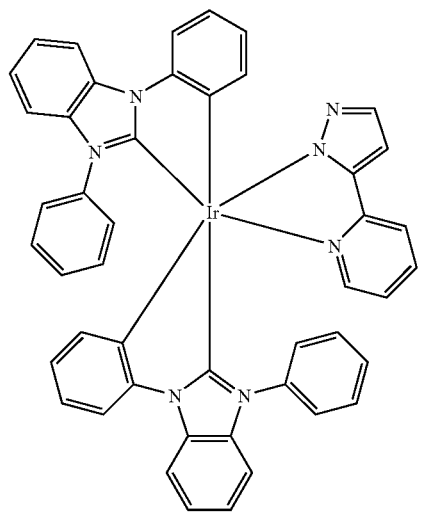
Ir(bpbi)₂(pypz)
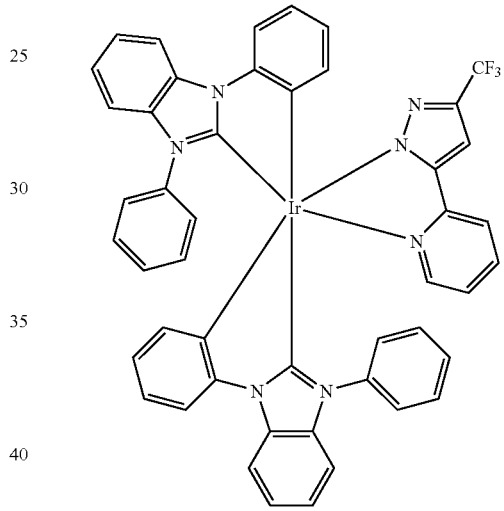
Ir(bpbi)₂(tfpypz)
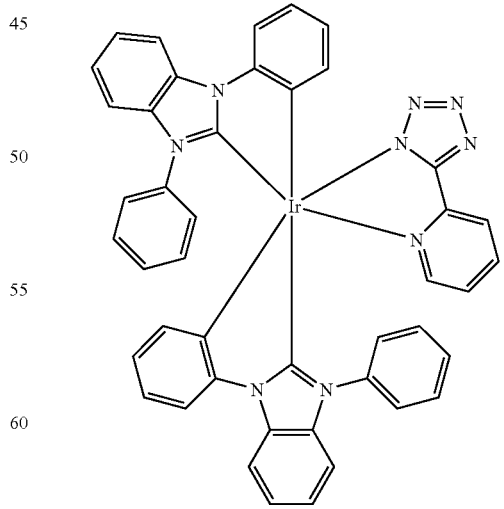
Ir(bpbi)₂(pytrz)

-continued
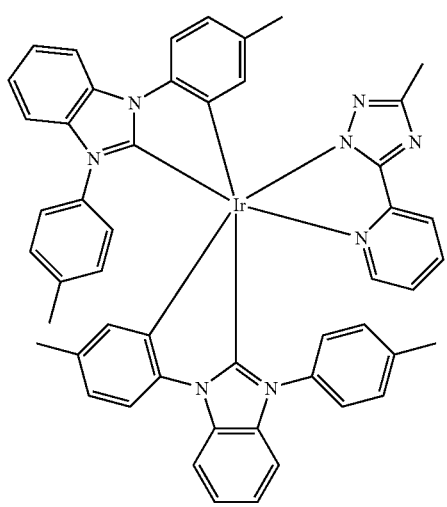
Ir(bmpbi)₂(mptz)
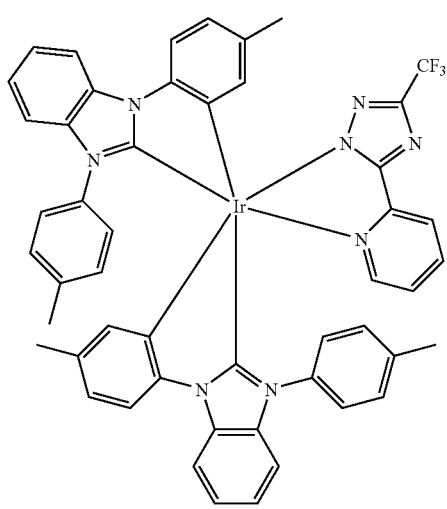
Ir(bmpbi)₂(tfptz)
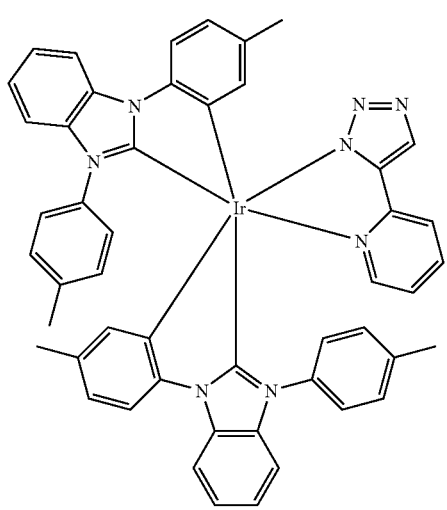
Ir(bmpbi)₂(pytz)
-continued
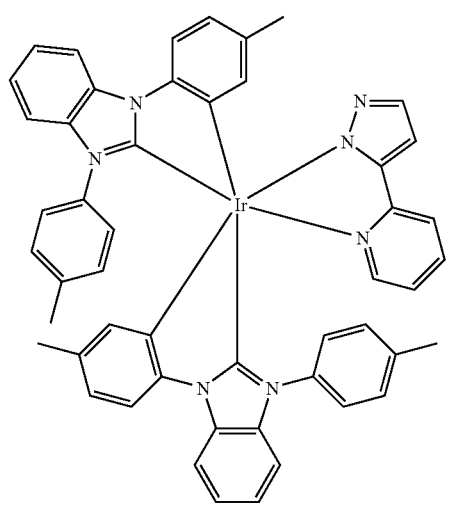
Ir(bmpbi)₂(pypz)
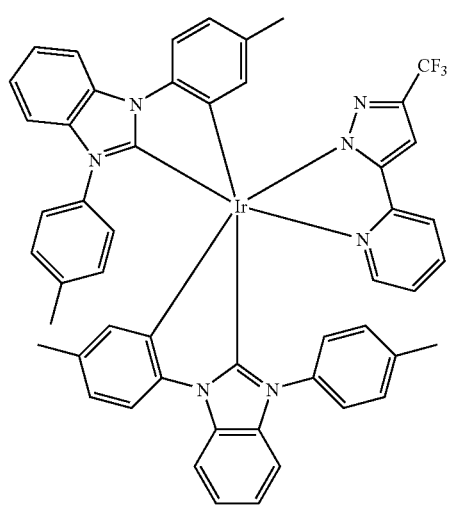
Ir(bmpbi)₂(tfpypz)
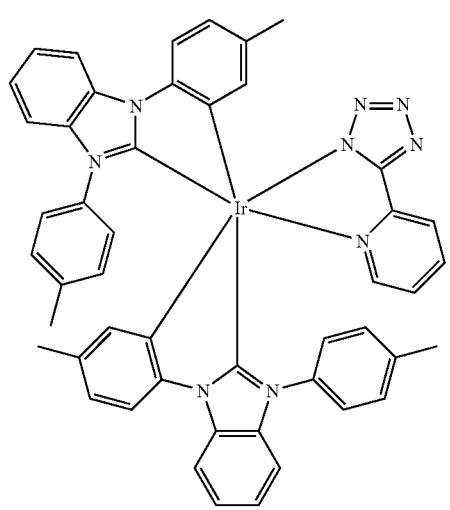
Ir(bmpbi)₂(pytrz)

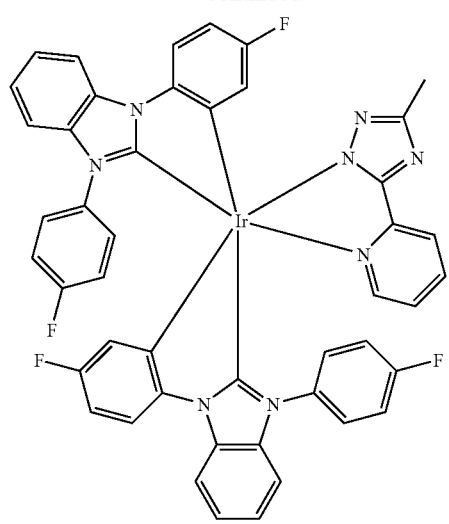
Ir(bfpbi)₂(mptz)
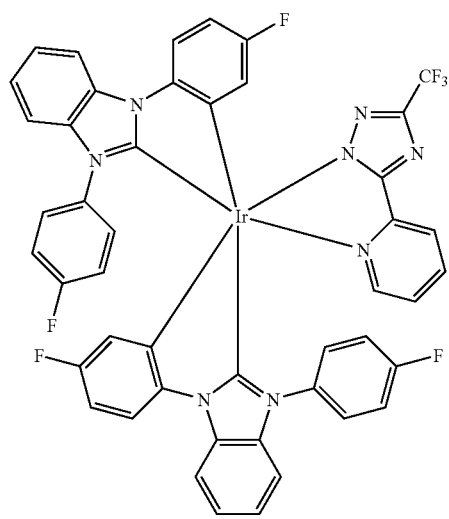
Ir(bfpbi)₂(tfptz)
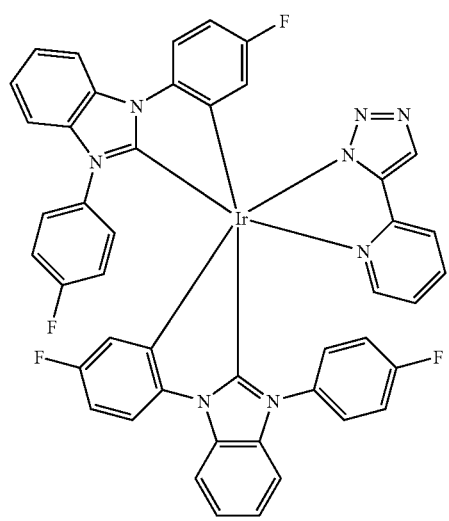
Ir(bfpbi)₂(pytz)
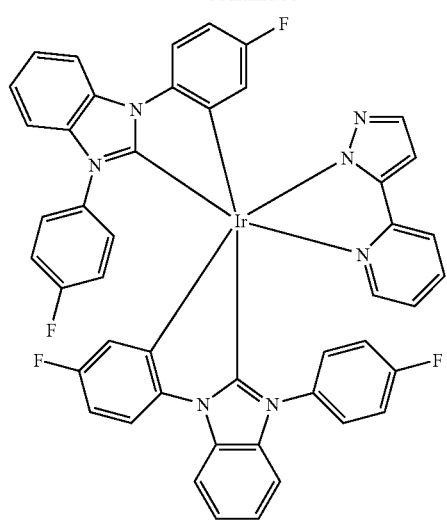
Ir(bfpbi)₂(pypz)
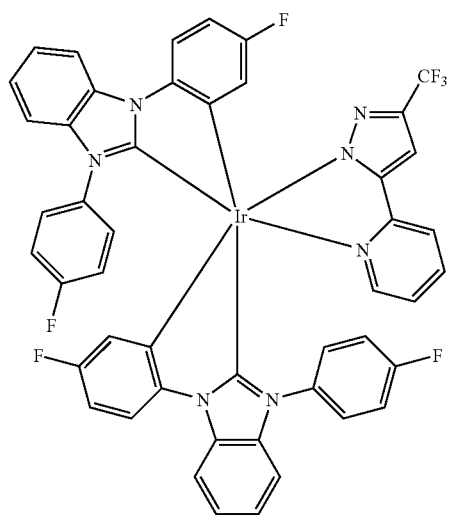
Ir(bfpbi)₂(tfpypz)
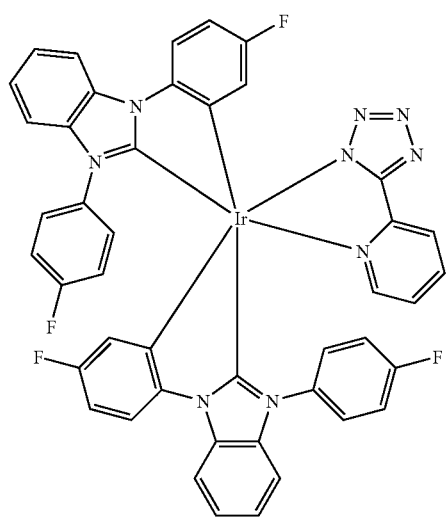
Ir(bfpbi)₂(pytrz)

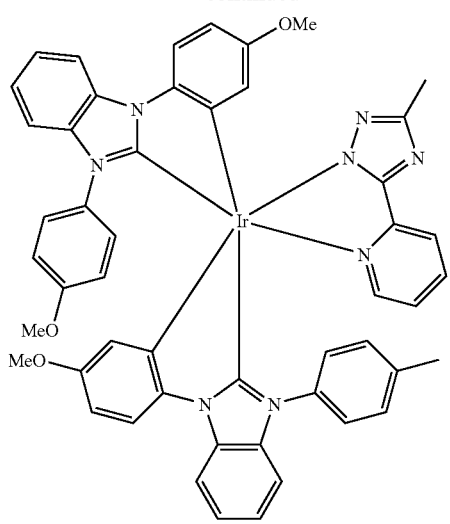
Ir(bmopbi)₂(mptz)
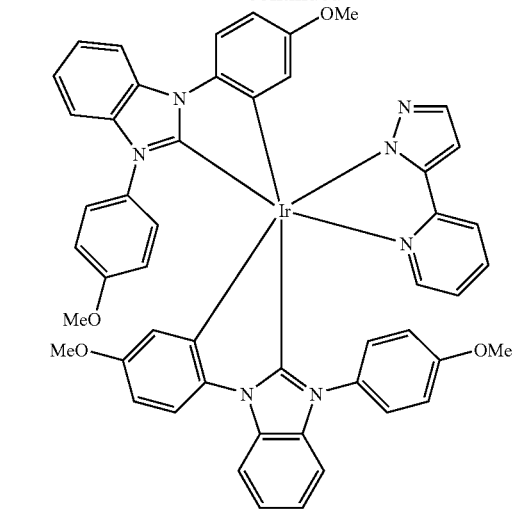
Ir(bmopbi)₂(pypz)
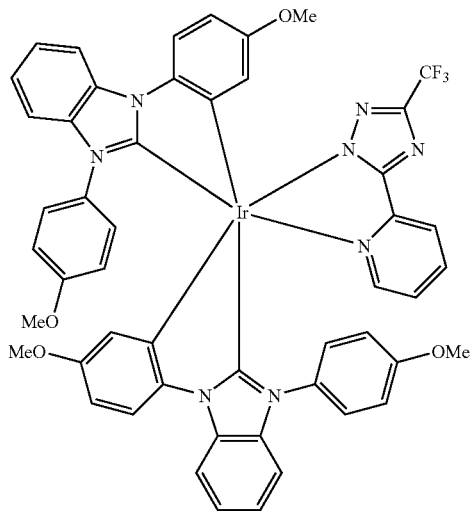
Ir(bmopbi)₂(tfptz)
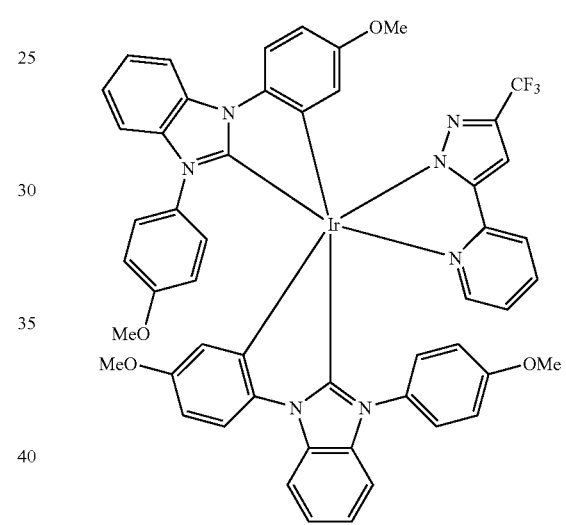
Ir(bmopbi)₂(tfpypz)
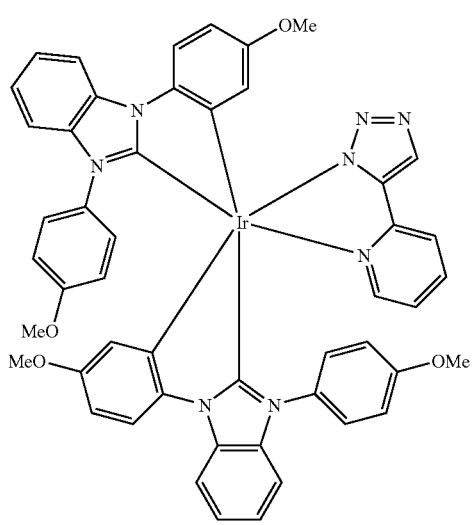
Ir(bmopbi)₂(pytz)
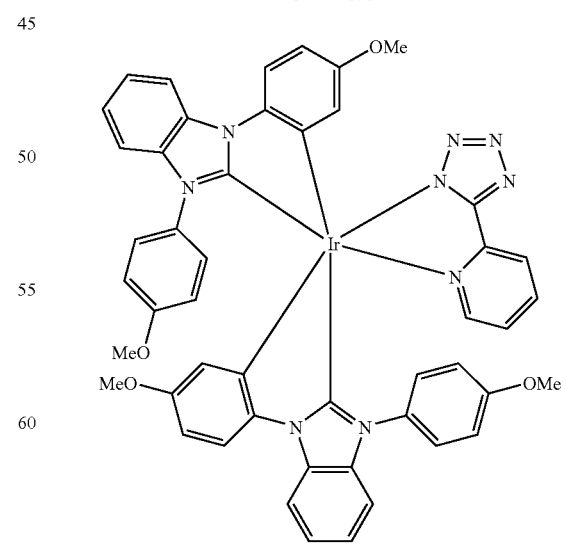
Ir(bmopbi)₂(pytrz)

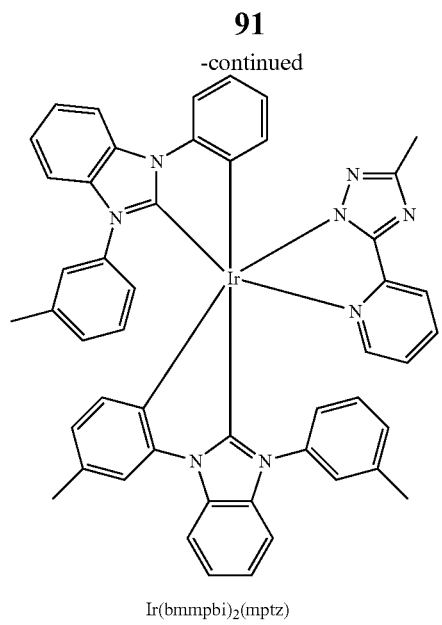
Ir(bmmpbi)₂(mptz)
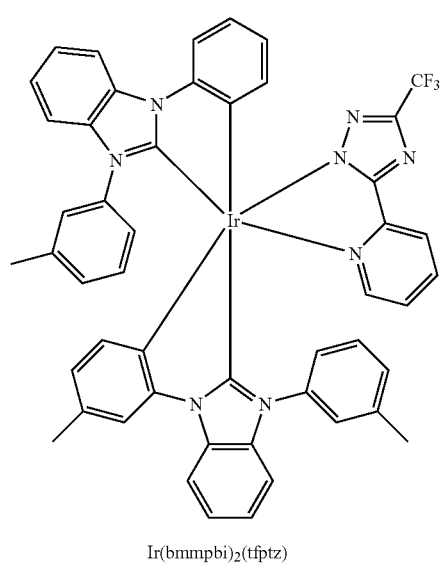
Ir(bmmpbi)₂(tfptz)
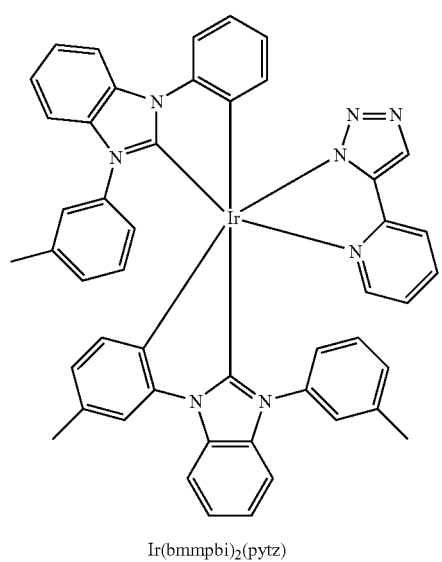
Ir(bmmpbi)₂(pytz)
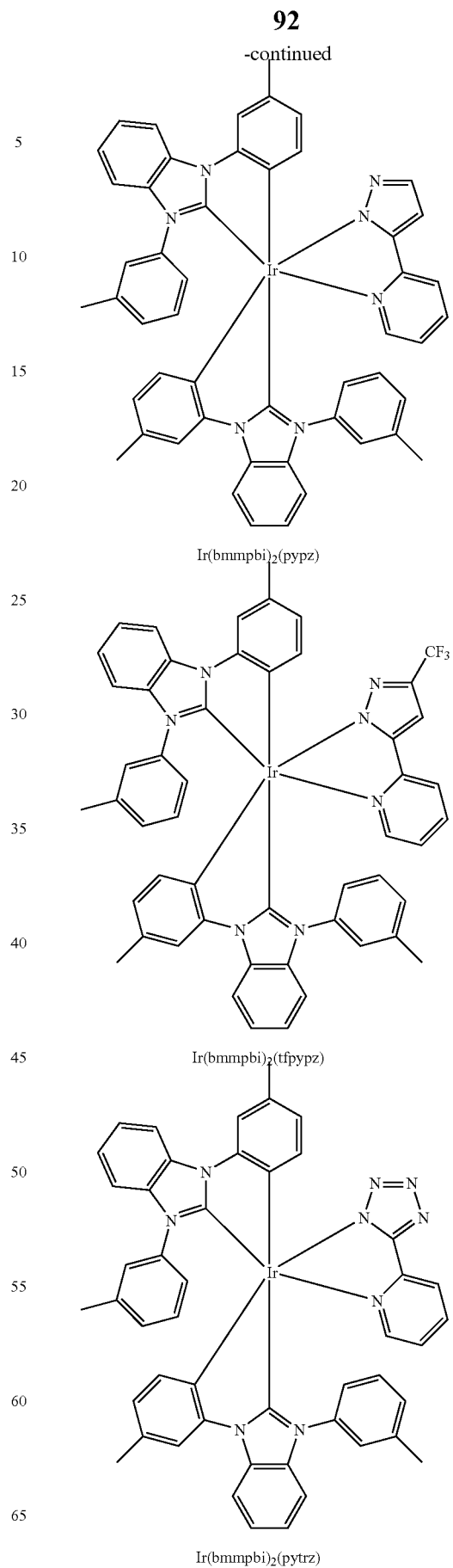
Ir(bmmpbi)₂(pypz)
Ir(bmmpbi)₂(tfpypz)
Ir(bmmpbi)₂(pytrz)

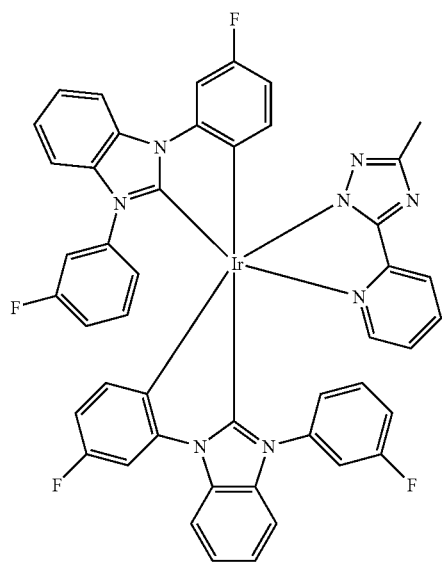
Ir(bmfpbi)₂(mptz)
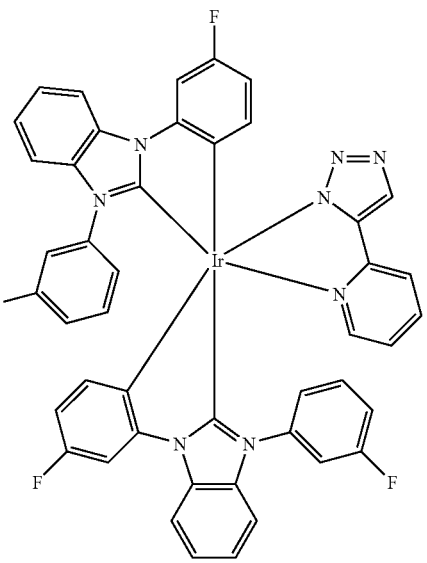
Ir(bmfpbi)₂(pytz)
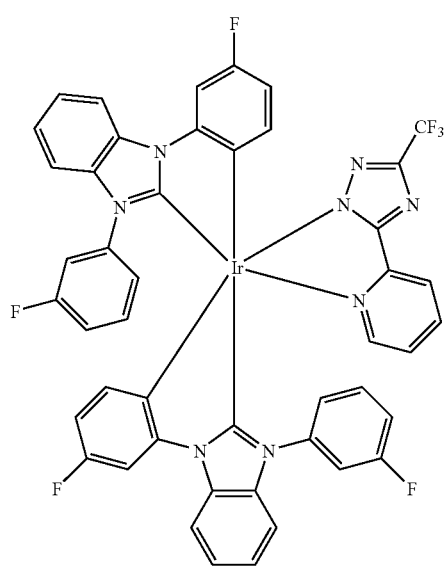
Ir(bmfpbi)₂(tfptz)
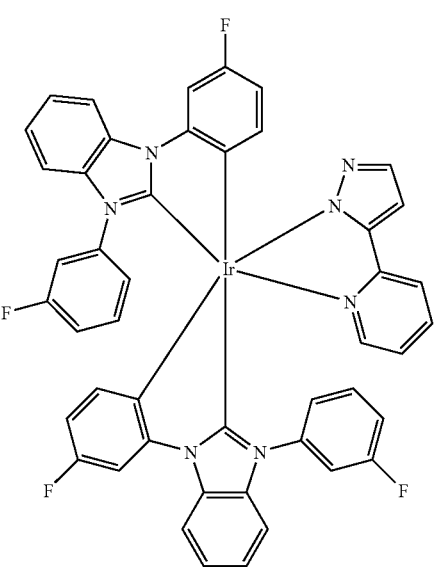
Ir(bmfpbi)₂(pypz)

-continued
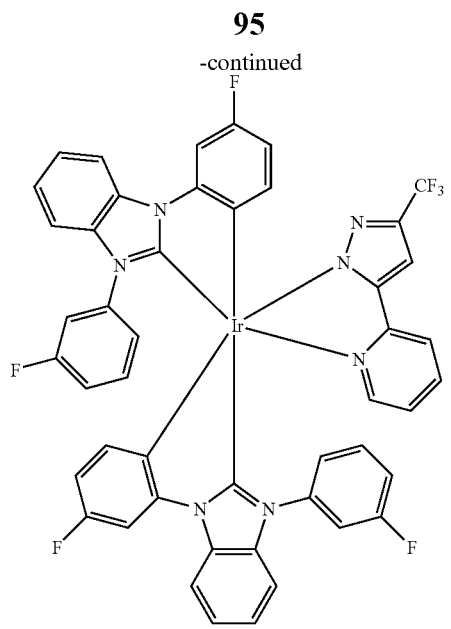
Ir(bmfpbi)₂(tfpypz)
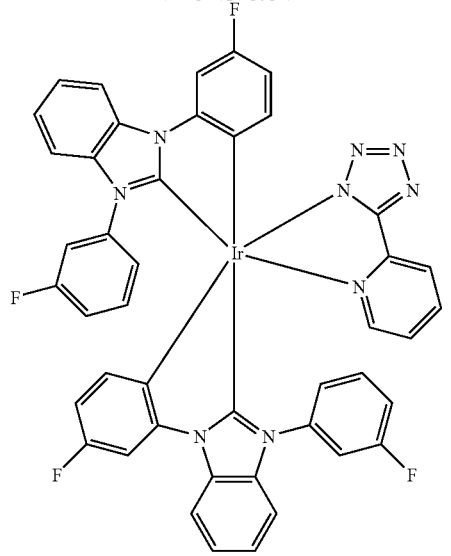
Ir(bmfpbi)₂(pytrz)
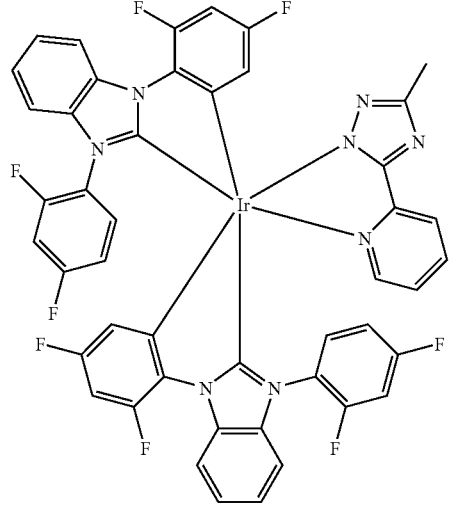
Ir(bdfpbi)₂(mptz)
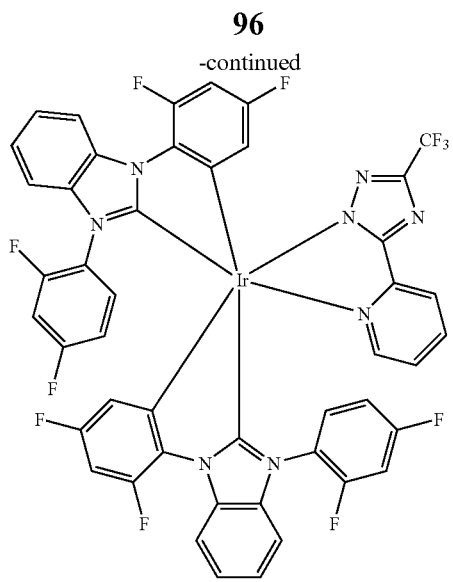
Ir(bdfpbi)₂(tfptz)
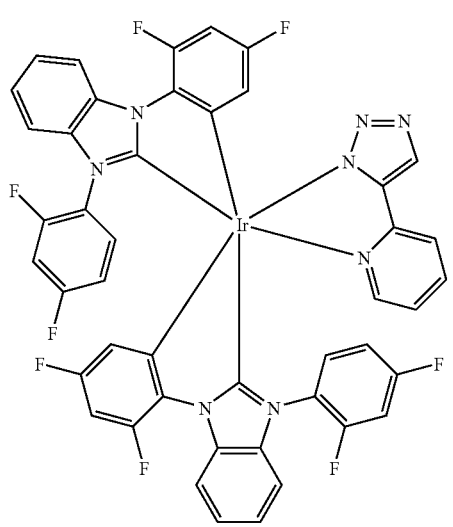
Ir(bdfpbi)₂(pytz)
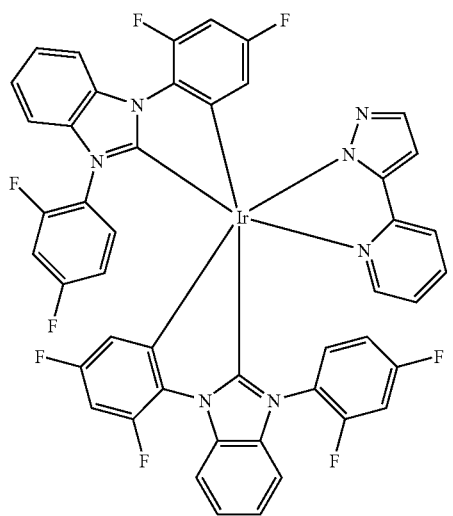
Ir(bdfpbi)₂(pypz)

-continued
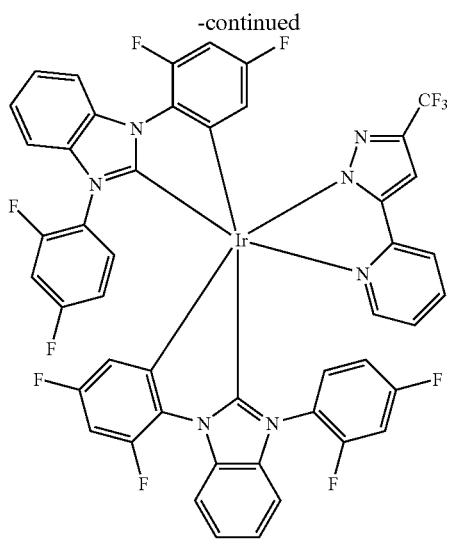
Ir(bdfpbi)₂(tfpypz)
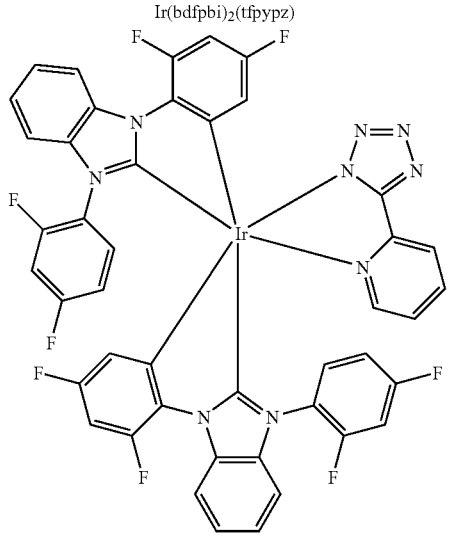
Ir(bdfpbi)₂(pytrz)
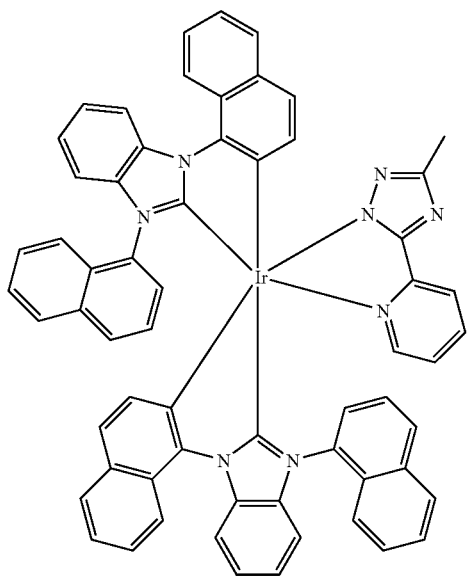
Ir(bnbi)₂(mptz)
-continued
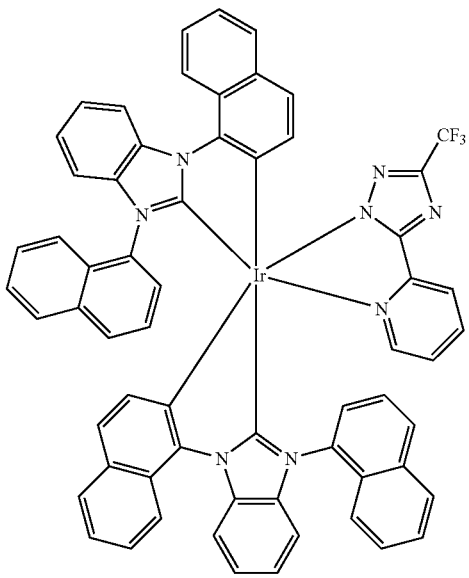
Ir(bnbi)₂(tfptz)
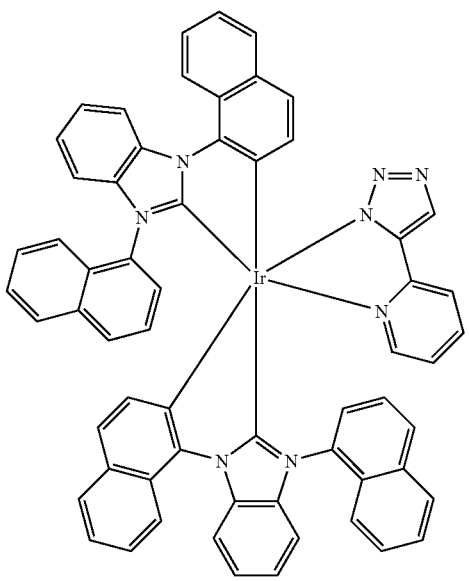
Ir(bnbi)₂(pytz)

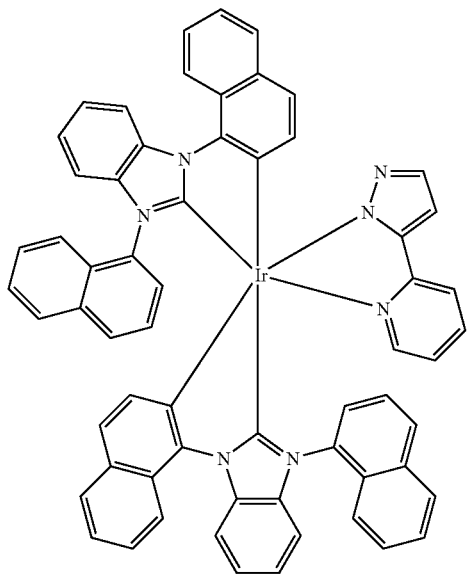
Ir(bnbi)₂(pypz)
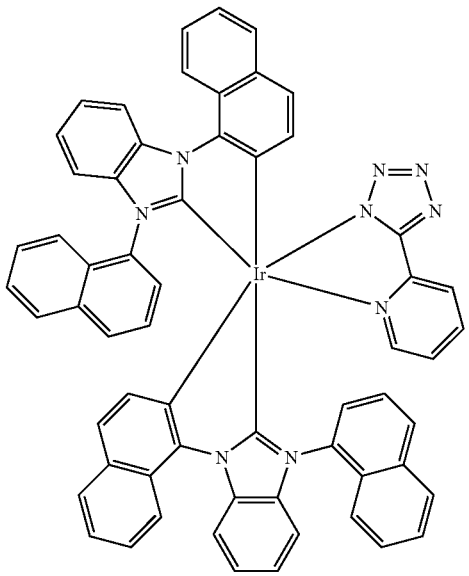
Ir(bnbi)₂(pytrz)
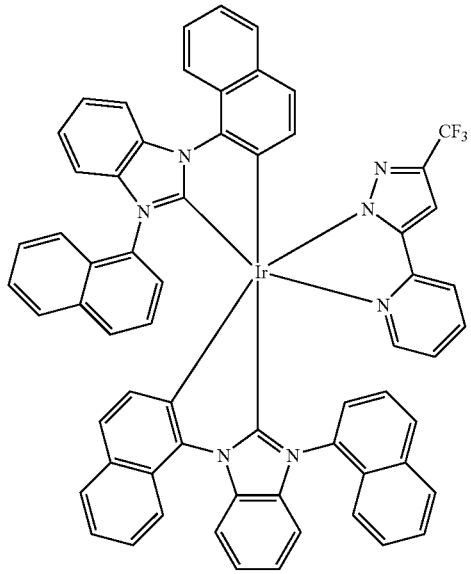
Ir(bnbi)₂(tfpypz)
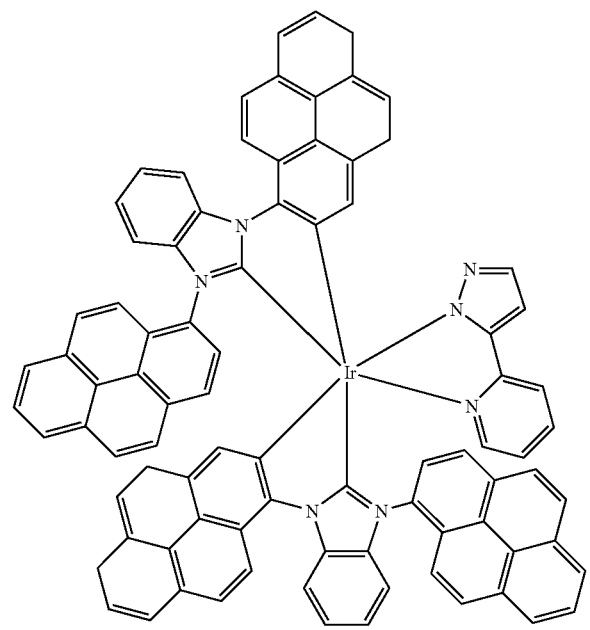
Ir(bpybi)₂(pypz)

101
-continued
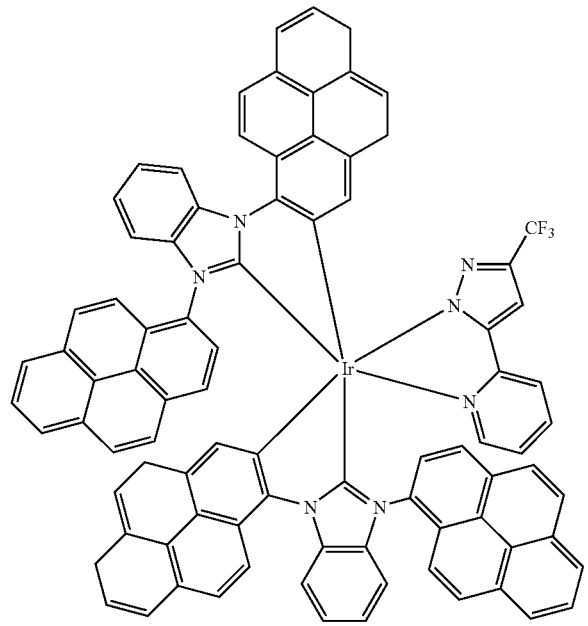
Ir(bpybi)₂(tfpypz)
102
-continued
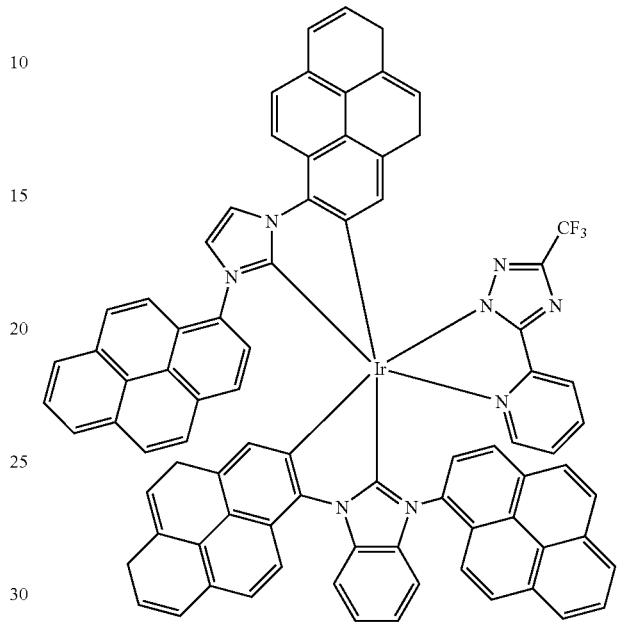
Ir(bpybi)₂(tfptz)
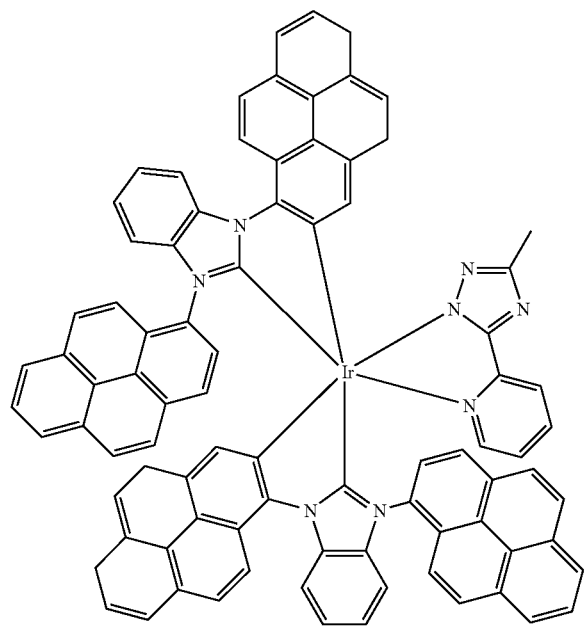
Ir(bpybi)₂(mptz)
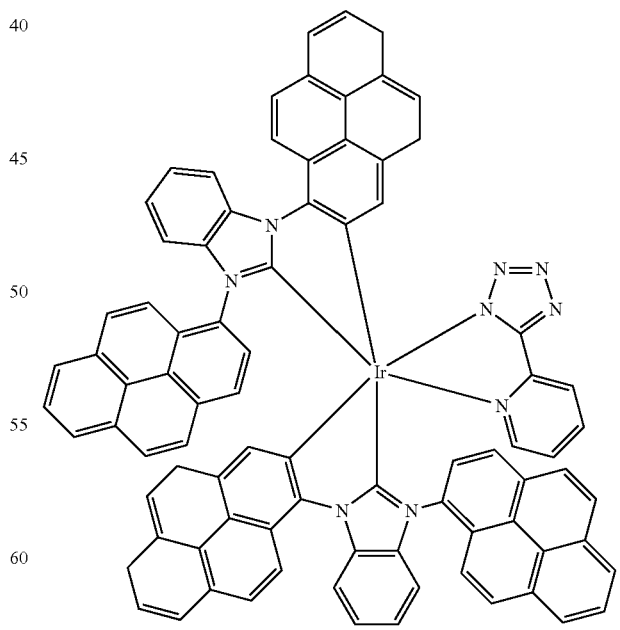
Ir(bpybi)₂(pytrz)

103
-continued
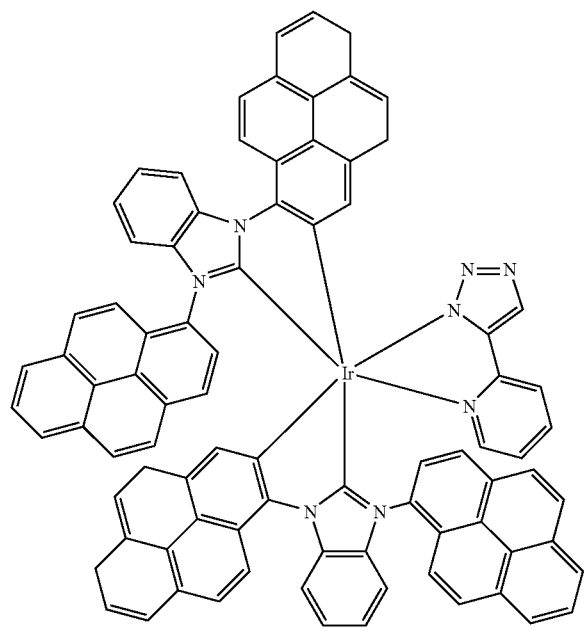
Ir(bpybi)₂(pytz)
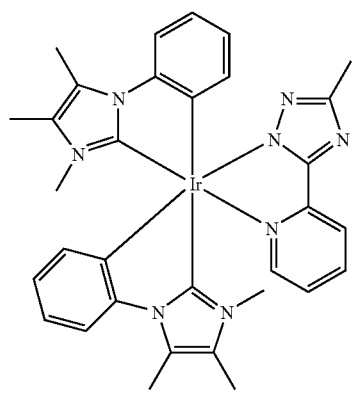
Ir(ptmi)₂(mptz)
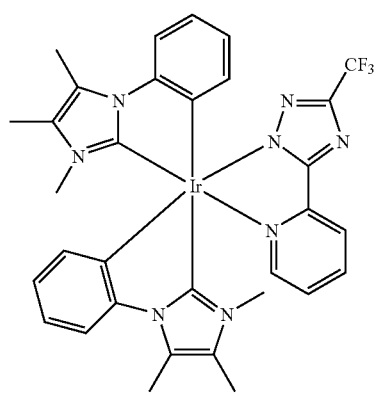
Ir(ptmi)₂(tfptz)
104
-continued
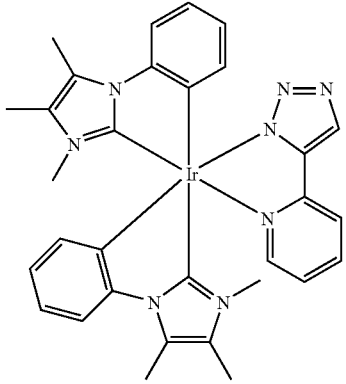
Ir(ptmi)₂(pytz)
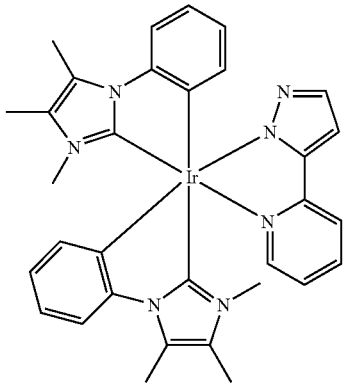
Ir(ptmi)₂(pypz)
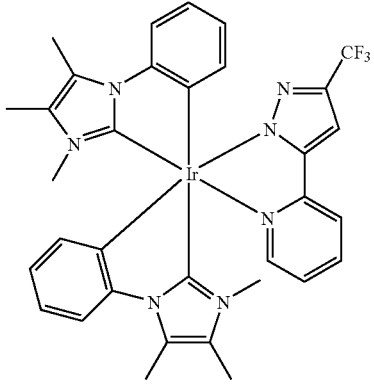
Ir(ptmi)₂(tfpypz)
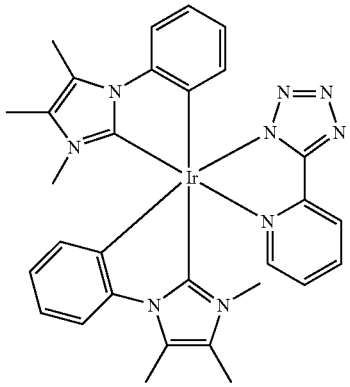
Ir(ptmi)₂(pytrz)

-continued
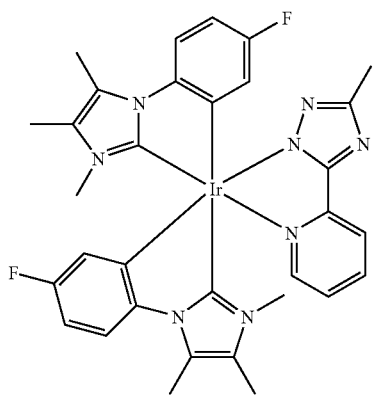
Ir(fptmi)₂(mptz)
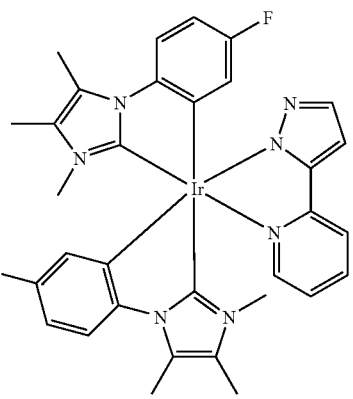
Ir(fptmi)₂(pypz)
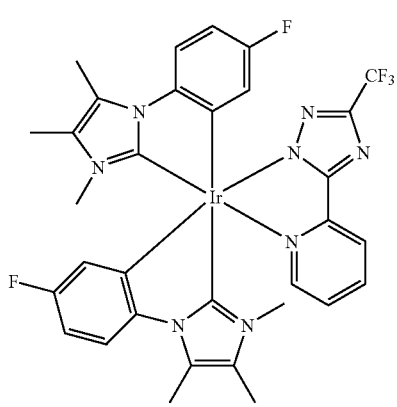
Ir(fptmi)₂(tfptz)
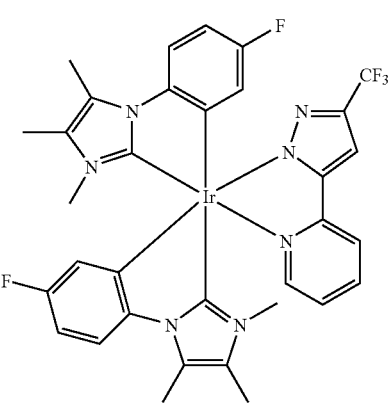
Ir(fptmi)₂(tfpypz)
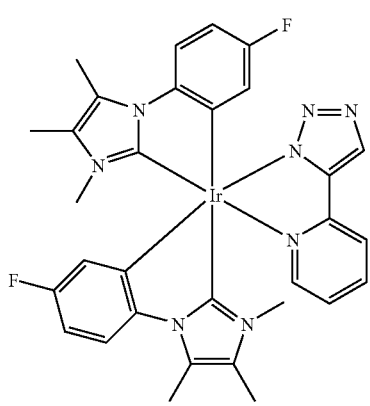
Ir(fptmi)₂(pytz)
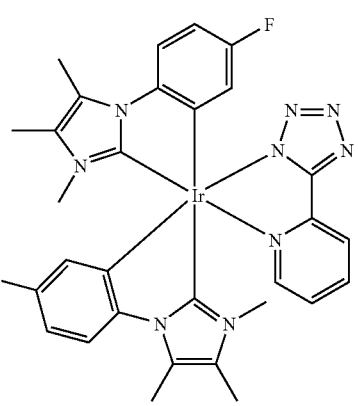
Ir(fptmi)₂(pytrz)

-continued
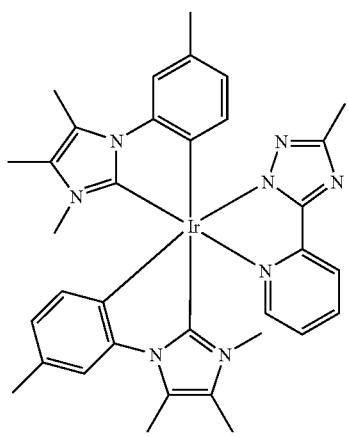
Ir(mmptmi)₂(mptz)
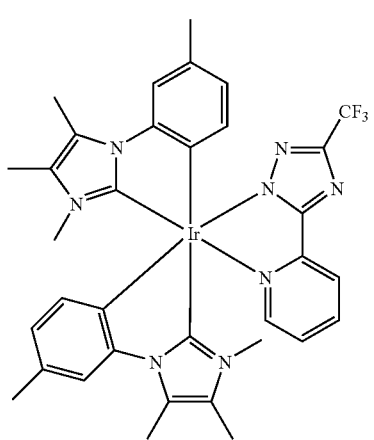
Ir(mmptmi)₂(tfptz)
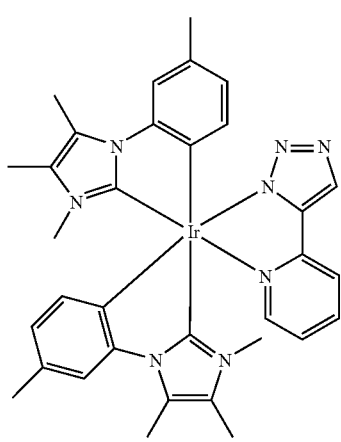
Ir(mmptmi)₂(pytz)
-continued
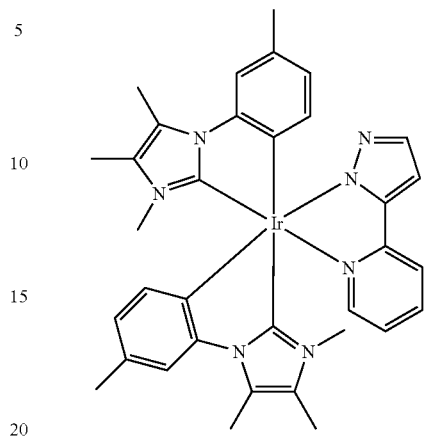
Ir(mmptmi)₂(pypz)
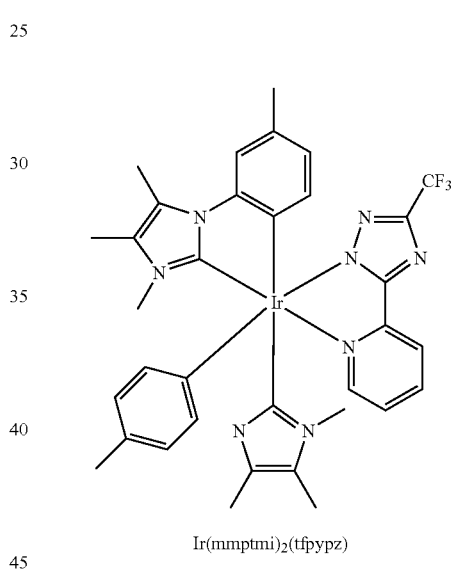
Ir(mmptmi)₂(tfpypz)
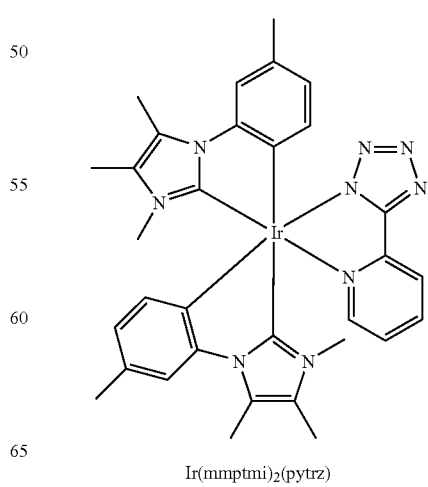
Ir(mmptmi)₂(pytrz)

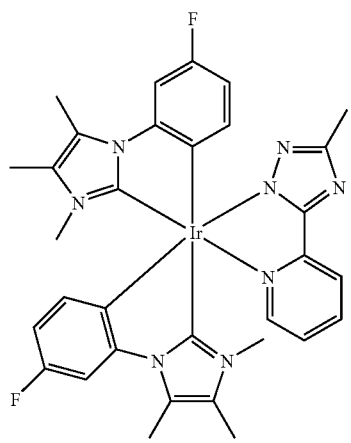
Ir(mfptmi)₂(mptz)
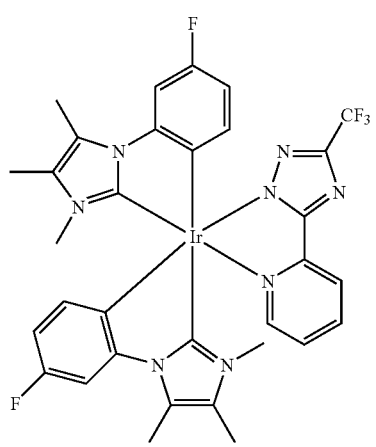
Ir(mfptmi)₂(tfptz)
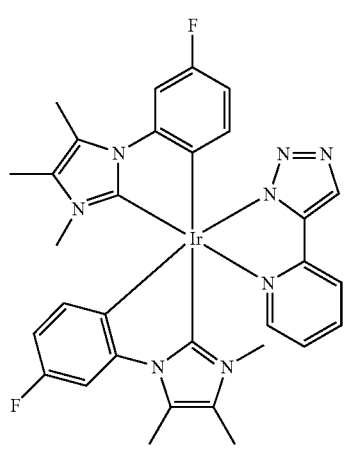
Ir(mfptmi)₂(pytz)
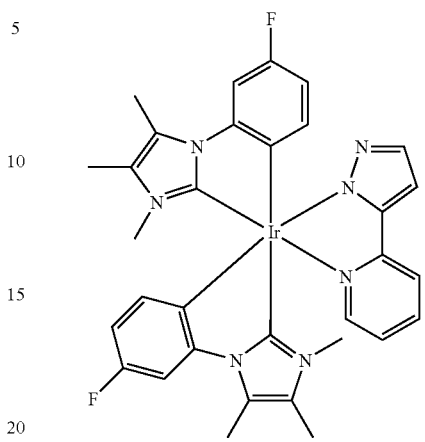
Ir(mtptmi)₂(pypz)
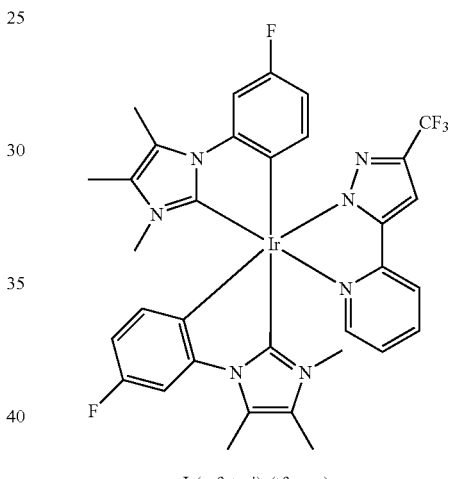
Ir(mfptmi)₂(tfpypz)
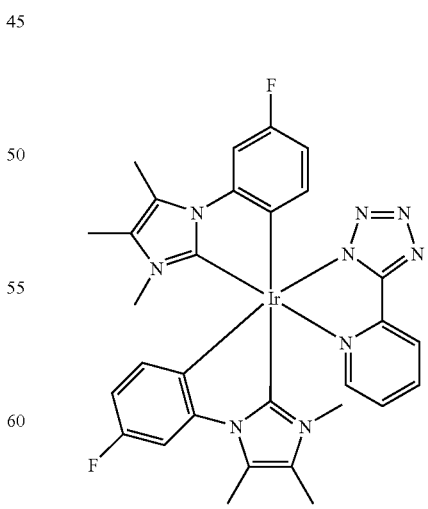
Ir(mfptmi)₂(pytrz)

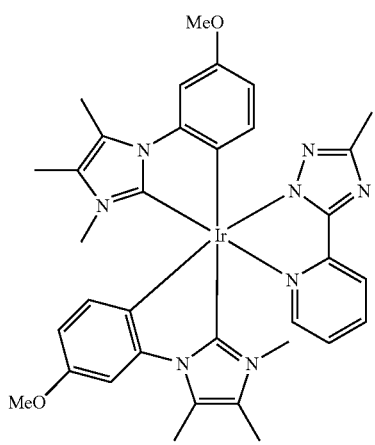
Ir(momptmi)₂(mptz)
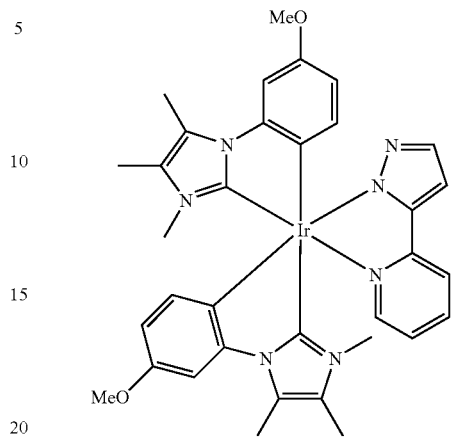
Ir(momptmi)₂(pypz)
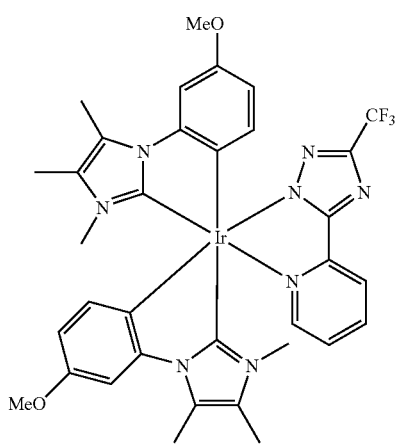
Ir(momptmi)₂(tfptz)
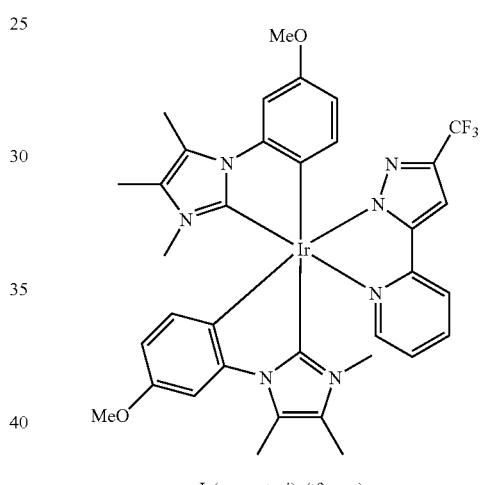
Ir(momptmi)₂(tfpypz)
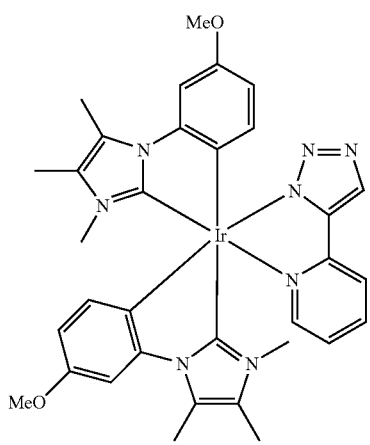
Ir(momptmi)₂(pytz)
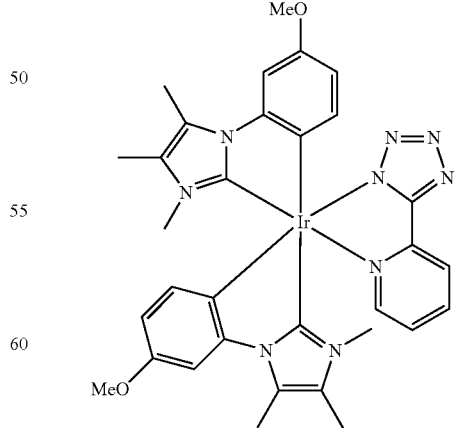
Ir(momptmi)₂(pytrz)

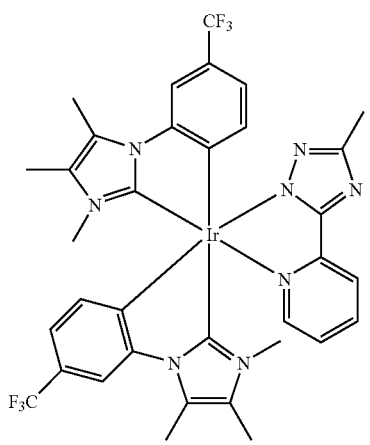
Ir(mtfptmi)₂(mptz)
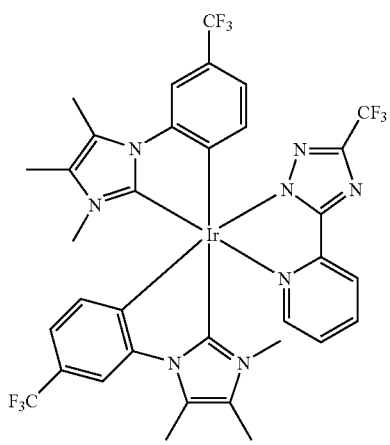
Ir(mtfptmi)₂(tfptz)
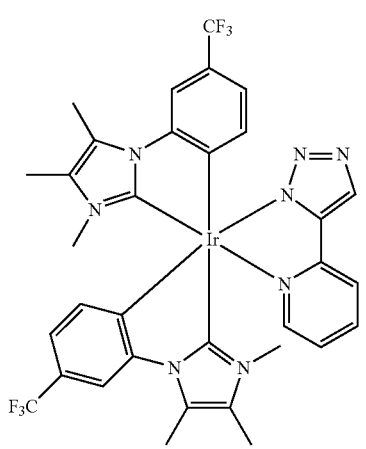
Ir(mtfptmi)₂(pytz)
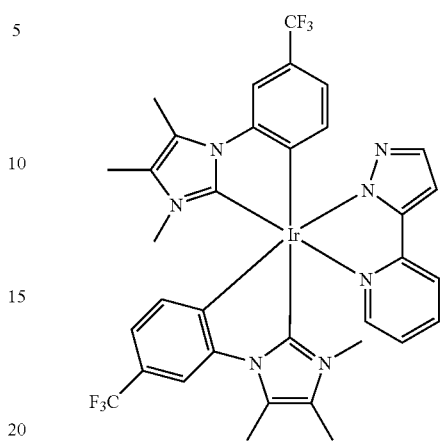
Ir(mfptmi)₂(pypz)
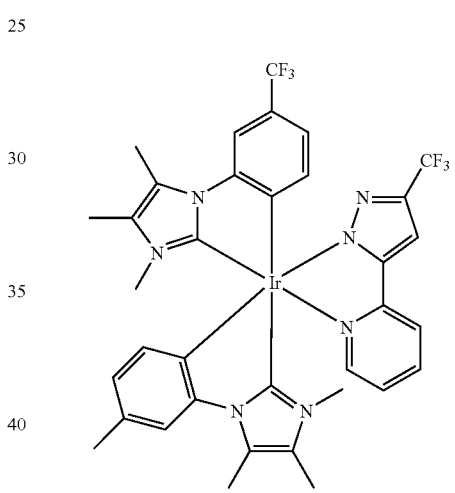
Ir(mfptmi)₂(tfpypz)
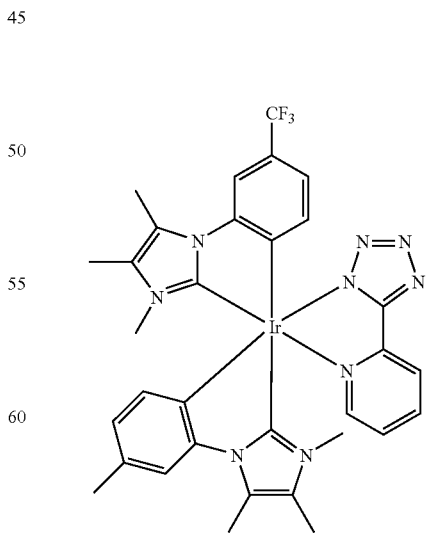
Ir(mtfptmi)₂(pytrz)

-continued
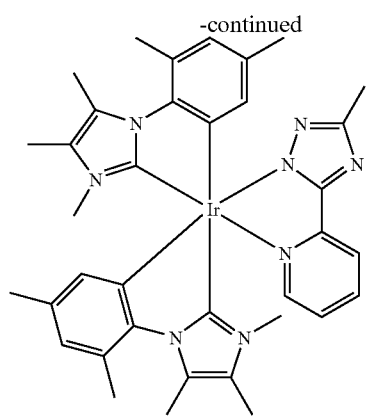
Ir(dmptmi)₂(mptz)
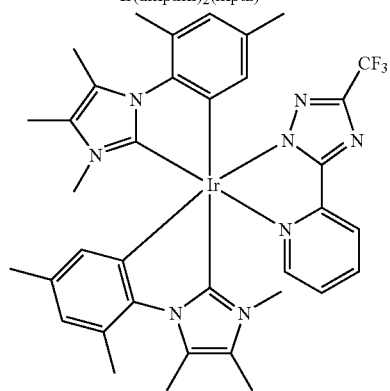
Ir(dmptmi)₂(tfptz)
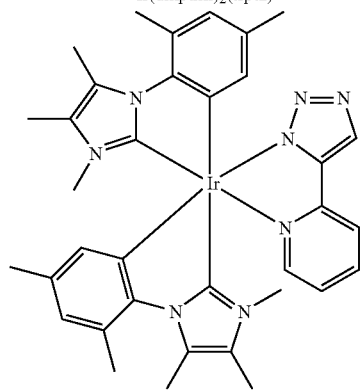
Ir(dmptmi)₂(pytz)
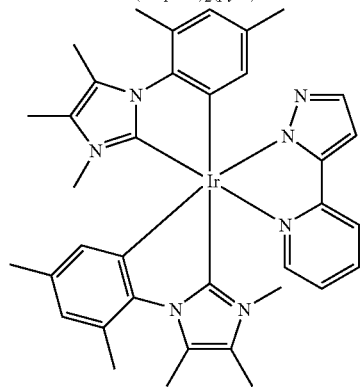
Ir(dmfptmi)₂(pypz)
-continued
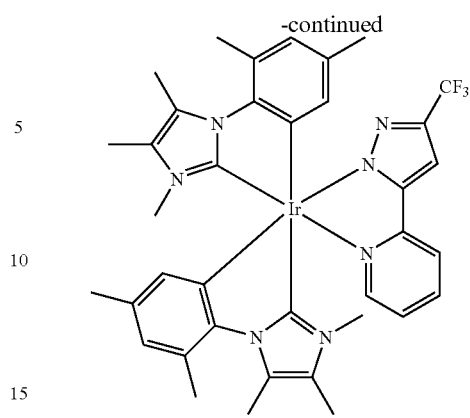
Ir(dmptmi)₂(tfpypz)
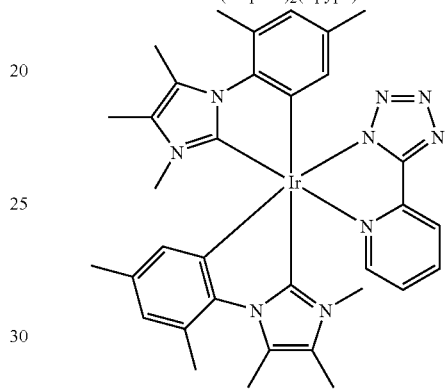
Ir(dmptmi)₂(pytrz)
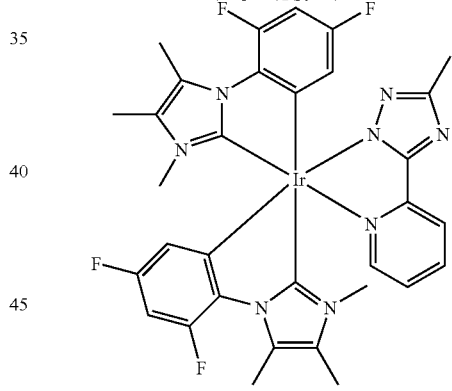
Ir(dfptmi)₂(mptz)
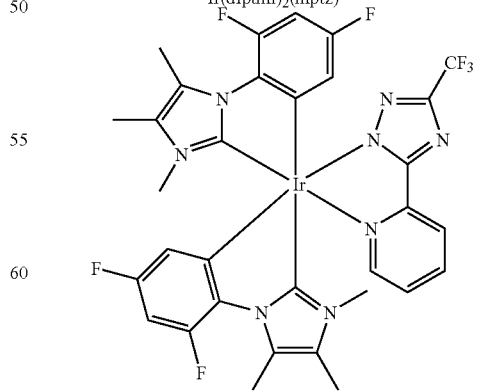
Ir(dfptmi)₂(tfptz)

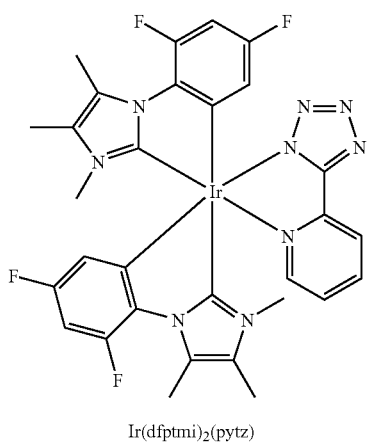
Ir(dfptmi)₂(pytz)
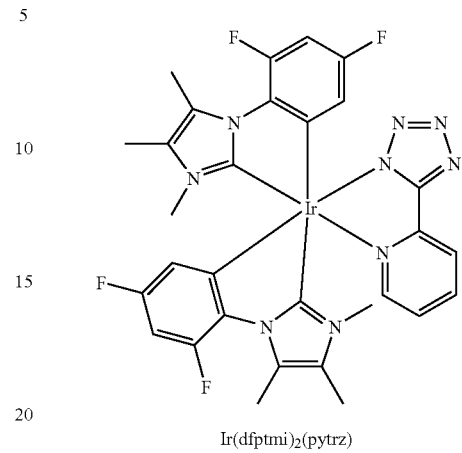
Ir(dfptmi)₂(pytrz)
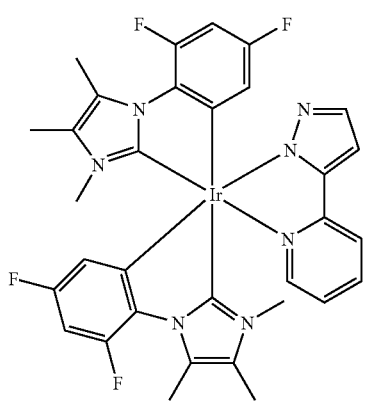
Ir(dfptmi)₂(pypz)
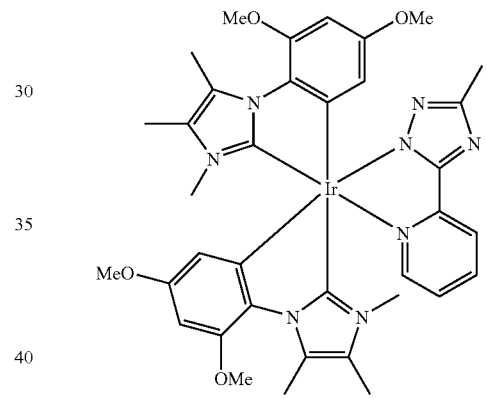
Ir(dmoptmi)₂(mptz)
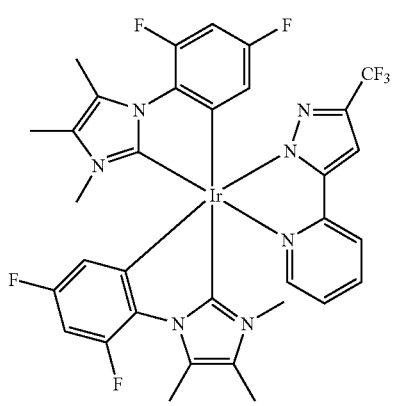
Ir(dfptmi)₂(tfpypz)
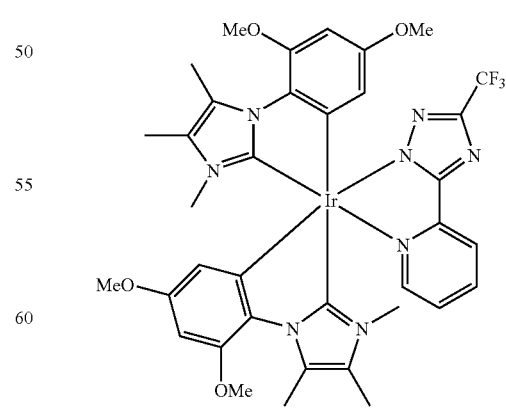
Ir(dmoptmi)₂(tfptz)

119
-continued
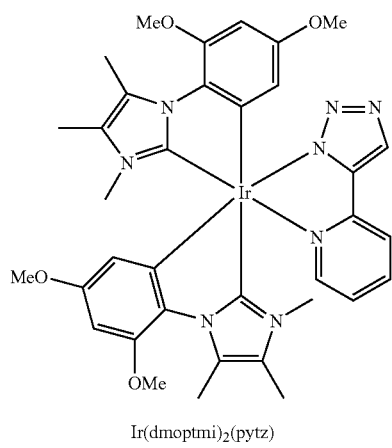
Ir(dmoptmi)₂(pytz)
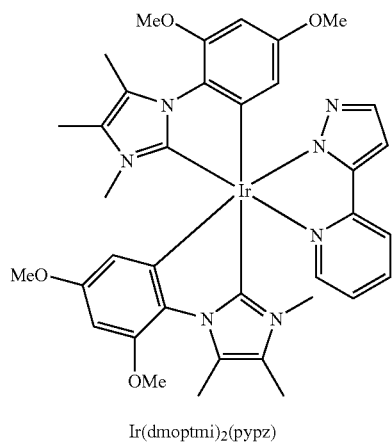
Ir(dmoptmi)₂(pypz)
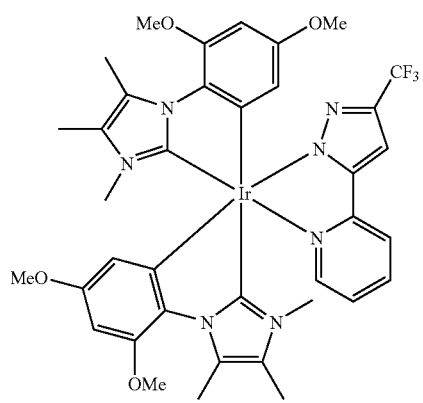
Ir(dmoptmi)₂(tfpypz)
120
-continued
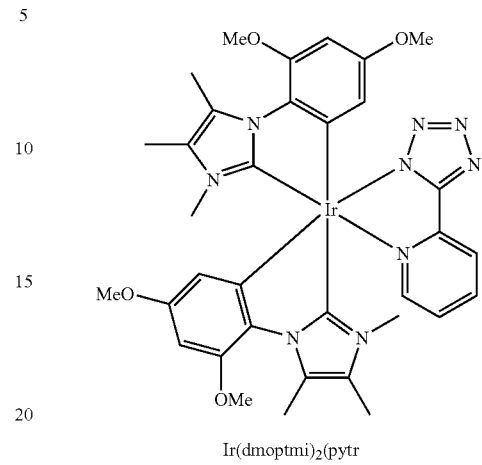
Ir(dmoptmi)₂(pytr)
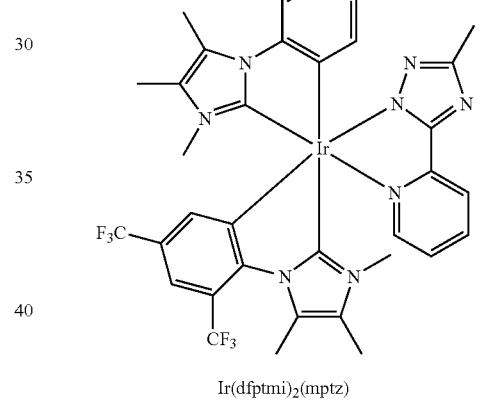
Ir(dfptmi)₂(mptz)
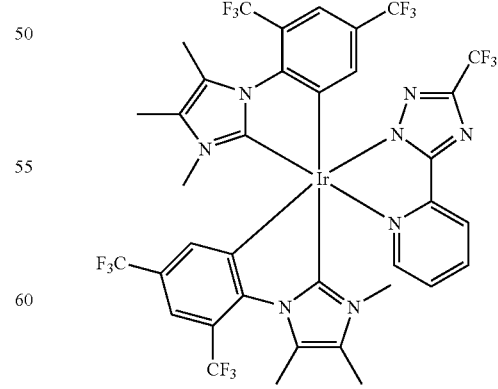
Ir(dfptmi)₂(tfptz)

121
-continued
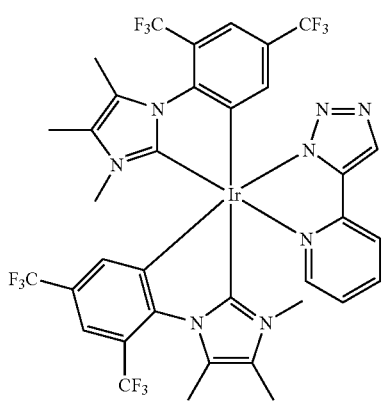
Ir(dfptmi)₂(pytz)
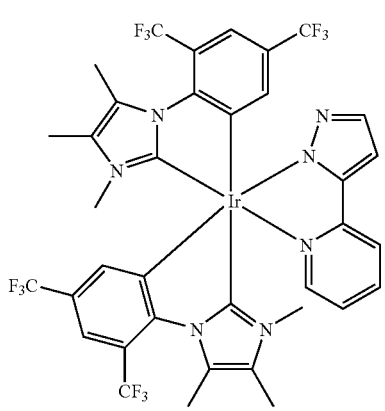
Ir(dfptmi)₂(pypz)
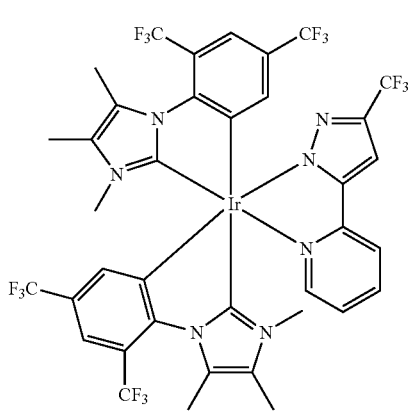
Ir(dfptmi)₂(tfpypz)
122
-continued
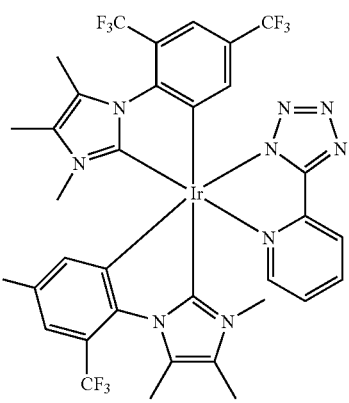
Ir(dfptmi)₂(pytrz)
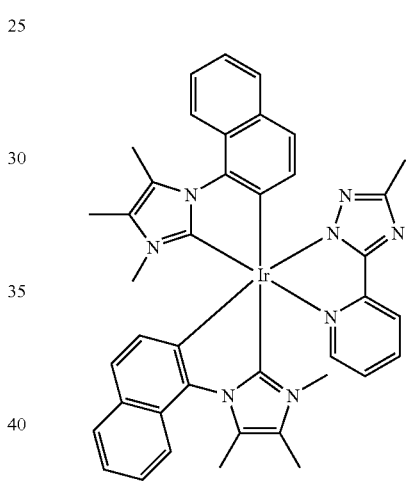
Ir(ntmi)₂(mptz)
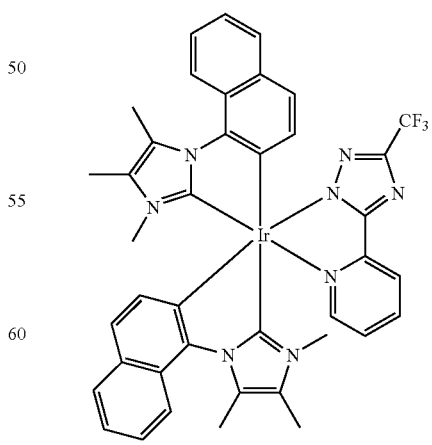
Ir(ntmi)₂(tfptz)

123
-continued
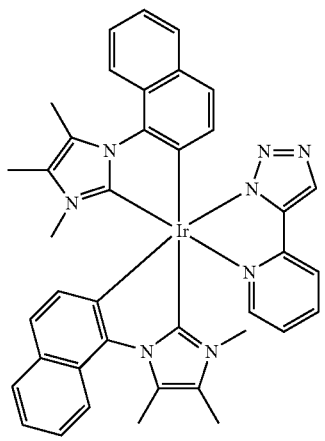
Ir(ntmi)$_2$(pytz)
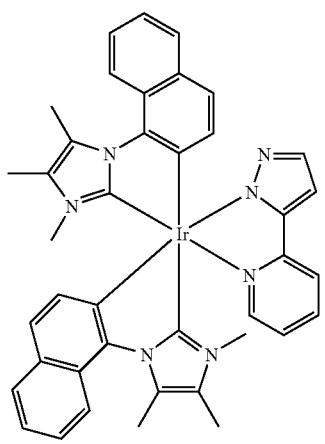
Ir(ntmi)$_2$(pypz)
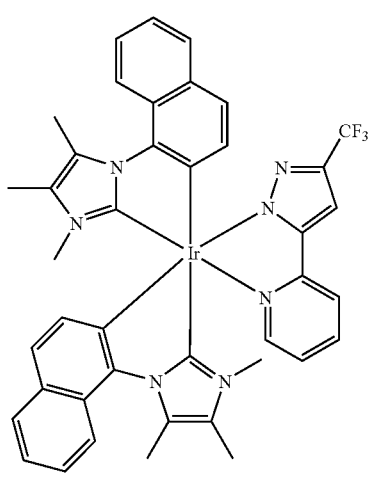
Ir(ntmi)$_2$(tfpypz)
124
-continued
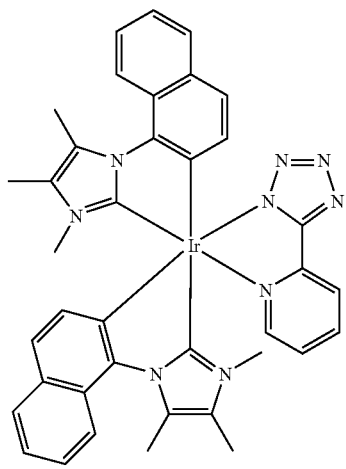
Ir(ntmi)$_2$(pytrz)
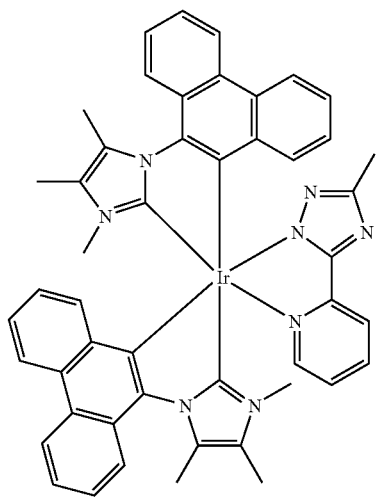
Ir(pntmi)$_2$(mptz)
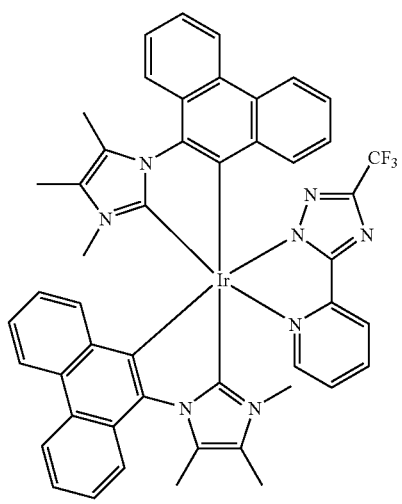
Ir(pntmi)$_2$(tfptz)

125
-continued
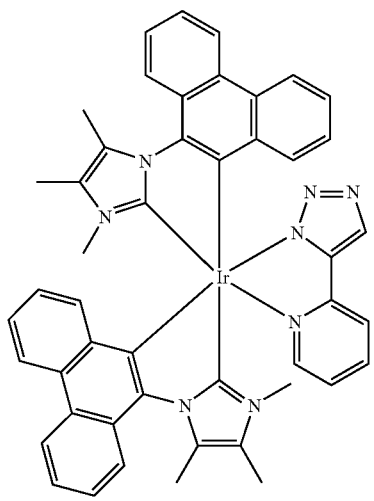
Ir(pntmi)₂(pytz)
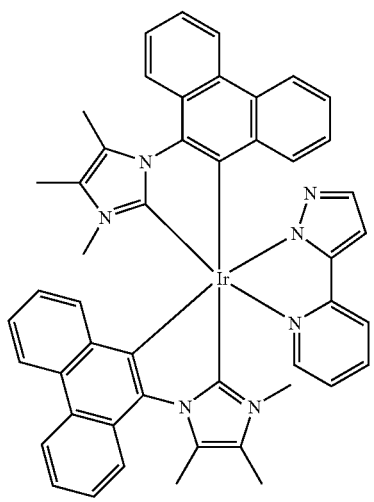
Ir(pntmi)₂(pypz)
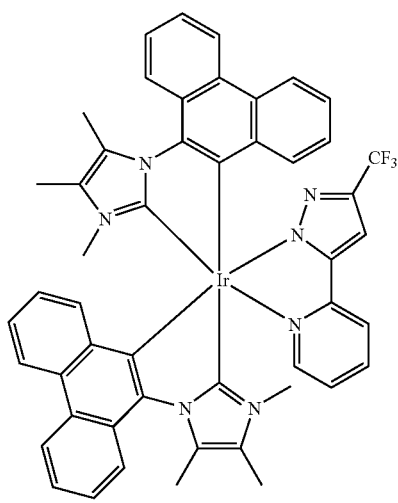
Ir(pntmi)₂(tfpypz)
126
-continued
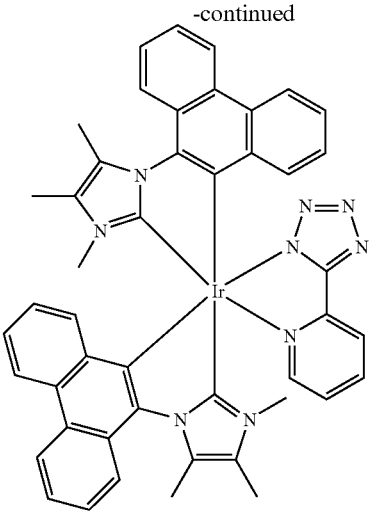
Ir(pntmi)₂(pytrz)
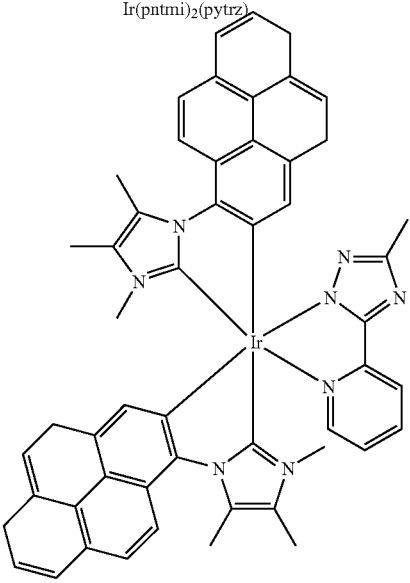
Ir(pytmi)₂(mptz)
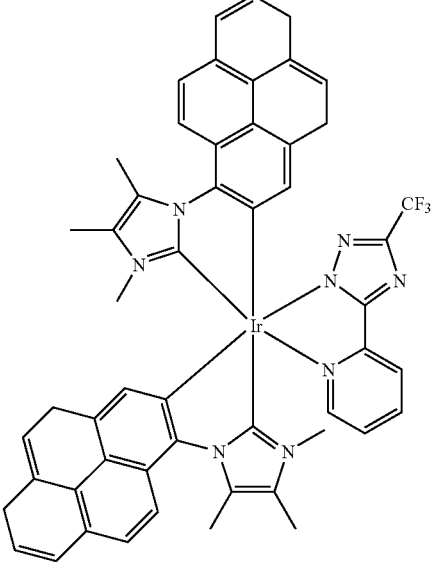
Ir(pytmi)₂(tfptz)

127
-continued
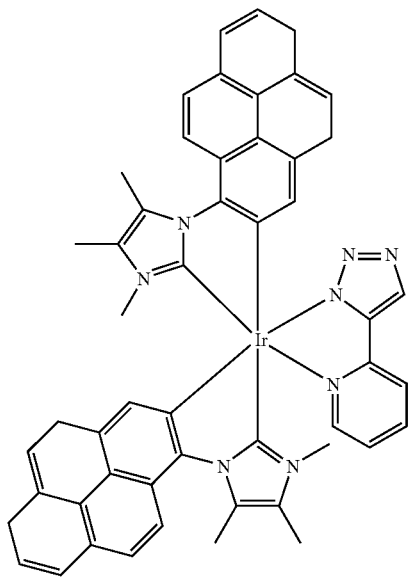
Ir(pytmi)$_2$(pytz)
128
-continued
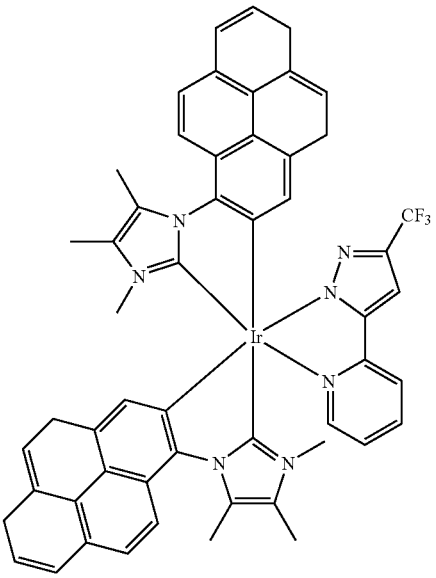
Ir(pytmi)$_2$(tfpypz)
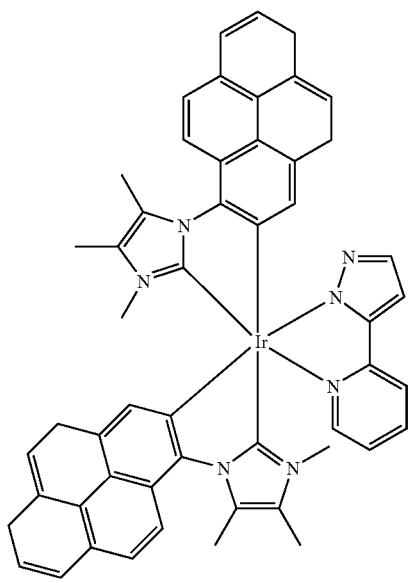
Ir(pytmi)$_2$(pypz)
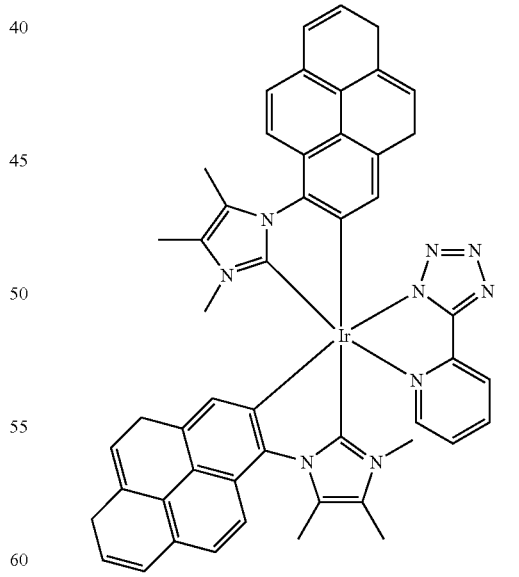
Ir(pytmi)$_2$(pytrz)

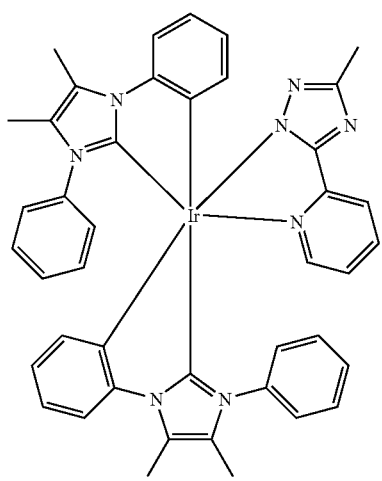
Ir(bpdmi)₂(mptz)
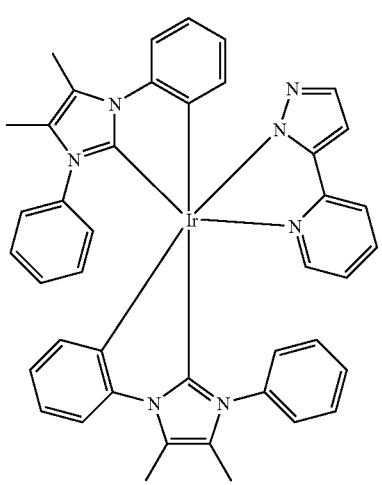
Ir(bpdmi)₂(pypz)
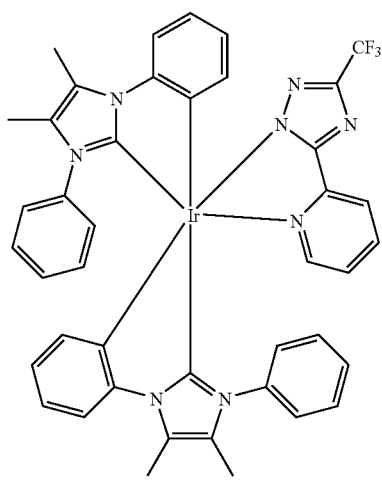
Ir(bpdmi)₂(tfptz)
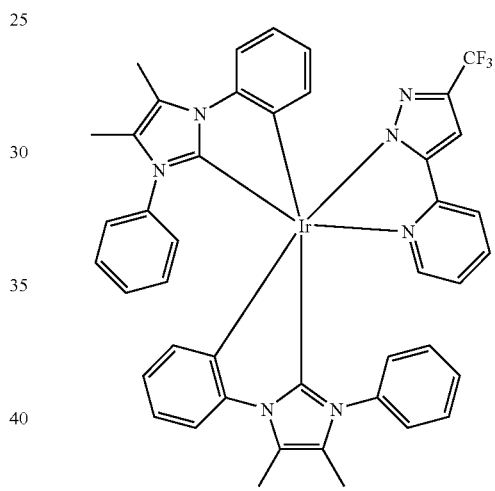
Ir(bpdmi)₂(tfpypz)
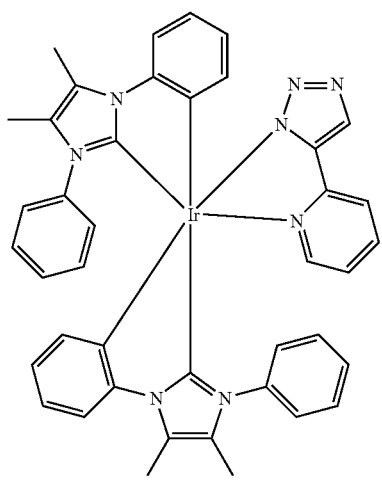
Ir(bpdmi)₂(pytz)
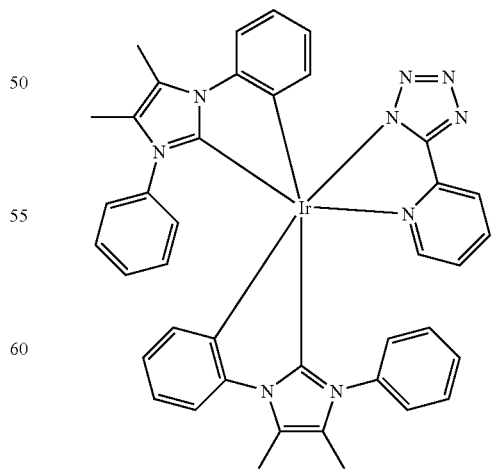
Ir(bpdmi)₂(pytrz)

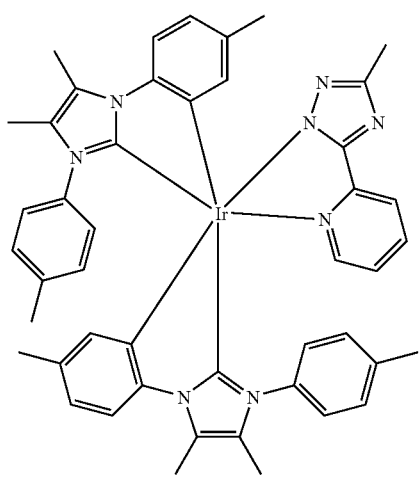
Ir(bmpdmi)₂(mptz)
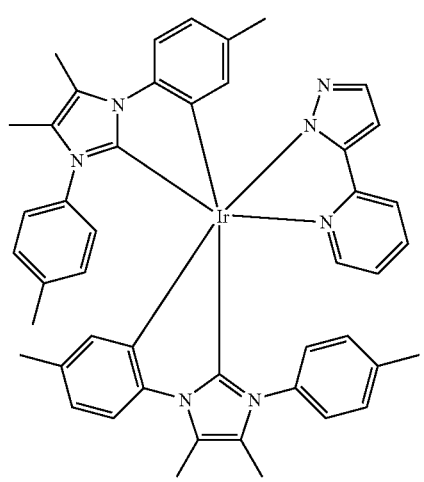
Ir(bmpdmi)₂(pypz)
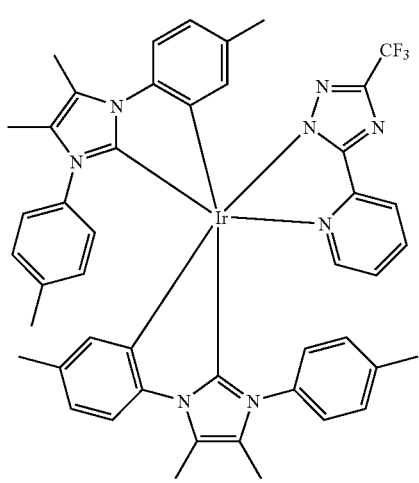
Ir(bmpdmi)₂(tfptz)
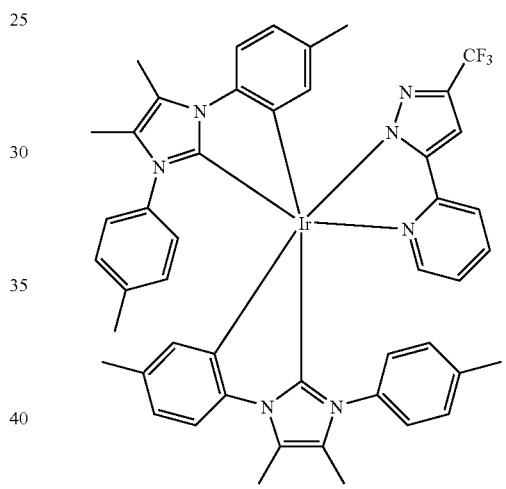
Ir(bmpdmi)₂(tfpypz)
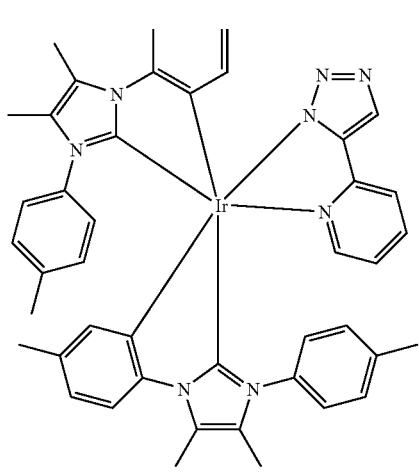
Ir(bmpdmi)₂(pytz)
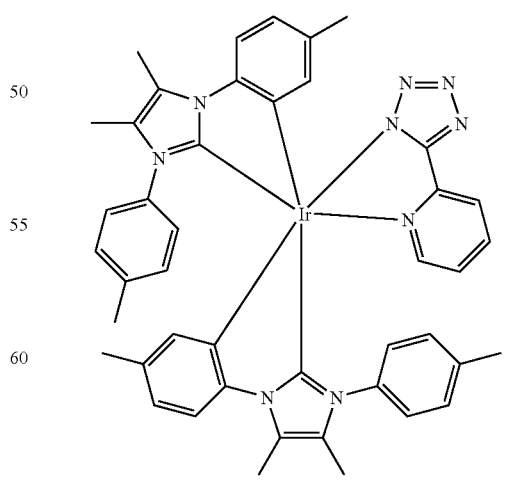
Ir(bmpdmi)₂(pytrz)

133
-continued
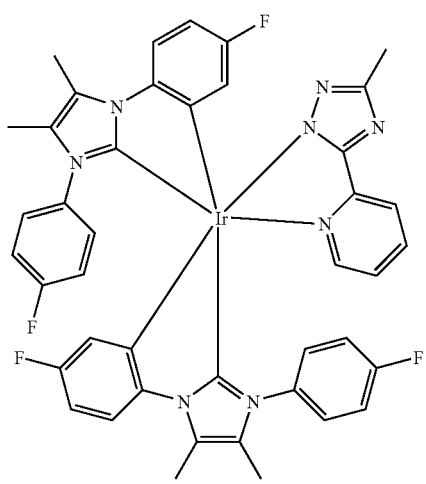
Ir(bfpdmi)₂(mptz)
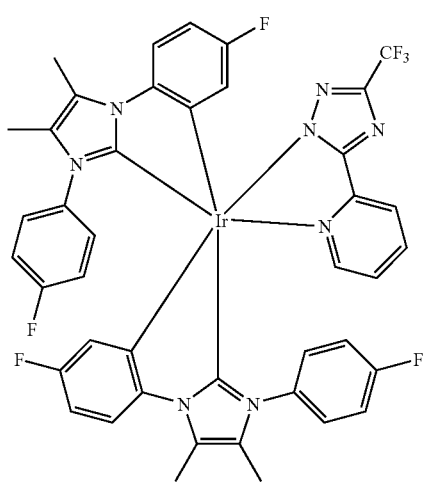
Ir(bfpdmi)₂(tfptz)
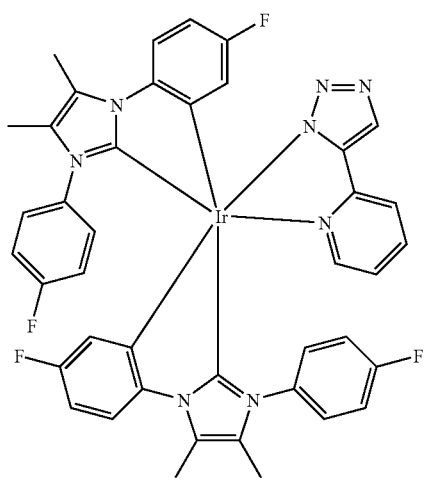
Ir(bfpdmi)₂(pytz)
134
-continued
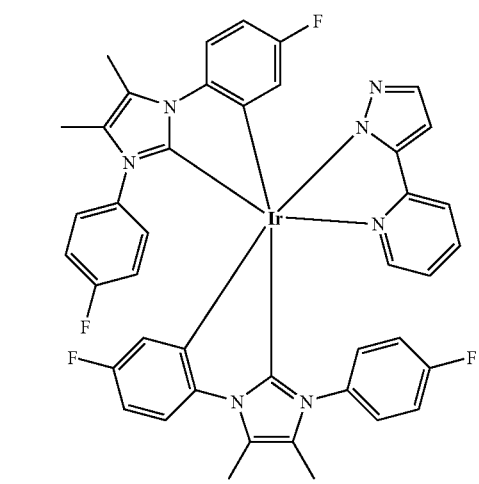
Ir(bfpdmi)₂(pypz)
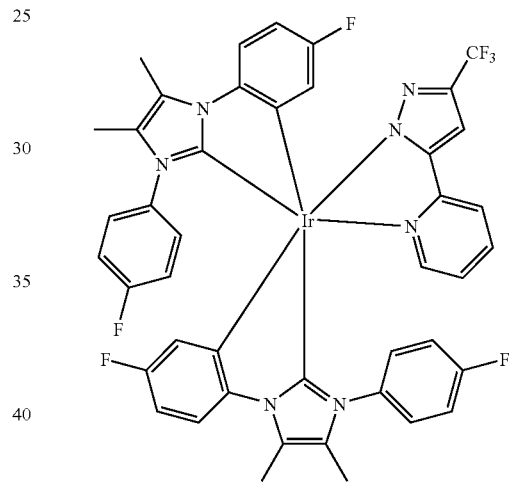
Ir(bfpdmi)₂(tfpypz)
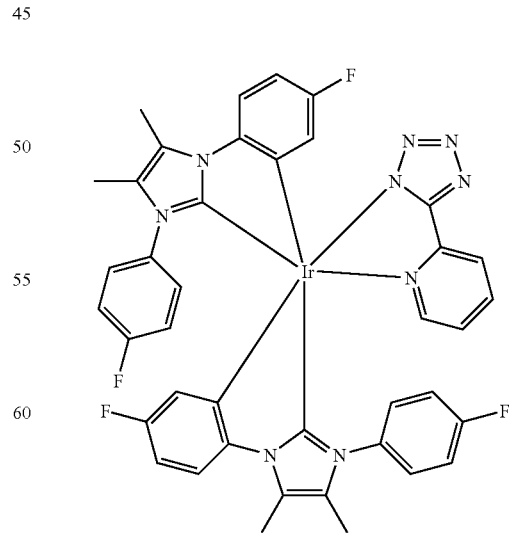
Ir(bfpdmi)₂(pytrz)

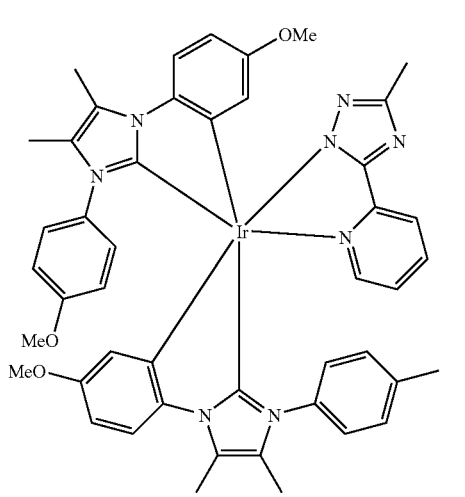
Ir(bmopdmi)₂(mptz)
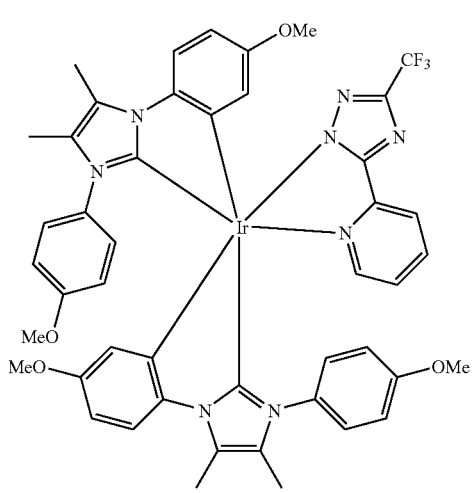
Ir(bmopdmi)₂(tfptz)
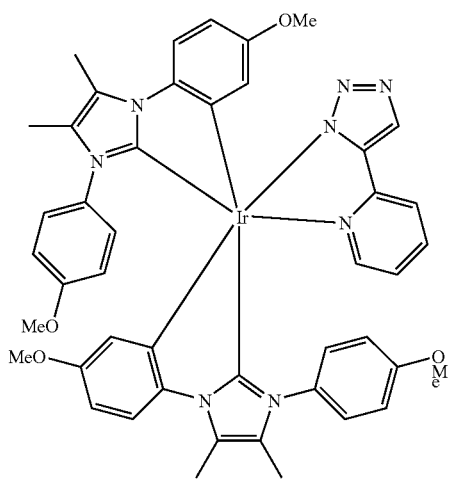
Ir(bmopdmi)₂(pytz)
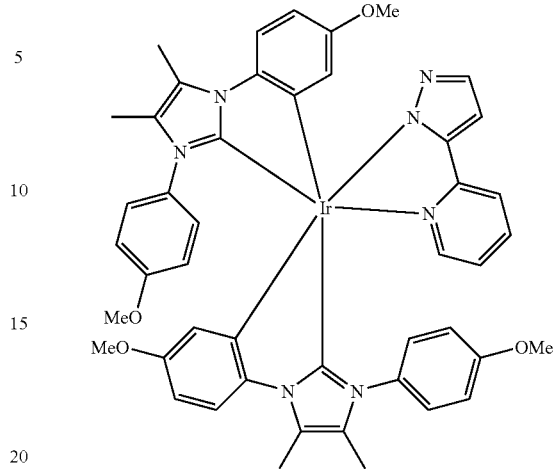
Ir(bmopdmi)₂(pypz)
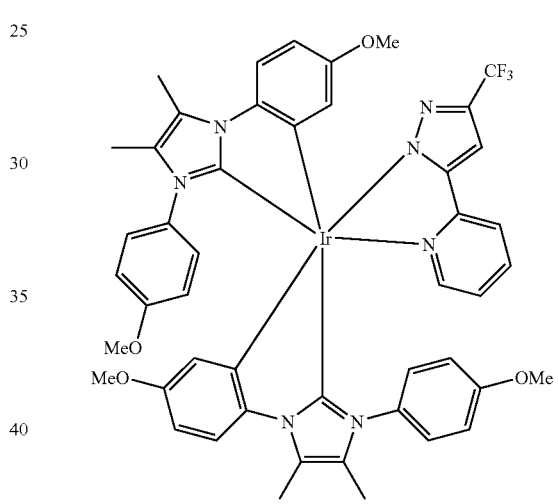
Ir(bmopdmi)₂(tfpypz)
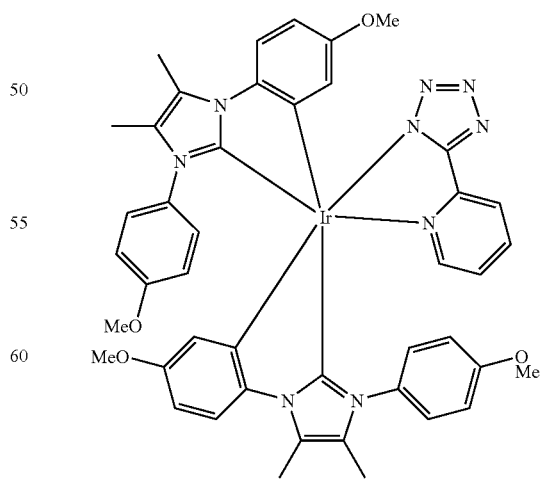
Ir(bmopdmi)₂(pytrz)

-continued
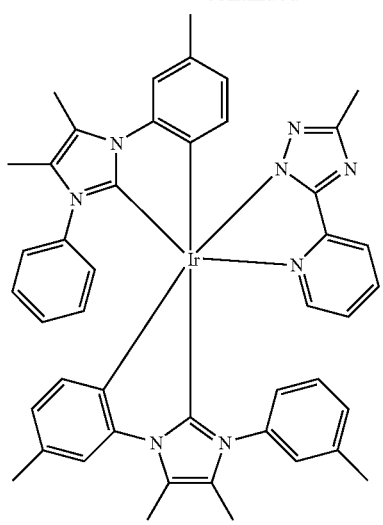
Ir(bmmpdmi)₂(mptz)
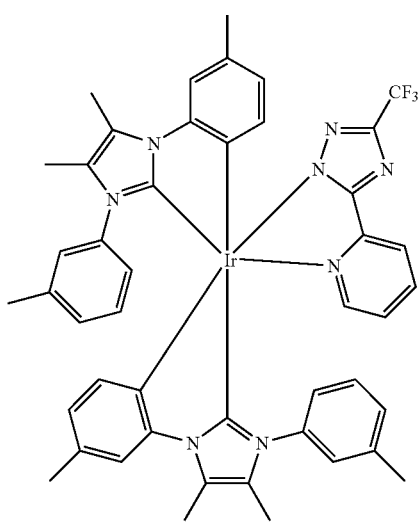
Ir(bmmpdmi)₂(tfptz)
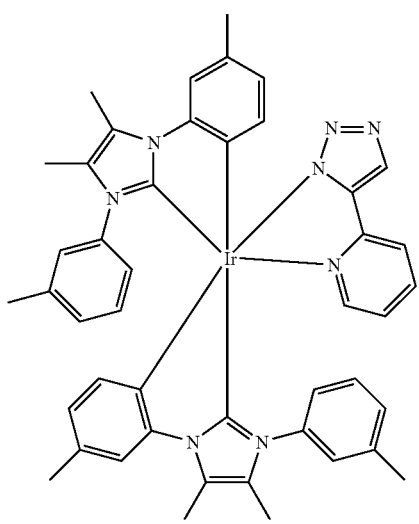
Ir(bmmpdmi)₂(pytz)
-continued
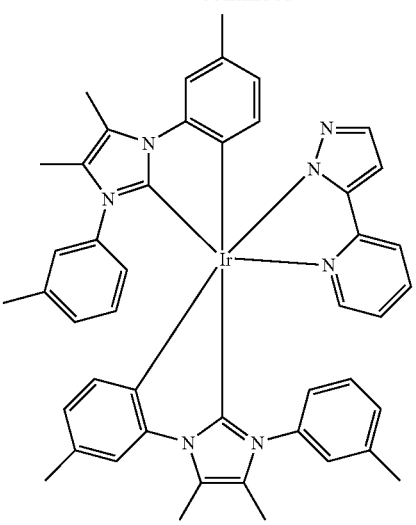
Ir(bmmpdmi)₂(pypz)
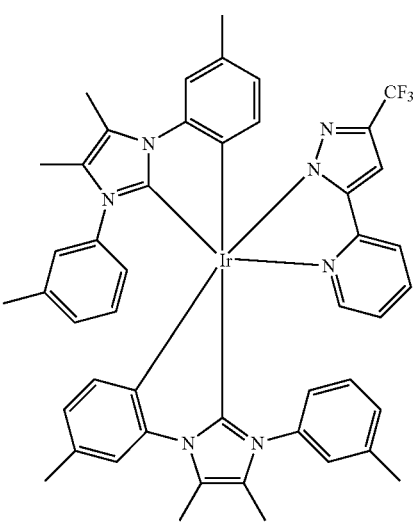
Ir(bmmpdmi)₂(tfpypz)
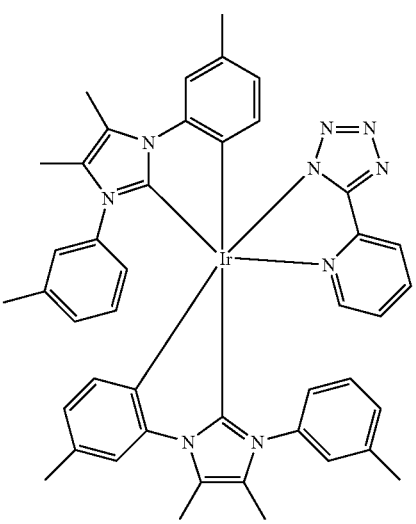
Ir(bmmpdmi)₂(pytrz)

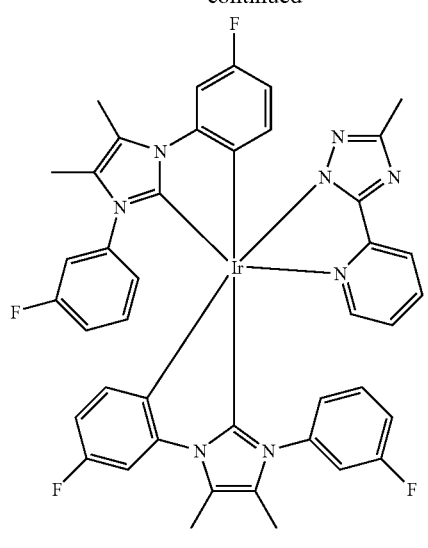
Ir(bmfpdmi)₂(mptz)
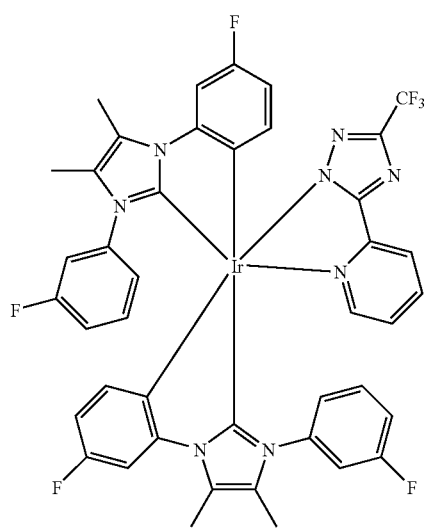
Ir(bmfpdmi)₂(tfptz)
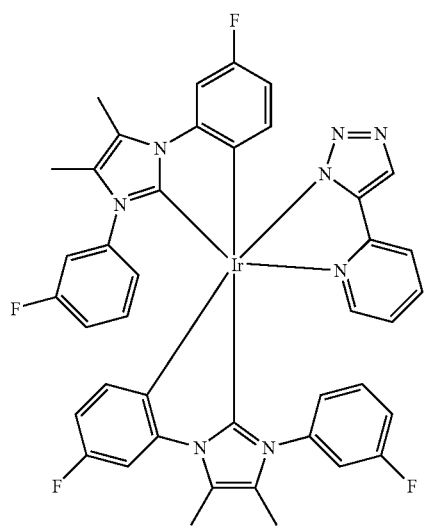
Ir(bmfpdmi)₂(pytz)
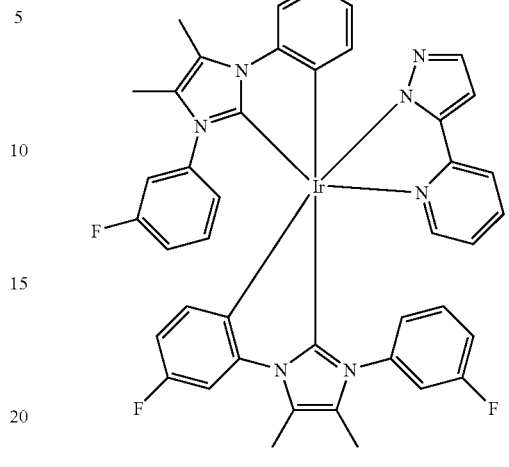
Ir(bmfpdmi)₂(pypz)
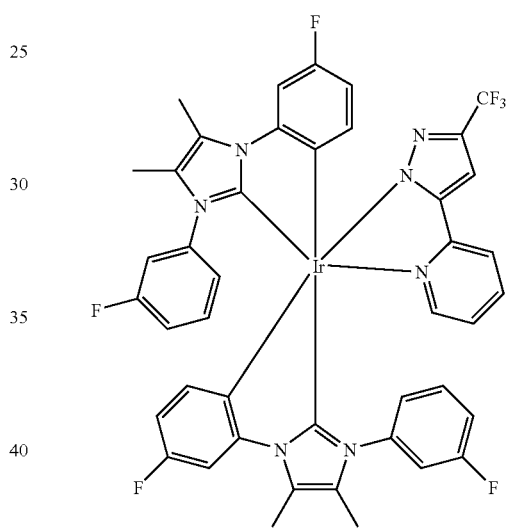
Ir(bmfpdmi)₂(tfpypz)
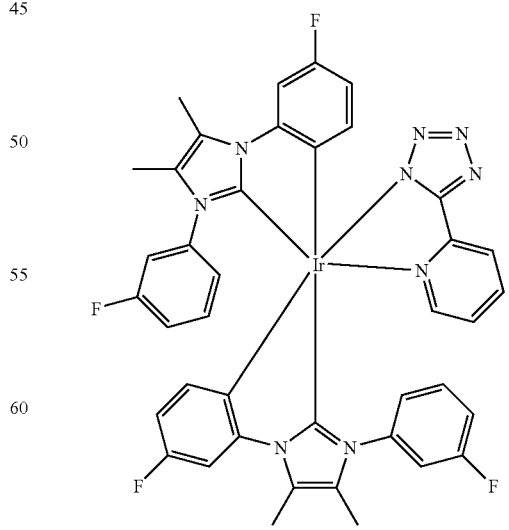
Ir(bmfpdmi)₂(pytrz)

141
-continued
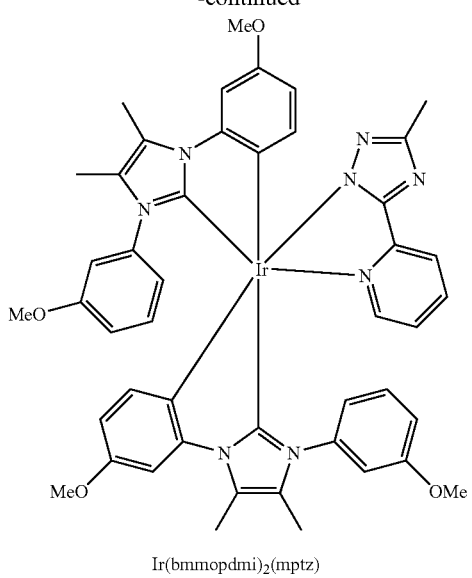
Ir(bmmopdmi)₂(mptz)
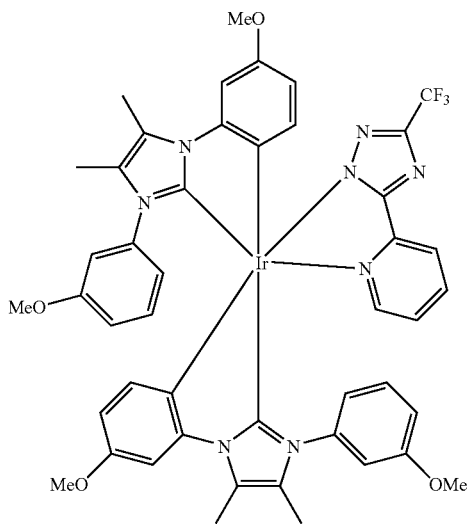
Ir(bmmopdmi)₂(tfptz)
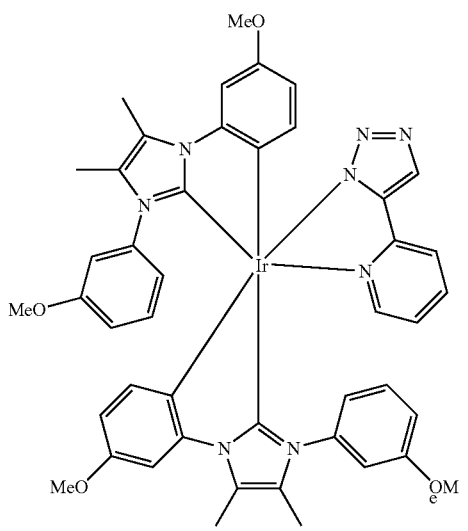
Ir(bmmopdmi)₂(pytz)
142
-continued
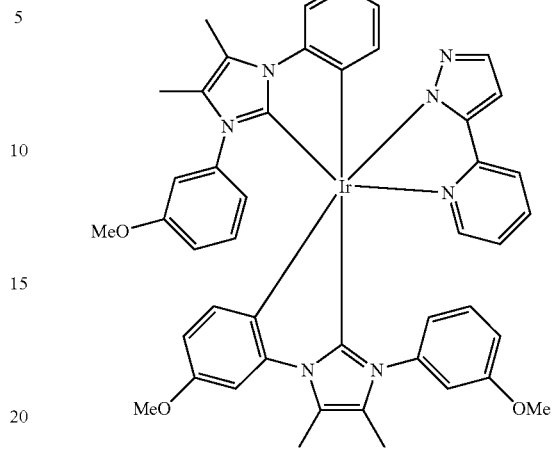
Ir(bmmopdmi)₂(pypz)
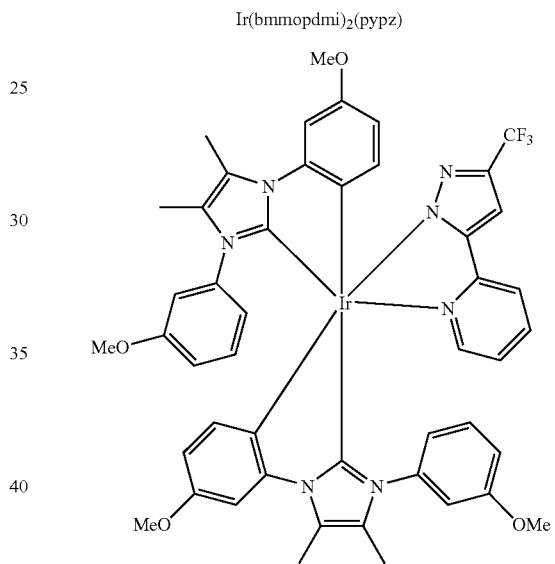
Ir(bmmopdmi)₂(tfpypz)
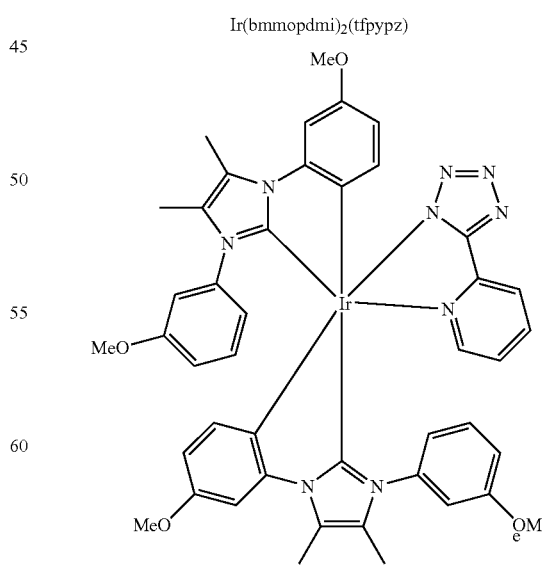
Ir(bmmopdmi)₂(pytrz)

-continued
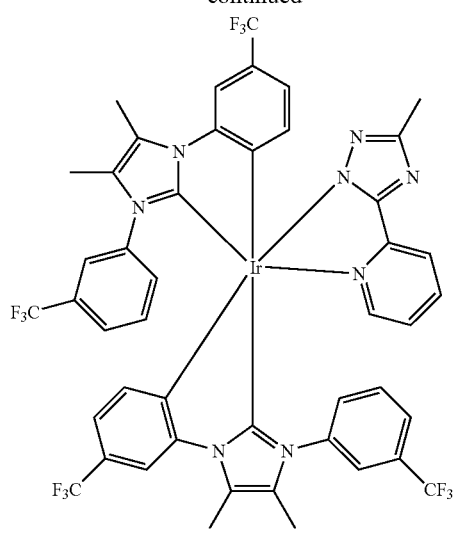
Ir(bmtfpdmi)₂(mptz)
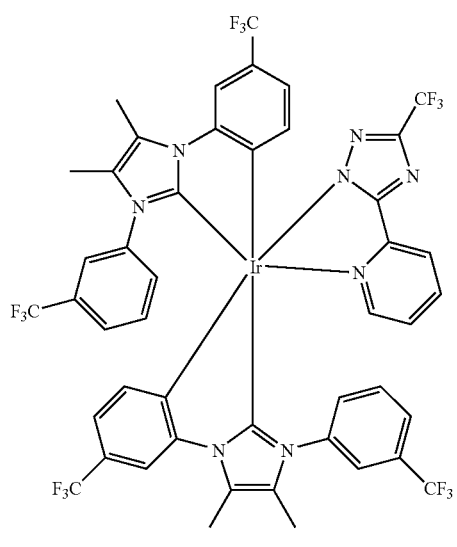
Ir(bmtfpdmi)₂(tfptz)
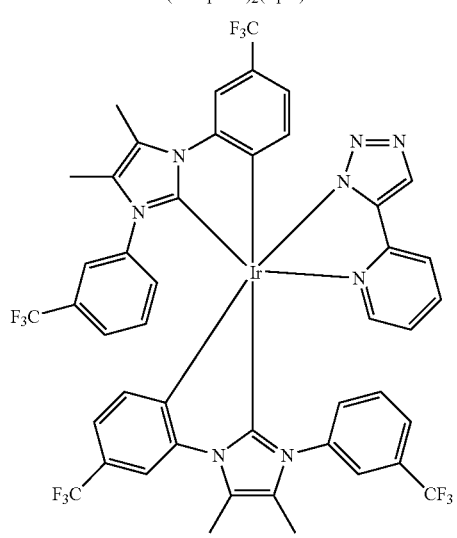
Ir(bmtfpdmi)₂(pytz)
-continued
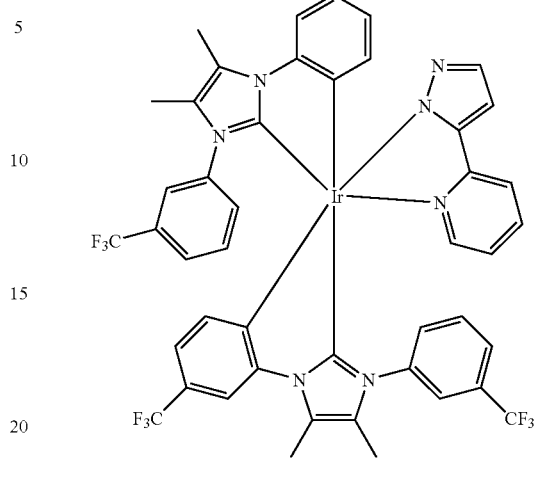
Ir(bmtfpdmi)₂(pypz)
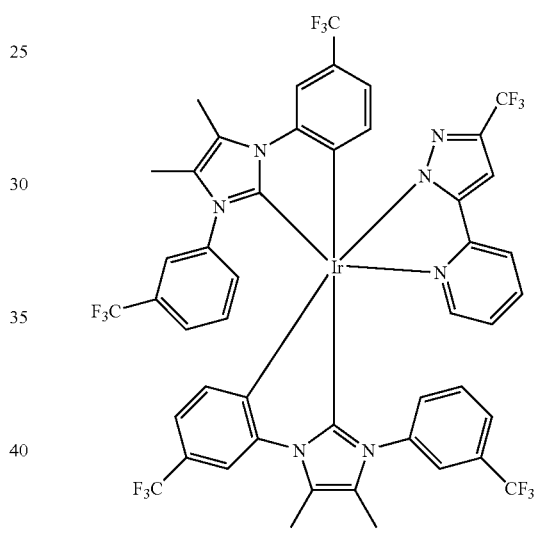
Ir(bmtfpdmi)₂(tfpypz)
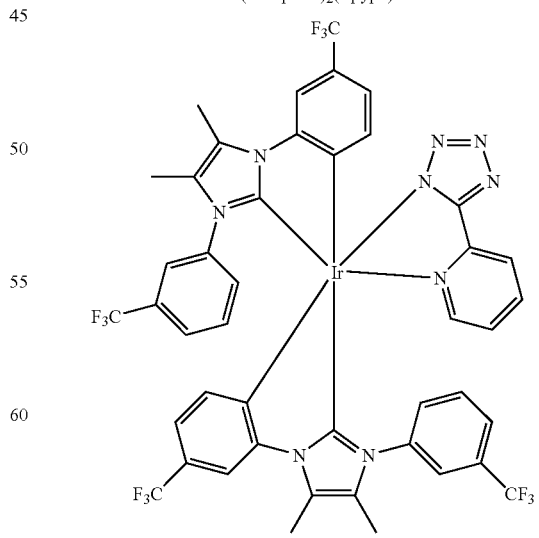
Ir(bmtfpdmi)₂(pytrz)

-continued
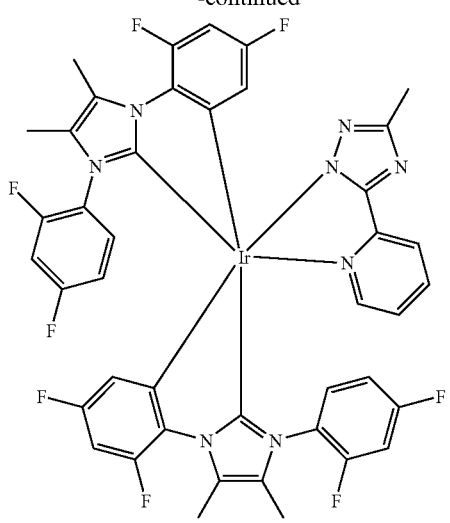
Ir(bdfpdmi)₂(mptz)
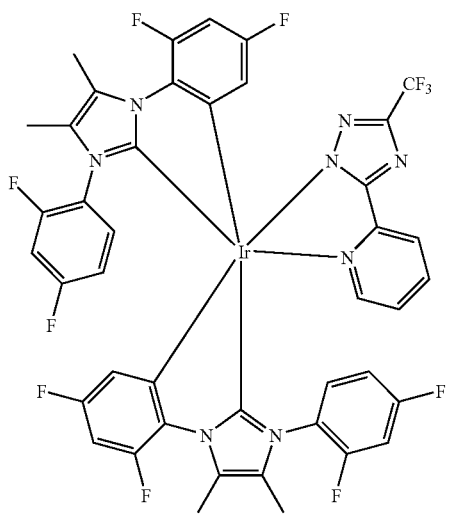
Ir(bdfpdmi)₂(tfptz)
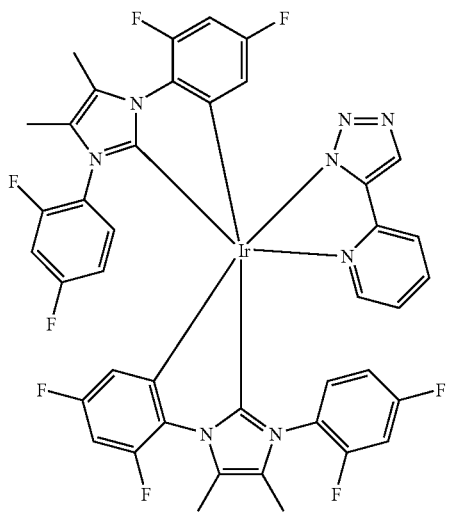
Ir(bdfpdmi)₂(pytz)
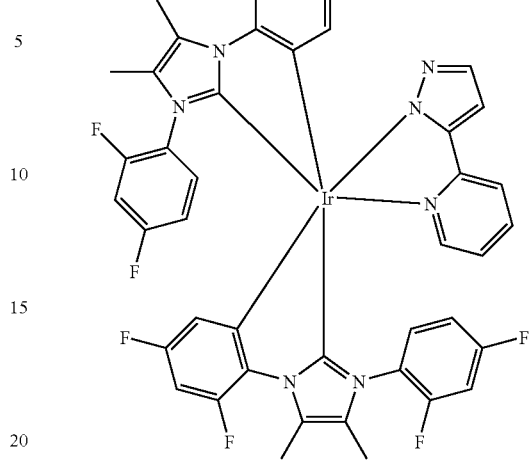
Ir(bdfpdmi)₂(pypz)
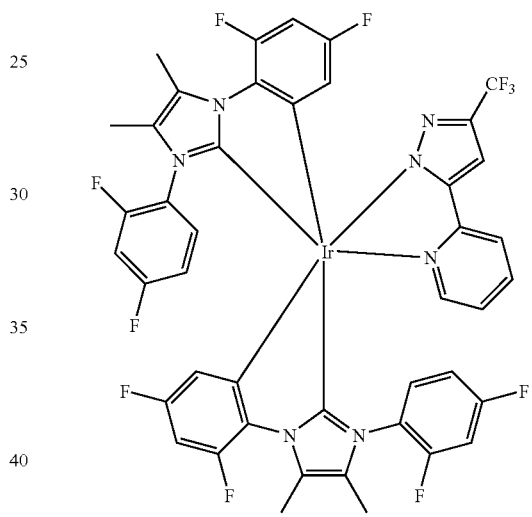
Ir(bdfpdmi)₂(tfpypz)
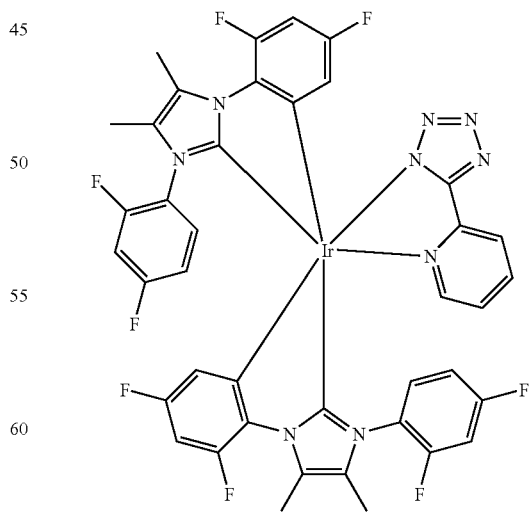
Ir(bdfpdmi)₂(pytrz)

147
-continued
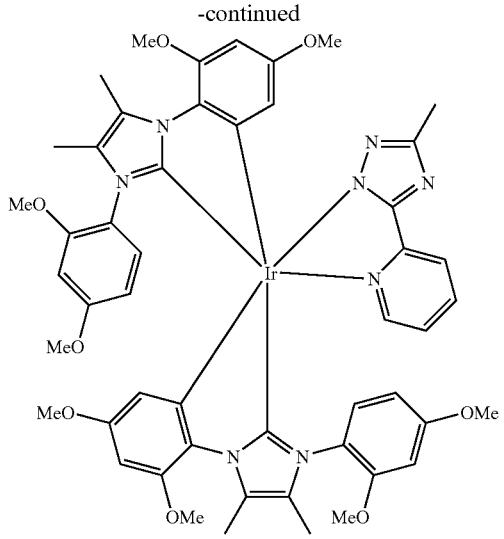
Ir(bdmopdmi)₂(mptz)
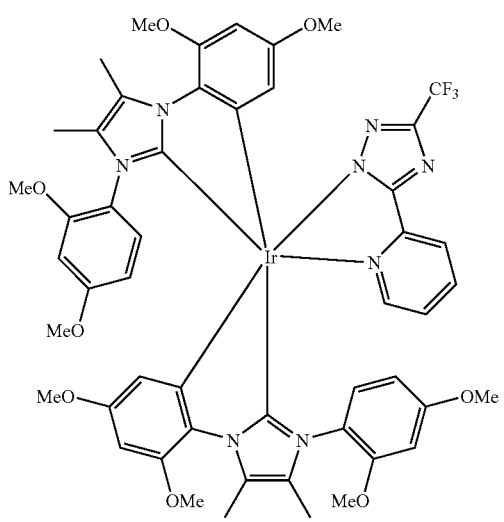
Ir(bdmopdmi)₂(tfptz)
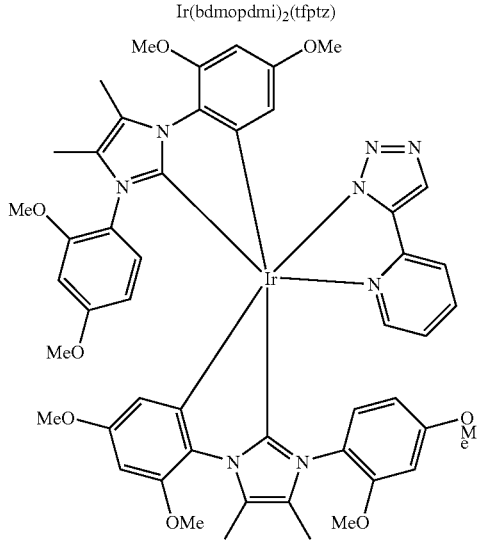
Ir(bdmopdmi)₂(pytz)
148
-continued
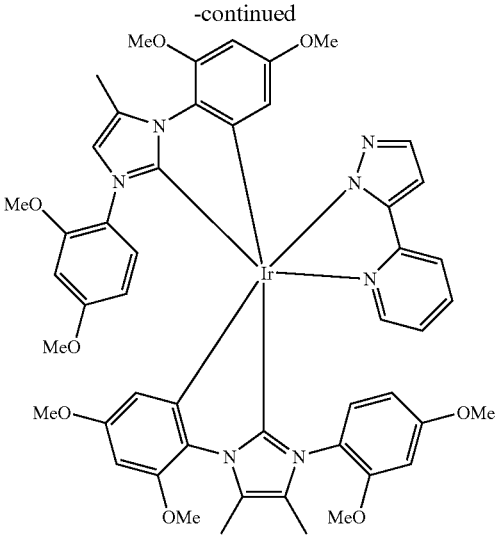
Ir(bdmopdmi)₂(pypz)
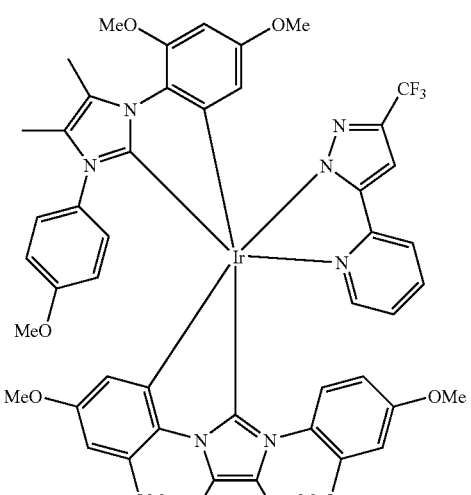
Ir(bdmopdmi)₂(tfpypz)
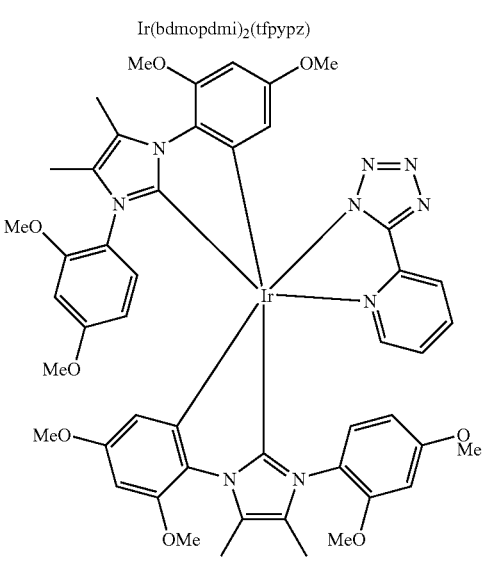
Ir(bdmopdmi)₂(pytrz)

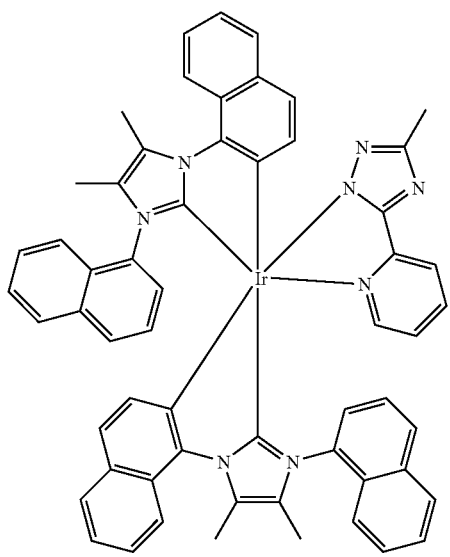
Ir(bndmi)₂(mptz)
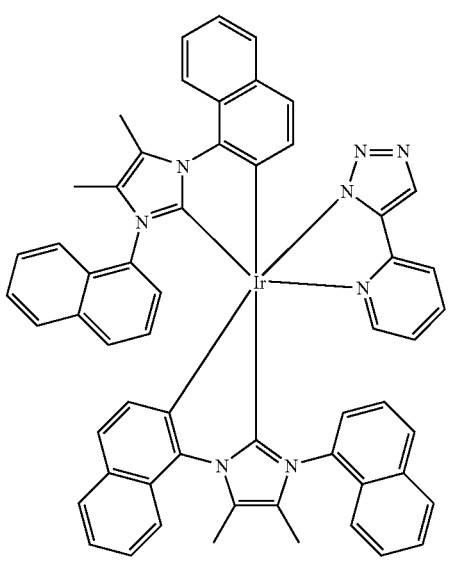
Ir(bndmi)₂(pytz)
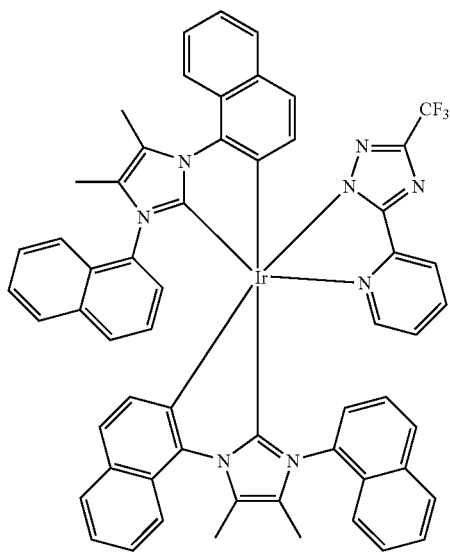
Ir(bndmi)₂(tfptz)
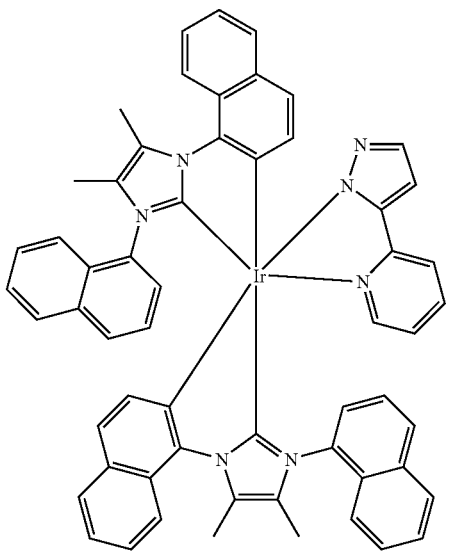
Ir(bndmi)₂(pypz)

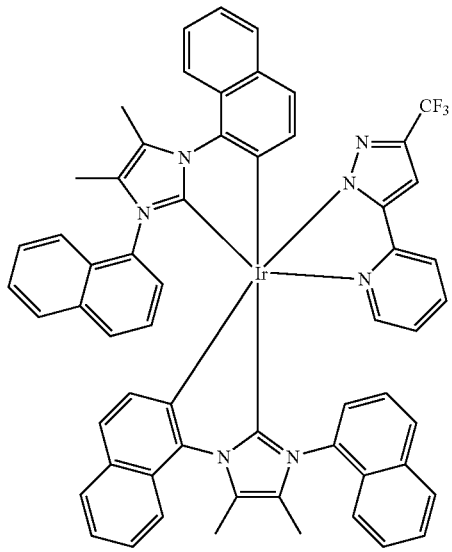
Ir(bndmi)₂(tfpypz)
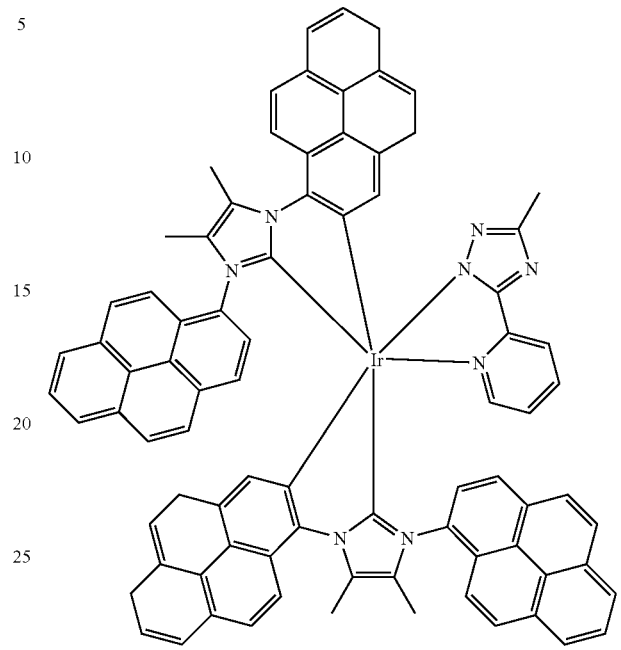
Ir(bpydmi)₂(mptz)
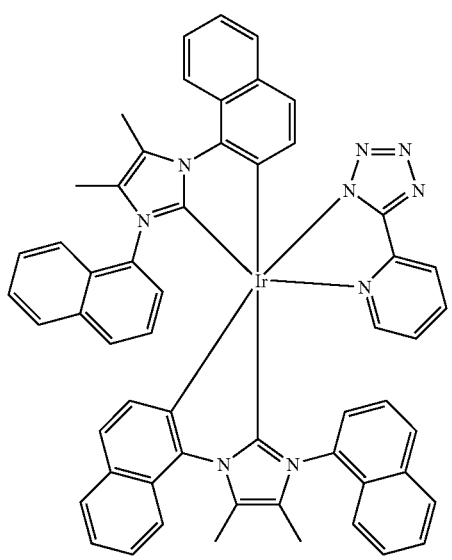
Ir(bndmi)₂(pytrz)
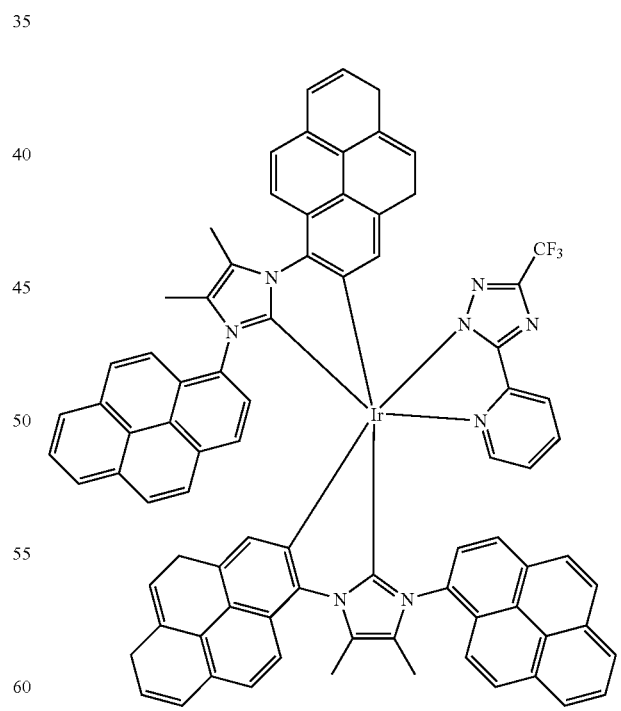
Ir(bpydmi)₂(tfptz)

153
-continued
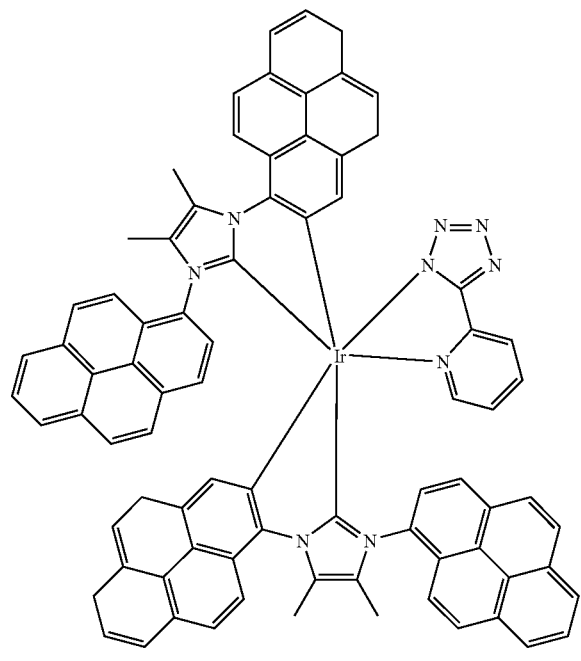
Ir(bpydmi)$_2$(pytrz)
154
-continued
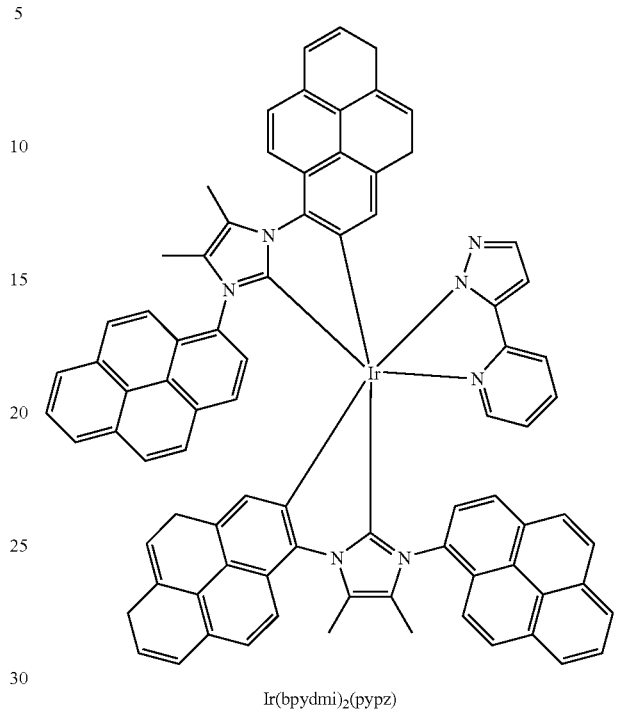
Ir(bpydmi)$_2$(pypz)
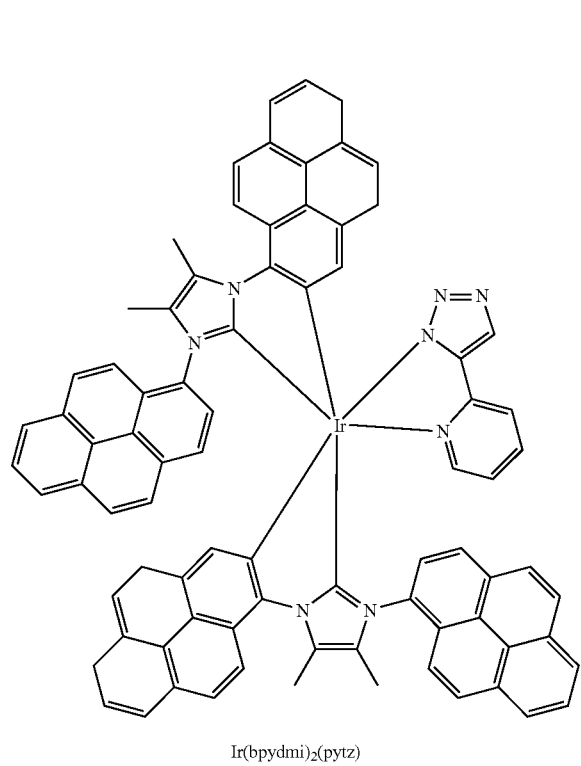
Ir(bpydmi)$_2$(pytz)
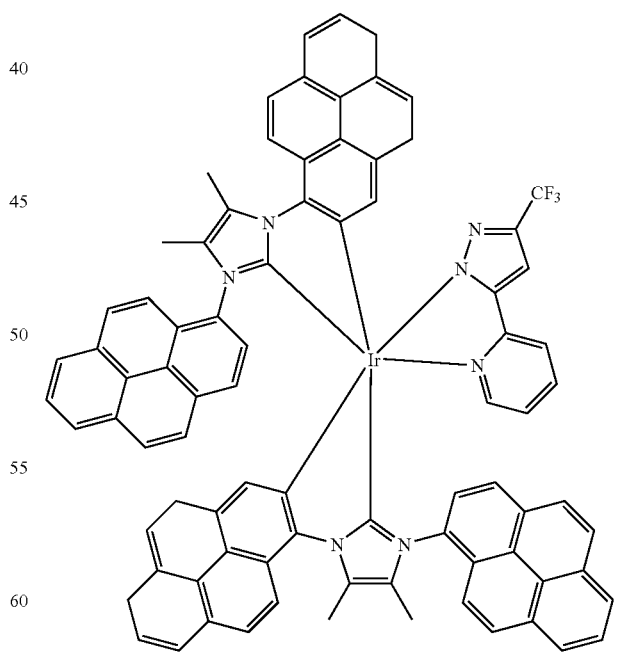
Ir(bpydmi)$_2$(tfpypz)

-continued
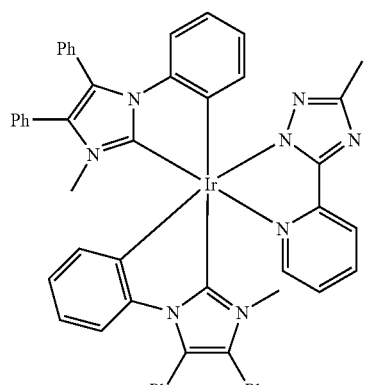
Ir(pmdpi)₂(mptz)
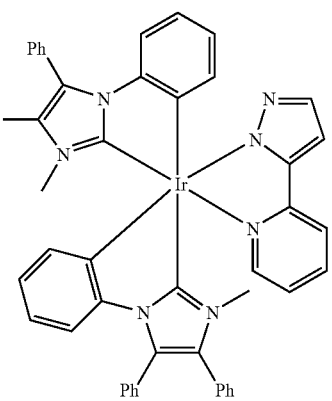
Ir(pmdpi)₂(pypz)
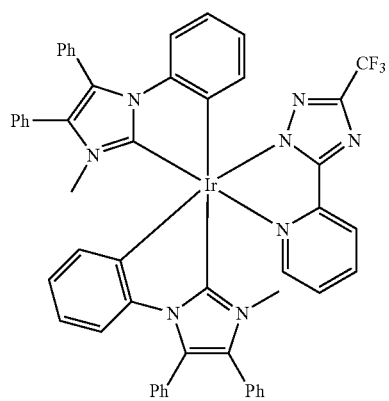
Ir(pmdpi)₂(tfptz)
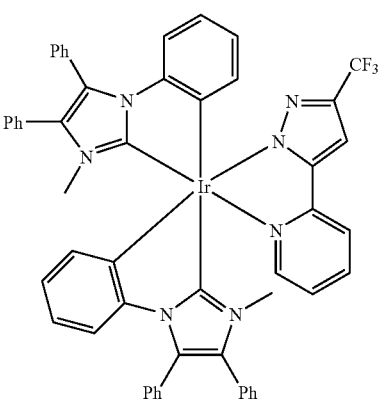
Ir(pmdpi)₂(tfpypz)
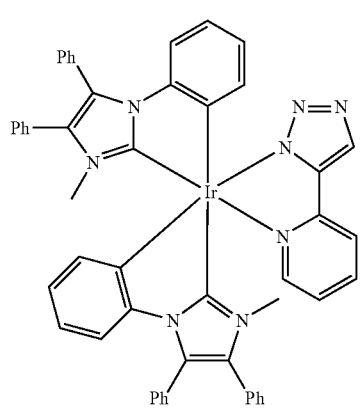
Ir(pmdpi)₂(pytz)
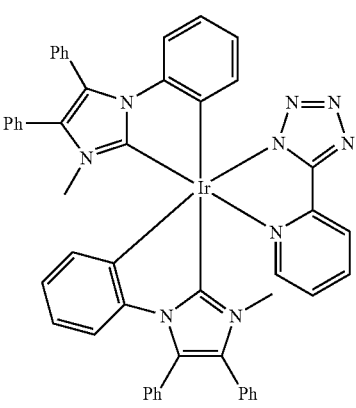
Ir(pmdpi)₂(pytrz)

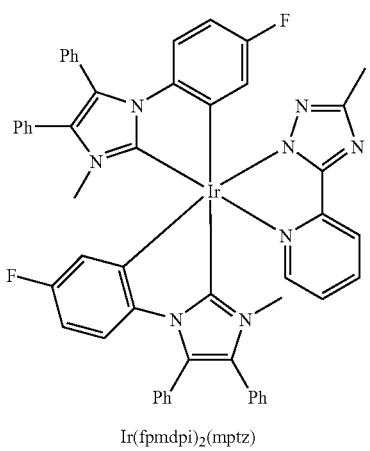
Ir(fpmdpi)₂(mptz)
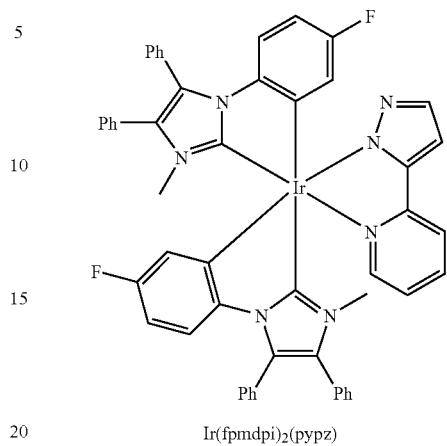
Ir(fpmdpi)₂(pypz)
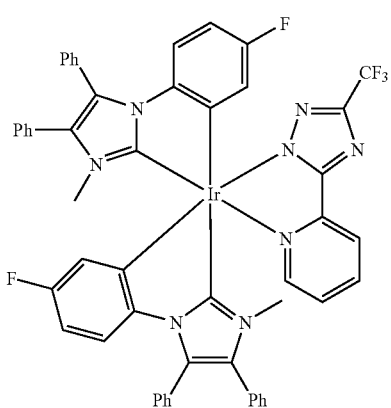
Ir(fpmdpi)₂(tfptz)
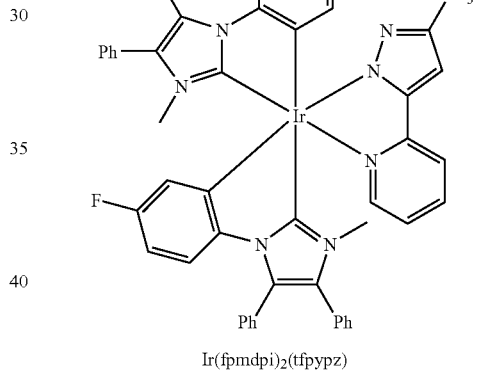
Ir(fpmdpi)₂(tfpypz)
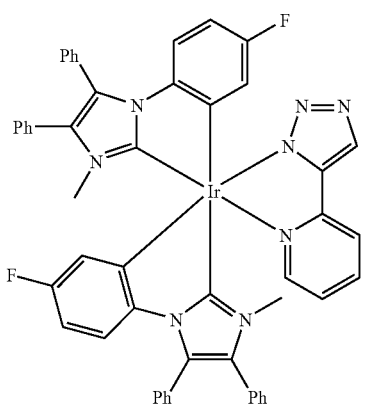
Ir(fpmdpi)₂(pytz)
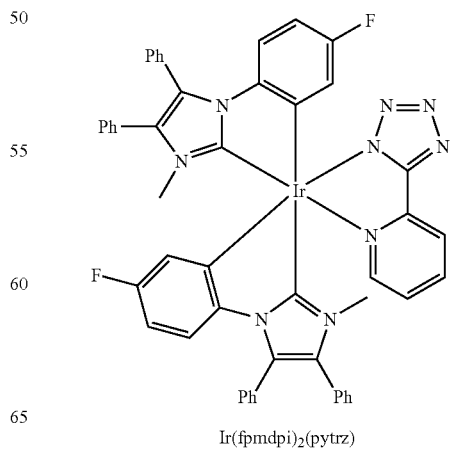
Ir(fpmdpi)₂(pytrz)

-continued
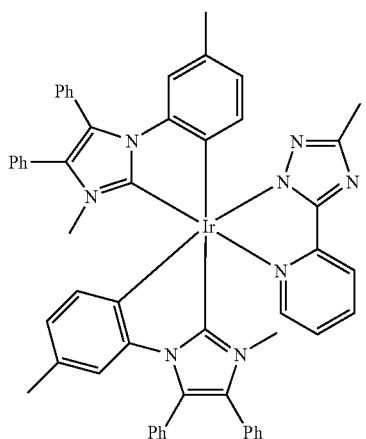
Ir(mmpmdpi)₂(mptz)
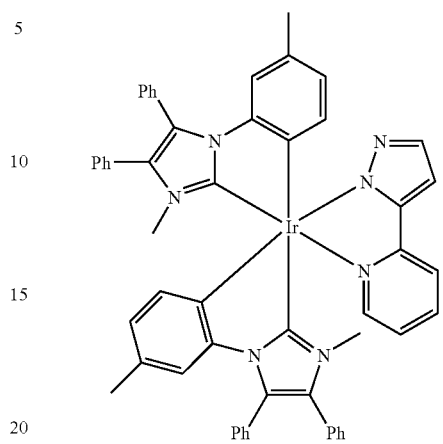
Ir(mmpmdpi)₂(pypz)
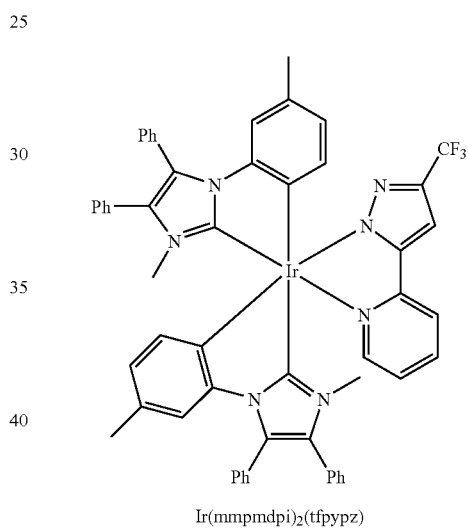
Ir(mmpmdpi)₂(tfpypz)
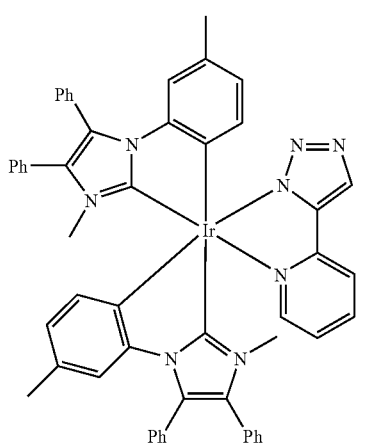
Ir(mmpmdpi)₂(pytz)
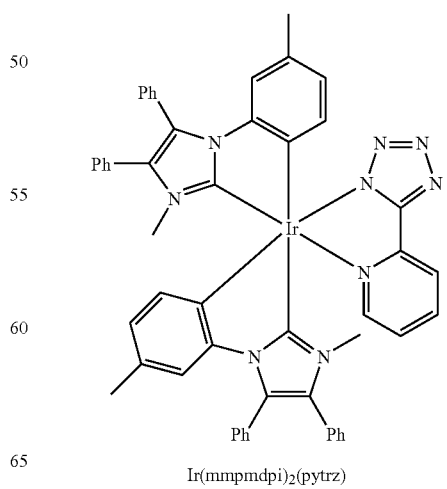
Ir(mmpmdpi)₂(pytrz)

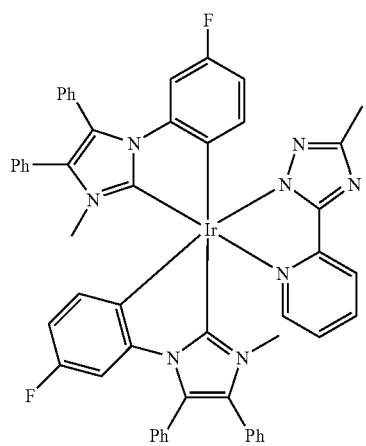
Ir(mfpmdpi)₂(mptz)
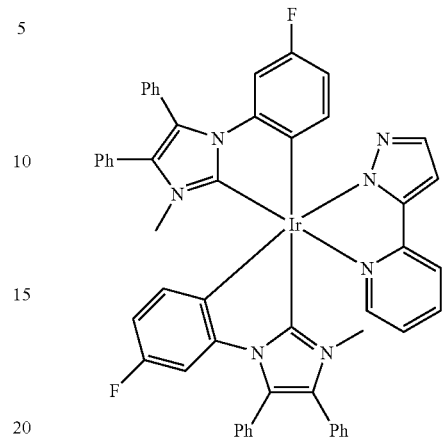
Ir(mfpmdpi)₂(pypz)
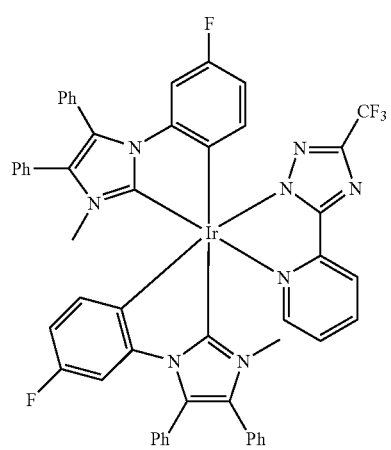
Ir(mfpmdpi)₂(tfptz)
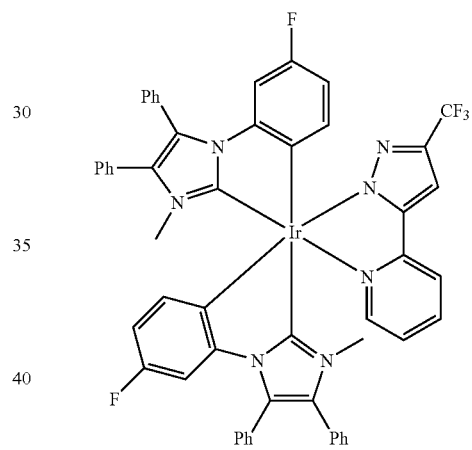
Ir(mfpmdpi)₂(tfpypz)
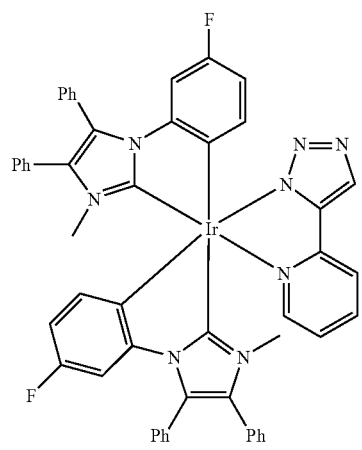
Ir(mfpmdpi)₂(pytz)
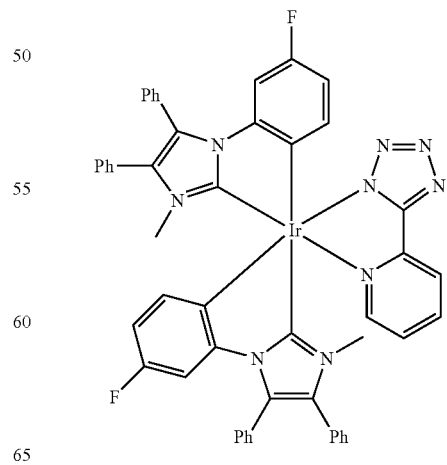
Ir(mfpmdpi)₂(pytrz)

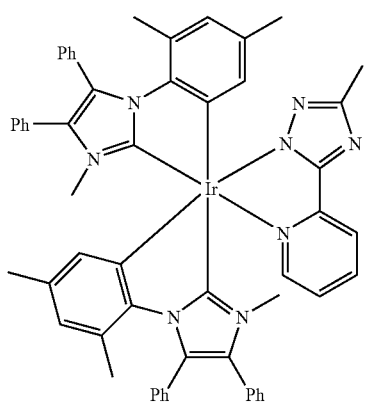
Ir(dmptmi)₂(mptz)
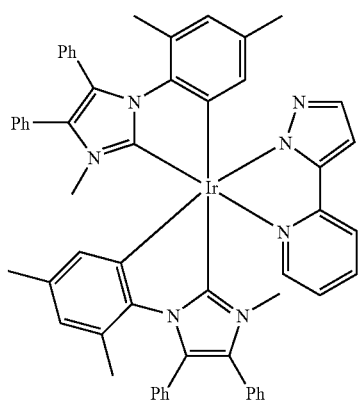
Ir(dmpmdpi)₂(pypz)
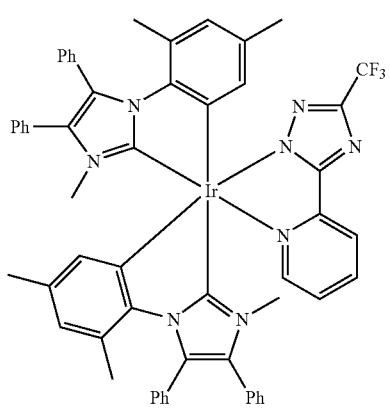
Ir(dmptmi)₂(tfptz)
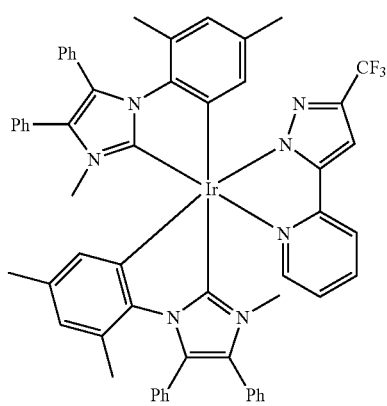
Ir(dmpmdpi)₂(tfpypz)
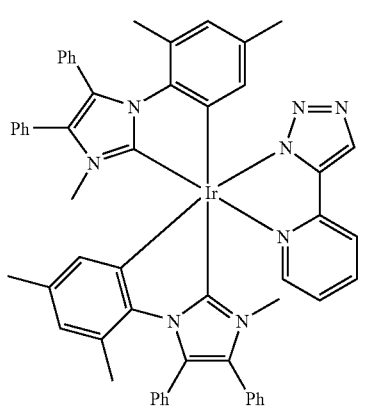
Ir(dmptmi)₂(pytz)
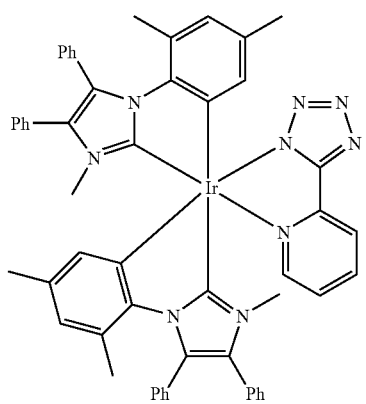
Ir(dmpmdpi)₂(pytrz)

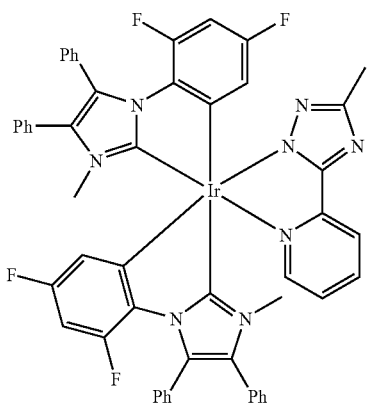
Ir(dfpmdpi)₂(mptz)
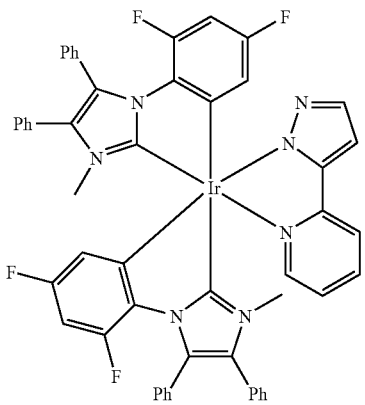
Ir(dfpmdpi)₂(pypz)
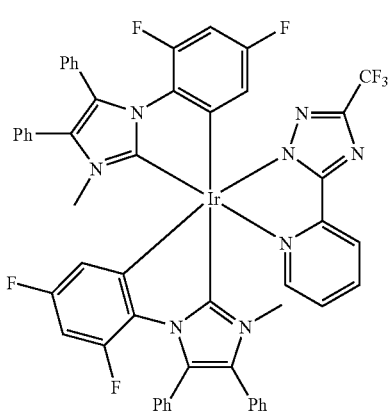
Ir(dfpmdpi)₂(tfptz)
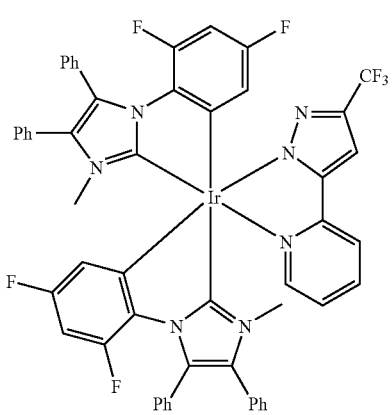
Ir(dfpmdpi)₂(tfpypz)
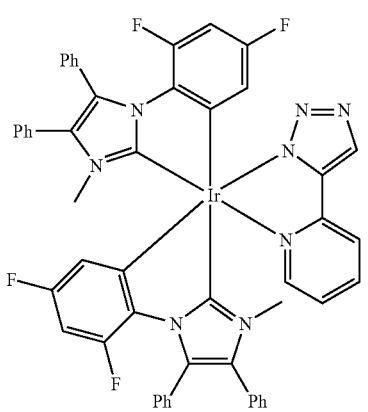
Ir(dfpmdpi)₂(pytz)
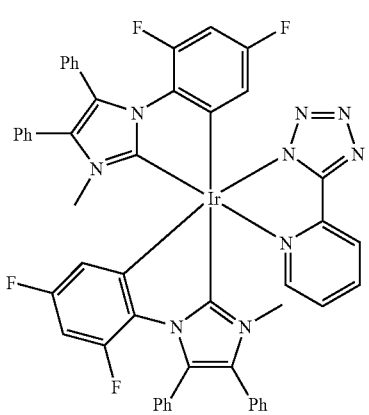
Ir(dfpmdpi)₂(pytrz)

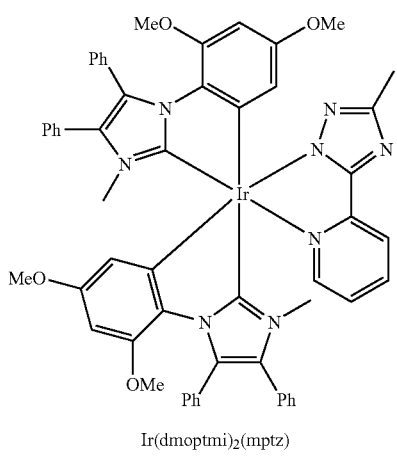
Ir(dmoptmi)₂(mptz)
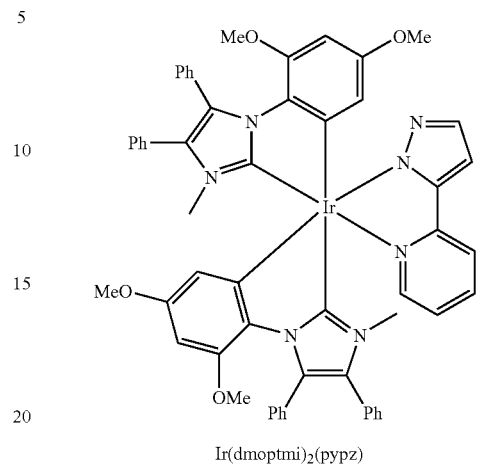
Ir(dmoptmi)₂(pypz)
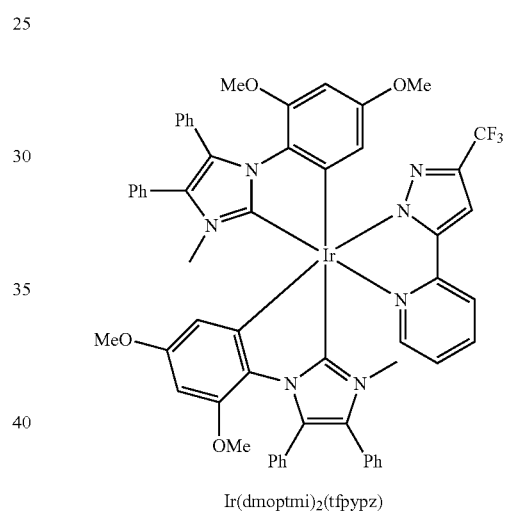
Ir(dmoptmi)₂(tfpypz)
Ir(dmoptmi)₂(tfptz)
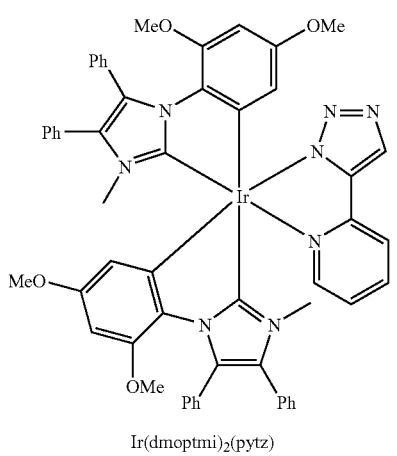
Ir(dmoptmi)₂(pytz)
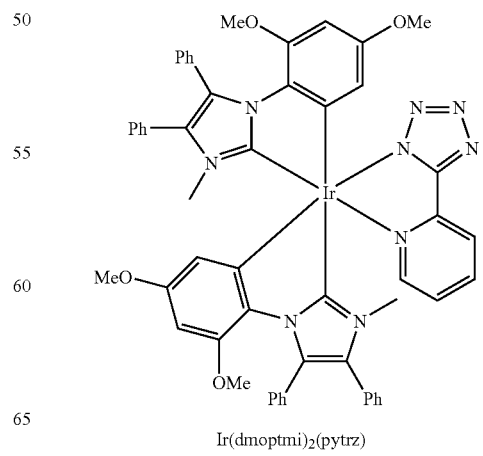
Ir(dmoptmi)₂(pytrz)

169
-continued
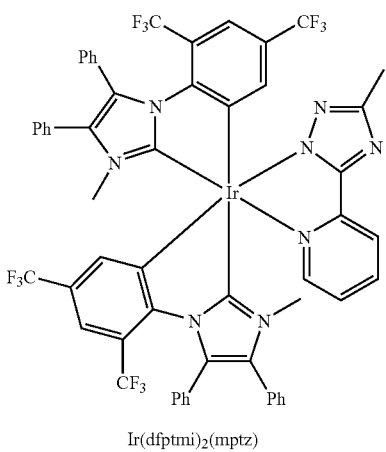
Ir(dfptmi)₂(mptz)
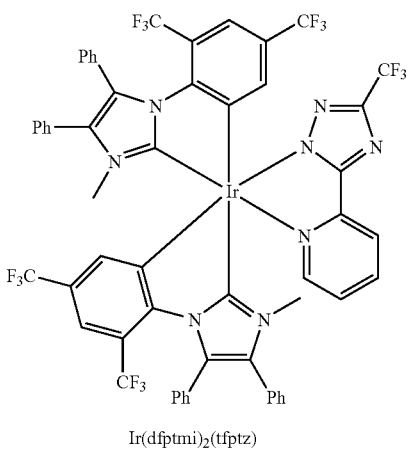
Ir(dfptmi)₂(tfptz)
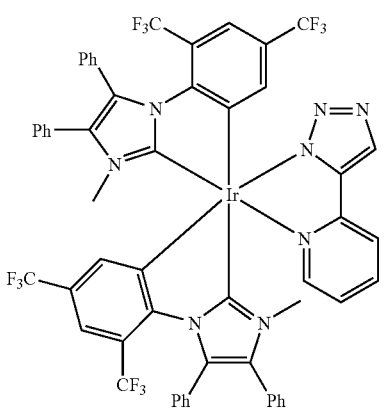
Ir(dfptmi)₂(pytz)
170
-continued
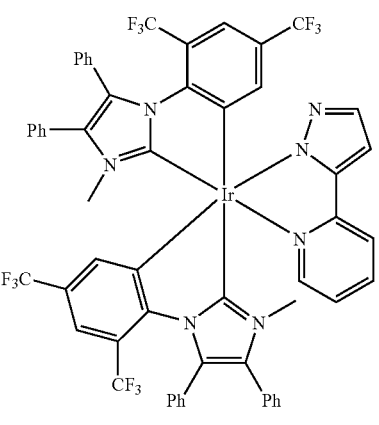
Ir(dfptmi)₂(pypz)
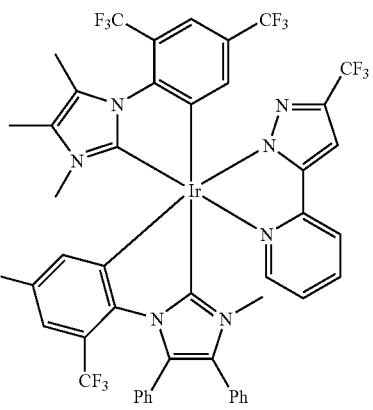
Ir(dfptmi)₂(tfpypz)
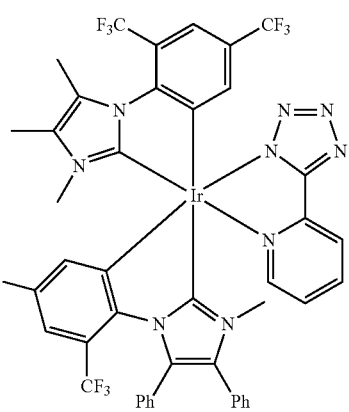
Ir(dfptmi)₂(pytrz)

-continued
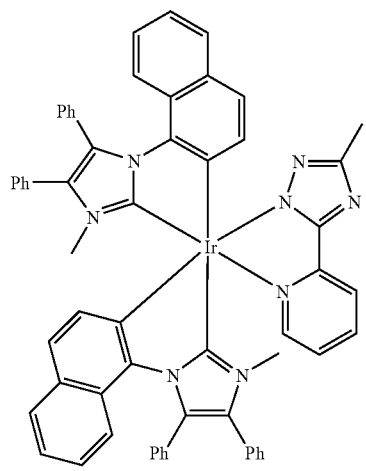
Ir(nmdpi)₂(mptz)
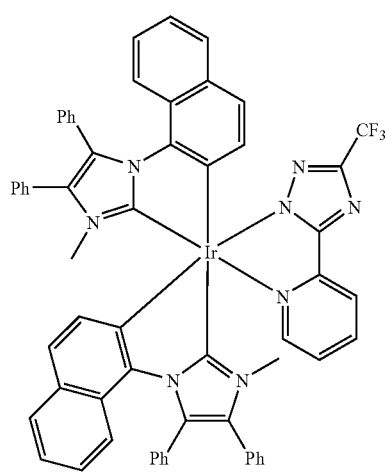
Ir(ntmdpi)₂(tfpypz)
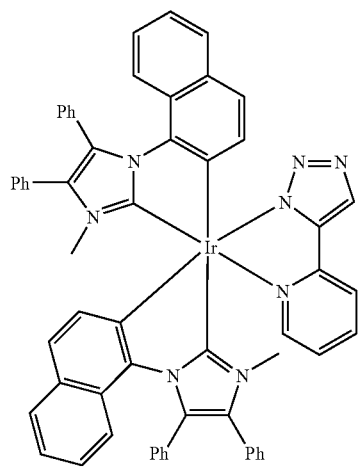
Ir(ntmdpi)₂(pytrz)
-continued
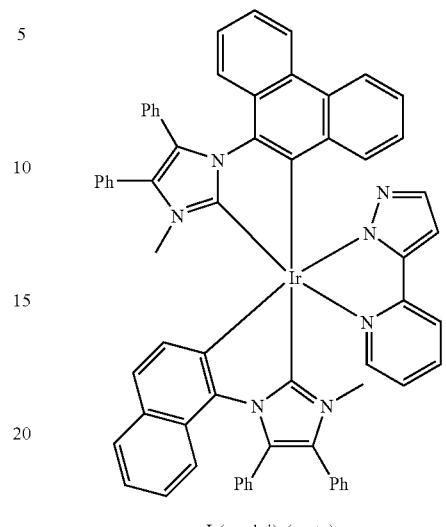
Ir(nmdpi)₂(mptz)
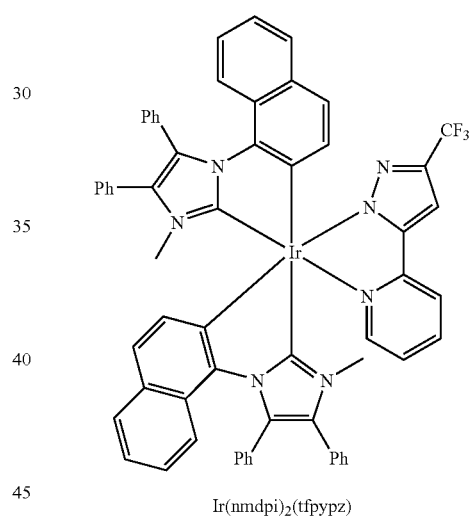
Ir(nmdpi)₂(tfpypz)
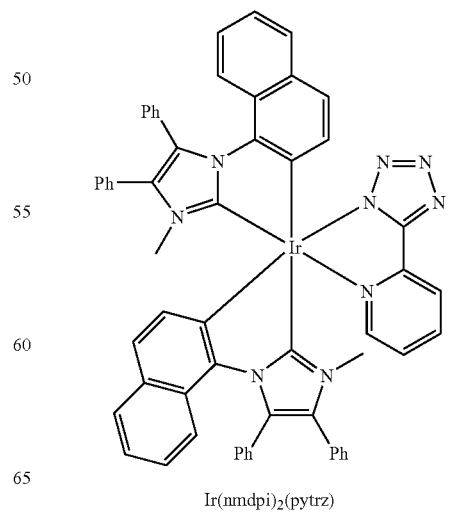
Ir(nmdpi)₂(pytrz)

173
-continued
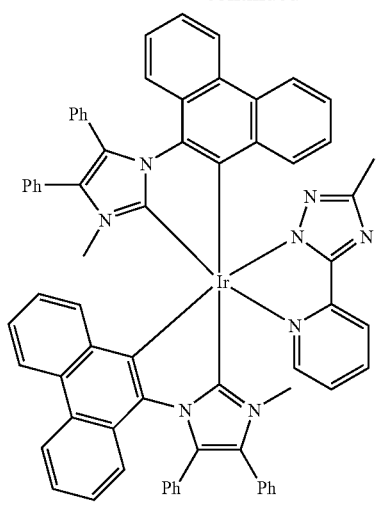
Ir(pnmdpi)₂(mptz)
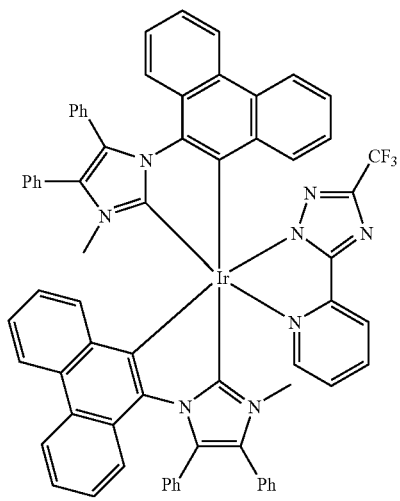
Ir(pnmdpi)₂(tfptz)
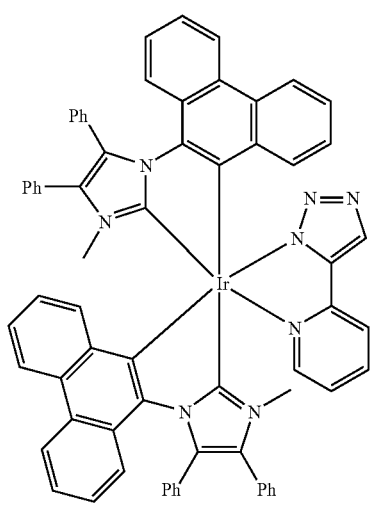
Ir(pnmdpi)₂(pytz)
174
-continued
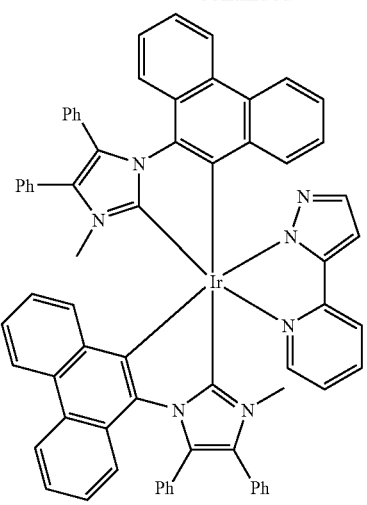
Ir(pnmdpi)₂(pypz)
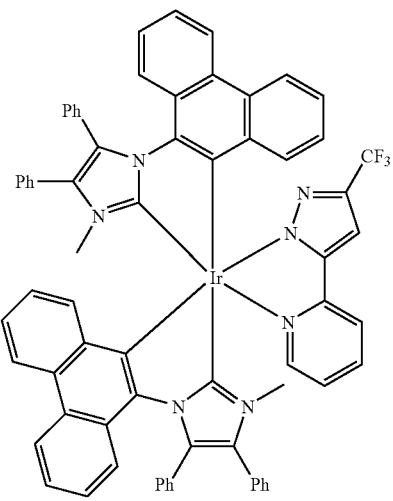
Ir(pnmdpi)₂(tfpypz)
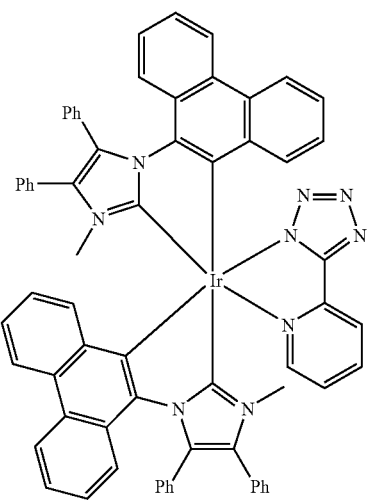
Ir(pnmdpi)₂(pytrz)

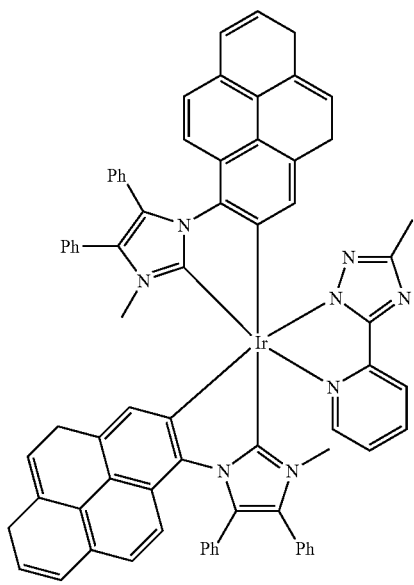
Ir(pymdpi)₂(mptz)
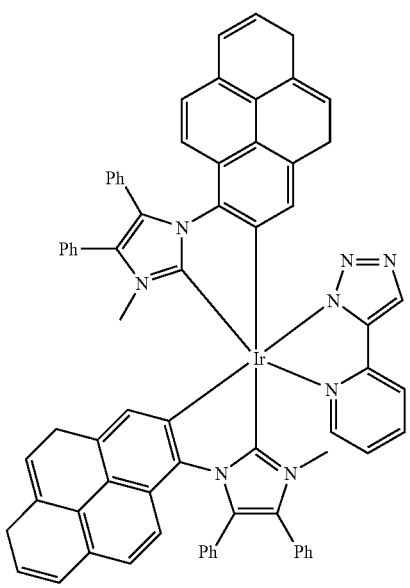
Ir(pymdpi)₂(pytz)
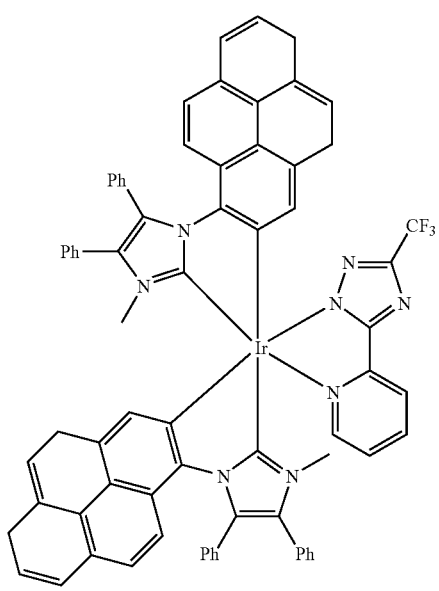
Ir(pymdpi)₂(tfptz)
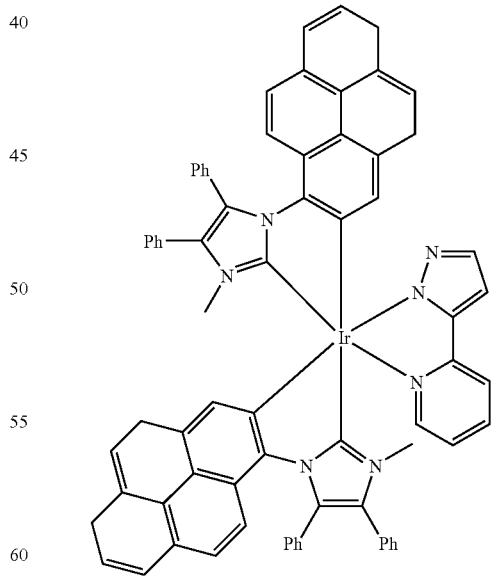
Ir(pymdpi)₂(pypz)

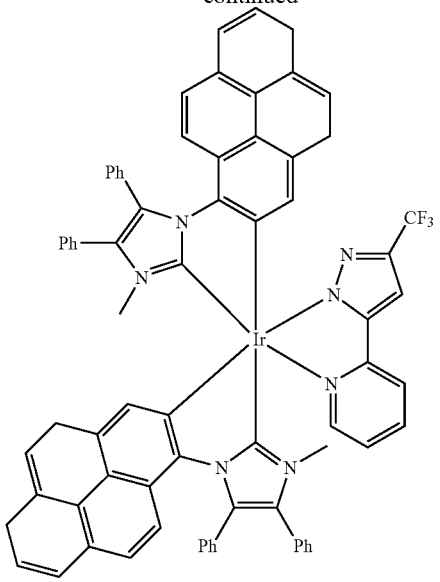
Ir(pymdpi)₂(tfpypz)
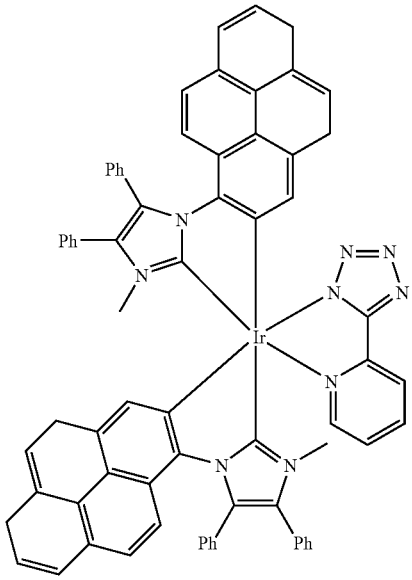
Ir(pymdpi)₂(pytrz)
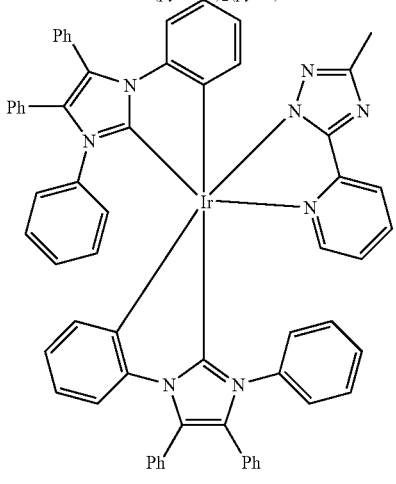
Ir(bpdpi)₂(mptz)
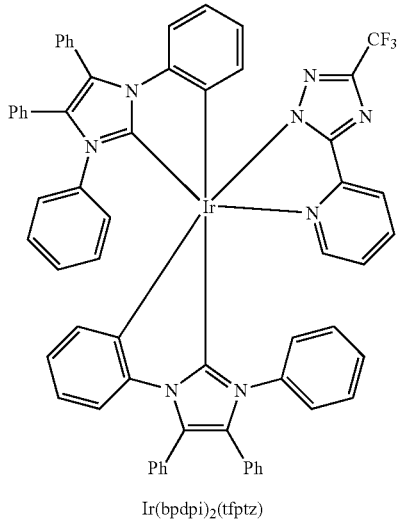
Ir(bpdpi)₂(tfptz)
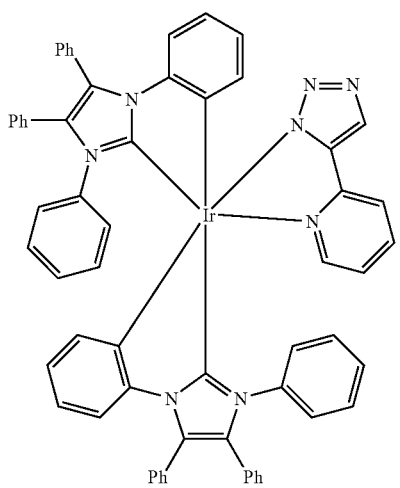
Ir(bpdpi)₂(pytz)
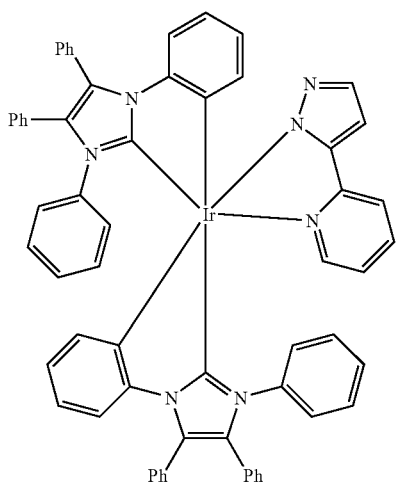
Ir(bpdpi)₂(pypz)

-continued
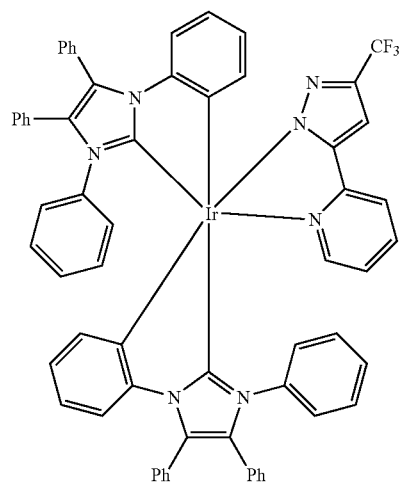
Ir(bpdpi)₂(tfpypz)
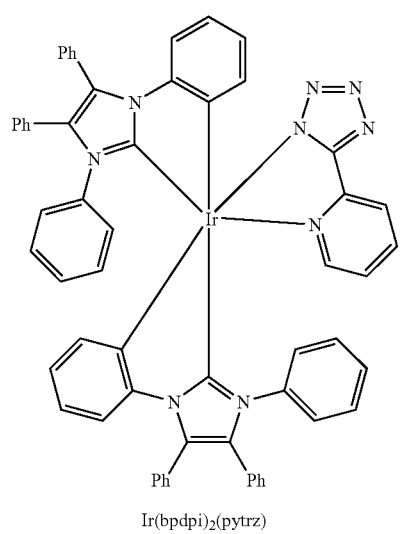
Ir(bpdpi)₂(pytrz)
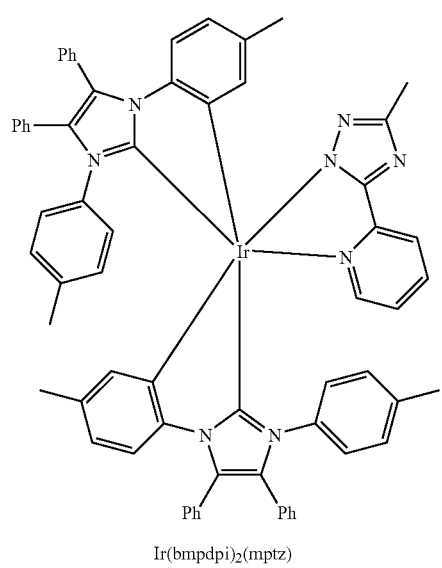
Ir(bmpdpi)₂(mptz)
-continued
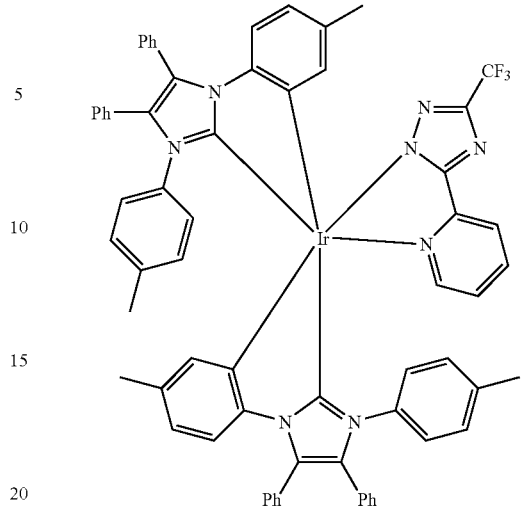
Ir(bmpdpi)₂(tfptz)
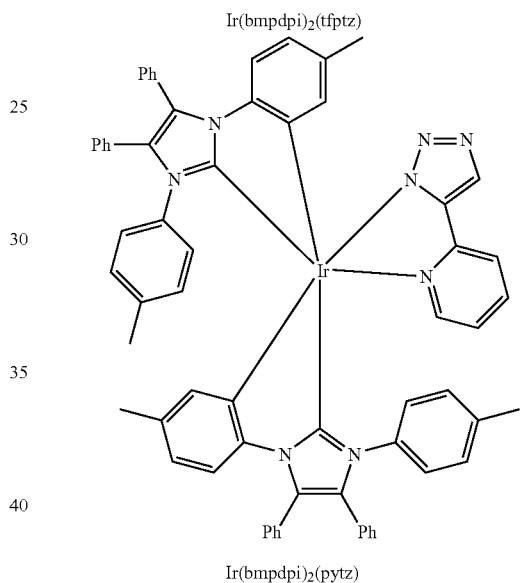
Ir(bmpdpi)₂(pytz)
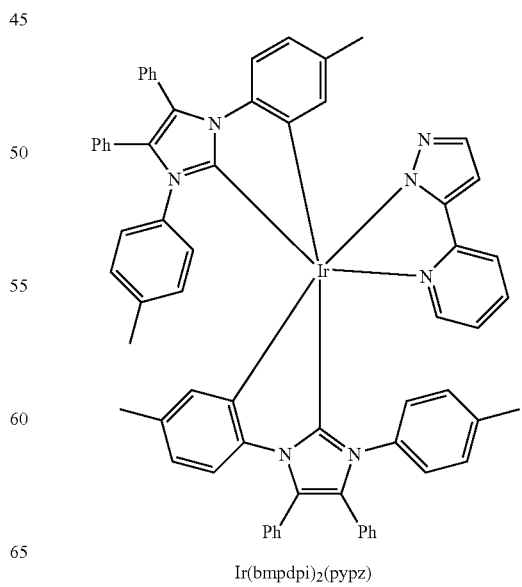
Ir(bmpdpi)₂(pypz)

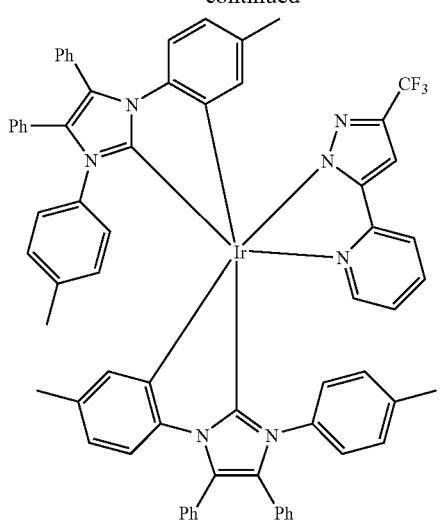
Ir(bmpdpi)₂(tfpypz)
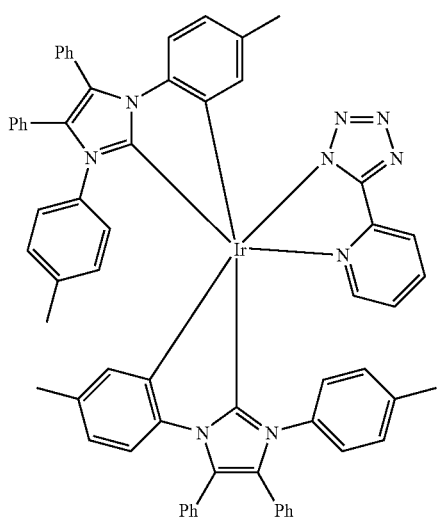
Ir(bmpdpi)₂(pytrz)
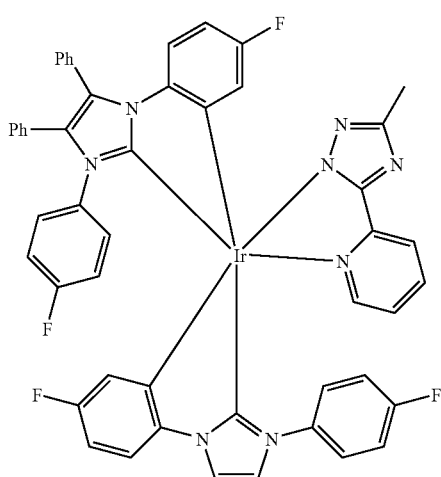
Ir(bmpdpi)₂(mptz)
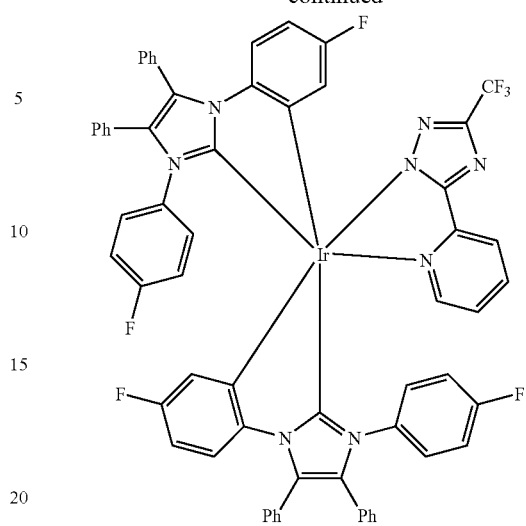
Ir(bfpdpi)₂(tfptz)
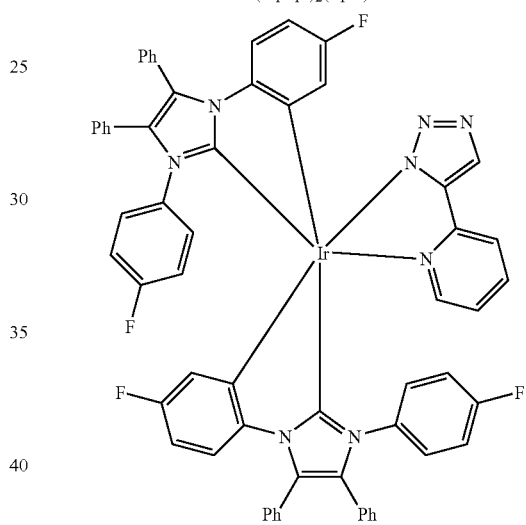
Ir(bfpdpi)₂(pytz)
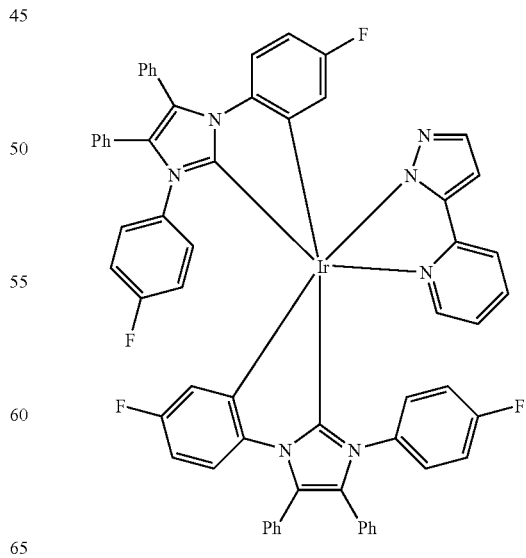
Ir(bfpdpi)₂(pypz)

-continued
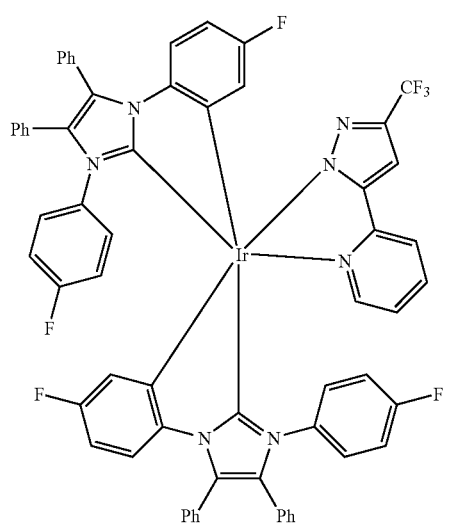
Ir(bfpdpi)₂(tfpypz)
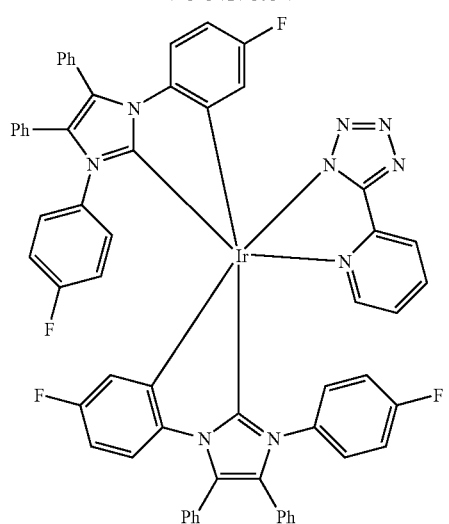
Ir(bfpdpi)₂(pytrz)
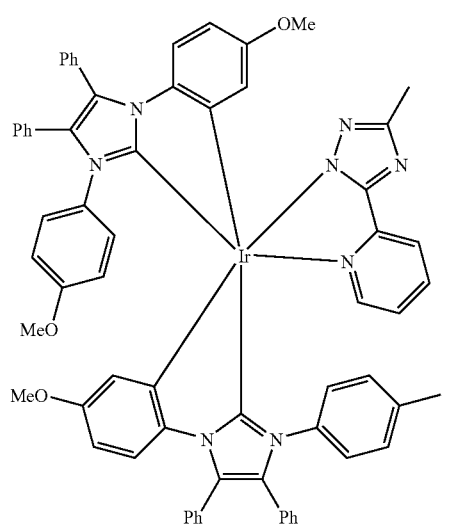
Ir(bmopdpi)₂(mptz)
-continued
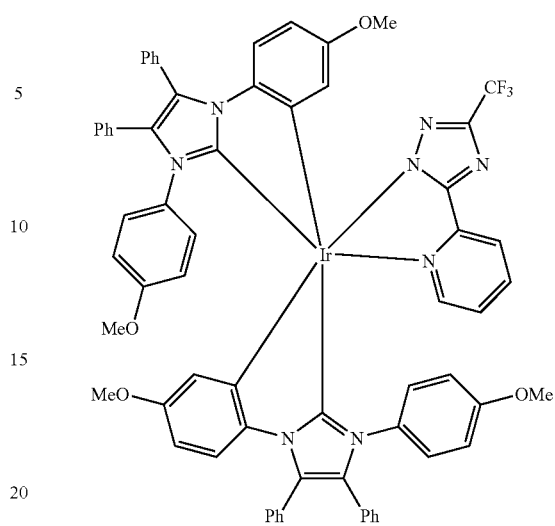
Ir(bmopdpi)₂(tfptz)
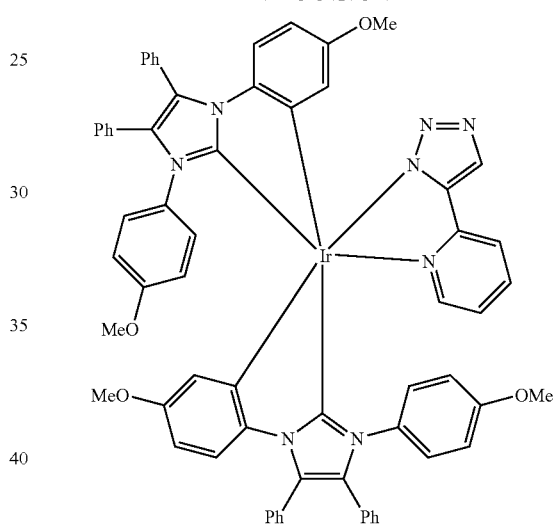
Ir(bmopdpi)₂(pytz)
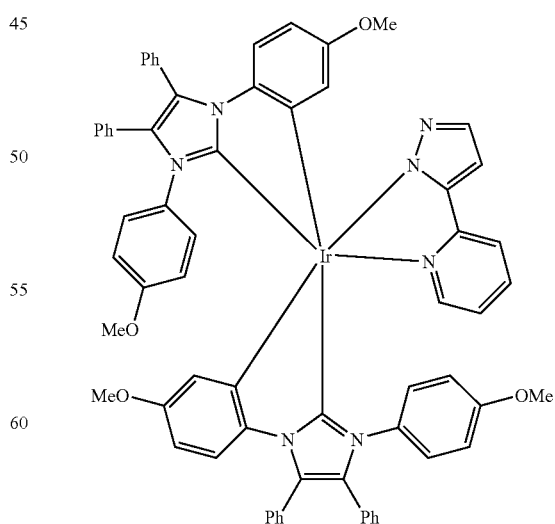
Ir(bmopdpi)₂(pypz)

185
-continued
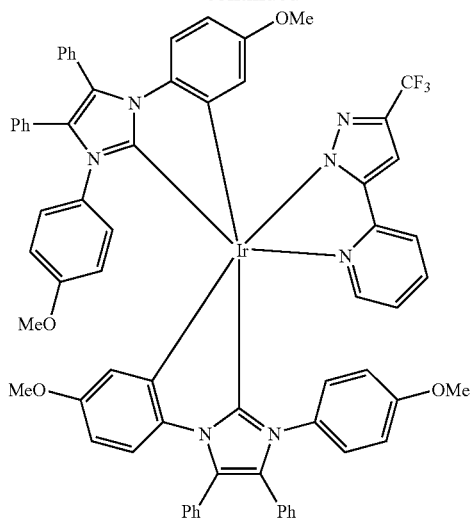
Ir(bmopdpi)₂(tfpypz)
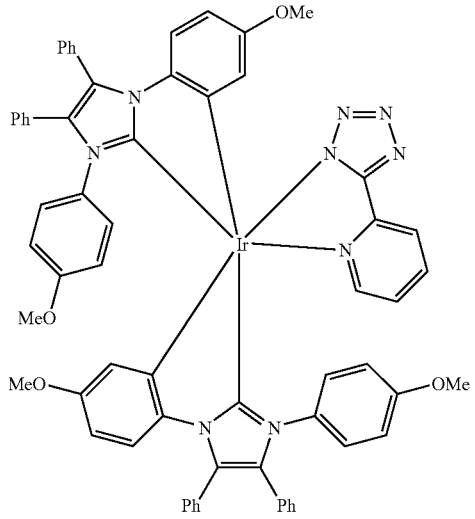
Ir(bmopdpi)₂(pytrz)
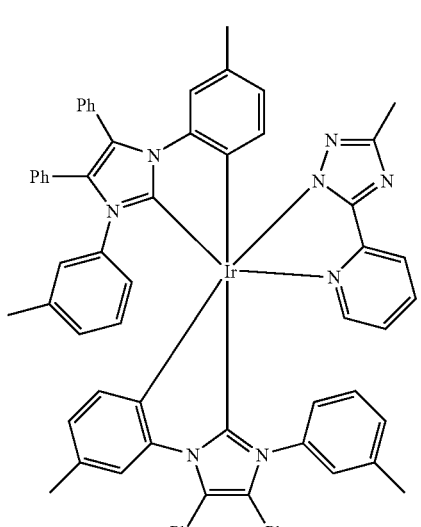
Ir(bmmpdpi)₂(mptz)
186
-continued
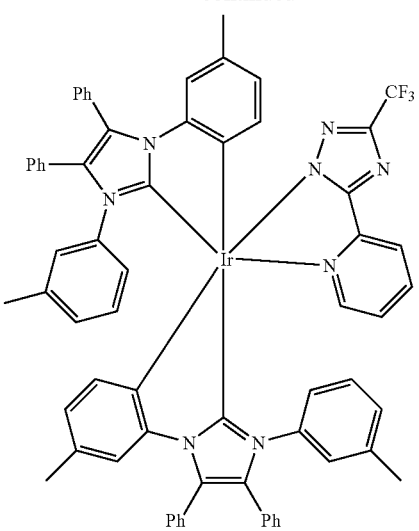
Ir(bmmpdpi)₂(tfptz)
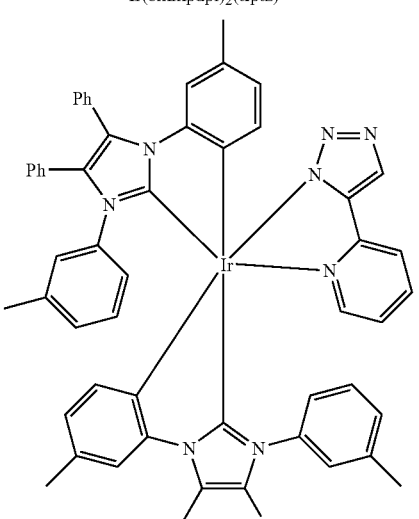
Ir(bmmpdpi)₂(pytz)
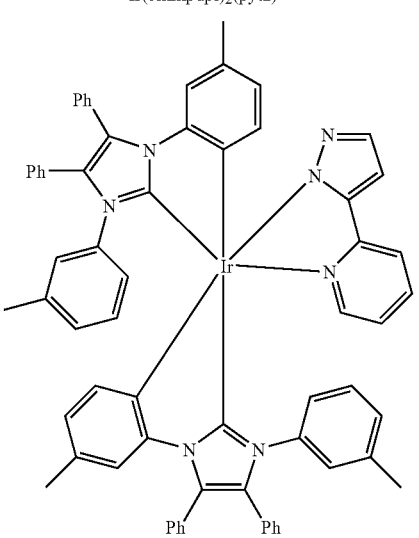
Ir(bmmpdpi)₂(pypz)

-continued
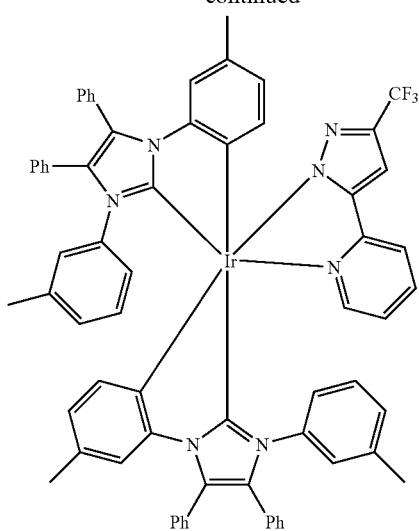
Ir(bmmpdpi)₂(tfpypz)
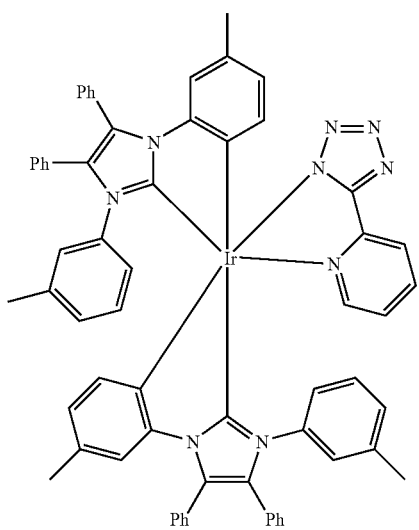
Ir(bmmpdpi)₂(pytrz)
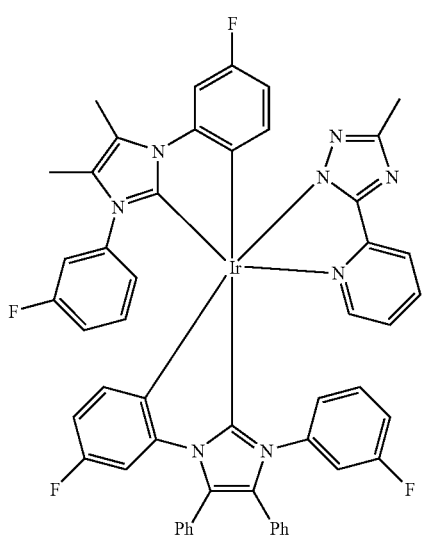
Ir(bmfpdpi)₂(mptz)
-continued
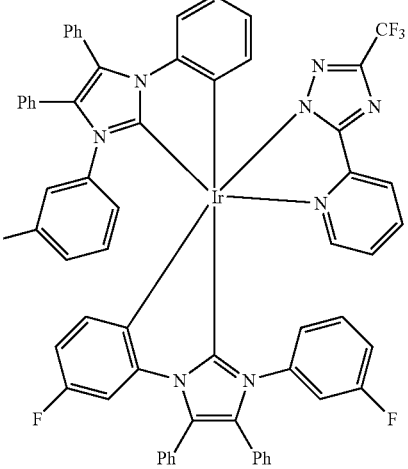
Ir(bmfpdpi)₂(tfptz)
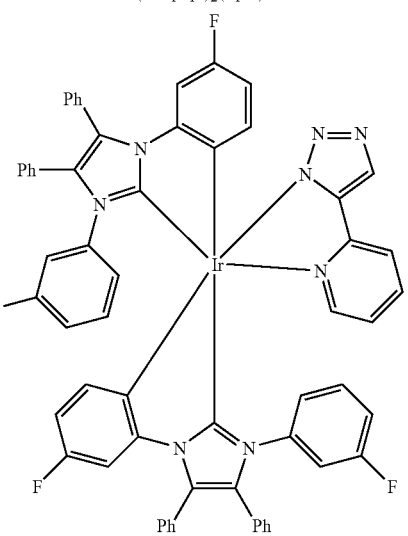
Ir(bmfpdpi)₂(pytz)
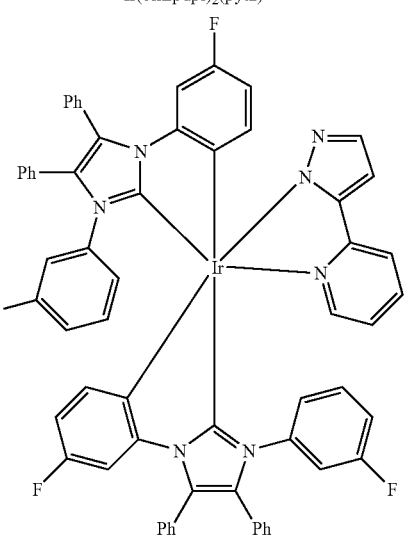
Ir(bmfpdpi)₂(pypz)

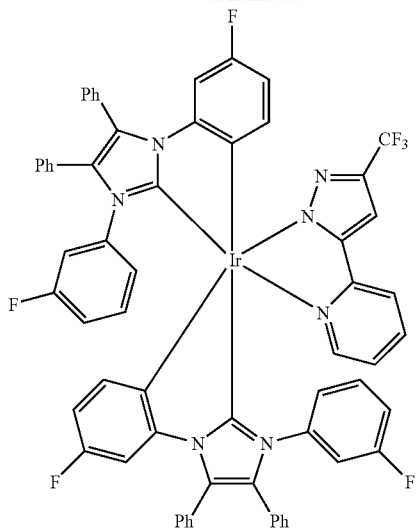
Ir(bmfpdpi)₂(tfpypz)
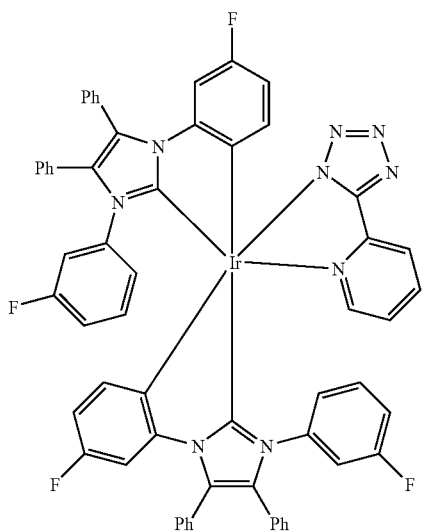
Ir(bmfpdpi)₂(pytrz)
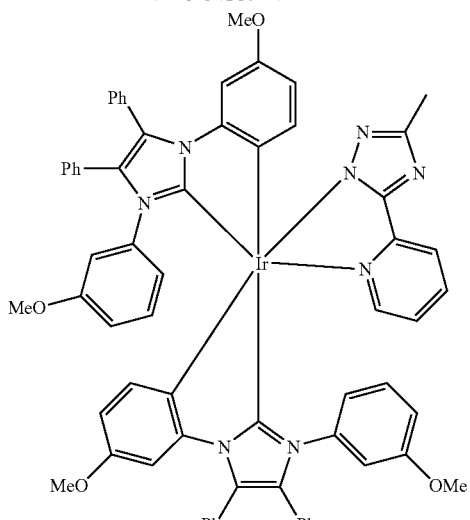
Ir(bmmopdpi)₂(mptz)
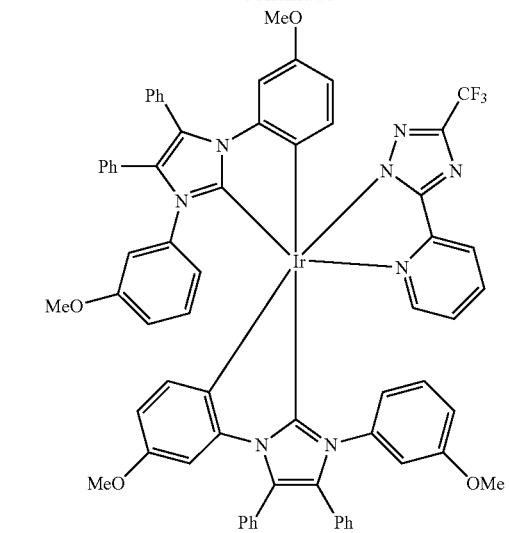
Ir(bmmopdpi)₂(tfptz)
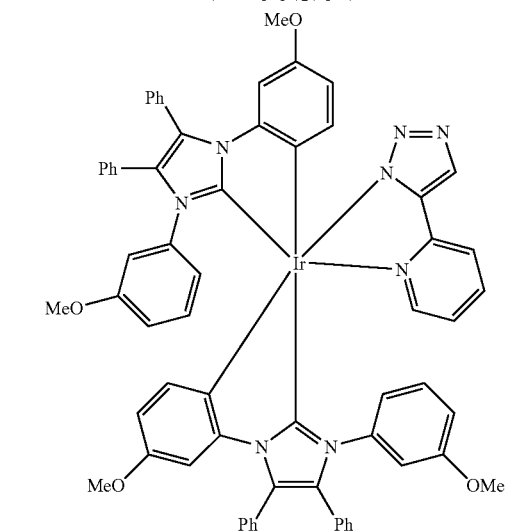
Ir(bmmopdpi)₂(pytz)
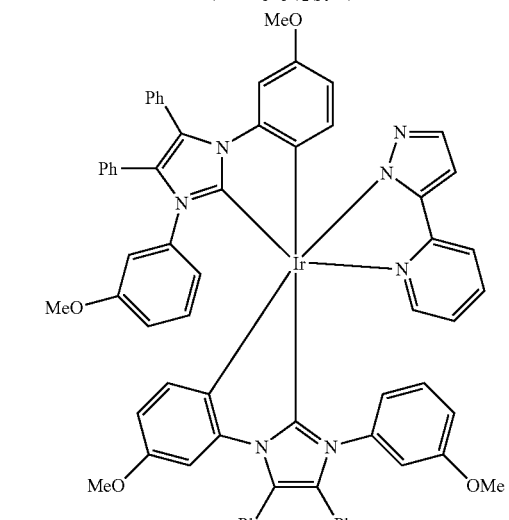
Ir(bmmopdpi)₂(pypz)

-continued
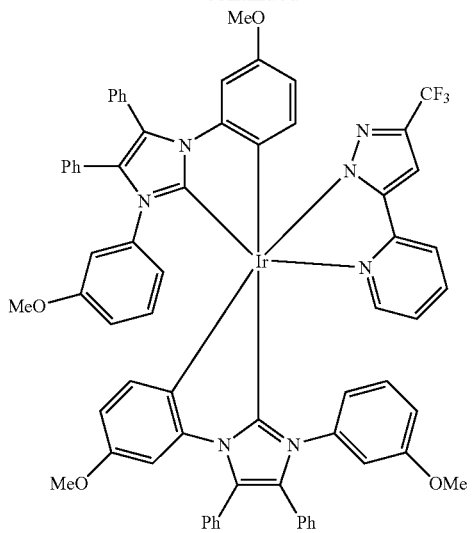
Ir(bmmopdpi)₂(tfpypz)
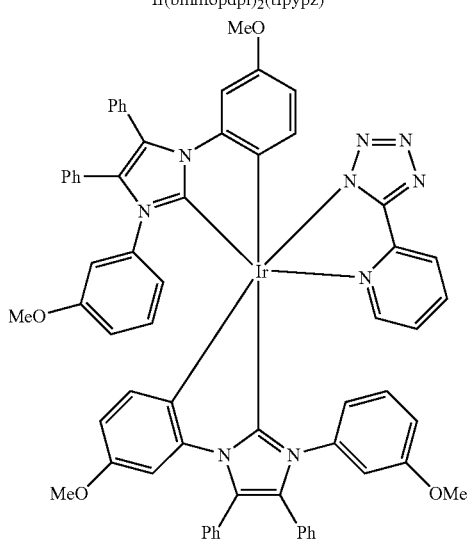
Ir(bmmopdpi)₂(pytrz)
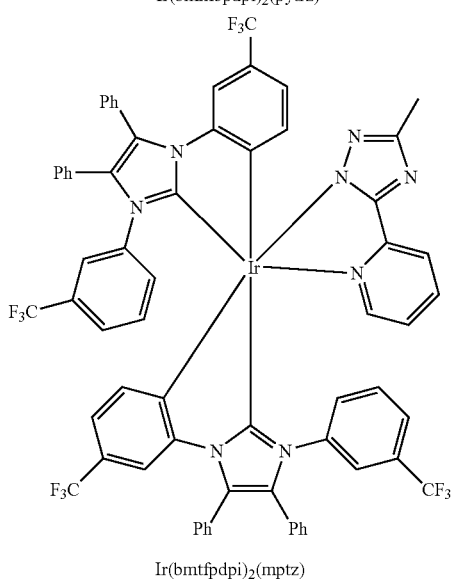
Ir(bmtfpdpi)₂(mptz)
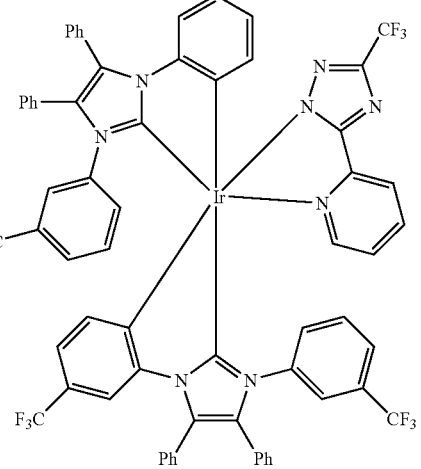
Ir(bmtfpdpi)₂(tfptz)
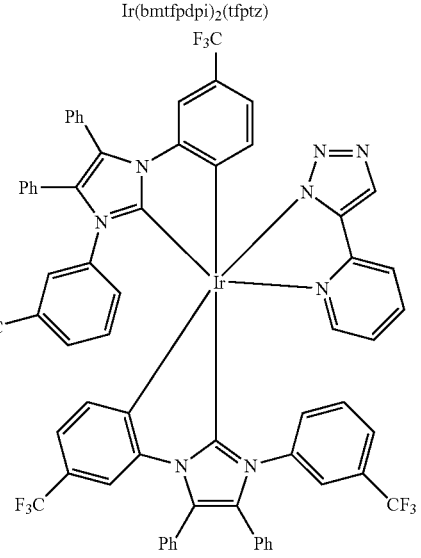
Ir(bmtfpdpi)₂(pytz)
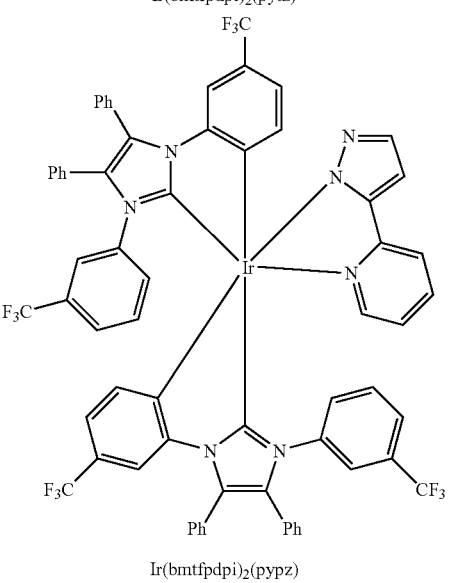
Ir(bmtfpdpi)₂(pypz)

-continued
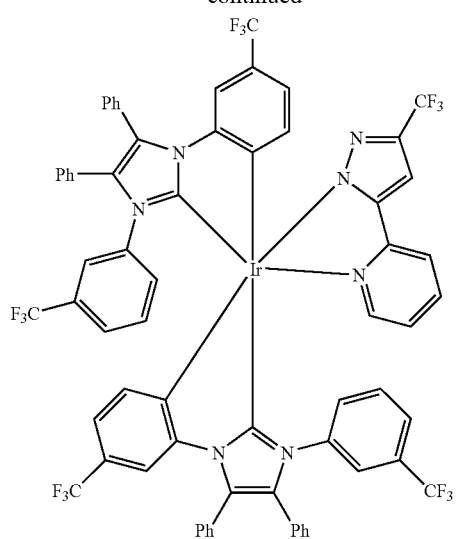
Ir(bmtfpdpi)₂(tfpypz)
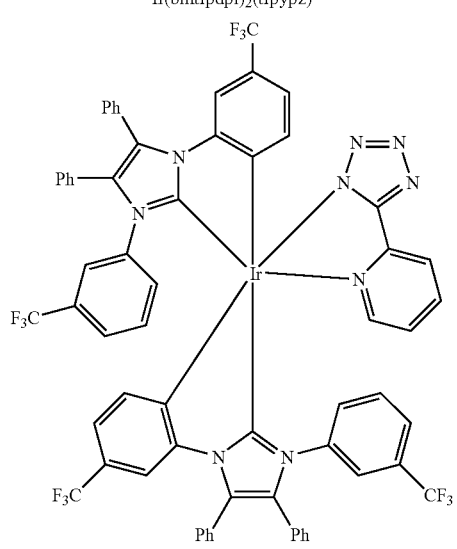
Ir(bmtfpdpi)₂(pytrz)
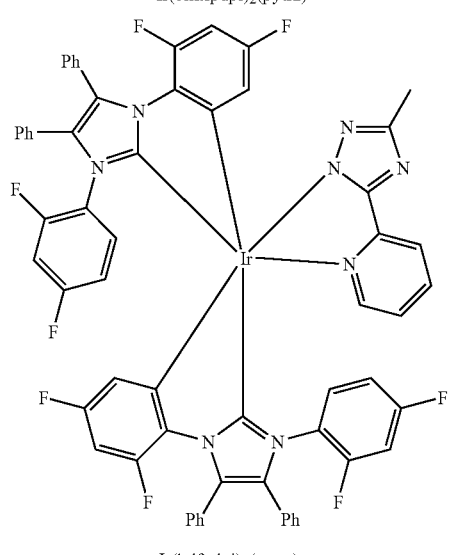
Ir(bdfpdpi)₂(mptz)
-continued
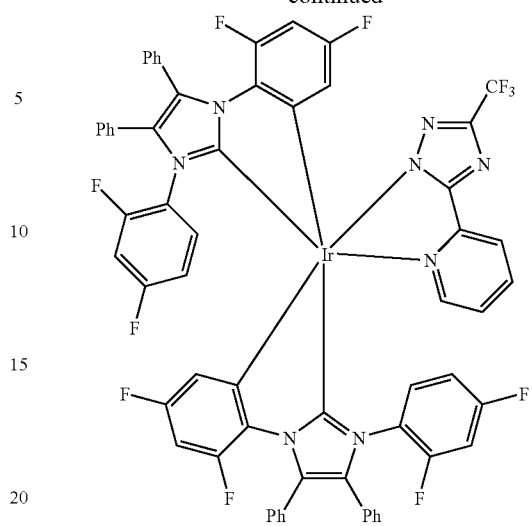
Ir(bdfpdpi)₂(tfptz)
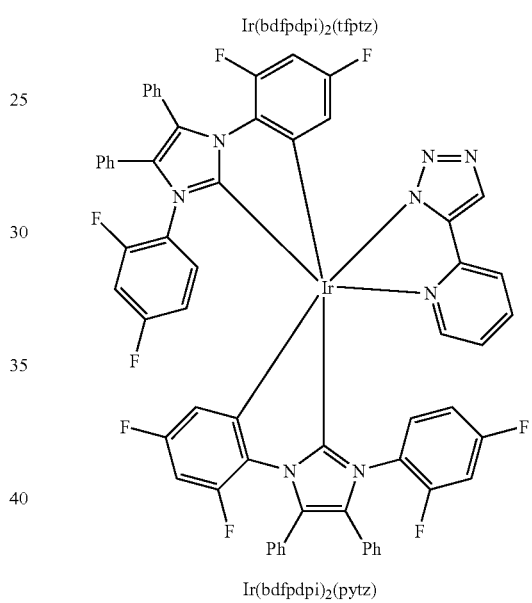
Ir(bdfpdpi)₂(pytz)
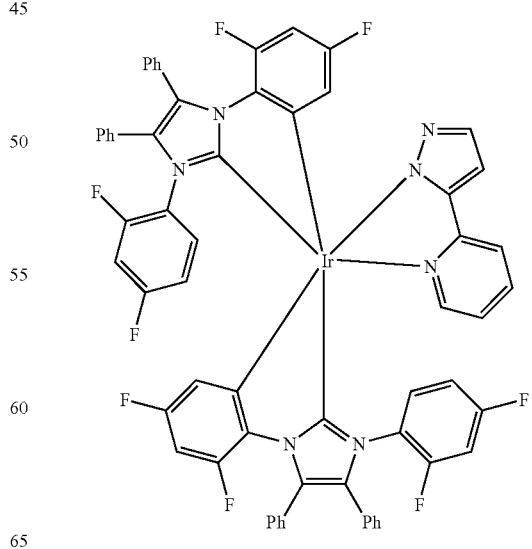
Ir(bdfpdpi)₂(pypz)

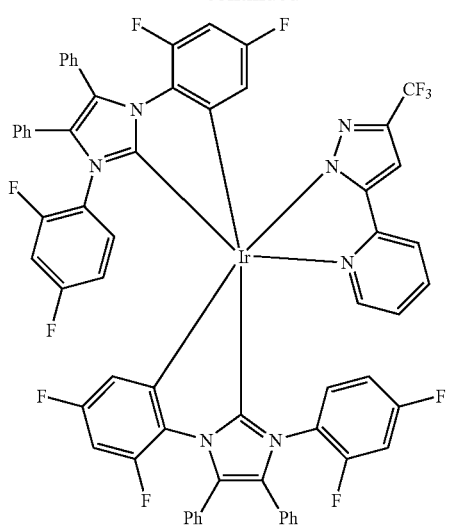
Ir(bdfpdpi)₂(tfpypz)
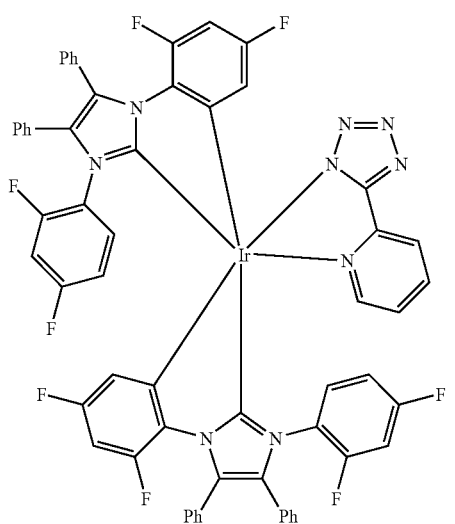
Ir(bdfpdpi)₂(pytrz)
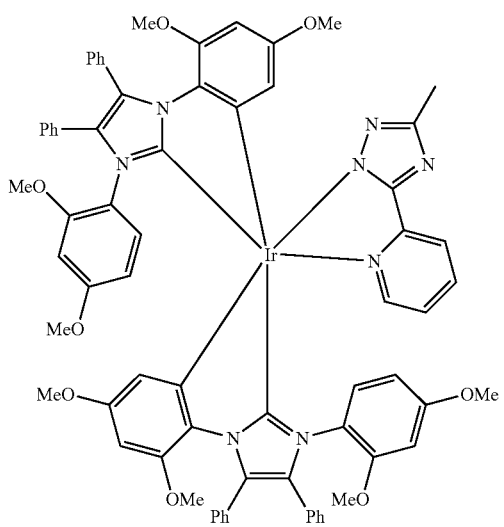
Ir(bdmopdpi)₂(mptz)
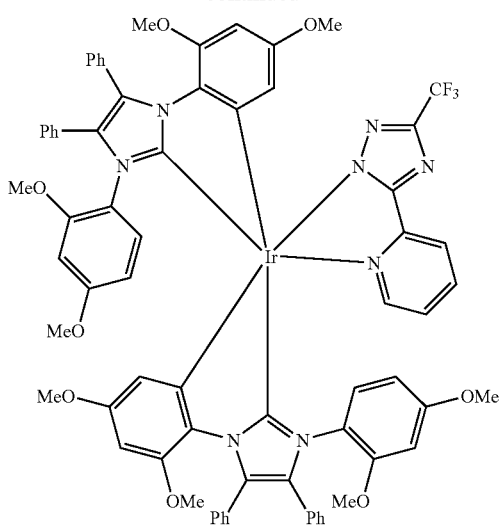
Ir(bdmopdpi)₂(tfptz)
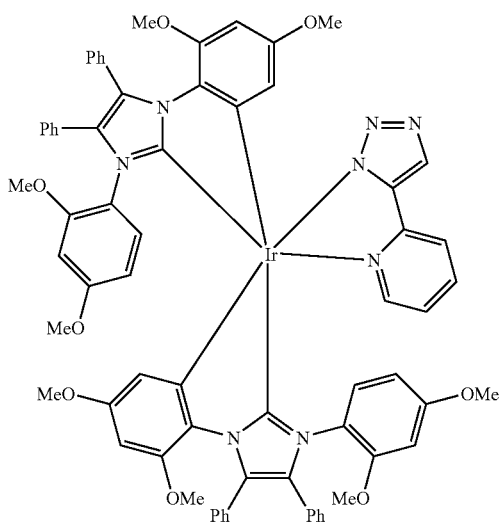
Ir(bdmopdpi)₂(pytz)
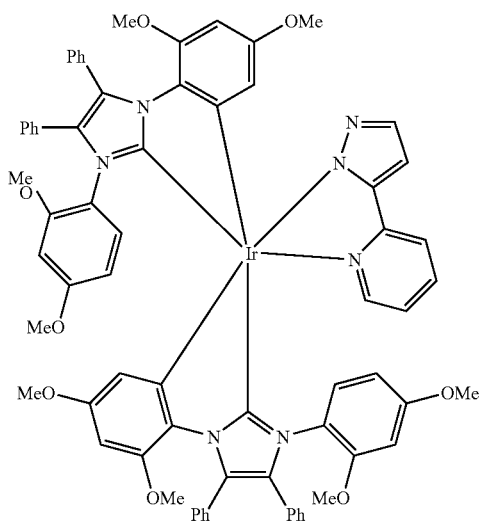
Ir(bdmopdpi)₂(pypz)

-continued
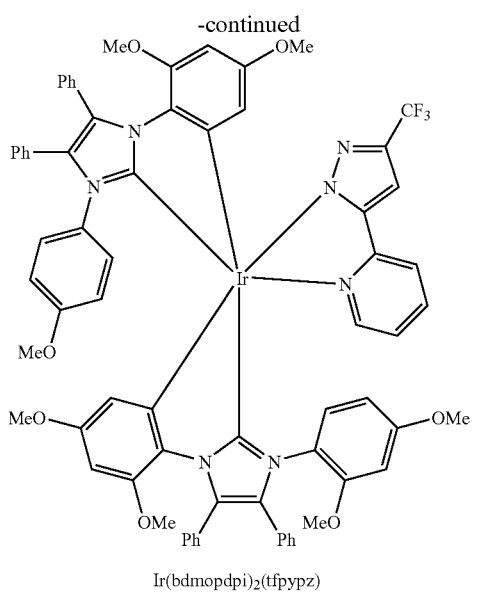
Ir(bdmopdpi)₂(tfpypz)
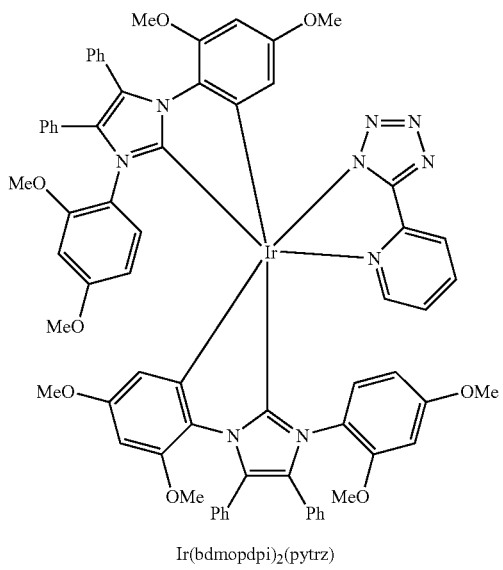
Ir(bdmopdpi)₂(pytrz)
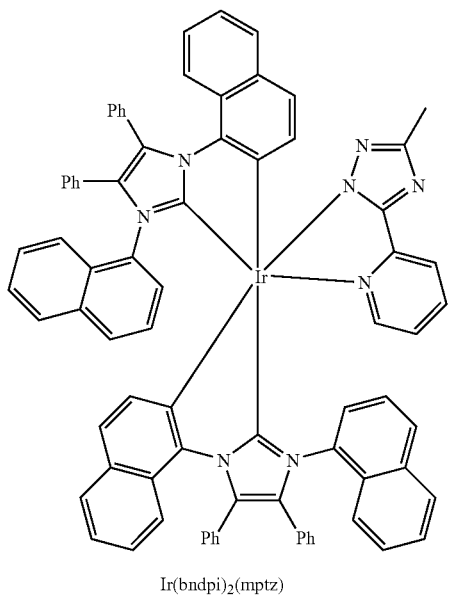
Ir(bndpi)₂(mptz)
-continued
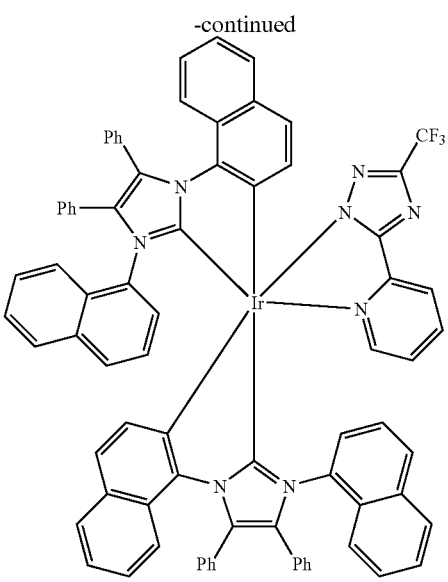
Ir(bndpi)₂(tfptz)
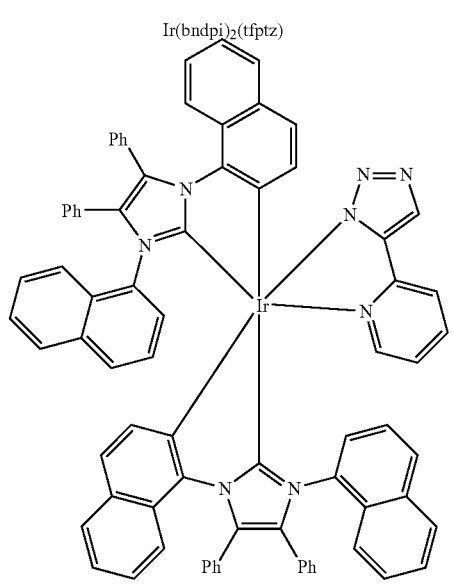
Ir(bndpi)₂(pytz)
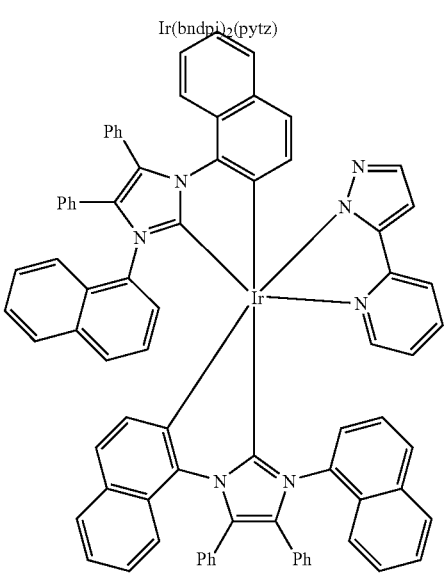
Ir(bndpi)₂(pypz)

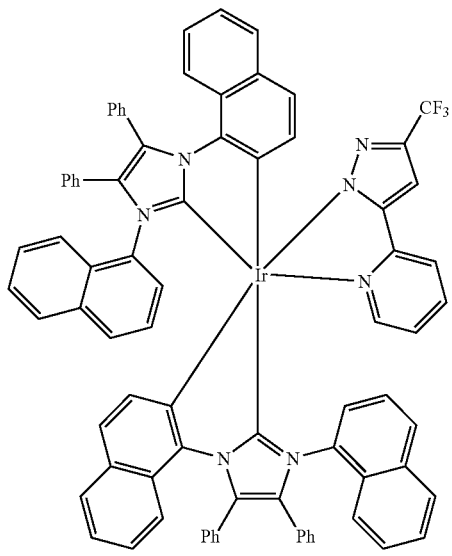
Ir(bndpi)₂(tfpypz)
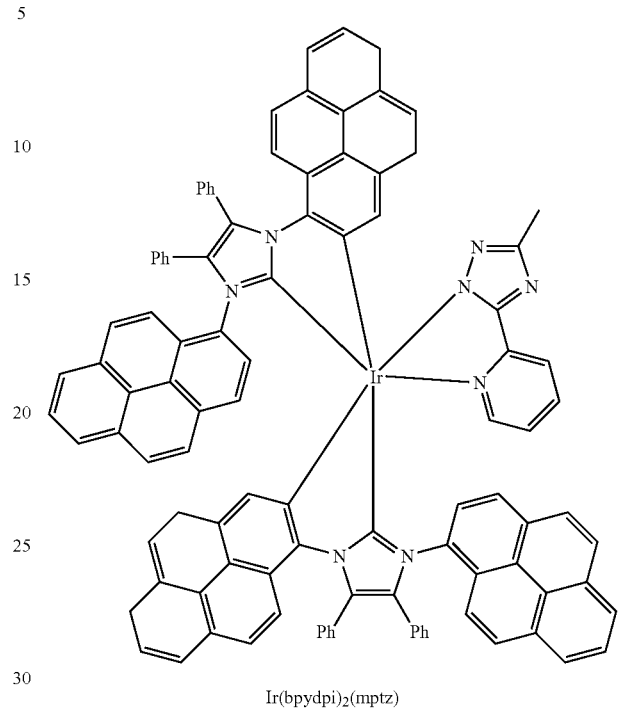
Ir(bpydpi)₂(mptz)
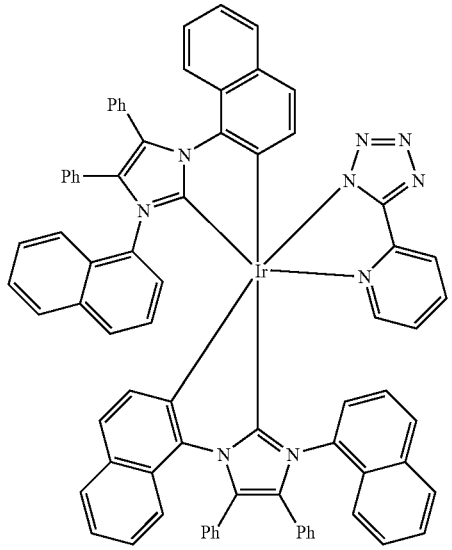
Ir(bndpi)₂(pytrz)
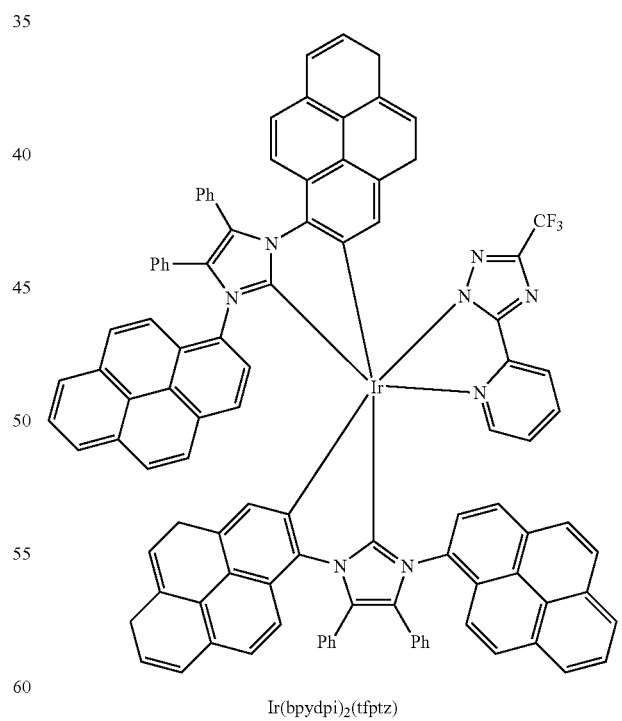
Ir(bpydpi)₂(tfptz)

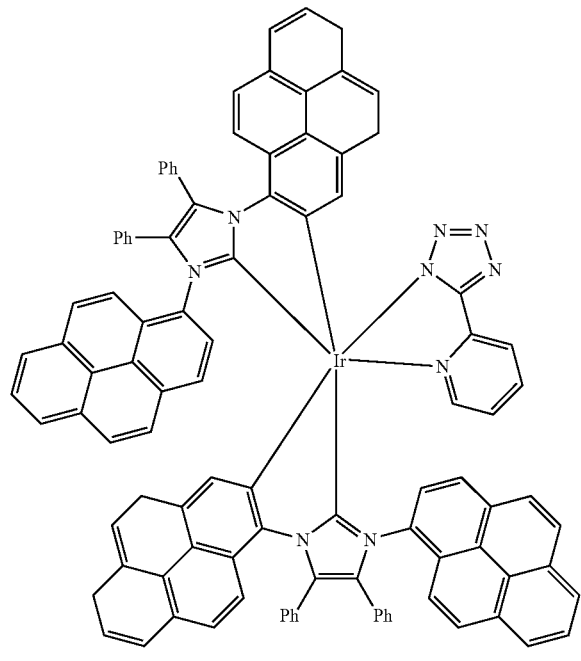

Ir(bpydpi)₂(pytrz)

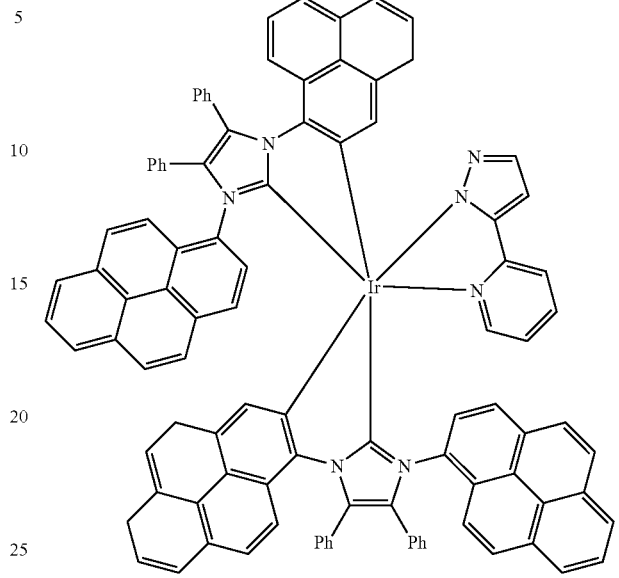

Ir(bpydpi)₂(pypz)

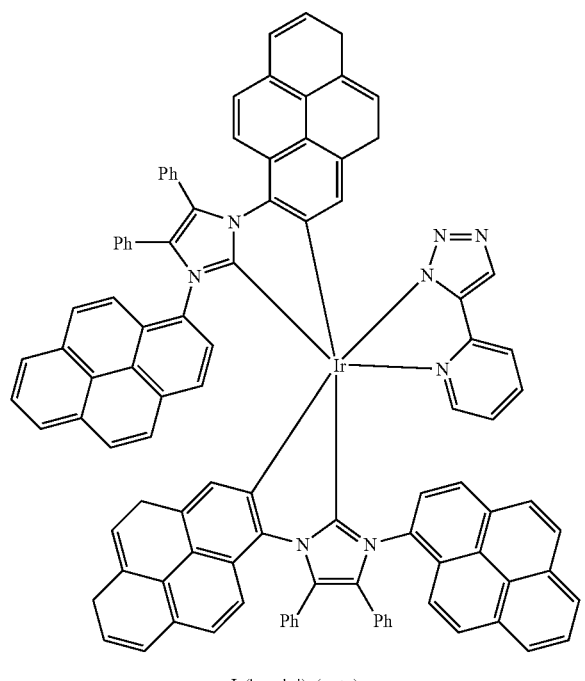

Ir(bpydpi)₂(pytz)

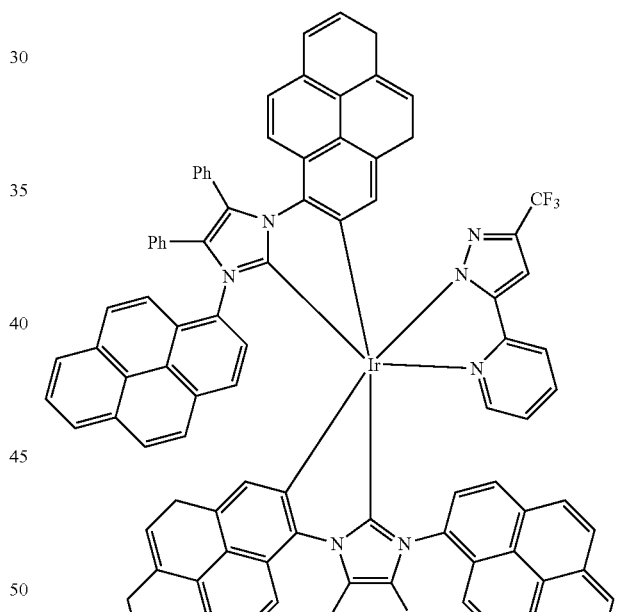

Ir(bpydpi)₂(tfpypz)

The disclosed transition metal complex with carbene ligand can be used in electroluminescent devices and/or phosphorescent devices, especially be used as the emitting material, electron transport material, or hole transport material in electroluminescent/phosphorescent devices. In addition, the disclosed transition metal complex can also be used as the electron transport material or hole transport material in other organic electronic devices, such as organic solar cells, organic thin-film transistors, organic photo-conductors or other organic semiconductor devices known to those skilled in the art.

Example 1

General Process for Forming Iridium-Based Metal Complex with Carbene Ligand

General Process for Forming Iridium-Based Dimer

As shown below, compound 5 is formed by reacting compound 4 with iridium chloride ($IrCl_3$).

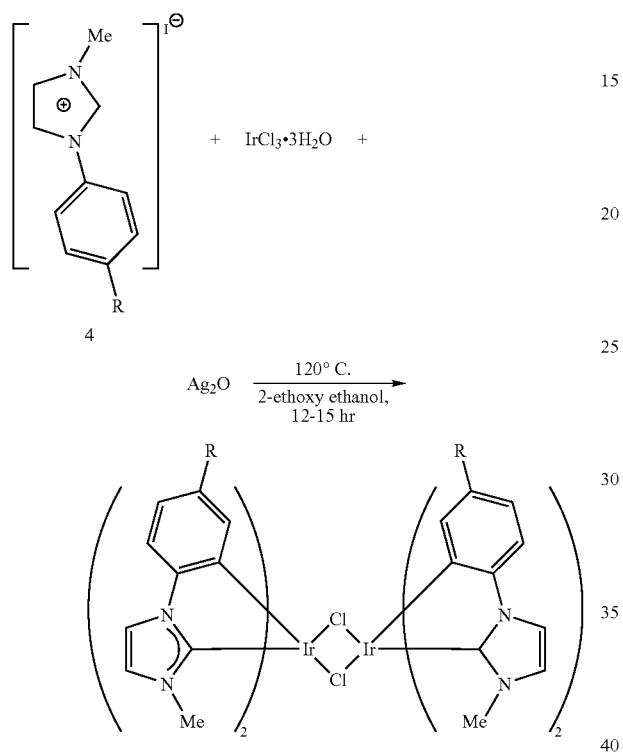

R = H, F, Me

Detailed steps will be described below. First, add silver oxide ($Ag_2O$) (926 mg, 4 mmole) into a reactor. Next, add compound 4 (1.22 g, 4 mmole) and iridium chloride with crystalline hydrate (353 mg, 1 mmole), and 4 ml ethylene glycol monoethyl ether (or 2-ethoxyethanol) as the solvent. Then, wrap the reactor up with aluminum foil and put it in a 120° C. oil-bath for 12-15 hours.

In the following step, add water to deposit out the solid and then filter it. Next, remove the filtrate and wash the solid with dichloromethane to separate the insoluble silver oxide from the soluble product. Then, concentrate the filtrate to obtain the solid, and re-crystallize the solid with ethanol to obtain the gray compound 5 with a yield of 35% (203 mg).

General Process for Forming the Transition Metal Complex with Carbene Ligand

Referring to the following reaction path, in this example, the transition metal complex with carbene ligand (compound 8, 10, 12) are obtained by reacting compound 6 with varying types of compound 7, 9, and 11, respectively.

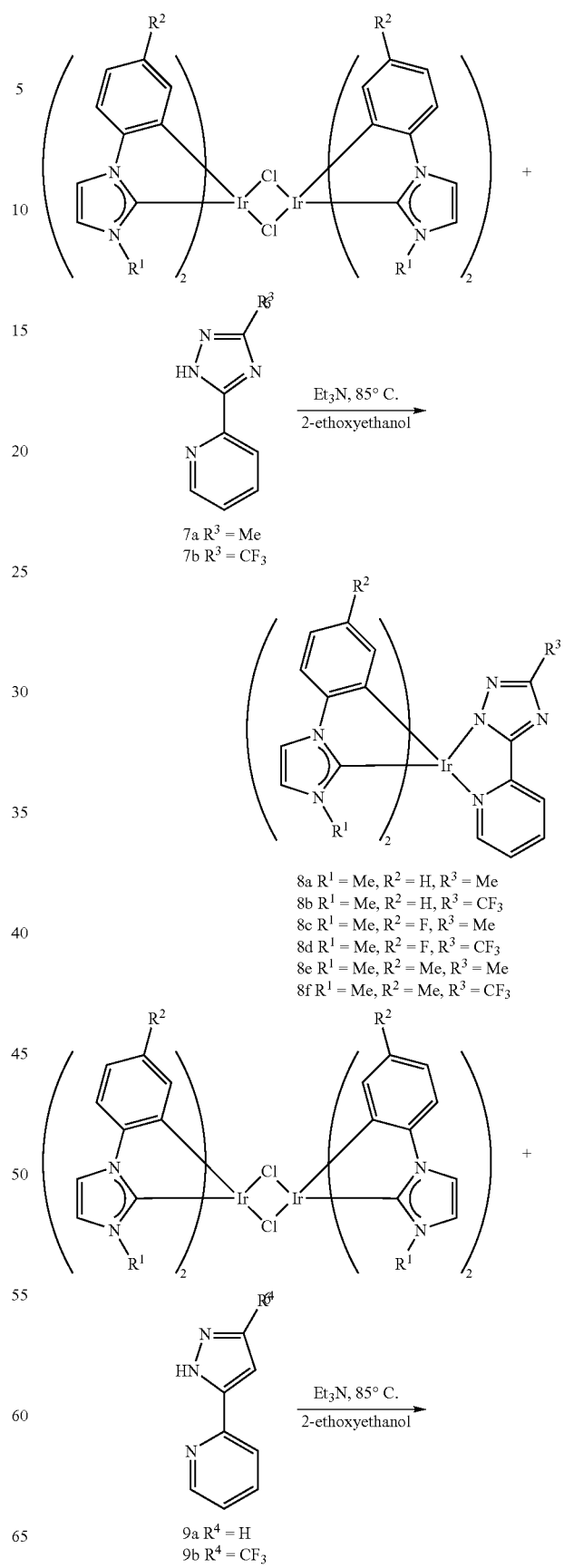

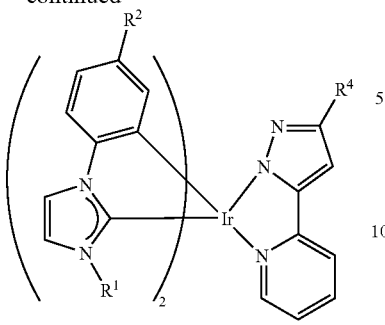

10a R¹ = Me, R² = H, R⁴ = H
10b R¹ = Me, R² = H, R⁴ = CF₃
10c R¹ = Me, R² = F, R⁴ = H
10d R¹ = Me, R² = F, R⁴ = CF₃
10e R¹ = Me, R² = Me, R⁴ = H
10f R¹ = Me, R² = Me, R⁴ = CF₃

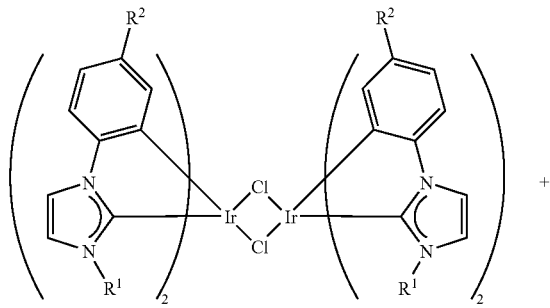

6

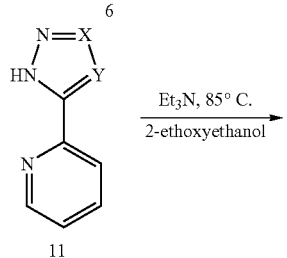

11

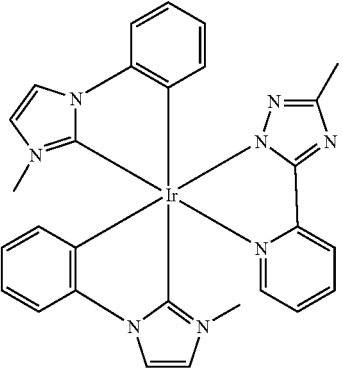

12a R¹ = Me, R² = H, X = N, Y = C
12b R¹ = Me, R² = H, X = N, Y = N
12c R¹ = Me, R² = F, X = N, Y = C
12d R¹ = Me, R² = F, X = N, Y = N
12e R¹ = Me, R² = Me, X = N, Y = C
12f R¹ = Me, R² = Me, X = N, Y = N

In the case of compound 9b, compound 6 (50 mg, 0.0434 mmole) is first added in a reactor along with compound 9b (21 mg, 0.0955 mmole) and triethylamine (14 mg, 0.0955 mmole). Next, add 2 ml 2-ethoxyethanol as the solvent, and put the reaction system in a 120° C. oil-bath for 10 hours. Slow precipitation of solids will be observed. After complete reaction, apply direct filtration to the product and wash the obtained solid with methanol. Finally, re-crystallize the solid obtained with ethanol to obtain the desired final product 10d, which is white solid, with a yield of 71% (43 mg).

Example 2

Iridium(III)bis(1-phenyl-3-methylimdazolin-2-ylidene-C, C²')(2-(5-Methyl-2H-1,2,4-triazol-3-yl)-pyridine)

[Will be referred to as Ir(pmi)₂(mptz) hereinafter]

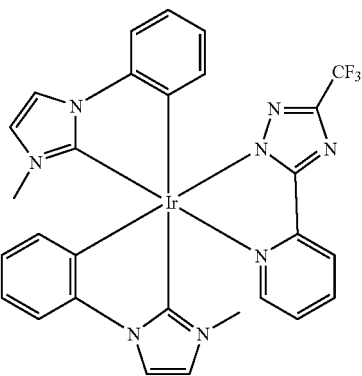

¹H NMR (CD₂Cl₂, 400 MHz) δ 8.04 (d, 1H, CH—N), 7.94 (d, 1H), 7.73 (td, 1H), 7.45 (d, 1H), 7.43 (d, 1H), 7.13-7.11 (m, 2H), 6.96-6.89 (m, 3H), 6.85 (d, 2H), 6.71-6.63 (m, 2H), 6.53 (d, 1H), 6.43 (d, 1H), 3.09 (s, 3H), 2.99 (s, 3H), 2.33 (s, 3H).

Example 3

Iridium(III)bis(1-phenyl-3-methylimdazolin-2-ylidene-C, C²')(2-(5-Trifloromethyl-2H-1,2,4-triazol-3-yl)-pyridine)

[Will be referred to as Ir(pmi)₂(tfptz) hereinafter]

¹H NMR (CD₂Cl₂, 400 MHz) δ 8.19 (d, 1H, CH—N), 7.96 (d, 1H), 7.75 (t, 1H), 7.39 (d, 2H), 7.08-7.02 (m, 2H), 6.91-6.78 (m, 5H), 6.70-6.61 (m, 2H), 6.48 (d, 1H), 6.39 (d, 1H), 3.08 (s, 3H), 2.95 (s, 3H).

Example 4

Iridium(III)bis(1-phenyl-3-methylimdazolin-2-ylidene-C, C²')(2-(2H-Pyrazol-3-yl)-pyridine)

[Will be referred to as Ir(pmi)$_2$(pypz) hereinafter]

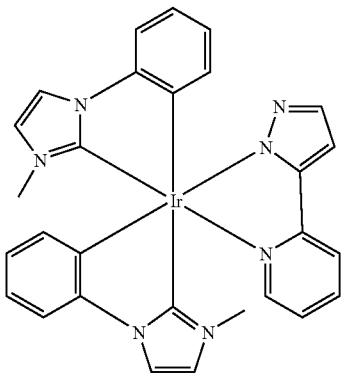

$^1$H NMR (CD$_2$Cl$_2$, 400 MHz) δ 7.90-7.92 (m, 1H, CH—N), 7.59-7.68 (m, 2H), 7.46 (d, 1H), 7.42 (dd, 2H), 7.11 (td, 2H), 6.85-6.93 (m, 2H), 6.83 (d, 1H), 6.82 (d, 1H), 6.76-6.80 (m, 1H), 6.72 (d, 1H), 6.69 (td, 1H), 6.63 (td, 1H), 6.48 (d, 1H), 6.56 (dd, 1H), 6.45 (dd, 1H), 3.04 (s, 3H), 2.98 (s, 3H); HRMS Calcd. for C$_{28}$H$_{24}$IrN$_7$ 651.1722, Found: 651.1725.

Example 5

Iridium(III)bis(1-phenyl-3-methylimdazolin-2-ylidene-C, C²')(2-(5-Trifluoromethyl-2H-pyrazol-3-yl)-pyridine)

[Will be referred to as Ir(pmi)$_2$(tfpypz) hereinafter]

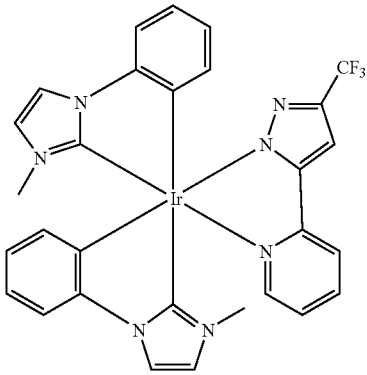

$^1$H NMR (CD$_2$Cl$_2$, 400 MHz) δ 7.95-7.93 (m, 1H, CH—N), 7.72-7.65 (m, 2H), 7.47 (d, 1H), 7.42 (d, 2H), 7.13-7.10 (m, 2H), 6.98 (s, 1H), 6.82 (d, 1H), 6.94-6.85 (m, 5H), 6.71-6.64 (m, 2H), 6.50 (dd, 1H), 6.42 (dd, 1H), 3.01 (s, 3H), 3.00 (s, 3H); HRMS Calcd. for C$_{29}$H$_{23}$F$_3$IrN$_7$ 719.1596, Found: 719.1592.

Example 6

Iridium(III)bis(1-phenyl-3-methylimdazolin-2-ylidene-C, C²')(5-(pyridine-2-yl)-1H-triazolate)

[Will be referred to as Ir(pmi)$_2$(pytz) hereinafter]

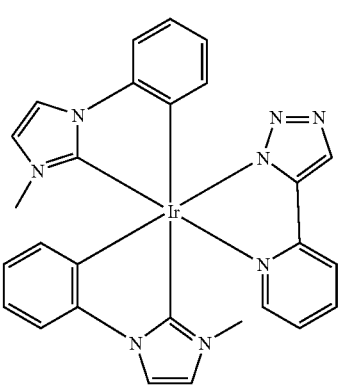

$^1$H NMR (CD$_2$Cl$_2$, 400 MHz) δ 8.15 (s, 1H), 7.95-7.94 (m, 1H), 7.77-7.68 (m, 2H), 7.46 (d, 1H), 7.44 (d, 1H), 7.15-7.12 (m, 2H), 6.96-6.84 (m, 5H), 6.73-6.65 (m, 2H), 6.55 (dd, 1H), 6.47 (dd, 1H), 3.00 (s, 3H), 2.99 (s, 3H); HRMS Calcd. for C$_{27}$H$_{23}$IrN$_8$ 652.1675, Found: 652.1677.

Example 7

Iridium(III)bis(1-phenyl-3-methylimdazolin-2-ylidene-C, C²')(2-(1H-tetrazol-5-yl)pyridine)

[Will be referred to as Ir(pmi)$_2$(pytrz) hereinafter]

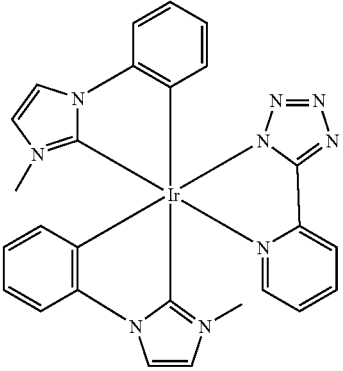

$^1$H NMR (CD$_2$Cl$_2$, 400 MHz) δ 8.33 (d, 1H), 8.02 (d, 1H), 7.86 (td, 1H), 7.46 (d, 1H), 7.44 (d, 1H), 7.16-7.10 (m, 3H), 6.98-6.90 (m, 2H), 6.87 (d, 1H), 6.84 (d, 1H), 6.74-6.66 (m, 2H), 6.53 (dd, 1H), 6.45 (dd, 1H), 2.98 (s, 3H), 2.95 (s, 3H); HRMS Calcd. for C$_{26}$H$_{22}$IrN$_9$ 653.1627, Found: 653.1627.

Example 8

Iridium(III)bis(1-(4-fluorophenyl)-3-methylimdazo-lin-2-ylidene-C, C$^{2'}$) Chloride Dimer

[Will be referred to as Ir(fpmi)$_2$ dimer hereinafter]

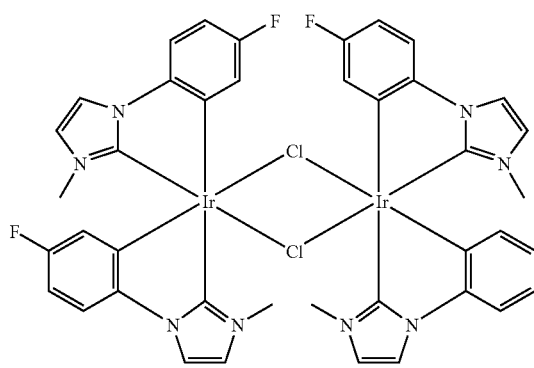

$^1$H NMR (CD$_2$Cl$_2$, 400 MHz) δ 7.56 (d, 4H), 7.19 (d, 4H), 6.96 (dd, 4H), 6.46 (td, 4H), 5.75 (dd, 4H), 3.87 (s, 12H)

Example 9

Iridium(III)bis(1-(4-fluorophenyl)-3-methylimdazo-lin-2-ylidene-C, C$^{2'}$)(2-(5-Methyl-2H-1,2,4-triazol-3-yl)-pyridine)

[Will be referred to as Ir(fpmi)$_2$(mptz) hereinafter]

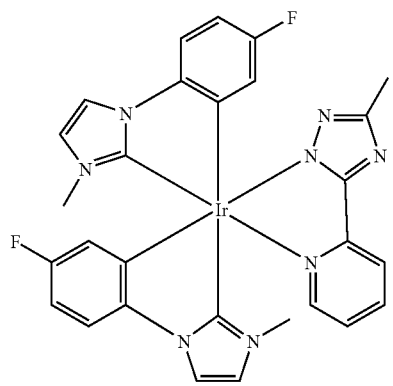

$^1$H NMR (CD$_2$Cl$_2$, 400 MHz) δ 8.05 (d, 1H, CH—N), 7.93 (d, 1H), 7.75 (td, 1H), 7.42 (d, 1H), 7.39 (d, 1H), 7.12-7.06 (m, 2H), 6.99-6.96 (m, 1H), 6.86 (d, 2H), 6.66-6.57 (m, 2H), 6.19 (dd, 1H), 6.08 (dd, 1H), 3.08 (s, 3H), 2.98 (s, 3H), 2.33 (s, 3H).

Example 10

Iridium(III) bis(1-(4-fluorophenyl)-3-methylimdazo-lin-2-ylidene-C, C$^{2'}$)(2-(5-Trifluoromethyl-2H-1,2,4-triazol-3-yl)-pyridine)

[Will be referred to as Ir(fpmi)$_2$(tfptz) hereinafter]

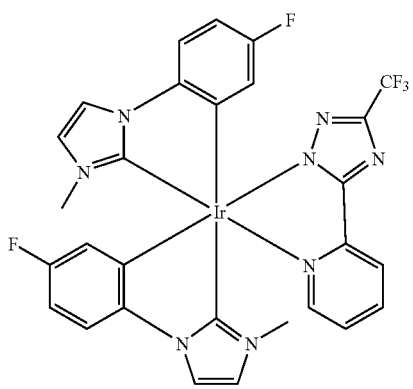

$^1$H NMR (CD$_2$Cl$_2$, 400 MHz) δ 8.19-8.17 (m, 1H, CH—N), 7.99 (d, 1H), 7.84 (td, 1H), 7.44 (d, 2H), 7.41 (d, 2H), 7.13-7.09 (m, 3H), 6.88 (d, 2H), 6.68-6.56 (m, 2H), 6.17 (dd, 1H), 6.06 (dd, 1H), 3.04 (s, 3H), 2.97 (s, 3H).

Example 11

Iridium(III)bis(1-(4-fluorophenyl)-3-methylimdazo-lin-2-ylidene-C, C$^{2'}$) (2-(2H-Pyrazol-3-yl)-pyridine)

[Will be referred to as Ir(fpmi)$_2$(pypz) herein after]

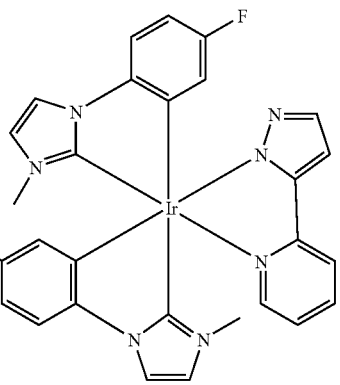

$^1$H NMR (CD$_2$Cl$_2$, 400 MHz) δ 7.90 (dd, 1H, CH—N), 7.68-7.61 (m, 2H), 7.47 (d, 1H), 7.40 (dd, 2H), 7.11-7.04 (m, 2H), 6.85-6.79 (m, 3H), 6.71 (d, 1H), 6.64-6.54 (m, 2H), 6.23 (dd, 1H), 6.09 (dd, 1H), 3.03 (s, 3H), 2.97 (s, 3H); HRMS Calcd. for C$_{28}$H$_{24}$F$_2$IrN$_7$ 689.1690, Found: 689.1687.

Example 12

Iridium(III)bis(1-(4-fluorophenyl)-3-methylimdazolin-2-ylidene-C, C²')(2-(5-Trifluoromethyl-2H-pyrazol-3-yl)-pyridine)

[Will be referred to as Ir(fpmi)$_2$(tfpypz) hereinafter]

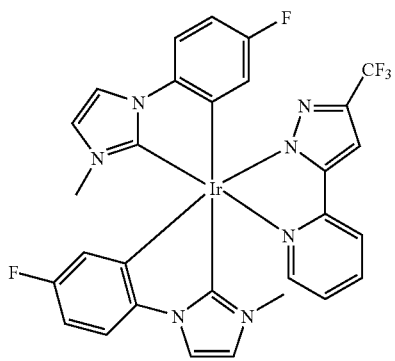

$^1$H NMR (CD$_2$Cl$_2$, 400 MHz) δ 7.93 (d, 1H, CH—N), 7.71-7.69 (m, 2H), 7.43 (d, 1H), 7.39 (dd, 2H), 7.11-7.07 (m, 2H), 6.98 (s, 1H), 6.92-6.90 (m, 1H), 6.89-6.85 (m, 2H), 6.63-6.59 (m, 2H), 6.16 (dd, 1H), 6.06 (dd, 1H), 3.00 (s, 3H), 2.99 (s, 3H); HRMS Calcd. for C$_{29}$H$_{21}$F$_5$IrN$_7$ 755.1408, Found: 755.1406.

Example 13

Iridium(III) bis(1-(4-fluorophenyl)-3-methylimdazolin-2-ylidene-C, C²') (5-(pyridine-2-yl)-1H-triazolate)

[Will be referred to as Ir(fpmi)$_2$(pytz) hereinafter]

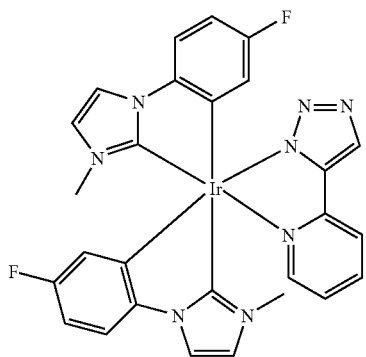

$^1$H NMR (CD$_2$Cl$_2$, 400 MHz) δ 8.15 (s, 1H), 7.94-7.92 (m, 1H), 7.77-7.69 (m, 2H), 7.43 (d, 1H), 7.40 (d, 1H), 7.13-7.07 (m, 2H), 6.93-6.90 (m, 1H), 6.86 (d, 1H), 6.85 (d, 1H), 6.67-6.58 (m, 2H), 6.22 (dd, 1H), 6.11 (dd, 1H), 2.99 (s, 3H), 2.98 (s, 3H); HRMS Calcd. for C$_{27}$H$_{21}$F$_2$IrN$_8$ 688.1486, Found: 688.1486.

Example 14

Iridium(III)bis(1-(4-fluorophenyl)-3-methylimdazolin-2-ylidene-C, C²') (2-(1H-tetrazol-5-yl)pyridine)

[Will be referred to as Ir(fpmi)$_2$(pytrz) hereinafter]

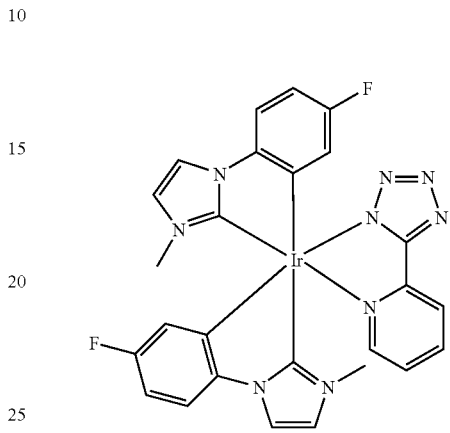

$^1$H NMR (CD$_2$Cl$_2$, 400 MHz) δ 8.35-8.33 (m, 1H), 8.03-8.01 (m, 1H), 7.89 (td, 1H), 7.43 (d, 1H), 7.42 (d, 1H), 7.18-7.09 (m, 3H), 6.88 (d, 1H), 6.85 (d, 1H), 6.69-6.60 (m, 2H), 6.20 (dd, 1H), 6.09 (dd, 1H), 2.97 (s, 3H), 2.94 (s, 3H); HRMS Calcd. for C$_{26}$H$_{20}$F$_2$IrN$_9$ 689.1439, Found: 689.1441.

Example 15

Iridium(III)bis(1-(4-methylphenyl)-3-methylimdazolin-2-ylidene-C, C²') Chloride Dimer

[Will be referred a Ir(mpmi)$_2$ dimer hereinafter]

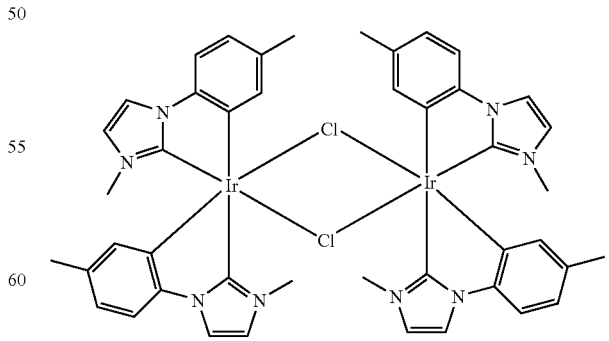

$^1$H NMR (CD$_2$Cl$_2$, 400 MHz) δ 7.47 (d, 4H), 7.05 (d, 4H), 6.77 (d, 4H), 6.42 (dd, 4H), 5.96 (s, 4H), 3.84 (s, 12H), 1.95 (s, 12H)

Example 16

Iridium(III)bis(1-(4-methylphenyl)-3-methylimdazolin-2-ylidene-C, C²')(2-(5-Methyl-2H-1,2,4-triazol-3-yl)-pyridine)

[Will be referred to as Ir(mpmi)$_2$(mptz) hereinafter]

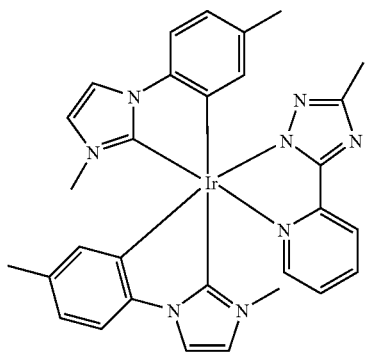

$^1$H NMR (CD$_2$Cl$_2$, 400 MHz) δ 8.02 (d, 1H, CH—N), 7.96 (d, 1H), 7.72 (td, 1H), 7.42 (d, 1H), 7.39 (d, 1H), 7.02 (d, 1H), 7.00 (d, 1H), 6.96-6.93 (m, 1H), 6.83 (d, 2H), 6.74-6.69 (m, 2H), 6.30 (d, 1H), 6.20 (d, 1H), 3.08 (s, 3H), 2.97 (s, 3H), 2.33 (s, 3H), 2.14 (s, 3H), 2.13 (s, 3H).

Example 17

Iridium(III) bis(1-(4-methylphenyl)-3-methylimdazolin-2-ylidene-C, C²') (2-(5-Trifluoromethyl-2H-1,2,4-triazol-3-yl)-pyridine)

[Will be referred as Ir(mpmi)$_2$(tfptz) hereinafter]

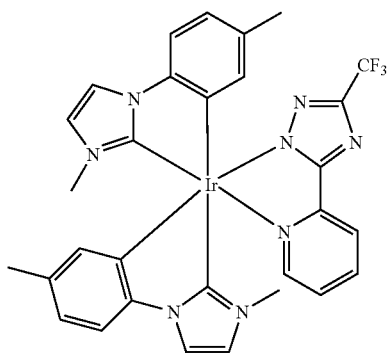

$^1$H NMR (CD$_2$Cl$_2$, 400 MHz) δ 8.16 (d, 1H, CH—N), 8.02 (d, 1H), 7.80 (td, 1H), 7.44 (d, 1H), 7.40 (d, 1H), 7.09-7.02 (m, 3H), 6.86-6.85 (m, 2H), 6.76-6.72 (m, 2H), 6.28 (s, 1H), 6.19 (s, 1H), 3.04 (s, 3H), 2.96 (s, 3H), 2.15 (s, 3H), 2.14 (s, 3H).

Example 18

Iridium(III)bis(1-(4-methylphenyl)-3-methylimdazolin-2-ylidene-C, C²') (2-(2H-Pyrazol-3-yl)-pyridine)

[Will be referred to as Ir(mpmi)$_2$(pypz) hereinafter]

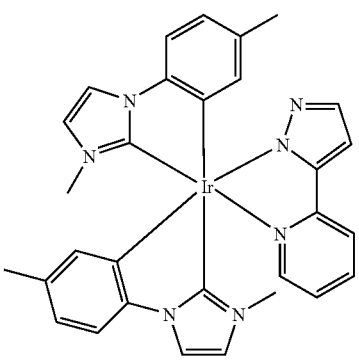

$^1$H NMR (CD$_2$Cl$_2$, 400 MHz) δ 7.93 (d, 1H, CH—N), 7.67-7.59 (m, 2H), 7.45 (d, 1H), 7.40 (d, 1H), 7.39 (d, 1H), 7.01 (d, 2H), 7.00 (d, 2H), 6.82-6.77 (m, 3H), 6.73-6.68 (m, 2H), 6.71 (d, 2H), 6.35 (s, 1H), 6.22 (s, 1H), 3.01 (s, 3H), 2.97 (s, 3H), 2.15 (s, 3H), 2.13 (s, 3H).

Example 19

Iridium(III)bis(1-(4-methylphenyl)-3-methylimdazolin-2-ylidene-C, C²') (2-(5-Trifluoromethyl-2H-pyrazol-3-yl)-pyridine)

[Will be referred to as Ir(mpmi)2(tfpypz) hereinafter]

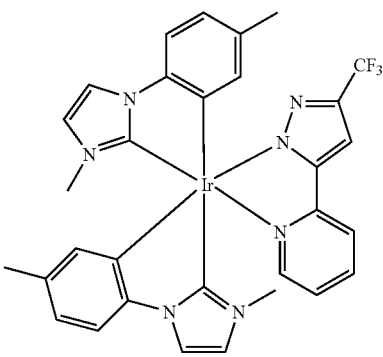

$^1$H NMR (CD$_2$Cl$_2$, 400 MHz) δ 7.96 (d, 1H, CH—N), 7.70-7.64 (m, 2H), 7.43 (d, 1H), 7.39 (d, 1H), 7.02 (d, 2H), 7.00 (d, 2H), 6.96 (s, 1H), 6.90-6.86 (m, 1H), 6.83 (d, 2H), 6.74-6.70 (m, 2H), 6.28 (s, 1H), 6.19 (s, 1H), 2.99 (s, 3H), 2.98 (s, 3H), 2.15 (s, 3H), 2.14 (s, 3H).

Example 20

Iridium(III)bis(1-(4-methylphenyl)-3-methylimdazo-lin-2-ylidene-C, C²')(5-(pyridine-2-yl)-1H-triazolate)

[Will be referred to as Ir(mpmi)₂(pytz) hereinafter]

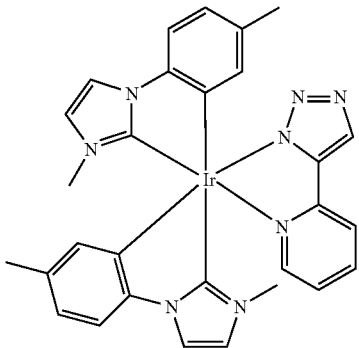

$^1$H NMR (CD$_2$Cl$_2$, 400 MHz) δ 8.14 (s, 1H), 7.95 (d, 1H), 7.75-7.66 (m, 2H), 7.43 (d, 1H), 7.40 (d, 1H), 7.03 (d, 1H), 7.01 (d, 1H), 6.90-6.87 (m, 1H), 6.84-6.82 (m, 2H), 6.74-6.70 (m, 2H), 6.32 (s, 1H), 6.23 (s, 1H), 2.99 (s, 3H), 2.97 (s, 3H), 2.15 (s, 3H), 2.14 (s, 3H).

Example 21

Iridium(III)bis(1-(4-methylphenyl)-3-methylimdazo-lin-2-ylidene-C, C²') (2-(1H-tetrazol-5-yl)pyridine)

[Will be referred to as Ir(mpmi)₂(pytrz) hereinafter]

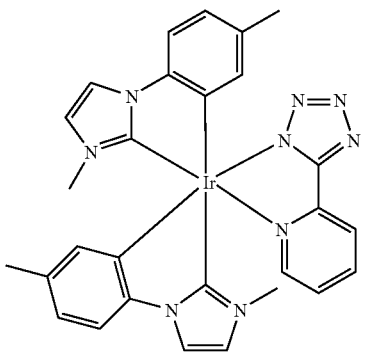

$^1$H NMR (CD$_2$Cl$_2$, 400 MHz) δ 8.32 (d, 1H), 8.03 (d, 1H), 7.85 (td, 1H), 7.43 (d, 1H), 7.41 (d, 1H), 7.14-7.11 (m, 1H), 7.05 (d, 1H), 7.03 (d, 1H), 6.84 (d, 1H), 6.82 (d, 1H), 6.77-6.72 (m, 2H), 6.30 (d, 1H), 6.21 (d, 1H), 2.97 (s, 3H), 2.93 (s, 3H), 2.15 (s, 3H), 2.14 (s, 3H).

The second embodiment of the present invention discloses an electroluminescent device which comprises a pair of electrodes and at least one organic layer disposed between said electrodes. The above at least one organic layer comprises an emitting layer and a transition metal complex with carbene ligand, wherein the transition metal complex is represented by the following formula:

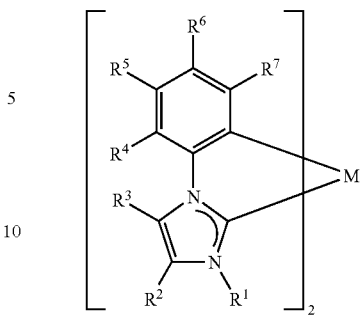

In the above formula, M is a transition metal and is selected from the group consisting of the following: ruthenium, rhodium, tungsten, rhenium, osmium, iridium, platinum; $R^1$ is selected from the group consisting of the following: C1-C20 alkyl group, C1-C20 cycloalkyl group, cycloalkenyl group, conjugated aromatic group, heterocyclic aromatic group; $R^2$~$R^7$ can be identical or different, and are independently selected from the group consisting of the following: H atom, halogen atom, C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group (—CN), nitro group, conjugated aromatic group, heterocyclic aromatic group, cycloalkenyl group.

Preferably, each of the pairs $R^2$-$R^3$, $R^4$-$R^5$, $R^5$-$R^6$, $R^6$-$R^7$ optionally forms one selected from the group consisting of the following: aromatic ring, heterocyclic aromatic group, cycloalkenyl group, or heterocyclic alkenyl group. The remaining ones of $R^2$~$R^7$ that do not form a cyclic group can be identical or different, and are independently selected from the group consisting of the following: H atom, halogen atom, C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group (—CN), nitro group, conjugated aromatic group, heterocyclic aromatic group.

The above aromatic ring, heterocyclic aromatic group, cycloalkenyl group, or heterocyclic alkenyl group can be a five-membered, six-membered or seven-membered ring. Moreover, they optionally comprises one or more substituent The substituent(s) can be identical or different, and are independently selected from the group consisting of the following: H atom, halogen atom such as fluorine (Fl), chlorine (Cl), bromine (Br), iodine (Id), aryl group, halogen substituted aryl group, halogen substituted aralkyl group, haloalkyl substituted aryl group, haloalkyl substituted aralkyl group, aryl substituted C1-C20 alkyl group, electron donating group such as C1-C20 alkyl group and C1-C20 cycloalkyl group (for example methyl, ethyl, butyl, and cyclohexyl group), C1-C20 alkoxy group, C1-C20 substituted amino group, substituted arylamino group (for example aniline), or electron withdrawing group such as halogen atoms, nitrile group, nitro group, carbonyl group, cyano group (—CN), halogen substituted C1-C20 alkyl group (for example trifluoromethyl group, CF$_3$), and heterocyclic ring.

In another preferred example of this embodiment, the transition metal complex is represented by the following formula:

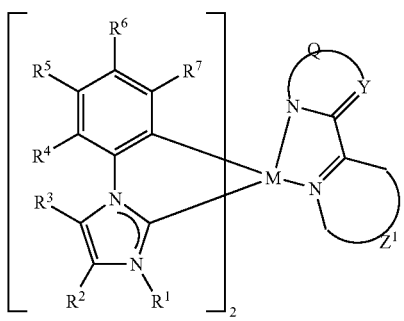

In the above formula, M is a transition metal and is selected from the group consisting of the following: ruthenium, rhodium, tungsten, rhenium, osmium, iridium, platinum; $R^1$ is selected from the group consisting of the following: C1-C20 alkyl group, C1-C20 cycloalkyl group, cycloalkenyl group, conjugated aromatic group, heterocyclic aromatic group; $R^2$~$R^7$ can be identical or different, and are independently selected from the group consisting of the following: H atom, halogen atom, C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group (—CN), nitro group, conjugated aromatic group, heterocyclic aromatic group, and cycloalkenyl group.

Preferably, each of the pairs $R^2$-$R^3$, $R^4$-$R^5$, $R^5$-$R^6$, $R^6$-$R^7$ optionally forms one selected from the group consisting of the following: aromatic ring, heterocyclic aromatic group, cycloalkenyl group, or heterocyclic alkenyl group. The above aromatic ring, heterocyclic aromatic group, cycloalkenyl group, or heterocyclic alkenyl group can be a five-membered, six-membered, or seven-membered ring. Moreover, they optionally comprises one or more substituents.

The remaining ones of $R^2$~$R^7$ which do not form a cyclic group can be identical or different, and are independently selected from the group consisting of the following: H atom, halogen atom, C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group (—CN), nitro group, conjugated aromatic group, heterocyclic aromatic group.

$Z^1$ can be any moiety that contributes to a nitrogen-containing heterocyclic aromatic group and nitrogen-containing heterocyclic alkenyl group, which can be a five-membered, six-membered, or seven-membered ring. Moreover, $Z^1$ optionally comprises one or more substituent. The substituent(s) can be identical or different, and are independently selected from the group consisting of the following: H atom, halogen atom such as fluorine (Fl), chlorine (Cl), bromine (Br), iodine (Id), aryl group, halogen substituted aryl group, halogen substituted aralkyl group, haloalkyl substituted aryl group, haloalkyl substituted aralkyl group, aryl substituted C1-C20 alkyl group, electron donating group such as C1-C20 alkyl group and C1-C20 cycloalkyl group (for example methyl, ethyl, butyl, and cyclohexyl group), C1-C20 alkoxy group, C1-C20 substituted amino group, substituted arylamino group (for example aniline), or electron withdrawing group such as halogen atoms, nitrile group, nitro group, carbonyl group, cyano group (—CN), halogen substituted C1-C20 alkyl group (for example trifluoromethyl group, $CF_3$), and heterocyclic ring.

Y is selected from the group consisting of the following: nitrogen (N), carbon (C), oxygen (O), sulfur (S); and Y optionally comprises a substituent. Q is a moiety comprising at least 2 atoms which contributes to a nitrogen-containing heterocycle, wherein Q comprises atom(s) selected from the group consisting of the following, or any combination thereof: nitrogen, carbon, oxygen, sulfur. The nitrogen-containing heterocycle optionally comprises one or more substituent. The substituent(s) can be identical or different, and are independently selected from the group consisting of the following: H atom, halogen atom such as fluorine (Fl), chlorine (Cl), bromine (Br), iodine (Id), aryl group, halogen substituted aryl group, halogen substituted aralkyl group, haloalkyl substituted aryl group, haloalkyl substituted aralkyl group, aryl substituted C1-C20 alkyl group, electron donating group such as C1-C20 alkyl group and C1-C20 cycloalkyl group (for example methyl, ethyl, butyl, and cyclohexyl group), C1-C20 alkoxy group, C1-C20 substituted amino group, substituted arylamino group (for example aniline), or electron withdrawing group such as halogen atoms, nitrile group, nitro group, carbonyl group, cyano group (—CN), halogen substituted C1-C20 alkyl group (for example trifluoromethyl group, $CF_3$), and heterocyclic ring.

In another preferred example of this embodiment, the transition metal complex is represented by the following formula:

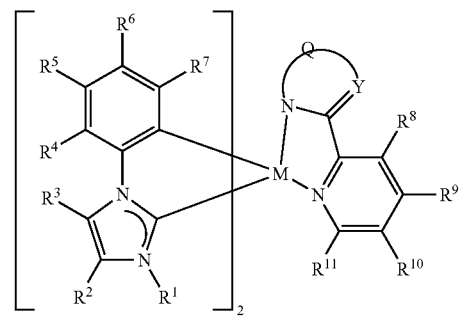

In the above formula, M is a transition metal and is selected from the group consisting of the following: ruthenium, rhodium, tungsten, rhenium, osmium, iridium, platinum; $R^1$ is selected from the group consisting of the following: C1-C20 alkyl group, C1-C20 cycloalkyl group, cycloalkenyl group, conjugated aromatic group, heterocyclic aromatic group; $R^2$~$R^{11}$ can be identical or different, and are independently selected from the group consisting of the following: H atom, halogen atom, C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group (—CN), nitro group, conjugated aromatic group, heterocyclic aromatic group, and cycloalkenyl group.

Preferably, each of the pairs $R^2$-$R^3$, $R^4$-$R^5$, $R^5$-$R^6$, $R^6$-$R^7$, $R^8$-$R^9$, $R^9$-$R^{10}$, $R^{10}$-$R^{11}$ optionally forms one selected from the group consisting of the following: aromatic ring, heterocyclic aromatic group, cycloalkenyl group, or heterocyclic alkenyl group. The above aromatic ring, heterocyclic aromatic group, cycloalkenyl group, or heterocyclic alkenyl group can be a five-membered, six-membered, or seven-membered ring. The remaining ones of $R^2$~$R^7$ which do not form a cyclic group can be identical or different, and are independently selected from the group consisting of the following: H atom, halogen atom, C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group (—CN), nitro group, conjugated aromatic group, heterocyclic aromatic group.

The above aromatic ring, heterocyclic aromatic group, cycloalkenyl group, or heterocyclic alkenyl group can optionally comprise one or more substituent, wherein the substituent(s) can be identical or different and is independently selected from the group consisting of the following: H atom, halogen atom, C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group (—CN), nitro group, conjugated aromatic group, heterocyclic aromatic group.

Y is selected from the group consisting of the following: nitrogen (N), carbon (C), oxygen (O), sulfur (S); and Y optionally comprises a substituent. Q is a moiety comprising at least 2 atoms which contributes to a nitrogen-containing heterocycle, wherein Q comprises atom(s) selected from the group consisting of the following, or any combination thereof: nitrogen, carbon, oxygen, sulfur. The nitrogen-containing heterocycle optionally comprises one or more substituent. The substituent(s) can be identical or different and are independently selected from the group consisting of the following: H atom, halogen atom such as fluorine (Fl), chlorine (Cl), bromine (Br), iodine (Id), aryl group, halogen substituted aryl group, halogen substituted aralkyl group, haloalkyl substituted aryl group, haloalkyl substituted aralkyl group, aryl substituted C1-C20 alkyl group, electron donating group such as C1-C20 alkyl group and C1-C20 cycloalkyl group (for example methyl, ethyl, butyl, and cyclohexyl group), C1-C20 alkoxy group, C1-C20 substituted amino group, substituted arylamino group (for example aniline), or electron withdrawing group such as halogen atoms, nitrile group, nitro group, carbonyl group, cyano group (—CN), halogen substituted C1-C20 alkyl group (for example trifluoromethyl group, $CF_3$), and heterocyclic ring.

The aryl group is one selected from the group consisting of the following: phenyl, naphthyl, diphenyl, anthryl, pyrenyl, phenanthryl, fluorenyl group or other type of multi-phenyl group. The cycloalkenyl group is one selected from the group consisting of the following: cyclohexene, cyclohexadiene, cyclopentene, cyclopentadiene or other type of cycloalkenyl group. The heterocyclic aromatic group is one selected from the group consisting of the following: pyrane, pyrroline, furan, benzofuran, thiophene, benzothiophene, pyridine, quinoline, isoquinoline, pyrazine, pyrimidine, pyrrole, pyrazole, imidazole, indole, thiazole, isothiazole, oxazole, isoxazole, benzothiazole, benzoxazole, phenanthroline or other type of heterocyclic aromatic group. The above nitrogen-containing heterocycle is one selected from the group consisting of the following: pyridine, quinoline, isoquinoline, pyrazine, pyrimidine, pyrrole, pyrazole, imidazole, indole, thiazole, isothiazole, oxazole, isoxazole, benzothiazole, benzoxazole, phenanthroline or other type of heterocyclic group.
General Process for Fabricating Electroluminescent Device An ITO glass with etched circuitry is placed in a cleaning liquid (neutral cleanser:deionized water=1:50) and then be applied supersonic oscillation for 5 minutes. Next, the ITO glass is brushed using a soft brush, and then is placed in 50 mL of mixture of deionized water and electronic grade acetone for another oscillation for 5 minutes. Then, the ITO glass is blown dry with nitrogen.

The cleaned ITO glass is placed in an ultraviolet-ozone machine for 5 minutes and then taken out and secured on a substrate with the ITO face down. The substrate is then put in an evaporator chamber for thin film formation. The chamber is vacuumed to a pressure of $5 \times 10^{-6}$ torr for the process to take place. The formation rate of the organic film is controlled at 1~2 Å/s; the formation rate of the metal film is controlled at 5 Å/s for magnesium film and 0.5 Å/s for silver film, wherein ratio of magnesium to silver in the alloid is 10:1, and the total thickness of the metal film is 55 nm. Another silver film of 100 nm thickness is formed atop of the metal film for protection. If the metal film system is selected to be lithium floride/aluminum (LiF/Al), a LiF film is first formed at a rate of 0.1 Å/s til the thickness reaches 1 nm, then an aluminum film of 100 nm thickness if formed atop for protection.

During the formation process, the rotational rate of the evaporator is set to be 20 rpm. A 20 minute window is waited after the process has been completed in order for the metal electrode to cool down. Then the chamber pressure is brought back to normal.

After the eluminescent device is completed, the EL spectra and CIE coordination of the device is measured using Hitach F-4500 spectra scan spectrometer; other characteristics such as the current, voltage and brightness of the device is measured using Keithley 2400 programmable voltage-current source. The measurement is carried out at atmosphere pressure and room temperature (about 20° C.).

Example 22

Performance of the Electroluminescent Device

Comparison of the performance of several electroluminescent devices constructed according to this embodiment will be presented. It is noted that this example is not to limit the scope of the present invention, which should be determined in accordance with the claims.
Sample Device Structures The layered structure of the devices tested in this example is shown in FIG. 1. The tested devices comprises the above ITO glass as the substrate and the disclosed transition metal complex with carbene ligand as the guest emitting material. Impact of different electrode materials, host emitting materials and charge carrier materials on the performance of the electroluminescent devices are measured.

Tested electrode materials include Mg:Ag/Ag and LiF/Al; tested host emitting materials include mCP(3,5-Bis (N-carbazolyl)benzene), CzSi(9-(4-tert-butylphenyl)-3,6-bis (triphenylsilyl)-9H-carbazole), BSB (4,4'-bis-triphenylsilanyl-biphenyl), and UGH2 (p-bis(triphenyl-silyly)benzene), these materials have high energy gap and triplet energy, which is able to prevent energy transferred back to the host material from the triplet. When using BSB and UGH2 as the host emitting material, an mCP layer is added to lower the energy gap of hole injection. Test charge carrier materials include BCP (2,9-Dimethyl-4,7-diphenyl-[1,10]phenanthroline) and TPBI (2,9-Dimethyl-4,7-diphenyl-[1,10]phenanthroline) which can be used for the hole stopper layer or simultaneous hole stopper layer and electron transport layer. This is because the above charge carrier material BCP, TPBI or mCP which has a wide energy gap can inhibit the high energy triplet exciton diffuses from the host emitting layer to the charge carrier layer.

Figure 2:
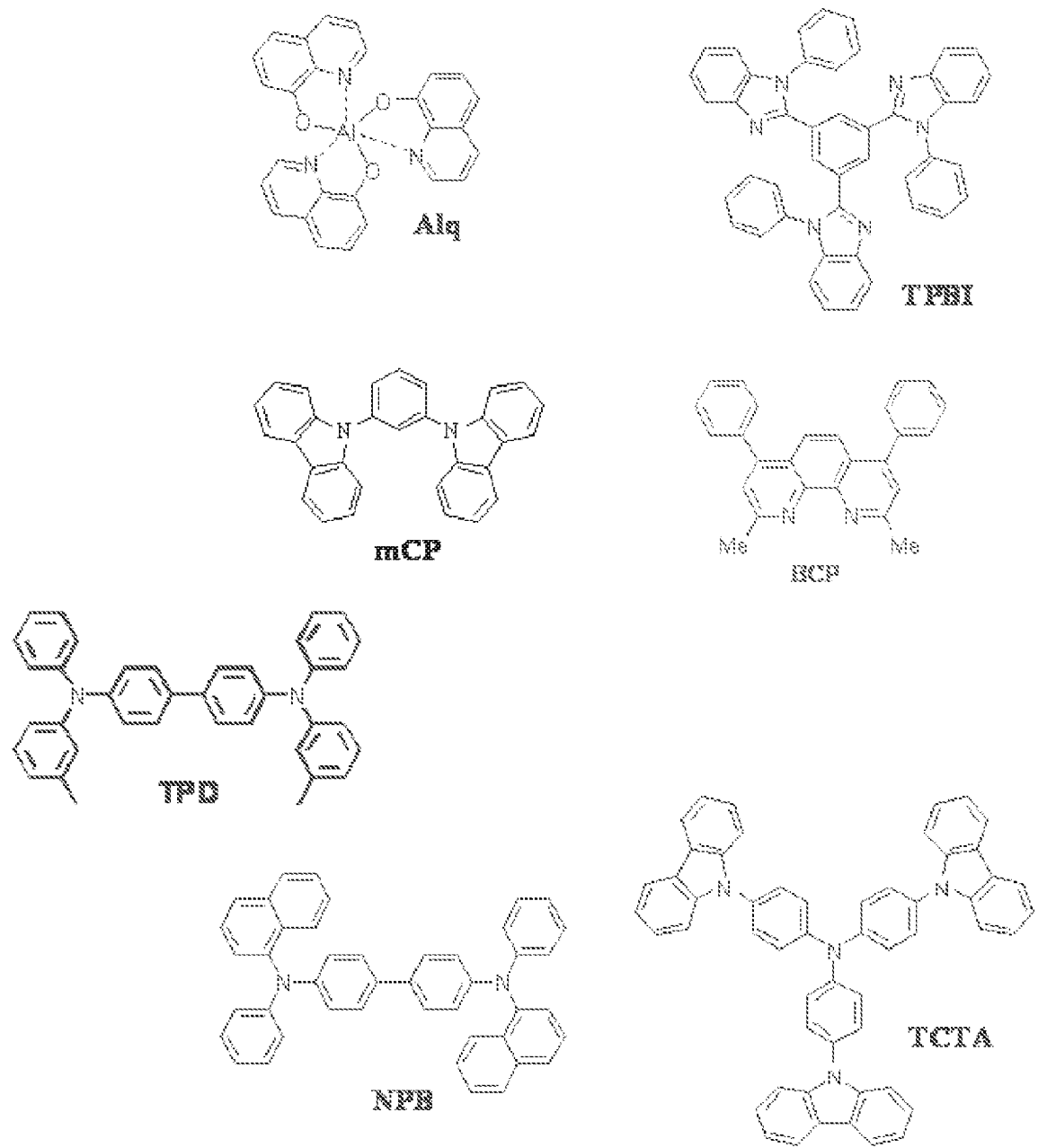
FIG. 2 is a schematic of the chemical structure of the materials for fabricating the electroluminescent device.

The structure of the materials mentioned above is shown in FIG. 2. Detailed structure of the tested devices are as follows:
Device A: ITO/TCTA (40)/complex:mCP (7%) (30)/BCP (15)/Alq (30)/Mg:Ag/Ag
Device B: ITO/NPB (20)/TCTA (10)/complex:CzSi (8%) (30)/BCP (15)/Alq (30)/Mg:Ag/Ag
Device C: ITO/TCTA (30)/mCP (20)/complex:BSB (7%) (30)/BCP (10)/Alq (30)/Mg:Ag/Ag
Device D: NPB (20)/TCTA (10)/complex:CzSi (8%) (30)/TPBI (30)/LiF/Al
Device E: ITO/TCTA (40)/mCP (15)/complex:UGH2 (7%) (30)/BCP (40)/Mg:Ag/Ag
Device F: ITO/TPD (20)/mCP (20)/complex:UGH2 (7%) (30)/BCP (40)/LiF/Al In the above devices, the anode is Mg:Ag(55)/Ag(100) or LiF(1)/Al(100). The thickness is measured in nm.

Comparison of the Device Performance

Comparison of the performance of the electroluminescent devices is shown in Table 1:

On the other hand, the device with the most blue Ir(fpmi)$_2$(tfpypz) complex must work with a high triplet energy host emitting material, therefore the complex Ir(fpmi)$_2$(tfpypz) can render higher device efficiency only when working with silicon-based host emitting material such as BSB nad UGH2. Moreover, as shown in the table, in device F, the complex Ir(fpmi)$_2$(tfpypz) can render a CIE coordination of (0.14, 0.09) and a device efficiency approaching 5%.

The foregoing description is not intended to be exhaustive or to limit the invention to the precise forms disclosed. Obvious modifications or variations are possible in light of the above teachings. In this regard, the embodiment or embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the inventions as determined by the appended claims when interpreted in accordance with the breath to which they are fairly and legally entitled.

TABLE 1

Comparison of device performance

| Device | Vd$^a$ (V) | ext$^c$ (%) | Lum$^b$ (cd/m$^2$) | Current Density at Maximum Illuminance (mA/cm$^2$) | c$^d$ cd/A | p$^e$ (lm/W) | C.I.E (8 V) (x, y) | Max Peak (nm) |
|---|---|---|---|---|---|---|---|---|
| | | | | Ir(pmi)$_2$(pypz) | | | | |
| A | 4.3 | 8.4 (9.0) | 25738 (14.5) | 362.4 | 16.9 (9.0) | 6.0 (8.5) | (0.14, 0.31) | 486 |
| B | 4.2 | 7.9 (10.0) | 13955 (16.0) | 398.8 | 13.1 (10.0) | 4.2 (9.5) | (0.15, 0.32) | 486 |
| | | | | Ir(pmi)$_2$(tfpypz) | | | | |
| A | 6.0 | 5.6 (10.0) | 7875 (16.0) | 249.8 | 10.1 (10.0) | 3.2 (9.5) | (0.14, 0.26) | 478 |
| B | 5.4 | 5.3 (11.0) | 6346 (20.0) | 193.2 | 9.8 (11.0) | 3.0 (10.0) | (0.14, 0.26) | 480 |
| C | 6.6 | 3.4 (12.5) | 5721 (18.0) | 386.3 | 5.5 (12.5) | 1.4 (12.0) | (0.14, 0.22) | 476 |
| | | | | Ir(fpmi)$_2$(pypz) | | | | |
| B | 4.1 | 8.0 (7.0) | 9669 (15.0) | 298.7 | 12.6 (7.0) | 5.7 (6.5) | (0.14, 0.21) | 472 |
| C | 4.6 | 7.5 (8.0) | 8428 (13.5) | 375.2 | 10.0 (8.0) | 4.0 (7.5) | (0.14, 0.16) | 466 |
| D | 5.2 | 6.2 (7.5) | 6245 (14.5) | 321.4 | 7.9 (7.5) | 3.5 (7.0) | (0.14, 0.15) | 464 |
| E | 6.8 | 8.8 (9.0) | 3759 (20.0) | 68.8 | 16.8 (9.0) | 5.9 (9.0) | (0.15, 0.27) | 478 |
| | | | | Ir(fpmi)$_2$(tfpypz) | | | | |
| B | 5.3 | 3.1 (8.5) | 2193 (13.0) | 236.5 | 3.0 (8.5) | 1.2 (7.5) | (0.14, 0.11) | 458 |
| C | 6.2 | 4.9 (9.5) | 3319 (17.0) | 342.3 | 5.7 (9.5) | 1.9 (9.5) | (0.14, 0.14) | 464 |
| D | 5.2 | 2.6 (7.5) | 2090 (13.0) | 251.7 | 2.2 (7.5) | 0.9 (7.5) | (0.15, 0.10) | 452 |
| E | 6.2 | 4.4 (10.0) | 3597 (16.0) | 222.6 | 5.4 (10.0) | 1.8 (9.0) | (0.14, 0.14) | 460 |
| F | 6.1 | 4.6 (9.5) | 2671 (16.5) | 272.4 | 2.7 (9.5) | 0.98 (8.5) | (0.14, 0.09) | 454 |

As shown, the bule Ir(fpmi)$_2$(pypz) complex renders a device efficiency of greater than 7%, and its Y CIE coordinates is lower than 0.20 and is located in the pure blue region (0.14, 0.16).

It is understood that several modifications, changes, and substitutions are intended in the foregoing disclosure and in some instances some features of the invention will be employed without a corresponding use of other features.

Accordingly, it is appropriate that the appended claims be construed broadly and in a manner consistent with the scope of the invention.

What is claimed is:

1. A transition metal complex with carbene ligand, represented by the following formula:

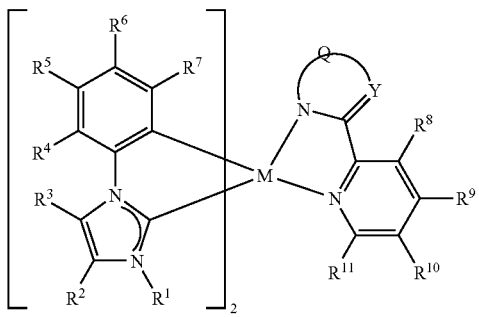

wherein M is a transition metal and is selected from the group consisting of the following: ruthenium, rhodium, tungsten, rhenium, osmium, iridium, platinum;

$R^1$ is selected from the group consisting of the following: C1-C20 alkyl group, C1-C20 cycloalkyl group, cycloalkenyl group, conjugated aromatic group, heterocyclic aromatic group;

$R^2$~$R^7$ can be identical or different, and are independently selected from the group consisting of the following: H atom, halogen atom, C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group (—CN), nitro group, conjugated aromatic group, heterocyclic aromatic group, cycloalkenyl group;

Q is a moiety comprising at least 2 atoms, contributing to a nitrogen-containing heterocycle, wherein Q comprises atom(s) selected from the group consisting of the following, or any combination thereof: nitrogen, carbon, oxygen, sulfur, and said nitrogen-containing heterocycle optionally comprises one or more substituent, wherein the substitutent(s) on said nitrogen-containing heterocycle partly constructed by Q can be identical or different, and are independently selected from the group consisting of the following: H atom, halogen atom, C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group(—CN), nitro group, conjugated aromatic group, heterocyclic aromatic group;

Y is selected from the group consisting of the following: nitrogen(N), carbon(C), oxygen(O), sulfur(S), wherein Y further comprises a substituent selected from the group consisting of the following: H atom, halogen atom, C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group(—CN), nitro group, conjugated aromatic group, heterocyclic aromatic group; and $R^8$~$R^{11}$ can be identical or different, and are independently selected from the group consisting of the following: H atom, halogen atom, C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group (—CN), nitro group, conjugated aromatic group, heterocyclic aromatic group, cyclo alkenyl group.

2. The transition metal complex according to claim 1, wherein said nitrogen-containing heterocycle is selected from the group consisting of the following: pyridine, quinoline, isoquinoline, pyrazine, pyrimidine, pyrrole, pyrazole, imidazole, indole, thiazole, isothiazole, oxazole, isoxazole, benzothiazole, benzoxazole, phenanthroline.

3. The transition metal complex according to claim 1, wherein said aryl group is selected from the group consisting of the following: phenyl, naphthyl, diphenyl, anthryl, pyrenyl, phenanthryl, and fluorenyl group.

4. The transition metal complex according to claim 1, wherein said cycloalkenyl group is selected from the group consisting of the following: cyclohexene, cyclohexadiene, cyclopentene, cyclopentadiene.

5. The transition metal complex according to claim 1, wherein said heterocyclic aromatic group is selected from the group consisting of the following: pyrane, pyrroline, furan, benzofuran, thiophene, benzothiophene, pyridine, quinoline, isoquinoline, pyrazine, pyrimidine, pyrrole, pyrazole, imidazole, indole, thiazole, isothiazole, oxazole, isoxazole, benzothiazole, benzoxazole, phenanthroline.

6. The transition metal complex according to claim 1, with the forming method thereof as the following:

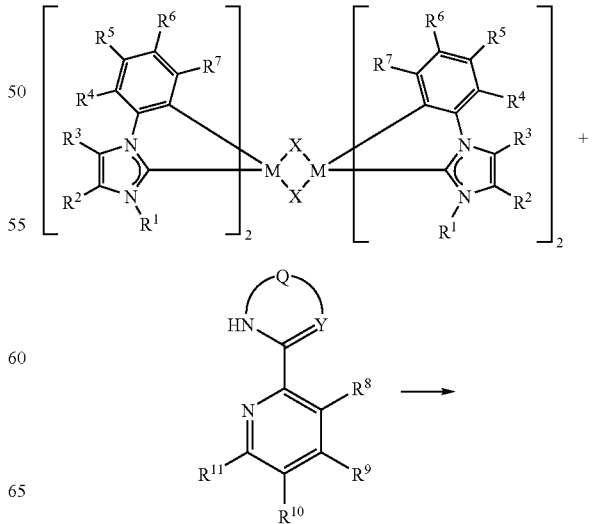

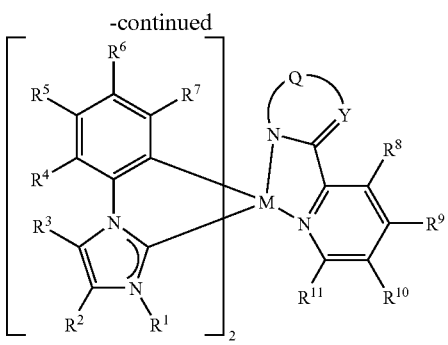

wherein X is a halogen atom.

7. An electroluminescent device, comprising a pair of electrodes and at least one organic layer disposed between said electrodes, said at least one organic layer comprises an emitting layer and a transition metal complex with carbene ligand, wherein said transition metal complex is represented by the following formula:

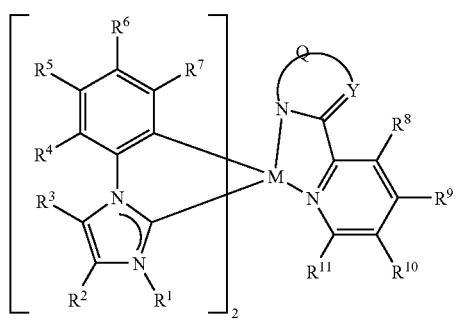

wherein M is a transition metal and is selected from the group consisting of the following: ruthenium, rhodium, tungsten, rhenium, osmium, iridium, platinum;

$R^1$ is selected from the group consisting of the following: C1-C20 alkyl group, C1-C20 cycloalkyl group, cycloalkenyl group, conjugated aromatic group, heterocyclic aromatic group;

$R^2 \sim R^7$ can be identical or different, and are independently selected from the group consisting of the following: H atom, halogen atom, C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group (—CN), nitro group, conjugated aromatic group, heterocyclic aromatic group;

Q is a moiety comprising at least 2 atoms, contributing to a nitrogen-containing heterocycle, wherein Q comprises atom(s) selected from the group consisting of the following, or any combination thereof: nitrogen, carbon, oxygen, sulfur, and said nitrogen-containing heterocycle optionally comprises one or more substituent, wherein the substitutent(s) on said nitrogen-containing heterocycle partly constructed by Q can be identical or different, and are independently selected from the group consisting of the following: H atom, halogen atom, C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group(—CN), nitro group, conjugated aromatic group, heterocyclic aromatic group, cyclo alkenyl group;

Y is selected from the group consisting of the following: nitrogen(N), carbon(C), oxygen(O), sulfur(S), wherein Y further comprises a substituent selected from the group consisting of the following: H atom, halogen atom, C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group(—CN), nitro group, conjugated aromatic group, heterocyclic aromatic group; and $R^8 \sim R^{11}$ can be identical or different, and are independently selected from the group consisting of the following: H atom, halogen atom, C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group (—CN), nitro group, conjugated aromatic group, heterocyclic aromatic group, cyclo alkenyl group.

8. The electroluminescent device according to claim 7, wherein said nitrogen-containing heterocycle is selected from the group consisting of the following: pyridine, quinoline, isoquinoline, pyrazine, pyrimidine, pyrrole, pyrazole, imidazole, indole, thiazole, isothiazole, oxazole, isoxazole, benzothiazole, benzoxazole, phenanthroline.

9. The electroluminescent device according to claim 7, wherein said aryl group is selected from the group consisting of the following: phenyl, naphthyl, diphenyl, anthryl, pyrenyl, phenanthryl, and fluorenyl group.

10. The electroluminescent device according to claim 7, wherein said cycloalkenyl group is selected from the group consisting of the following: cyclohexene, cyclohexadiene, cyclopentene, cyclopentadiene.

11. The electroluminescent device according to claim 7, wherein said heterocyclic aromatic group is selected from the group consisting of the following: pyrane, pyrroline, furan, benzofuran, thiophene, benzothiophene, pyridine, quinoline, isoquinoline, pyrazine, pyrimidine, pyrrole, pyrazole, imidazole, indole, thiazole, isothiazole, oxazole, isoxazole, benzothiazole, benzoxazole, phenanthroline.

12. The electroluminescent device according to claim 7, wherein the forming method for said transition metal complex is as the following:

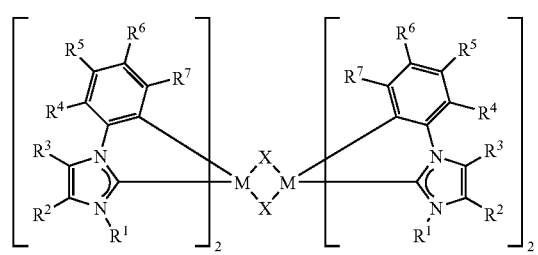
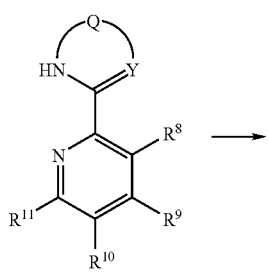
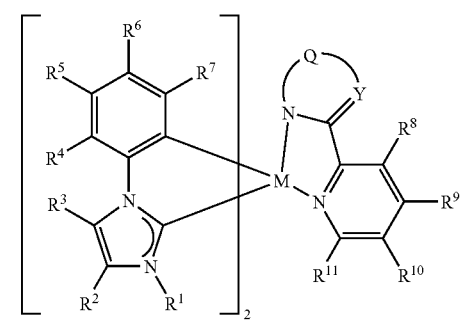
wherein X is a halogen atom.
13. The electroluminescent device according to claim 7, wherein said transition metal complex is represented by the formula selected from the group consisting of the following:
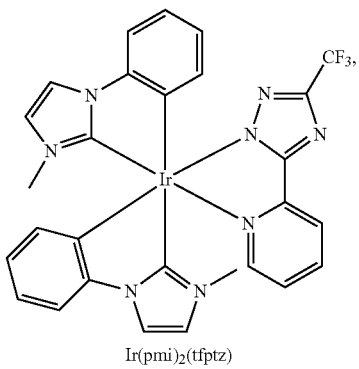
Ir(pmi)₂(tfptz)
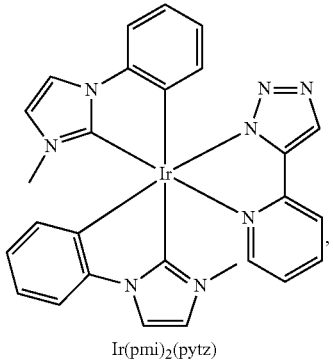
Ir(pmi)₂(pytz)
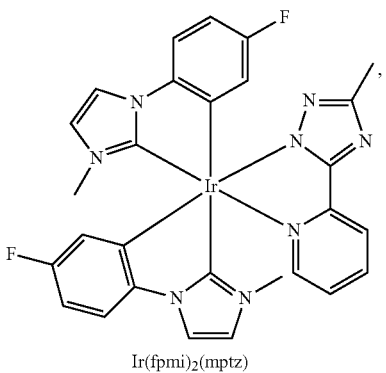
Ir(fpmi)₂(mptz)
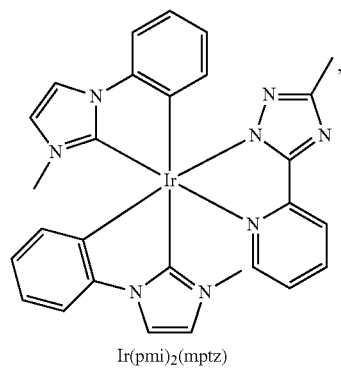
Ir(pmi)₂(mptz)
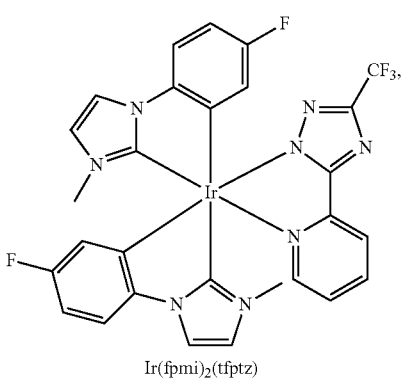
Ir(fpmi)₂(tfptz)

-continued
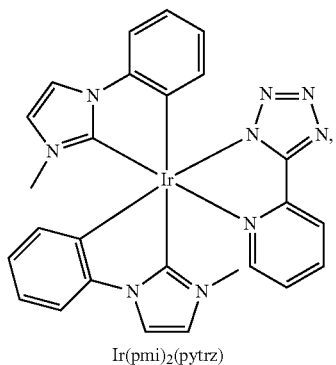
Ir(pmi)₂(pytrz)
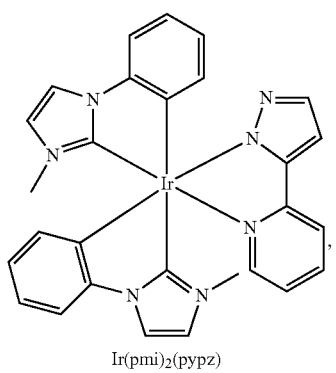
Ir(pmi)₂(pypz)
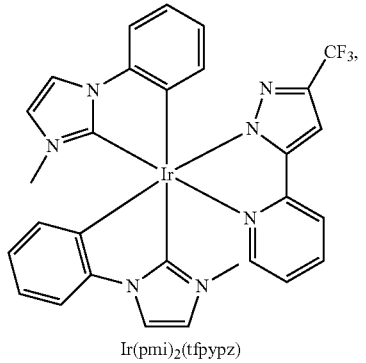
Ir(pmi)₂(tfpypz)
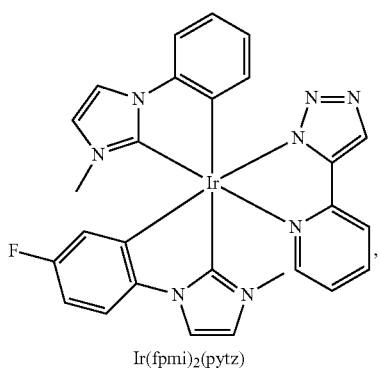
Ir(fpmi)₂(pytz)
-continued
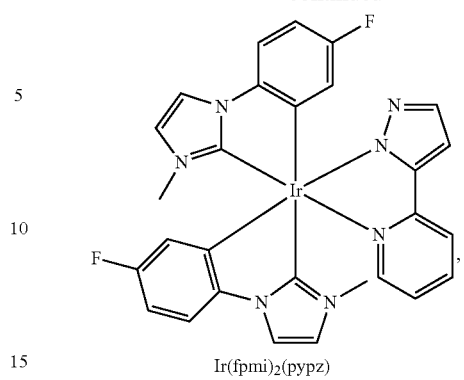
Ir(fpmi)₂(pypz)
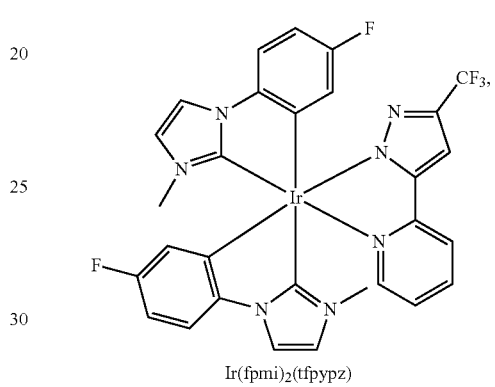
Ir(fpmi)₂(tfpypz)
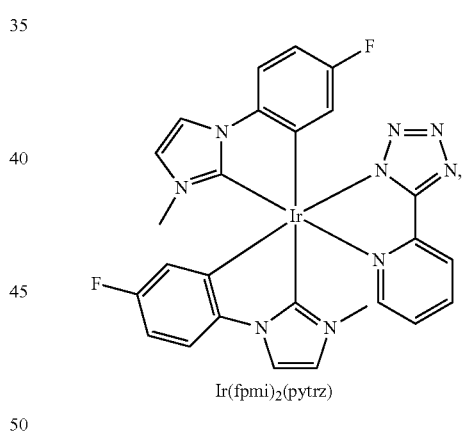
Ir(fpmi)₂(pytrz)
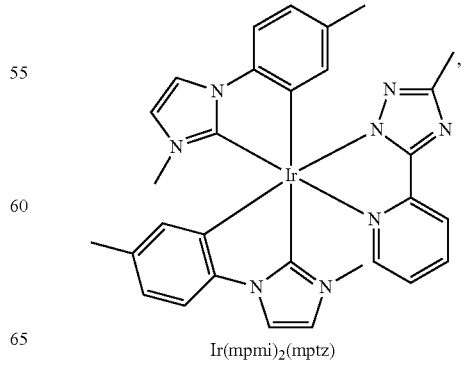
Ir(mpmi)₂(mptz)

-continued

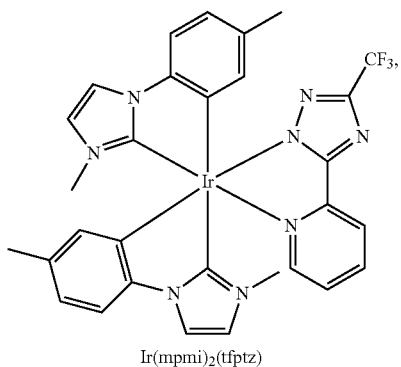

Ir(mpmi)₂(tfptz)

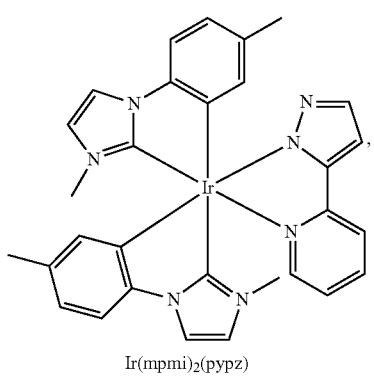

Ir(mpmi)₂(pypz)

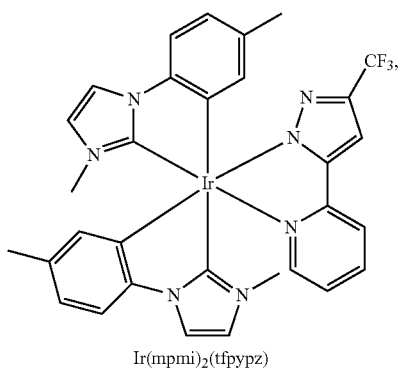

Ir(mpmi)₂(tfpypz)

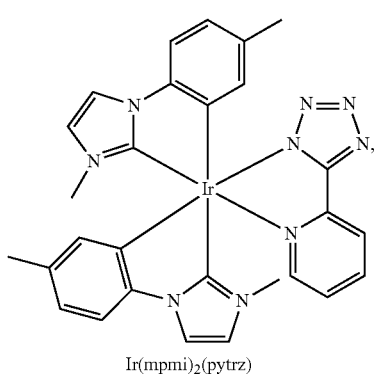

Ir(mpmi)₂(pytrz)

-continued

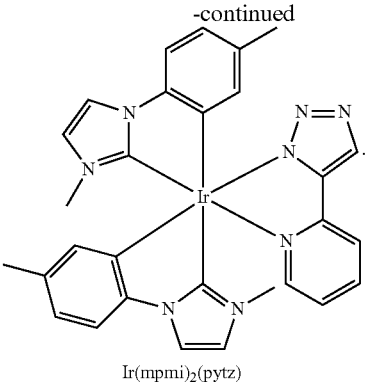

Ir(mpmi)₂(pytz)

14. A transition metal complex with carbene ligand, represented by the following formula:

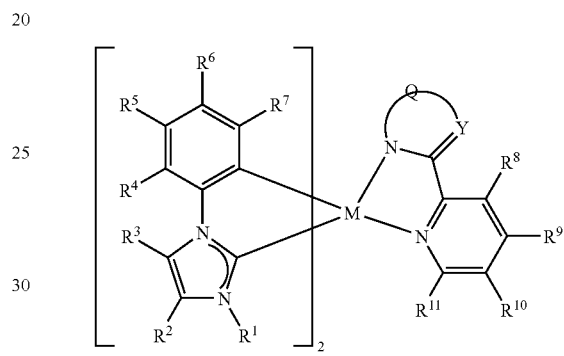

wherein M is a transition metal and is selected from the group consisting of the following: ruthenium, rhodium, tungsten, rhenium, osmium, iridium, platinum;

$R^1$ is selected from the group consisting of the following: C1-C20 alkyl group, C1-C20 cycloalkyl group, cycloalkenyl group, conjugated aromatic group, heterocyclic aromatic group;

wherein at least one of the pairs of $R^2$-$R^3$, $R^4$-$R^5$, $R^5$-$R^6$, $R^6$-$R^7$ forms an aromatic ring, heterocyclic aromatic group, cycloalkenyl group, or heterocyclic alkenyl group, wherein said formed aromatic ring, heterocyclic aromatic group, cycloalkenyl group, or heterocyclic alkenyl group optionally comprises one or more substituent, the remaining ones of $R^2$~$R^7$ that do not form a cyclic group can be identical or different, and are independently selected from the group consisting of the following: H atom, halogen atom, C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group(—CN), nitro group, conjugated aromatic group, heterocyclic aromatic group;

Q is a moiety comprising at least 2 atoms, contributing to a nitrogen-containing heterocycle, wherein Q comprises atom(s) selected from the group consisting of the following, or any combination thereof: nitrogen, carbon, oxygen, sulfur, and said nitrogen-containing heterocycle optionally comprises one or more substituent, wherein the substitutent(s) on said nitrogen-containing heterocycle partly constructed by Q can be identical or different, and are independently selected from the group consisting of the following: H atom, halogen atom, C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group(—CN), nitro group, conjugated aromatic group, heterocyclic aromatic group;

Y is selected from the group consisting of the following: nitrogen(N), carbon(C), oxygen(O), sulfur(S), wherein Y further comprises a substituent selected from the group consisting of the following: H atom, halogen atom, C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group(—CN), nitro group, conjugated aromatic group, heterocyclic aromatic group; and $R^8 \sim R^{11}$ can be identical or different, and are independently selected from the group consisting of the following: H atom, halogen atom, C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group (—CN), nitro group, conjugated aromatic group, heterocyclic aromatic group, cycloalkenyl group.

15. The transition metal complex according to claim 14, wherein said nitrogen-containing heterocycle is selected from the group consisting of the following: pyridine, quinoline, isoquinoline, pyrazine, pyrimidine, pyrrole, pyrazole, imidazole, indole, thiazole, isothiazole, oxazole, isoxazole, benzothiazole, benzoxazole, phenanthroline.

16. The transition metal complex according to claim 14, wherein said aryl group is selected from the group consisting of the following: phenyl, naphthyl, diphenyl, anthryl, pyrenyl, phenanthryl, and fluorenyl group.

17. The transition metal complex according to claim 14, wherein said cycloalkenyl group is selected from the group consisting of the following: cyclohexene, cyclohexadiene, cyclopentene, cyclopentadiene.

18. The transition metal complex according to claim 14, wherein said heterocyclic aromatic group is selected from the group consisting of the following: pyrane, pyrroline, furan, benzofuran, thiophene, benzothiophene, pyridine, quinoline, isoquinoline, pyrazine, pyrimidine, pyrrole, pyrazole, imidazole, indole, thiazole, isothiazole, oxazole, isoxazole, benzothiazole, benzoxazole, phenanthroline.

19. The transition metal complex according to claim 14, with the forming method thereof as the following:

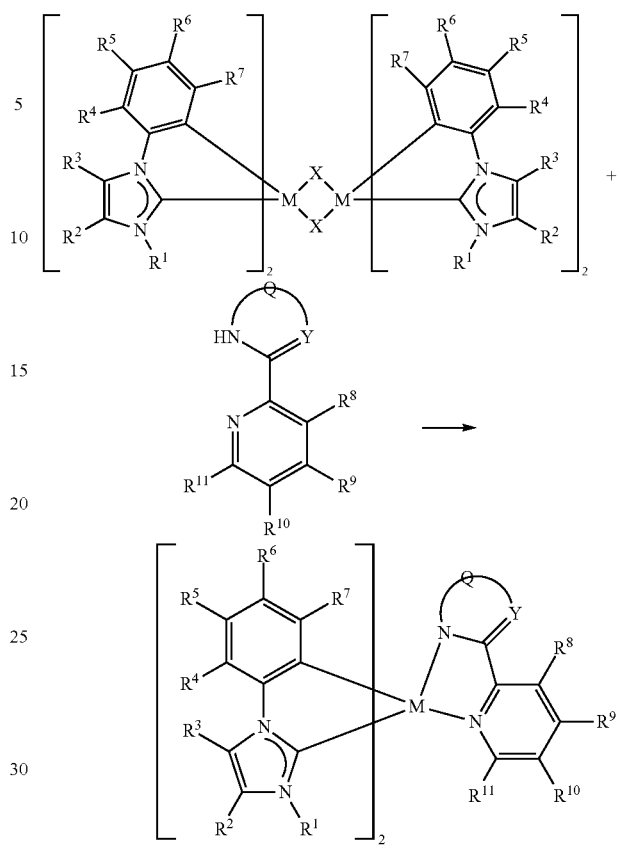

wherein X is a halogen atom.

20. An electroluminescent device, comprising a pair of electrodes and at least one organic layer disposed between said electrodes, said at least one organic layer comprises an emitting layer and a transition metal complex with carbene ligand, wherein said transition metal complex is represented by the following formula:

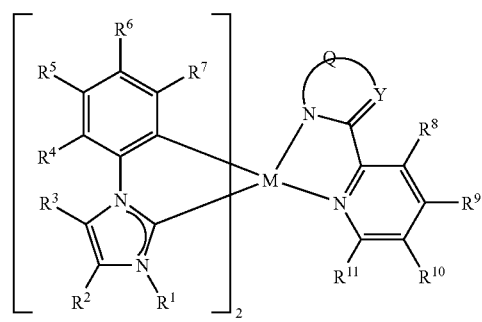

wherein M is a transition metal and is selected from the group consisting of the following: ruthenium, rhodium, tungsten, rhenium, osmium, iridium, platinum;

$R^1$ is selected from the group consisting of the following: C1-C20 alkyl group, C1-C20 cycloalkyl group, cycloalkenyl group, conjugated aromatic group, heterocyclic aromatic group;

wherein at least one of the pairs of $R^2$-$R^3$, $R^4$-$R^5$, $R^5$-$R^6$, $R^6$-$R^7$ forms an aromatic ring, heterocyclic aromatic group, cycloalkenyl group, or heterocyclic alkenyl group, wherein said formed aromatic ring, heterocyclic aromatic group, cycloalkenyl group, or heterocyclic alkenyl group optionally comprises one or more substituent, the remaining ones of $R^2$~$R^7$ that do not form a cyclic group can be identical or different, and are independently selected from the group consisting of the following: H atom, halogen atom, C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group(—CN), nitro group, conjugated aromatic group, heterocyclic aromatic group;

Q is a moiety comprising at least 2 atoms, contributing to a nitrogen-containing heterocycle, wherein Q comprises atom(s) selected from the group consisting of the following, or any combination thereof: nitrogen, carbon, oxygen, sulfur, and said nitrogen-containing heterocycle optionally comprises one or more substituent, wherein the substitutent(s) on said nitrogen-containing heterocycle partly constructed by Q can be identical or different, and are independently selected from the group consisting of the following: H atom, halogen atom, C1-C20 alkyl group, C1-C20 cycloalkyl group, alkoxy group, halogen substituted C1-C20 alkyl group, C1-C20 substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group(—CN), nitro group, conjugated aromatic group, heterocyclic aromatic group, cyclo alkenyl group;

Y is selected from the group consisting of the following: nitrogen(N), carbon(C), oxygen(O), sulfur(S), wherein Y further comprises a substituent selected from the group consisting of the following: H atom, halogen atom, C1-C20 alkyl group, C1-C20 cycloalkyl group, alkoxy group, halogen substituted C1-C20 alkyl group, C1-C20 substituted amino group, C1-C20 acyl group, $C1-C_{20}$ ester group, $C_1-C_{20}$ amide group, aryl group, halogen substituted aryl group, halogen substituted aralkyl group, haloalkyl substituted aryl group, haloalkyl substituted aralkyl group, cyano group(—CN), nitro group, conjugated aromatic group, heterocyclic aromatic group; and $R^8$~$R^{11}$ can be identical or different, and are independently selected from the group consisting of the following: H atom, halogen atom, C1-C20 alkyl group, C1-C20 cycloalkyl group, alkoxy group, halogen substituted C1-C20 alkyl group, $C1-C_{20}$ substituted amino group, C1-C20 acyl group, C1-C20 ester group, C1-C20 amide group, aryl group, halogen substituted aryl group, halogen substituted aralkyl group, haloalkyl substituted aryl group, haloalkyl substituted aralkyl group, cyano group (—CN), nitro group, conjugated aromatic group, heterocyclic aromatic group, cycloalkenyl group.

21. The electroluminescent device according to claim 20, wherein said nitrogen-containing heterocycle is selected from the group consisting of the following: pyridine, quinoline, isoquinoline, pyrazine, pyrimidine, pyrrole, pyrazole, imidazole, indole, thiazole, isothiazole, oxazole, isoxazole, benzothiazole, benzoxazole, phenanthroline.

22. The electroluminescent device according to claim 20, wherein said aryl group is selected from the group consisting of the following: phenyl, naphthyl, diphenyl, anthryl, pyrenyl, phenanthryl, and fluorenyl group.

23. The electroluminescent device according to claim 20, wherein said cycloalkenyl group is selected from the group consisting of the following: cyclohexene, cyclohexadiene, cyclopentene, cyclopentadiene.

24. The electroluminescent device according to claim 20, wherein said heterocyclic aromatic group is selected from the group consisting of the following: pyrane, pyrroline, furan, benzofuran, thiophene, benzothiophene, pyridine, quinoline, isoquinoline, pyrazine, pyrimidine, pyrrole, pyrazole, imidazole, indole, thiazole, isothiazole, oxazole, isoxazole, benzothiazole, benzoxazole, phenanthroline.

25. The electroluminescent device according to claim 20, wherein the forming method for said transition metal complex is as the following:

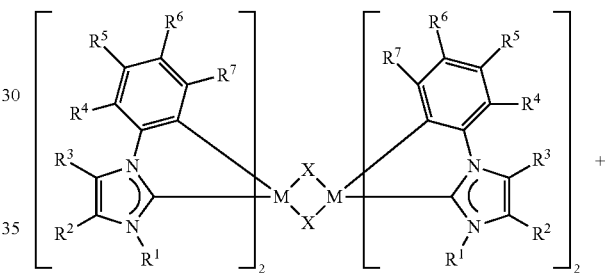

wherein X is a halogen atom.

26. The electroluminescent device according to claim 20, wherein said transition metal complex is represented by the formula selected from the group consisting of the following:

237
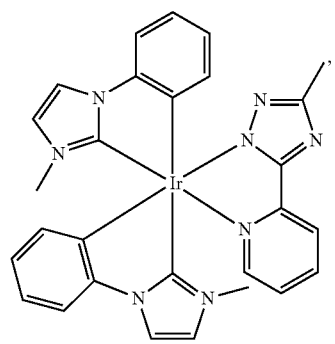
Ir(pmi)₂(mptz)
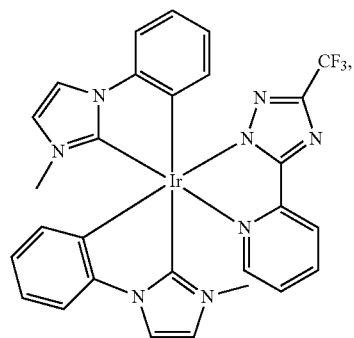
Ir(pmi)₂(tfptz)
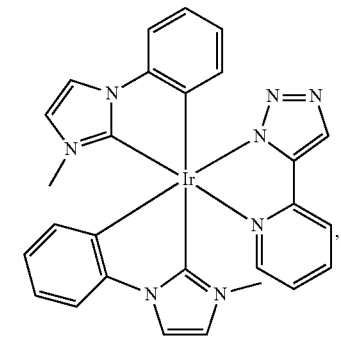
Ir(pmi)₂(pytz)
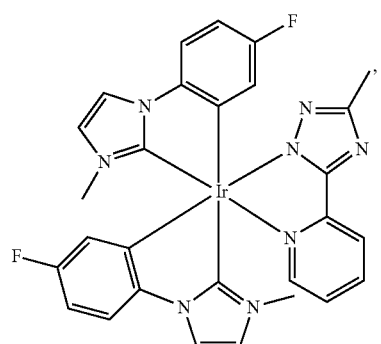
Ir(fpmi)₂(mptz)
238
-continued
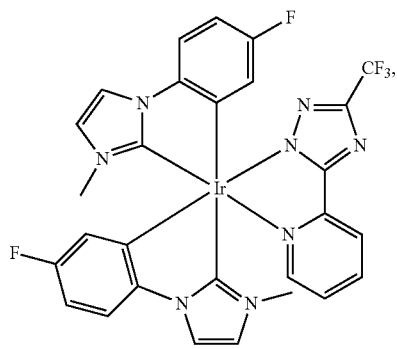
Ir(fpmi)₂(tfptz)
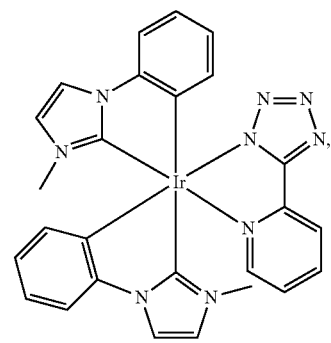
Ir(fpmi)₂(pytrz)
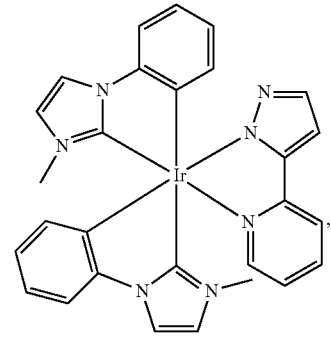
Ir(pmi)₂(pypz)
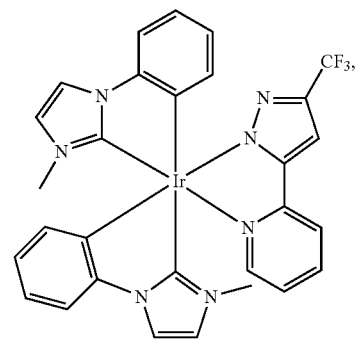
Ir(pmi)₂(tfpypz)

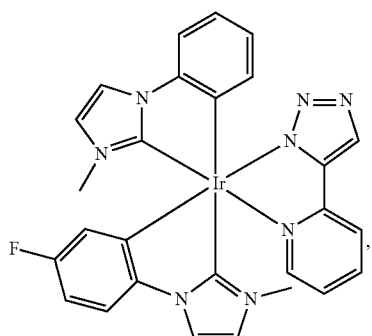
Ir(fpmi)₂(pytz)
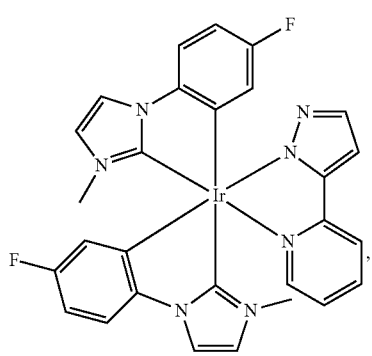
Ir(fpmi)₂(pypz)
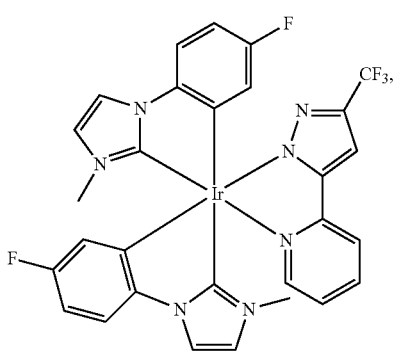
Ir(fpmi)₂(tfpypz)
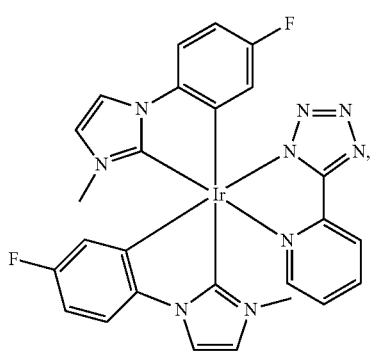
Ir(fpmi)₂(pytrz)
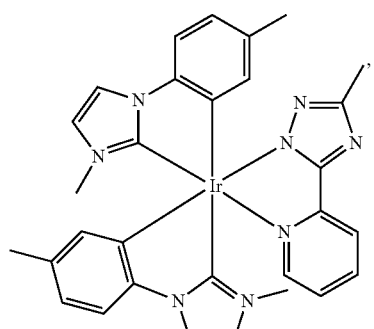
Ir(mpmi)₂(mptz)
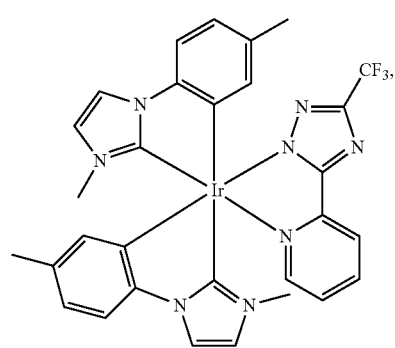
Ir(mpmi)₂(tfptz)
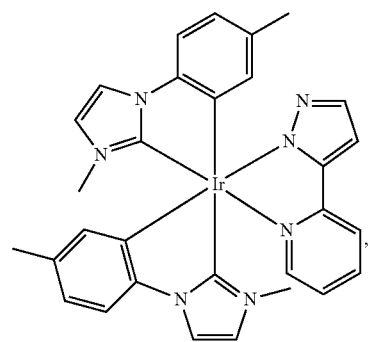
Ir(mpmi)₂(pypz)
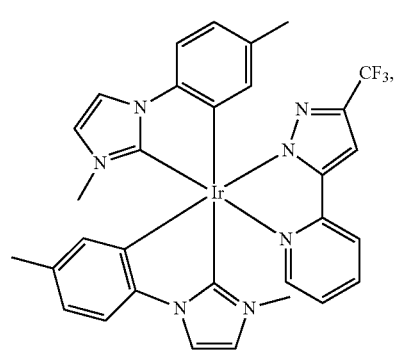
Ir(mpmi)₂(tfpypz)

241
-continued
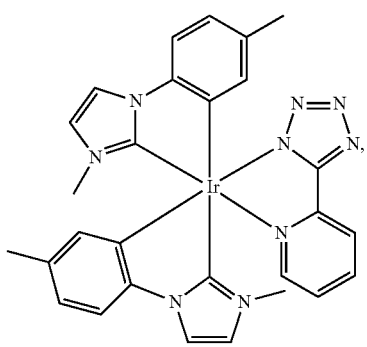
Ir(mpmi)₂(pytrz)
and
242
-continued
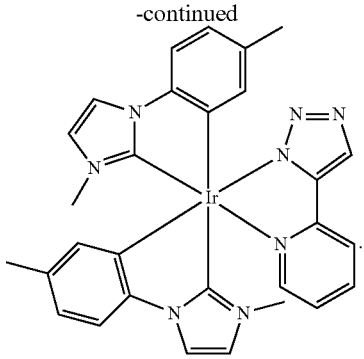
Ir(mpmi)₂(pytz)
* * * * *